(12) United States Patent
Yokoyama et al.

(10) Patent No.: US 10,818,844 B2
(45) Date of Patent: *Oct. 27, 2020

(54) ORGANIC ELECTROLUMINESCENT DEVICE

(71) Applicant: HODOGAYA CHEMICAL CO., LTD., Tokyo (JP)

(72) Inventors: Norimasa Yokoyama, Tokyo (JP); Takeshi Yamamoto, Tokyo (JP); Shuichi Hayashi, Tokyo (JP); Hideyoshi Kitahara, Tokyo (JP)

(73) Assignees: HODOGAYA CHEMICAL CO., LTD., Tokyo (JP); SFC CO., LTD., Chungcheongbuk-Do (KR)

( * ) Notice: Subject to any disclaimer, the term of this patent is extended or adjusted under 35 U.S.C. 154(b) by 272 days.

This patent is subject to a terminal disclaimer.

(21) Appl. No.: 15/324,133

(22) PCT Filed: Jul. 8, 2015

(86) PCT No.: PCT/JP2015/069641
§ 371 (c)(1),
(2) Date: Jan. 5, 2017

(87) PCT Pub. No.: WO2016/006629
PCT Pub. Date: Jan. 14, 2016

(65) Prior Publication Data
US 2017/0179398 A1    Jun. 22, 2017

(30) Foreign Application Priority Data

Jul. 9, 2014 (JP) .................................. 2014-141152

(51) Int. Cl.
*H01L 51/50* (2006.01)
*H01L 51/00* (2006.01)
(Continued)

(52) U.S. Cl.
CPC ........ *H01L 51/0059* (2013.01); *C07C 211/54* (2013.01); *C07C 211/61* (2013.01);
(Continued)

(58) Field of Classification Search
None
See application file for complete search history.

(56) References Cited

U.S. PATENT DOCUMENTS 5,639,914 A  6/1997  Tomiyama et al.
5,707,747 A  1/1998  Tomiyama et al.
(Continued)

FOREIGN PATENT DOCUMENTS

CN  102473856 A  5/2012
CN  102712639 A  10/2012
(Continued)

OTHER PUBLICATIONS

International Search Report issued in Patent Application No. PCT/JP2015/069641, dated Sep. 15, 2015.
(Continued)

*Primary Examiner* — Gregory D Clark
(74) *Attorney, Agent, or Firm* — Greenblum & Bernstein, P.L.C.

(57) ABSTRACT

The organic EL device of the present invention has an anode, a hole transport layer, a luminous layer, an electron transport
(Continued)

9 CATHODE
8 ELECTRON INJECTION LAYER
7 ELECTRON TRANSPORT LAYER
6 LUMINOUS LAYER
5 SECOND HOLE TRANSPORT LAYER
4 FIRST HOLE TRANSPORT LAYER
3 HOLE INJECTION LAYER
2 TRANSPARENT ELECTRODE
1 TRANSPARENT SUBSTRATE layer, and a cathode in this order, and the hole transport layer contains an arylamine compound represented by the following general formula (1):

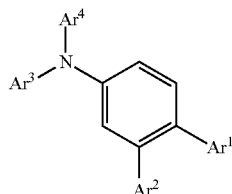

(1)

where
Ar$^1$ to Ar$^4$ each represent a monovalent aromatic hydrocarbon group or a monovalent aromatic heterocyclic group.

13 Claims, 78 Drawing Sheets

(51) Int. Cl.
    *C09K 11/06* (2006.01)
    *C07D 401/10* (2006.01)
    *C07C 211/54* (2006.01)
    *C07C 211/61* (2006.01)

(52) U.S. Cl.
    CPC ............ *C07D 401/10* (2013.01); *C09K 11/06* (2013.01); *H01L 51/006* (2013.01); *C07C 2603/18* (2017.05); *H01L 51/0052* (2013.01); *H01L 51/0058* (2013.01); *H01L 51/5056* (2013.01); *H01L 51/5064* (2013.01); *H01L 51/5072* (2013.01)

(56) References Cited

U.S. PATENT DOCUMENTS

| | | | |
|---|---|---|---|
| 5,792,557 | A | 8/1998 | Nakaya et al. |
| 7,759,030 | B2 | 7/2010 | Abe et al. |
| 7,799,492 | B2 | 9/2010 | Abe et al. |
| 8,021,764 | B2 | 9/2011 | Hwang et al. |
| 8,021,765 | B2 | 9/2011 | Hwang et al. |
| 8,188,315 | B2 | 5/2012 | Hwang et al. |
| 8,394,510 | B2 | 3/2013 | Mizuki et al. |
| 8,895,159 | B2 | 11/2014 | Mizuki et al. |
| 8,974,922 | B2 | 3/2015 | Hwang et al. |
| 9,478,754 | B2 | 10/2016 | Hwang et al. |
| 2005/0236976 | A1* | 10/2005 | Leung ............... C07C 211/54 313/504 |
| 2007/0252521 | A1 | 11/2007 | Kondakov et al. |
| 2009/0284140 | A1 | 11/2009 | Osaka et al. |
| 2009/0317539 | A1 | 12/2009 | Shitagaki et al. |
| 2010/0244008 | A1* | 9/2010 | Lee ............... C07D 409/10 257/40 |
| 2012/0181922 | A1 | 7/2012 | Kawamura et al. |
| 2012/0228598 | A1* | 9/2012 | Yokoyama ........... C07D 471/04 257/40 |
| 2013/0328027 | A1 | 12/2013 | Sotoyama et al. |
| 2013/0341604 | A1 | 12/2013 | Yokoyama et al. |
| 2014/0197402 | A1 | 7/2014 | Huh et al. |
| 2014/0239273 | A1 | 8/2014 | Mizutani et al. |
| 2014/0312287 | A1 | 10/2014 | Stoessel et al. |
| 2018/0269399 | A1* | 9/2018 | Stoessel ............. H01L 51/0059 |

FOREIGN PATENT DOCUMENTS

| | | | |
|---|---|---|---|
| JP | 8-048656 | | 2/1996 |
| JP | 3194657 | | 6/2001 |
| JP | 2003-201472 | | 7/2003 |
| JP | 2006-151979 | | 6/2006 |
| JP | 2009-535815 | | 10/2009 |
| JP | 2009-299049 | | 12/2009 |
| JP | 2010-202633 | | 9/2010 |
| JP | 4943840 | | 5/2012 |
| JP | 2013-258269 | | 12/2013 |
| KR | 2011-0018195 | A | 2/2011 |
| KR | 10-1216004 | | 12/2012 |
| KR | 2013051582 | * | 5/2013 ............. C09K 11/06 |
| TW | 201326145 | A | 7/2013 |
| WO | 2008/062636 | | 5/2008 |
| WO | 2010/035723 | | 4/2010 |
| WO | 2013/087142 | | 6/2013 |
| WO | 2014/129048 | | 8/2014 |

OTHER PUBLICATIONS

Chinese Office Action with English Translation in respect to Chinese Application No. 201580048317.5, dated Feb. 27, 2018.
Extended European Search Report in respect to European Application No. 15818378.0, dated Feb. 12, 2018.
Chinese Office Action issued with respect to Chinese Application No. 201580048317.5, dated Nov. 26, 2018.
Taiwanese Office Action issued with respect to Application No. 104122243, dated Oct. 11, 2018.

\* cited by examiner

9 CATHODE
8 ELECTRON INJECTION LAYER
7 ELECTRON TRANSPORT LAYER
6 LUMINOUS LAYER
5 SECOND HOLE TRANSPORT LAYER
4 FIRST HOLE TRANSPORT LAYER
3 HOLE INJECTION LAYER
2 TRANSPARENT ELECTRODE
1 TRANSPARENT SUBSTRATE (1 − 1)
pm-substituted benzene ring: 1

(1 − 2)
pm-substituted benzene ring: 1

(1 − 3)
pm-substituted benzene ring: 1

(1 − 4)
pm-substituted benzene ring: 1

(1 − 5)
pm-substituted benzene ring: 1

(1-6)
pm-substituted benzene ring: 1

(1-7)
pm-substituted benzene ring: 1

(1-8)
pm-substituted benzene ring: 1

(1-9)
pm-substituted benzene ring: 1

(1-117)
pm-substituted benzene rings: 2

(1-118)
pm-substituted benzene rings: 2

(1-119)
pm-substituted benzene rings: 2

(1-120)
pm-substituted benzene rings: 2

(1-14)
pm-substituted benzene ring: 1

(1-15)
pm-substituted benzene ring: 1

(1-16)
pm-substituted benzene ring: 1

(1-17)
pm-substituted benzene ring: 1

(1-18)
pm-substituted benzene ring: 1

(1-19)
pm-substituted benzene ring: 1

(1-20)
pm-substituted benzene ring: 1

(1-21)
pm-substituted benzene ring: 1

(1-22)
pm-substituted benzene ring: 1

(1-23)
pm-substituted benzene ring: 1

(1-24)
pm-substituted benzene ring: 1

(1-25)
pm-substituted benzene ring: 1

(1-26)
pm-substituted benzene ring: 1

(1-27)
pm-substituted benzene ring: 1

(1-28)
pm-substituted benzene ring: 1

(1-29)
pm-substituted benzene ring: 1

(1-30)
pm-substituted benzene ring: 1

(1-31)
pm-substituted benzene ring: 1

(1-37)
pm-substituted benzene ring: 1

(1-38)
pm-substituted benzene ring: 1

(1-39)
pm-substituted benzene ring: 1

(1-40)
pm-substituted benzene ring: 1

(1-41)
pm-substituted benzene ring: 1

(1-47)
pm-substituted benzene ring: 1

(1-48)
pm-substituted benzene ring: 1

(1-49)
pm-substituted benzene ring: 1

(1-50)
pm-substituted benzene ring: 1

(1-51)
pm-substituted benzene ring: 1

(1-52)
pm-substituted benzene ring: 1

(1-53)
pm-substituted benzene ring: 1

(1-54)
pm-substituted benzene ring: 1

(1-55)
pm-substituted benzene ring: 1

(1-56)
pm-substituted benzene ring: 1

(1-57)
pm-substituted benzene ring: 1

(1-58)
pm-substituted benzene ring: 1

(1-59)
pm-substituted benzene ring: 1

(1-60)
pm-substituted benzene ring: 1

(1-61)
pm-substituted benzene ring: 1

(1-62)
pm-substituted benzene ring: 1

(1-63)
pm-substituted benzene ring: 1

(1-64)
pm-substituted benzene ring: 1

(1-65)
pm-substituted benzene ring: 1

(1-66)
pm-substituted benzene ring: 1

(1-67)
pm-substituted benzene ring: 1

(1-68)
pm-substituted benzene ring: 1

(1-69)
pm-substituted benzene ring: 1

(1-70)
pm-substituted benzene ring: 1

(1-71)
pm-substituted benzene ring: 1

(1-72)
pm-substituted benzene ring: 1

(1-73)
pm-substituted benzene ring: 1

(1-74)
pm-substituted benzene ring: 1

(1-75)
pm-substituted benzene ring: 1

(1-76)
pm-substituted benzene ring: 1

(1-77)
pm-substituted benzene ring: 1

(1-78)
pm-substituted benzene ring: 1

(1-79)
pm-substituted benzene ring: 1

(1-80)
pm-substituted benzene ring: 1

(1-81)
pm-substituted benzene ring: 1

(1-82)
pm-substituted benzene ring: 1

(1-83)
pm-substituted benzene ring: 1

(1-84)
pm-substituted benzene ring: 1

(1-85)
pm-substituted benzene ring: 1

(1-86)
pm-substituted benzene ring: 1

(1-87)
pm-substituted benzene ring: 1

(1-88)
pm-substituted benzene ring: 1

(1-89)
pm-substituted benzene ring: 1

(1-90)
pm-substituted benzene ring: 1

(1-91)
pm-substituted benzene ring: 1

(1-92)
pm-substituted benzene ring: 1

(1-93)
pm-substituted benzene ring: 1

(1-94)
pm-substituted benzene rings: 2

(1-95)

pm-substituted benzene rings: 2

(1-96)

pm-substituted benzene rings: 2

(1-97)

pm-substituted benzene rings: 2

(1-98)

pm-substituted benzene rings: 2

(1-99)
pm-substituted benzene rings: 2

(1-100)
pm-substituted benzene rings: 2

(1-101)
pm-substituted benzene rings: 2

(1-102)
pm-substituted benzene rings: 2

(1-103)
pm-substituted benzene rings: 2

(1-104)
pm-substituted benzene rings: 2

(1-105)
pm-substituted benzene rings: 2

(1-106)
pm-substituted benzene rings: 2

(1-107)
pm-substituted benzene rings: 2

(1-108)
pm-substituted benzene rings: 2

(1-109)
pm-substituted benzene rings: 2

(1-110)
pm-substituted benzene rings: 2

(1-111)
pm-substituted benzene rings: 2

(1-112)
pm-substituted benzene rings: 2

(1-113)
pm-substituted benzene rings: 2

(1-114)
pm-substituted benzene rings: 2

(1-115)
pm-substituted benzene rings: 2

(1-116)
pm-substituted benzene rings: 2

(1-117)
pm-substituted benzene rings: 2

(1-118)
pm-substituted benzene rings: 2

(1-119)
pm-substituted benzene rings: 2

(1-120)
pm-substituted benzene rings: 2

(1-121)
pm-substituted benzene rings: 2

(1-122)
pm-substituted benzene rings: 2

(1-123)
pm-substituted benzene rings: 2

(1-124)
pm-substituted benzene rings: 2

(1-125)

pm-substituted benzene rings: 2

(1-126)

pm-substituted benzene rings: 2

(1-127)
pm-substituted benzene rings: 2

(1-128)
pm-substituted benzene rings: 2

(1-129)
pm-substituted benzene rings: 3

(1-130)
pm-substituted benzene rings: 3

(1-131)
pm-substituted benzene rings: 3

(1-132)
pm-substituted benzene rings: 3

(1-133)
pm-substituted benzene rings: 3

(1-134)
pm-substituted benzene ring: 1

(1-135)
pm-substituted benzene ring: 1

(1-136)
pm-substituted benzene ring: 1

(1-137)
pm-substituted benzene ring: 1

(1-138)
pm-substituted benzene ring: 1

(1-139)
pm-substituted benzene ring: 1

(1-140)
pm-substituted benzene ring: 1

(1-141)
pm-substituted benzene ring: 1

(1-142)
pm-substituted benzene ring: 1

(1-143)
pm-substituted benzene ring: 1

(1-144)
pm-substituted benzene ring: 1

(1-145)
pm-substituted benzene ring: 1

(1-146)
pm-substituted benzene ring: 1

(1-147)
pm-substituted benzene ring: 1

(1-148)
pm-substituted benzene ring: 1

(1-149)
pm-substituted benzene ring: 1

(1-150)
pm-substituted benzene ring: 1

(1-151)
pm-substituted benzene ring: 1

(1-152)
pm-substituted benzene ring: 1

(1-153)
pm-substituted benzene ring: 1

(1-154)
pm-substituted benzene ring: 1

(1-155)
pm-substituted benzene ring: 1

(1-156)
pm-substituted benzene ring: 1

(1-157)
pm-substituted benzene ring: 1

(1-158)
pm-substituted benzene ring: 1

(1-159)
pm-substituted benzene ring: 1

(2a-1)

(2a-2)

(2a-3)

(2a-4)

(2a-5)

(2a-6)

(2a-7)

(2a-8)

(2a-9)

(2a-10)

(2a-11)

(2a-12)

(2a-13)

(2a-14)

(2a-15)

(2a-16)

(2a-17)

(2a-18)

(2a-19)

(2a-20)

(2b-1)

(2b-2)

(2b-3)

(2b-4)

(2b-5)

(2b-6)

(2b-7)

(2b-8)

(2b-9)

(2b-10)

(2b-11)

(2b-12)

(2b-13)

(2b-14)

(2b-15)

(2b-16)

(2c-1)

(2c-2)

(2c-3)

(2c-4)

(2c-5)

(2c-6)

(2c-7)

(2c-8)

(2c-9)

(2c-10)

(2c-11)

(2c-12)

(2c-13)

(2c-14)

(2c-15)

(2c-16)

(2c-17)

(2c-18)

(2c-19)

(2c-20)

(2c-21)

(2c-22)

(2c-23)

(2c-24)

(2c-25)

(2c-26)

(2c-27)

(2c-28)

(2c-29)

(2c-30)

(3-1)

(3-2)

(3-3)

(3-4)

(3-5)

(3-11)

(3-12)

(3-13)

(3-14)

(3-15)

(3-16)

(3-17)

(3-18)

(3-19)

(3-20)

(3-21)

(3-22)

(3-23)

(3-24)

(3-25)

(3-26)

(3-27)

(3-28)

(3-29)

(3-30)

(3-31)

(3-38)

(3-39)

(3-40)

(3-41)

(4-1)

(4-2)

(4-3)

(4-4)

(4-5)

(4-6)

(4-7)

(4-8)

(4-9)

(4-10)

(4-11)

(4-12)

(4-13)

(4-14)

(4-15)

(4－16)

(4－17)

ORGANIC ELECTROLUMINESCENT DEVICE

TECHNICAL FIELD

This invention relates to an organic electroluminescent device (organic EL device) which is a self light-emitting device suitable for various display devices. Furthermore, the invention relates to a novel arylamine compound suitably used for a hole transport layer of the organic EL device.

BACKGROUND ART

Since an organic EL device is a self light-emitting device, it is brighter, better in visibility, and capable of clearer display, than a liquid crystal device. Hence, many researches have been conducted on organic EL devices.

In 1987, C. W. Tang et al. of Eastman Kodak worked out a laminated structure sharing various roles for light emission among various materials, thereby succeeding in the development of practical organic EL devices. Such an organic EL device is constituted by laminating a fluorescent body capable of transporting electrons, and an organic substance capable of transporting holes. The organic EL device is adapted to inject positive charges and negative charges into the layer of the fluorescent body to perform light emission, the devices was capable of attaining a high luminance of 1,000 cd/m$^2$ or more at a voltage of 10V or less (see, for example, Patent Document 1 and Patent Document 2).

Many improvements have been made to put the organic EL devices to practical use. For example, it is generally known that high efficiency and high durability are achieved by further allocating various roles of a laminated structure and forming an anode, a hole injection layer, a hole transport layer, a luminous layer, an electron transport layer, an electron injection layer, and a cathode provided on a substrate.

For a further increase in the luminous efficiency, it has been attempted to utilize triplet excitons, and the utilization of phosphorescent compounds has been considered.

Furthermore, devices utilizing light emission by thermally activated delayed fluorescence (TADF) have been developed. For example, Adachi et al. of Kyushu University realized in 2011 an external quantum efficiency of 5.3% by a device using a thermally activated delayed fluorescence material.

The luminous layer can also be prepared by doping a charge transporting compound, generally called a host material, with a fluorescent compound, a phosphorescent compound, or a material radiating delayed fluorescence. The selection of an organic material in the organic EL device greatly affects the characteristics of the device, such as efficiency and durability.

With the organic EL device, the charges injected from both electrodes recombine in the luminous layer to obtain light emission. In this case, how efficiently the charges of the holes and the electrons are transferred to the luminous layer is of importance, and the device needs to be excellent in carrier balance. Moreover, the luminous efficiency is improved by enhancing hole injection properties and electron blocking properties of blocking electrons injected from the cathode to increase recombination probability of holes and electrons, and by confining excitons generated within the luminous layer. Thus, the role of the hole transport material is so important that there has been a desire for a hole transport material having high hole injection properties, high hole mobility, high electron blocking properties, and high durability to electrons.

From the viewpoint of service life of the device, heat resistance and amorphousness of the material are also important. A material with low heat resistance is thermally decomposed even at a low temperature by heat produced during device driving, and the material deteriorates. With a material having low amorphousness, crystallization of a thin film occurs even in a short time, and the device deteriorates. Thus, high heat resistance and satisfactory amorphousness are required of the material to be used.

As hole transport materials so far used for organic EL devices, N,N'-diphenyl-N,N'-di(α-naphthyl)benzidine (NPD) and various aromatic amine derivatives have been known (see, for example, Patent Document 1 and Patent Document 2). NPD has satisfactory hole transport capability, but its glass transition point (Tg) serving as an index of heat resistance is as low as 96° C. Under high temperature conditions, therefore, device characteristics decline because of crystallization.

Among the aromatic amine derivatives described in Patent Documents 1 and 2 are compounds having excellent hole mobility of $10^{-3}$ cm$^2$/Vs or more. Since their electron blocking properties are insufficient, however, some of electrons pass through the luminous layer, and an increase in the luminous efficiency cannot be expected. For these and other reasons, there has been a desire for a material having higher electron blocking properties, more stable in the form of a thin film, and possessing higher heat resistance, in order to achieve an even higher efficiency.

Besides, highly durable aromatic amine derivatives have been reported (see, for example, Patent Document 3). However, they have been used as charge transport materials for electrophotographic photoreceptors, and there have been no examples of using them as organic EL devices.

As compounds improved in characteristics such as heat resistance and hole injection properties, arylamine compounds having substituted carbazole structures have been proposed (see, for example, Patent Document 4 and Patent Document 5). In devices using these compounds as hole injection layers or hole transport layers, heat resistance and luminous efficiency have been improved. However, the improved characteristics have not been sufficient, and an even lower driving voltage and an even higher luminous efficiency are desired.

In order to improve the device characteristics of an organic EL device and increase the yield of device preparation, it is desired to obtain a device, which enables holes and electrons to recombine with high efficiency, which has a high luminous efficiency, whose driving voltage is low, and whose service life is long, by combining materials excellent in the hole and electron injection/transport performance, thin film stability, and durability.

In order to improve the device characteristics of an organic EL device, moreover, it is desired to obtain a device, which is satisfactory in carrier balance, has a high efficiency, works at a low driving voltage, and has a long service life, by combining materials excellent in the hole and electron injection/transport performance, thin film stability, and durability.

PRIOR ART DOCUMENTS

Patent Documents

Patent Document 1: JP-A-8-048656
Patent Document 2: Japanese Patent No. 3194657

Patent Document 3: Japanese Patent No. 4943840
Patent Document 4: JP-A-2006-151979
Patent Document 5: WO2008/62636

SUMMARY OF THE INVENTION

Problems to be Solved by the Invention

It is an object of the present invention to provide an organic EL device with high efficiency, low driving voltage, and long service life by using various materials which excel in hole and electron injection/transport performance, electron blocking capability, thin film stability, and durability so that the characteristics possessed by the respective materials can be exhibited effectively, wherein the various materials are selected as materials for a highly efficient and highly durable organic EL device.

It is another object of the invention to provide a novel arylamine compound suitably used for the formation of the hole transport layer of the organic EL device.

Means for Solving the Problems

The present inventors have found that an arylamine compound having a specific structure excels in hole injection and transport capabilities, thin film stability, and durability, and also excels in electron blocking properties. Based on these findings, they have accomplished the present invention.

According to the present invention, there is provided an organic electroluminescent device having an anode, a hole transport layer, a luminous layer, an electron transport layer, and a cathode in this order, wherein the hole transport layer contains an arylamine compound represented by the following general formula (1):

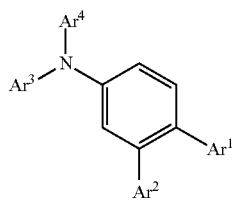

(1)

where
$Ar^1$ to $Ar^4$ each represent a monovalent aromatic hydrocarbon group or a monovalent aromatic heterocyclic group.

In the organic electroluminescent device (organic EL device) of the invention, it is preferred that the arylamine compound be represented by the following general formula (1a) or (1b).

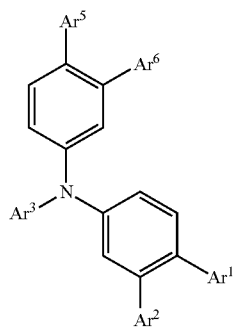

(1a)

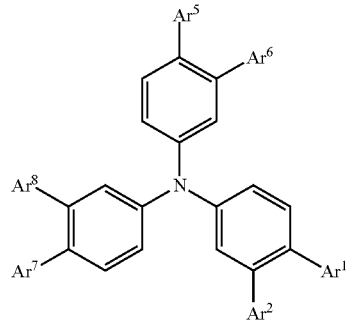

(1b)

In the formulas (1a) and (1b),
$Ar^1$ to $Ar^3$ each represent a group as defined above, and $Ar^5$, $Ar^6$, $Ar^7$ and $Ar^8$, like $Ar^1$ to $Ar^3$, each represent a monovalent aromatic hydrocarbon group or a monovalent aromatic heterocyclic group.

In the organic EL device of the invention, it is preferred for the electron transport layer to contain an anthracene derivative represented by the following general formula (2).

In the organic EL device of the invention, it is preferred for the electron transport layer to contain an anthracene derivative represented by the following formula (2).

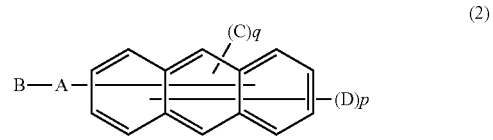

(2)

where
A represents a divalent aromatic hydrocarbon group, a divalent aromatic heterocyclic group, or a single bond,
B represents a monovalent aromatic heterocyclic group,
C represents a monovalent aromatic hydrocarbon group or a monovalent aromatic heterocyclic group,
D represents a hydrogen atom, a deuterium atom, a fluorine atom, a chlorine atom, a cyano group, an alkyl group having 1 to 6 carbon atoms, and
p and q are such that p denotes an integer of 7 or 8, and q denotes an integer of 1 or 2, provided that p and q total 9.

The above-mentioned anthracene derivative is preferably represented by the following general formula (2a), (2b) or (2c), in particular.

The anthracene derivative represented by the general formula (2a):

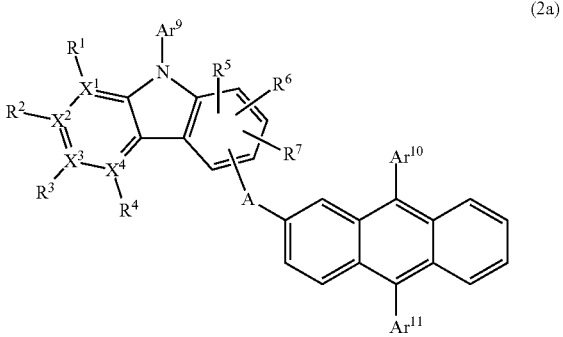

(2a)

where

A is as defined in the aforementioned general formula (2),
$Ar^9$, $Ar^{10}$ and $Ar^{11}$ each represent a monovalent aromatic hydrocarbon group or a monovalent aromatic heterocyclic group, $R^1$ to $R^7$ each represent a hydrogen atom, a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, a monovalent aromatic hydrocarbon group, a monovalent aromatic heterocyclic group, or an aryloxy group, and these groups may bind to each other via a single bond, a methylene group optionally having a substituent, an oxygen atom, or a sulfur atom to form a ring, and $X^1$, $X^2$, $X^3$ and $X^4$ each represent a carbon atom or a nitrogen atom, provided that only one of $X^1$, $X^2$, $X^3$ and $X^4$ represents a nitrogen atom, and any of $R^1$ to $R^4$, including a hydrogen atom, does not bind to the nitrogen atom.

The anthracene derivative represented by the general formula (2b):

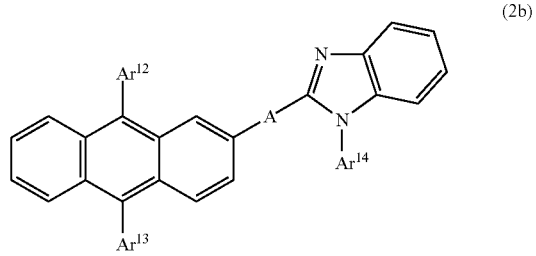

(2b)

where

A is as defined in the aforementioned general formula (2), and $Ar^{12}$, $Ar^{13}$ and $Ar^{14}$ each represent a monovalent aromatic hydrocarbon group or a monovalent aromatic heterocyclic group.

The anthracene derivative represented by the general formula (2c):

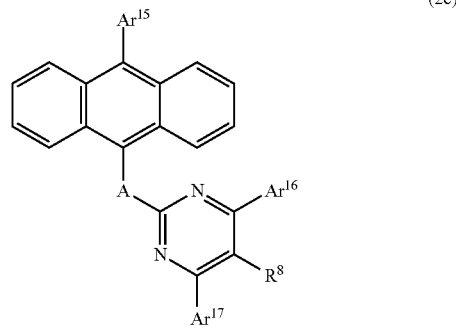

(2c)

where

A is as defined in the aforementioned general formula (2),
$Ar^{15}$, $Ar^{16}$ and $Ar^{17}$ each represent a monovalent aromatic hydrocarbon group or a monovalent aromatic heterocyclic group, and $R^8$ represents a hydrogen atom, a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, a monovalent aromatic hydrocarbon group, a monovalent aromatic heterocyclic group, or an aryloxy group.

In the organic EL device of the invention, moreover, it is preferred that the hole transport layer has a two-layer structure having a first hole transport layer and a second hole transport layer, and that the second hole transport layer is located on the luminous layer side, and contains the above arylamine compound.

In the organic EL device in which the hole transport layer has the two-layer structure, it is desirable that the first hole transport layer contains a triarylamine derivative different from the arylamine compound contained in the second hole transport layer, and that the triarylamine derivative is preferably a compound which has a molecular structure having two triarylamine skeletons coupled together by a single bond or a divalent hydrocarbon group, and which has 2 to 6 triarylamine skeletons in the entire molecule.

Furthermore, a compound represented by the following general formula (3) or (4) is preferably used as the above triarylamine derivative contained in the first hole transport layer.

The triarylamine derivative represented by the general formula (3):

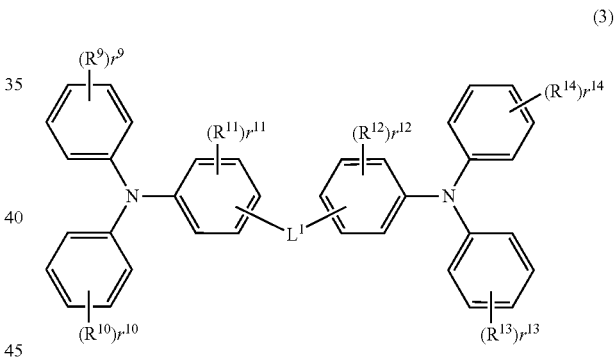

(3)

where $r^9$, $r^{10}$, $r^{13}$ and $r^{14}$ each denote an integer of 0 to 5,
$r^{11}$ and $r^{12}$ each denote an integer of 0 to 4,
$R^9$ to $R^{14}$ each represent a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, a monovalent aromatic hydrocarbon group, a monovalent aromatic heterocyclic group, or an aryloxy group and, if a plurality of these groups are present on the same benzene ring, these groups may bind to each other via a single bond, a methylene group optionally having a substituent, an oxygen atom, or a sulfur atom to form a ring, and $L^1$ represents a single bond, or a divalent group represented by the following structural formula (B), (C), (D), (E), (F) or (G).

(B)
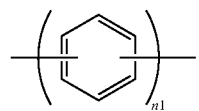
where n1 denotes an integer of 1 to 4.
(C)
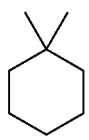
(D)
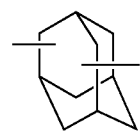
-continued
(E)
—CH$_2$—
(F)
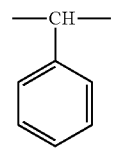
(G)
The triarylamine derivative represented by the general formula (4):
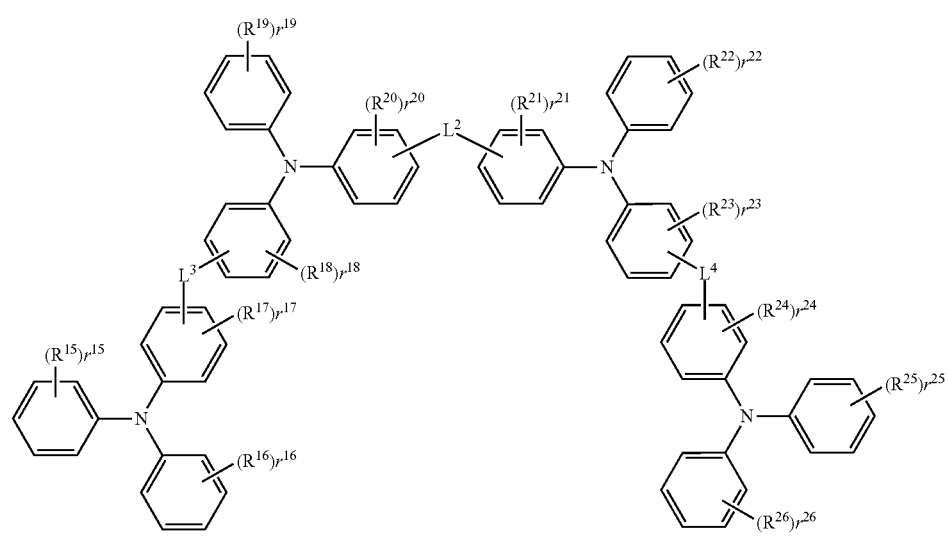

Where $r^{15}, r^{16}, r^{19}, r^{22}, r^{25}$, and $r^{26}$ each denote an integer of 0 to 5, $r^{17}, r^{18}, r^{20}, r^{21}, r^{23}$, and $r^{24}$ each denote an integer of 0 to 4, $R^{15}$ to $R^{26}$ each represent a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, a monovalent aromatic hydrocarbon group, a monovalent aromatic heterocyclic group, or an aryloxy group and, if a plurality of these groups are present on the same benzene ring, these groups may bind to each other via a single bond, a methylene group optionally having a substituent, an oxygen atom, or a sulfur atom to form a ring, and $L^2$, $L^3$ and $L^4$ each represent a single bond, or a divalent group represented by the following structural formula (B'), or the structural formula (C), (D), (E), (F) or (G) in the aforementioned general formula (3).

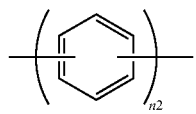
(B')

where n2 denotes an integer of 1 to 3.

According to the present invention, there is also provided the arylamine compound represented by the aforementioned general formula (1).

Effects of the Invention

In the organic EL device of the present invention, the arylamine compound represented by the general formula (1), which is contained in the hole transport layer, has the structural features that two monovalent aromatic hydrocarbon groups or monovalent aromatic heterocyclic groups are bound, as substituents, to the benzene ring bound to the nitrogen atom, and these substituents bind to the p-position and the m-position of the benzene ring with respect to the nitrogen atom. Such an arylamine compound is a novel compound, and has (1) satisfactory hole injection properties, (2) high hole mobility, (3) excellent electron blocking capability, (4) stable thin film state, and (5) excellent heat resistance.

That is, in the organic EL device of the present invention, the arylamine compound having the above properties is contained in the hole transport layer. Thus, holes can be efficiently injected into and transported to the luminous layer, light emission with a high efficiency and at a low driving voltage can be achieved and, further, the long service life of the device can be realized.

In the present invention, moreover, the electron transport layer formed from the anthracene derivative represented by the general formula (2), as well as the hole transport layer containing the above arylamine compound, is provided. Hence, holes and electrons can be injected into and transported to the luminous layer more efficiently, a high carrier balance can be ensured, so that a higher improvement in the characteristics can be achieved.

Furthermore, in the present invention, the hole transport layer is configured as a two-layer structure having the first hole transport layer and the second hole transport layer, and the second hole transport layer located on the side adjacent to the luminous layer is formed from the above arylamine compound of the general formula (1). By so doing, the electron blocking performance of the arylamine compound can be maximized, and an organic EL device having a higher efficiency and a longer service life can be realized.

MODE FOR CARRYING OUT THE INVENTION

Figure 1:
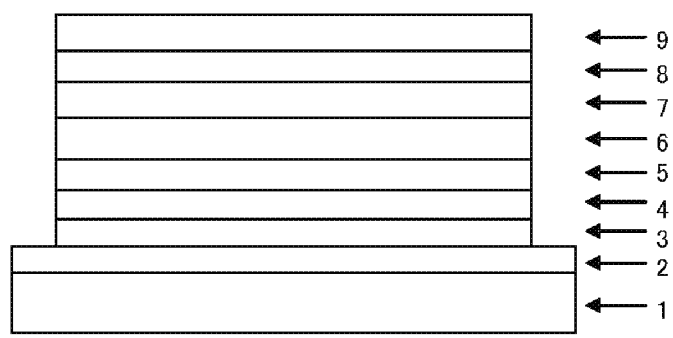
FIG. 1 is a view showing the preferred layer structure adopted in Examples in the organic EL device of the present invention.

The organic EL device of the present invention has a basic structure in which an anode, a hole transport layer, a luminous layer, an electron transport layer, and a cathode are formed in this sequence on a transparent substrate such as a glass substrate or a transparent plastic substrate (e.g., polyethylene terephthalate substrate). As long as the organic EL device has such a basic structure, its layer structure can take various forms. For example, the hole transport layer can be configured as a two-layer structure having a first hole transport layer located on the anode side, and a second hole transport layer adjacent to the luminous layer, and a hole injection layer can be provided between the transparent electrode and the hole transport layer. Further, an electron injection layer can be provided between the electron transport layer and the cathode. FIG. 1, for example, shows a layer structure adopted in the Examples to be described later. In this example, an anode 2, a hole injection layer 3, a first hole transport layer 4, a second hole transport layer 5, a luminous layer 6, an electron transport layer 7, an electron injection layer 8, and a cathode 9 are formed in this sequence on a transparent substrate 1.

The respective layers constituting the organic EL device of the present invention will be described below.

<Anode>

The anode 2 is formed on the transparent substrate 1 by vapor deposition of an electrode material having a high work function, such as ITO or gold.

<Hole Transport Layer>

The hole transport layer is provided between the above anode 2 and the luminous layer 6. In the present invention, this hole transport layer contains an arylamine compound represented by the following general formula (1):

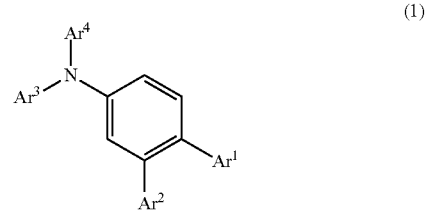

(1)

where

Ar$^1$ to Ar$^4$ each represent a monovalent aromatic hydrocarbon group or a monovalent aromatic heterocyclic group.

Such an arylamine compound is a triarylamine with all the three hydrogen atoms being substituted by aromatic groups, and has, in particular, a novel structure having at least one benzene ring (hereinafter, this benzene ring may be abbreviated as pm-substituted benzene ring) which has a monovalent aromatic hydrocarbon group or a monovalent aromatic heterocyclic group as a substituent (e.g., Ar$^1$ and Ar$^2$ in the formula (1)) bound to each of the p-position and the m-position with respect to the nitrogen atom of the amino group.

The arylamine compound of the above structure has a high glass transition point Tg (e.g., 100° C. or higher) as will be understood from the Examples (to be described later), and thus has a stable thin film state and excellent heat resistance. Moreover, the arylamine compound has a high work function in comparison with the work function (about 5.4 eV) of an ordinary hole transport material. Hence, the arylamine compound has excellent hole transport properties, high hole mobility, satisfactory hole injection properties and, furthermore, excellent electron blocking properties.

In the above general formula (1), Ar$^1$ to Ar$^4$ may be the same or different, and the monovalent aromatic hydrocarbon group or the monovalent aromatic heterocyclic group, represented by Ar$^1$ to Ar$^4$, can be exemplified by the following:

The monovalent aromatic hydrocarbon group:

A phenyl group, a biphenylyl group, a terphenylyl group, a naphthyl group, an anthracenyl group, a phenanthrenyl group, a fluorenyl group, an indenyl group, a pyrenyl group, a perylenyl group, a fluoranthenyl group, and a triphenylenyl group.

The monovalent aromatic heterocyclic group:

A pyridyl group, a pyrimidinyl group, a triazinyl group, a furyl group, a pyrrolyl group, a thienyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzimidazolyl group, a pyrazolyl group, a dibenzofuranyl group, a dibenzothienyl group, a naphthyridinyl group, a phenanthrolinyl group, an acridinyl group, and a carbolinyl group.

The above monovalent aromatic hydrocarbon group and the monovalent aromatic heterocyclic group may each have a substituent.

Such a substituent can be exemplified by the following in addition to a deuterium atom, a cyano group, and a nitro group:

a halogen atom, for example, a fluorine atom, a chlorine atom, a bromine atom, or an iodine atom;

an alkyl group having 1 to 6 carbon atoms, for example, a methyl group, an ethyl group, an n-propyl group, an isopropyl group, an n-butyl group, an isobutyl group, a tert-butyl group, an n-pentyl group, an isopentyl group, a neopentyl group, or an n-hexyl group;

an alkyloxy group having 1 to 6 carbon atoms, for example, a methyloxy group, an ethyloxy group, or a propyloxy group;

an alkenyl group, for example, a vinyl group or an allyl group;

an aryl group, for example, a phenyl group, a biphenylyl group, a terphenylyl group, a naphthyl group, an anthracenyl group, a phenanthrenyl group, a fluorenyl group, an indenyl group, a pyrenyl group, a perylenyl group, a fluoranthenyl group, or a triphenylenyl group;

an aryloxy group, for example, a phenyloxy group or a tolyloxy group;

an arylalkyloxy group, for example, a benzyloxy group or a phenethyloxy group;

an aromatic heterocyclic group, for example, a pyridyl group, a pyrimidinyl group, a triazinyl group, a thienyl group, a furyl group, a pyrrolyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzimidazolyl group, a pyrazolyl group, a dibenzofuranyl group, a dibenzothienyl group, or a carbolinyl group;

an arylvinyl group, for example, a styryl group, or a naphthylvinyl group; and an acyl group, for example, an acetyl group, or a benzoyl group.

Any of these substituents may further have the above exemplary substituent.

In the above-mentioned general formula (1), as the group Ar$^1$, a phenyl group, a biphenylyl group, a terphenylyl group, a naphthyl group, a phenanthrenyl group, an anthracenyl group, a fluorenyl group, a carbazolyl group, an indolyl group, a dibenzofuranyl group, or a dibenzothienyl group is preferred. Among them, the aromatic hydrocarbon group, for example, a phenyl group, a biphenylyl group, a terphenylyl group, a naphthyl group, a phenanthrenyl group, or a fluorenyl group, is particularly preferred. Needless to say, any of these groups may have a substituent.

As the group Ar$^2$, the aromatic hydrocarbon group is preferred. Of the aromatic hydrocarbon groups, a phenyl group, a biphenylyl group, a terphenylyl group, a naphthyl group, a phenanthrenyl group, an anthracenyl group, and a fluorenyl group are more preferred. Further preferred are a phenyl group and a biphenylyl group. Any of these groups may have a substituent, but the most preferred group are an unsubstituted phenyl group and an unsubstituted biphenylyl group.

As the groups Ar$^3$ and Ar$^4$, the aromatic hydrocarbon groups are preferred. Among them, a phenyl group, a biphenylyl group, a terphenylyl group, and a fluorenyl group are more preferred. Any of these groups may have a substituent. The particularly preferred Ar$^3$ and Ar$^4$ are an unsubstituted biphenylyl group, an unsubstituted terphenylyl group, a phenyl group having a substituent, and a fluorenyl group having a substituent. As the substituent for the phenyl group, a naphthyl group or a fluorenyl group is preferred. As the substituent for the fluorenyl group, a methyl group or a phenyl group is preferred.

In the present invention, the arylamine compound represented by the aforementioned general formula (1) is structurally characterized by having at least one pm-substituted benzene ring, as stated earlier.

For example, the arylamine compound represented by the following general formula (1a) has at least two of the above pm-substituted benzene rings, while the arylamine compound represented by the following general formula (1b) has three of the pm-substituted benzene rings:

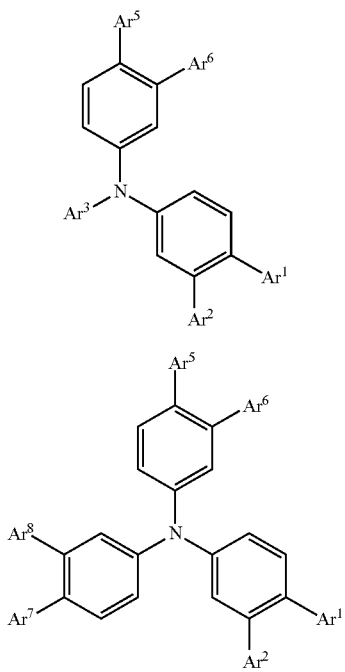

In the above formulas (1a) and (1b), $Ar^1$ to $Ar^3$ each represent a group as defined above, and $Ar^5$, $Ar^6$, $Ar^7$ and $Ar^8$, like $Ar^1$ to $Ar^3$, each represent a monovalent aromatic hydrocarbon group or a monovalent aromatic heterocyclic group.

That is, $Ar^5$ to $Ar^8$ can also be exemplified by the same groups as those illustrated in connection with $Ar^1$ to $Ar^3$.

The compound of the formula (1a) above is one in which the group $Ar^4$ in the formula (1) is the aforementioned group having the pm-substituted benzene ring, and $Ar^5$ and $Ar^6$ in the formula (1a) correspond to the two substituents which the pm-substituted benzene ring has.

In this formula (1a), it is preferred from the point of view of synthesis that $Ar^1$ and $Ar^5$ (the groups bound to the p-position of each benzene ring with respect to the nitrogen atom) are identical groups and that $Ar^2$ and $Ar^6$ (the groups bound to the m-position of the benzene ring with respect to the nitrogen atom) are identical groups.

The compound of the general formula (1b) above is one in which the groups $Ar^3$ and $Ar^4$ in the general formula (1) are the groups each having the pm-substituted benzene ring as above, and $Ar^5$, $Ar^6$ and $Ar^7$, $Ar^8$ in the formula (1b), respectively, correspond to the two substituents which each pm-substituted benzene ring has.

In this general formula (1b), as in the case with the above general formula (1a), it is preferred from the point of view of synthesis that the groups $Ar^1$, $Ar^5$ and $Ar^7$ are identical groups and that the groups $Ar^2$, $Ar^6$ and $Ar^8$ are identical groups.

Concrete examples of the arylamine compound represented by the general formula (1) (or the general formula (1a) or the general formula (1b)) include the compounds (1-1) to (1-159) having the structural formulas shown in FIGS. 39 to 75.

These drawings also show the number of the pm-substituted aromatic rings which each compound has.

The compound represented by the general formula (1) is a novel compound, and can be synthesized using a publicly known method such as Suzuki coupling, as will be indicated in the Examples to be described later. The purification of the synthesized compound can be performed, for example, by purification using a column chromatograph, adsorption purification using silica gel, activated carbon, activated clay, or the like, recrystallization or crystallization using a solvent, or sublimation purification.

The compound for use in the organic EL device of the present invention is finally purified by sublimation purification before use.

The arylamine compound having the single pm-substituted benzene ring, for example, can be produced in the following manner:

An N,N-bisarylamine (di-substituted aromatic amine) having aromatic groups substituted for two hydrogen atoms is reacted with an m-substituted halogenated aromatic compound having a halogen atom, such as a bromine atom, at the m-position, whereby an m-substituted benzene ring group is introduced into the nitrogen atom of the di-substituted aromatic amine. Then, a brominating agent such as N-bromosuccinimide is reacted with the resulting product to introduce a halogen group into the p-position of the m-substituted benzene ring group, and a corresponding boronic acid and a coupling agent such as tetrakis(triphenylphosphine)palladium are reacted with the brominated aromatic amine to introduce an aromatic group at the p-position of the m-substituted benzene ring group. In this manner, the desired arylamine compound having the single pm-substituted benzene ring can be produced.

The arylamine compound having two pm-substituted benzene rings can be produced in the following manner:

An N,N-bis(m-substituted aromatic)amine having m-substituted aromatic groups, namely, substituted with aromatic groups at the m-positions, is synthesized. Then, a brominating agent such as N-bromosuccinimide is reacted with the synthesized di-substituted amine to introduce halogen groups at the p-positions of the m-substituted benzene ring groups, and then a corresponding boronic acid and a phenyl coupling agent such as tetrakis(triphenylphosphine)palladium are reacted with the brominated aromatic amine to introduce aromatic groups at the p-positions of the m-substituted benzene ring groups. In this manner, the desired arylamine compound having two pm-substituted benzene rings can be produced.

Further, the arylamine compound having three pm-substituted benzene rings can be produced in the following manner:

A tris(m-substituted aromatic)amine having m-substituted aromatic groups, namely, substituted with aromatic groups at the m-positions, is prepared. Then, aromatic groups are introduced in the same manner as above into the p-positions of the three m-substituted aromatic groups that this triarylamine has. By so doing, the desired arylamine compound having three of the pm-substituted benzene rings can be produced.

In the present invention, the arylamine compounds represented by the general formula (1) can each be used alone, or can be used as a mixture of two or more. Alternatively, they can be used in combination with publicly known hole transport materials to form a hole transport layer, as far as the excellent properties of the arylamine compounds are not impaired.

Examples of such publicly known hole transport materials include benzidine derivatives such as N,N'-diphenyl-N,N'-di(m-tolyl)benzidine (TPD), N,N'-diphenyl-N,N'-di(α-naphthyl)benzidine (NPD), and N,N,N',N'-tetrabiphenylylbenzidine; 1,1-bis[4-(di-4-tolylamino)phenyl]cyclohexane (TAPC); arylamine compounds represented by the general formula (3) or the general formula (4) to be described later; and various other triphenylamine trimers.

In the hole transport layer, p-dopants such as tris(bromophenyl)aminium hexachloroantimonate or radialene derivatives (see, for example, WO2014/009310), or polymeric compounds containing the molecular structures of benzidine derivatives such as TPD can also be used in combination.

The above-mentioned hole transport layer is preferably formed by vapor deposition or co-vapor deposition of a gas containing the arylamine compound of the general formula (1), but can also be formed by a publicly known method such as a spin coating method or an ink jet method.

The thickness of the hole transport layer is usually of the order of 25 to 60 nm. Since light emission can take place at a low driving voltage, however, even a large thickness of 100 nm or more, for example, enables a rise in the driving voltage to be suppressed. That is, the degree of freedom of the thickness of the hole transport layer is so high that a thickness, for example, of 20 to 300 nm, particularly 20 to 200 nm, makes it possible to maintain practical driving voltage.

In the present invention, moreover, the hole transport layer containing the above-described arylamine compound preferably has the two-layer structure having the first hole transport layer 4 located on the anode side and the second hole transport layer 5 located beside the luminous layer 6, as shown, for example, in FIG. 1.

The hole transport layer of the two-layer structure will be described later.

<Luminous Layer>

The luminous layer is the same as that used in conventionally known organic EL devices, and is formed by a publicly known method such as vapor deposition, spin coating method, or ink jet method, according to the type of the material to be used.

For example, the luminous layer can be formed using luminescent materials such as metal complexes of quinolinol derivatives such as $Alq_3$; complexes of various metals such as zinc, beryllium, and aluminum; anthracene derivatives; bisstyrylbenzene derivatives; pyrene derivatives; oxazole derivatives; and polyparaphenylenevinylene derivatives.

Also, a material which emits delayed fluorescence, such as a CDCB derivative, for example, PIC-TRZ, CC2TA, PXZ-TRZ, or 4CzIPN, can be used as the luminescent material (see, for example, Appl. Phys. Let., 98, 0833302).

The luminous layer can also be formed using a host material and a dopant material (guest material).

In this case, an anthracene derivative is preferably used as the host material. In addition, the above luminescent materials, heterocyclic compounds having an indole ring as a partial structure of a condensed ring, heterocyclic compounds having a carbazole ring as a partial structure of a condensed ring, carbazole derivatives, thiazole derivatives, benzimidazole derivatives, and polydialkylfluorene derivatives can be used as the host materials.

As the dopant material, a blue-emitting material, for example, a pyrene derivative having a pyrene skeleton in the molecule is preferably used. In addition, the following example can be used as the dopant materials: amine derivatives having a fluorene ring as a partial structure of a condensed ring; quinacridone, coumarin, rubrene, perylene and derivatives thereof; pyrene; benzopyran derivatives; indenophenanthrene derivatives; rhodamine derivatives; and aminostyryl derivatives.

Furthermore, a phosphorescent body can be used as the guest material. As the phosphorescent body, a phosphorescent body in the form of a metal complex containing iridium, platinum or the like can be used. For example, a green phosphorescent body such as $Ir(ppy)_3$; a blue phosphorescent body such as FIrpic or FIr6; or a red phosphorescent body such as $Btp_2Ir(acac)$ is used.

As the host material in this case, a hole injecting/transporting host material, such as a carbazole derivative, for example, 4,4'-di(N-carbazolyl)biphenyl (CBP), TCTA, or mCP, can be used. An electron transporting host material such as p-bis(triphenylsilyl)benzene (UGH2) or 2,2',2''-(1,3,5-phenylene)-tris(1-phenyl-1H-benzimidazole) (TPBI) can also be used. By using such a host material, a high performance organic EL device can be prepared.

Doping of the host material with the phosphorescent body is preferably performed by code position in a range of 1 to 30% by weight based on the entire luminous layer in order to avoid concentration quenching.

The luminous layer described above is not limited to a single layer structure, but may be of a laminated structure in which layers formed using the various compounds mentioned above are stacked. It is also possible to mix the various compounds, thereby forming the luminous layer.

<Electron Transport Layer>

In the present invention, the electron transport layer (e.g., the layer indicated by the numeral 7 in FIG. 1) provided on the above-described luminous layer can be formed by a publicly known method, such as vapor deposition, spin coating method, or ink jet method, with the use of a publicly known electron transporting material.

The electron transport layer may be formed from an electron transport material publicly known per se. Its examples include, in addition to metal complexes of quinolinol derivatives such as $Alq_3$; various metal complexes of zinc, beryllium, aluminum, and the like; triazole derivatives; triazine derivatives; oxadiazole derivatives; thiadiazole derivatives; carbodiimide derivatives; quinoxaline derivatives; phenanthroline derivatives; and silole derivatives.

In the present invention, moreover, it is preferred that an anthracene derivative represented by the general formula (2) shown below is used as an electron transport material to form the electron transport layer. Such an anthracene derivative is excellent in electron injection and transporting capabilities, thin film stability, and durability. The electron transport layer formed from the anthracene derivative is combined with the hole transport layer containing the arylamine compound of the general formula (1), whereby holes and electrons can be efficiently injected into the luminous layer. By so doing, an optimum carrier balance can be ensured, and the properties of the result organic EL device can be enhanced greatly.

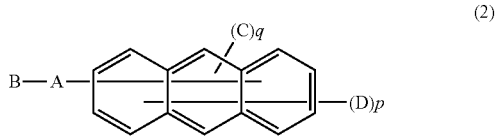

(2)

Where

A represents a divalent aromatic hydrocarbon group, a divalent aromatic heterocyclic group, or a single bond, B represents a monovalent aromatic heterocyclic group, C represents a monovalent aromatic hydrocarbon group or a monovalent aromatic heterocyclic group, D represents a hydrogen atom, a deuterium atom, a fluorine atom, a chlorine atom, a cyano group, or an alkyl group having 1 to 6 carbon atoms, and p and q are such that p denotes an integer of 7 or 8, and q denotes an integer of 1 or 2, provided that p and q total 9.

As will be understood from the above general formula (2), this anthracene derivative has a molecular structure in which the anthracene ring and the group B are coupled together by a divalent group or a single bond, and 1 or 2 monovalent aromatic hydrocarbon group(s) or monovalent aromatic heterocyclic group(s) (group C) is or are bound as a substituent(s) to the anthracene ring having the group B connected thereto.

In the formula (2), A denotes a single bond or a divalent group. Such a divalent group is a divalent aromatic hydrocarbon group or a divalent aromatic heterocyclic group, and its concrete examples are as follows.

The divalent aromatic hydrocarbon group is formed from an aromatic hydrocarbon ring having two bonds. Examples of this aromatic hydrocarbon ring include benzene, biphenyl, terphenyl, tetrakisphenyl, styrene, naphthalene, anthracene, acenaphthalene, fluorene, phenanthrene, indane, pyrene, and triphenylene.

The divalent aromatic heterocyclic group is formed from an aromatic heterocyclic ring having two bonds. Examples of this aromatic heterocyclic ring include pyridine, pyrimidine, triazine, pyrrole, furan, thiophene, quinoline, isoquinoline, benzofuran, benzothiophene, indoline, carbazole, carboline, benzoxazole, benzothiazole, quinoxaline, benzoimidazole, pyrazole, dibenzofuran, dibenzothiophene, naphthyridine, phenanthroline, and acridan.

The above aromatic hydrocarbon ring and aromatic heterocyclic ring may have a substituent, and may have an introducible substituent as long as the excellent properties of the anthracene derivative are not impaired thereby.

Such a substituent is the same as the substituent optionally possessed by the monovalent aromatic hydrocarbon group or monovalent aromatic heterocyclic group represented by $Ar^1$ to $Ar^4$ in the aforementioned general formula (1).

In the present invention, the particularly preferred A is derived from a substituted or unsubstituted benzene ring, biphenyl ring, naphthalene ring, or phenanthrene ring.

The group B in the general formula (2) is a monovalent aromatic heterocyclic group, which can be exemplified by a triazinyl group, a pyridyl group, a pyrimidinyl group, a furyl group, a pyrrolyl group, a thienyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzimidazolyl group, a pyrazolyl group, a dibenzofuranyl group, a dibenzothienyl group, a naphthyridinyl group, a phenanthrolinyl group, an acridinyl group, and a carbolinyl group.

The monovalent aromatic heterocyclic group, as the group B, may have a substituent which does not impair the excellent properties of the anthracene derivative. The substituent can be exemplified by the following in addition to a deuterium atom, a cyano group, and a nitro group:

a halogen atom, for example, a fluorine atom, a chlorine atom, a bromine atom, or an iodine atom;

an alkyl group having 1 to 6 carbon atoms, for example, a methyl group, an ethyl group, an n-propyl group, an isopropyl group, an n-butyl group, an isobutyl group, a tert-butyl group, an n-pentyl group, an isopentyl group, a neopentyl group, or an n-hexyl group;

a cycloalkyl group having 5 to 10 carbon atoms, for example, a cyclopentyl group, a cyclohexyl group, a 1-admantyl group, or a 2-adamantyl group;

an alkyloxy group having 1 to 6 carbon atoms, for example, a methyloxy group, an ethyloxy group, or a propyloxy group;

a cycloalkyloxy group having 5 to 10 carbon atoms, for example, a cyclopentyloxy group, a cyclohexyloxy group, a 1-admantyloxy group, or a 2-adamantyloxy group;

an alkenyl group, for example, a vinyl group or an allyl group;

an aryloxy group, for example, a phenyloxy group, a tolyloxy group, a biphenylyloxy group, a naphthyloxy group, an anthracenyloxy group, or a phenanthrenyloxy group;

an arylalkyloxy group, for example, a benzyloxy group or a phenethyloxy group;

an aromatic hydrocarbon group, for example, a phenyl group, a biphenylyl group, a terphenylyl group, a naphthyl group, an anthracenyl group, a phenanthrenyl group, a fluorenyl group, an indenyl group, a pyrenyl group, a perylenyl group, a fluoranthenyl group, or a triphenylenyl group;

an aromatic heterocyclic group, for example, a pyridyl group, a pyrimidinyl group, a triazinyl group, a thienyl group, a furyl group, a pyrrolyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzimidazolyl group, a pyrazolyl group, a dibenzofuranyl group, a dibenzothienyl group, or a carbolinyl group;

an arylvinyl group, for example, a styryl group, or a naphthylvinyl group; and an acyl group, for example, an acetyl group, or a benzoyl group.

The substituents exemplified above may be present independently of each other, but may bind to each other via a single bond, a methylene group optionally having a substituent, an oxygen atom, or a sulfur atom to form a ring.

In the present invention, the monovalent aromatic heterocyclic group preferred as the group B is a nitrogen-containing aromatic heterocyclic group, for example, a pyridyl group, a pyrimidinyl group, a pyrrolyl group, a quinolyl group, an isoquinolyl group, an indolyl group, a carbazolyl group, a benzoxazolyl group, a benzothiazolyl group, a quinoxalinyl group, a benzimidazolyl group, a pyrazolyl group, or a carbolinyl group. Among these groups, a pyridyl group, a pyrimidinyl group, a quinolyl group, an isoquinolyl group, an indolyl group, a pyrazolyl group, a benzimidazolyl group, or a carbolinyl group is more preferred.

The character C in the general formula (2) represents a monovalent aromatic hydrocarbon group or a monovalent aromatic heterocyclic group, which can be exemplified by the same groups as those illustrated in connection with $Ar^1$ to $Ar^4$ in the general formula (1). The monovalent aromatic hydrocarbon group and the monovalent aromatic heterocyclic group may have a substituent, like the aforementioned $Ar^1$ to $Ar^4$.

If two of the groups C are present in the molecule (q=2 in the formula (2)), the two groups C may be identical or different.

Further, D in the general formula (2) is a hydrogen atom, a deuterium atom, a fluorine atom, a chlorine atom, a cyano group, or an alkyl group having 1 to 6 carbon atoms. Examples of the alkyl group having 1 to 6 carbon atoms include a methyl group, an ethyl group, an n-propyl group, an isopropyl group, an n-butyl group, an isobutyl group, a tert-butyl group, an n-pentyl group, an isopentyl group, a neopentyl group, or an n-hexyl group.

Any of these alkyl groups may have a substituent, for example, a deuterium atom, a fluorine atom, a chlorine atom, or a cyano group.

A plurality of the D's, if any, may be identical or different.

In the present invention, the most preferred D is a hydrogen atom.

In the anthracene derivative of the general formula (2), it is preferred that B is a nitrogen-containing heterocycle and D be a hydrogen atom. This preferred anthracene derivative is represented, in particular, by the following general formula (2a), (2b) or (2c):

The anthracene derivative represented by the general formula (2a):

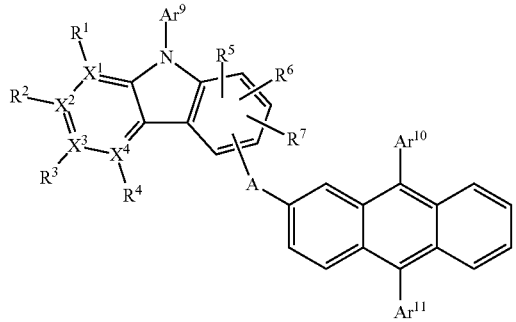

(2a)

In the general formula (2a), A is as defined in the formula (2), and represents a divalent aromatic hydrocarbon group, a divalent aromatic heterocyclic group, or a single bond.

The nitrogen-containing heterocycle of the tricyclic structure, to which A is bound, corresponds to the group B in the general formula (2).

In the formula (2a), $X^1$, $X^2$, $X^3$ and $X^4$ are endocyclic elements constituting a part of the above nitrogen-containing heterocycle, and each represent a carbon atom or a nitrogen atom, provided that only one of them is a nitrogen atom. $R^1$ to $R^7$ and $Ar^9$ represent groups bound to this nitrogen-containing heterocycle.

That is, for the ring formed by $X^1$, $X^2$, $X^3$ and $X^4$, $R^1$ to $R^4$ are indicated as the substituents. If any of the endocyclic elements is a nitrogen atom, any of $R^1$ to $R^4$ (including a hydrogen atom) is not to be bound to this nitrogen atom. This means that if $X^1$ is a nitrogen atom, $R^1$ does not exist; if $X^2$ is a nitrogen atom, $R^2$ does not exist; if $X^3$ is a nitrogen atom, $R^3$ does not exist; and if $X^4$ is a nitrogen atom, $R^4$ does not exist.

$R^1$ to $R^7$ bound to the above nitrogen-containing heterocycle each represent a hydrogen atom, a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, a monovalent aromatic hydrocarbon group, a monovalent aromatic heterocyclic group, or an aryloxy group.

The above alkyl group having 1 to 6 carbon atoms can be exemplified by the same groups as those illustrated in connection with D of the general formula (2).

The cycloalkyl group having 5 to 10 carbon atoms can be exemplified by a cyclopentyl group, a cyclohexyl group, a 1-admantyl group, and a 2-adamantyl group.

The alkenyl group having 2 to 6 carbon atoms can be exemplified by a vinyl group, an allyl group, an isopropenyl group, and a 2-butenyl group.

The alkyloxy group having 1 to 6 carbon atoms can be exemplified by a methyloxy group, an ethyloxy group, an n-propyloxy group, an isopropyloxy group, an n-butyloxy group, a tert-butyloxy group, an n-pentyloxy group, and an n-hexyloxy group.

The cycloalkyloxy group having 5 to 10 carbon atoms can be exemplified by a cyclopentyloxy group, a cyclohexyloxy group, a cycloheptyloxy group, a cyclooctyloxy group, a 1-admantyloxy group, and a 2-adamantyloxy group.

The monovalent aromatic hydrocarbon group and the monovalent aromatic heterocyclic group can be exemplified by the same groups as those illustrated in connection with $Ar^1$ to $Ar^4$ in the general formula (1).

The aryloxy group can be exemplified by a phenyloxy group, a biphenylyloxy group, a terphenylyloxy group, a naphthyloxy group, an anthracenyloxy group, a phenanthrenyloxy group, a fluorenyloxy group, an indenyloxy group, a pyrenyloxy group, and a perylenyloxy group.

The respective groups represented by $R^1$ to $R^7$ mentioned above may have substituents, which can be exemplified by the same groups as those illustrated as the substituents which the groups $Ar^1$ to $Ar^4$ in the general formula (1) have, as far as they satisfy the conditions regarding the number of carbon atoms.

These substituents may be present independently of each other, but may bind to each other via a single bond, a methylene group optionally having a substituent, an oxygen atom, or a sulfur atom to form a ring.

Furthermore, $Ar^9$ in the general formula (2a) is a substituent bound to the nitrogen-containing aromatic ring, and $Ar^{10}$ and $Ar^{11}$ correspond to C in the general formula (2) (that is, q=2).

The above $Ar^9$ to $Ar^{11}$ each represent a monovalent aromatic hydrocarbon group or a monovalent aromatic heterocyclic group, which can be exemplified by the same groups as those illustrated in connection with $Ar^1$ to $Ar^4$ in the general formula (1). The monovalent aromatic hydrocarbon group and the monovalent aromatic heterocyclic group may also have a substituent, like the aforementioned $Ar^1$ to $Ar^4$.

Concrete examples of the anthracene derivative represented by the general formula (2a) include the compounds (2a-1) to (2a-20) having the structural formulas shown in FIGS. 76 to 79.

The anthracene derivative represented by the general formula (2b):

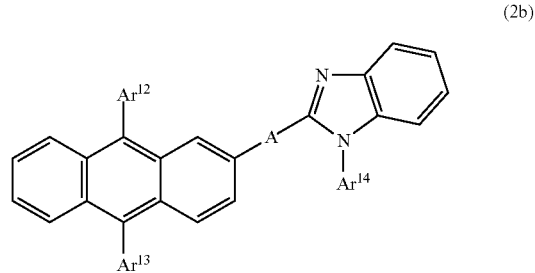

(2b)

In the general formula (2b), A is as defined in the formula (2), and represents a divalent aromatic hydrocarbon group, a divalent aromatic heterocyclic group, or a single bond.

The nitrogen-containing heterocycle, to which A is bound, corresponds to the group B in the general formula (2).

In the general formula (2b), moreover, $Ar^{12}$ and $Ar^{13}$ correspond to C in the general formula (2) (that is, q=2), and $Ar^{14}$ is a substituent bound to the nitrogen-containing aromatic ring.

The above $Ar^{12}$ to $Ar^{14}$ each represent a monovalent aromatic hydrocarbon group or a monovalent aromatic heterocyclic group, which can be exemplified by the same groups as those illustrated in connection with $Ar^1$ to $Ar^4$ in the general formula (1). The monovalent aromatic hydrocarbon group and the monovalent aromatic heterocyclic group may also have a substituent, like the aforementioned $Ar^1$ to $Ar^4$.

Concrete examples of the anthracene derivative represented by the general formula (2b) include the compounds (2b-1) to (2b-16) having the structural formulas shown in FIGS. 80 to 83.

The anthracene derivative represented by the general formula (2c):

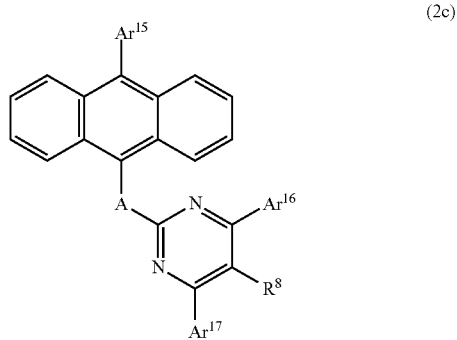

(2c)

In the general formula (2c), A is as defined in the formula (2), and represents a divalent aromatic hydrocarbon group, a divalent aromatic heterocyclic group, or a single bond.

The nitrogen-containing heterocycle, to which A is bound, corresponds to the group B in the general formula (2).

In the formula (2c), moreover, $Ar^{15}$ corresponds to C in the formula (2) (that is, q=1), and $Ar^{16}$, $Ar^{17}$ and $R^8$ are substituents bound to the nitrogen-containing heterocycle.

The above $Ar^{15}$ to $Ar^{17}$ each represent a monovalent aromatic hydrocarbon group or a monovalent aromatic heterocyclic group, which can be exemplified by the same groups as those illustrated in connection with $Ar^1$ to $Ar^4$ in the formula (1). The monovalent aromatic hydrocarbon group and the monovalent aromatic heterocyclic group may also have a substituent, like the aforementioned $Ar^1$ to $Ar^4$.

$R^8$ bound to the above nitrogen-containing heterocycle is the same as $R^1$ to $R^7$ in the general formula (2a), and represents a hydrogen atom, a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, a monovalent aromatic hydrocarbon group, a monovalent aromatic heterocyclic group, or an aryloxy group.

Each group represented by $R^8$ may have the same substituent as the substituent that $R^1$ to $R^7$ have. If this substituent is present in plural numbers, a plurality of the substituents are preferably present independently of each other. However, the plurality of substituents may bind to each other via a single bond, a methylene group optionally having a substituent, an oxygen atom, or a sulfur atom to form a ring.

Concrete examples of the anthracene derivative represented by the general formula (2c) include the compounds (2c-1) to (2c-30) having the structural formulas shown in FIGS. 84 to 91.

In the present invention, it is desirable that the electron transport layer be formed from the above-described anthracene derivative. The various anthracene derivatives illustrated above can be synthesized by methods publicly known per se (see, for example, WO2011/0593000, WO2003/060956, and Korean Unexamined Patent Publication 2013-060956).

These anthracene derivatives may each form the electron transport layer by itself, or may, as a mixture of two or more.

<Cathode>

In connection with the cathode of the organic EL device of the present invention, a metal with a low work function such as aluminum, or an alloy having a lower work function, such as a magnesium-silver alloy, a magnesium-indium alloy, or an aluminum-magnesium alloy, is used as an electrode material.

<Other Layers>

The organic EL device of the present invention may have other layers, if desired. In the example shown in FIG. 1, for example, the hole injection layer 3 is provided between the anode and the hole transport layer, and the electron injection layer 8 is provided between the cathode and the electron transport layer. Further, an electron blocking layer can be provided between the hole transport layer and the luminous layer, and a hole blocking layer can be provided between the luminous layer and the electron transport layer.

Each layer provided, as appropriate, may be formed from a material publicly known per se, and is formed by a publicly known method such as vapor deposition, spin coating method, or ink jet method, according to the type of the material to be used.

Hole Injection Layer:

The hole injection layer 3, which is formed, as appropriate, between the anode and the hole transport layer, can be formed using a material publicly known per se, for example, materials such as triphenylamine derivatives of starburst type, and various triphenylamine tetramers; porphyrin compounds typified by copper phthalocyanine; and acceptor type heterocyclic compounds such as hexacyanoazatriphenylene, and coating type polymeric materials.

Moreover, the arylamine compounds represented by the aforementioned general formula (1) show high hole mobility. Thus, the hole injection layer can be formed using such arylamine compounds.

Electron Injection Layer:

The electron injection layer 8, which is provided, as appropriate, between the cathode and the electron transport layer, can be formed using an alkali metal salt such as lithium fluoride or cesium fluoride, an alkaline earth metal salt such as magnesium fluoride, or a metal oxide such as aluminum oxide.

Electron Blocking Layer:

The electron blocking layer is to be provided between the hole transport layer and the luminous layer, although not shown in FIG. 1, and is formed to block the transmission of electrons from the luminous layer, thereby increasing the luminous efficiency. Various compounds having electron blocking properties can be used as materials for formation of the electron blocking layer, and the following carbazole derivatives are typical examples:
4,4',4''-tri(N-carbazolyl)triphenylamine (TCTA);
9,9-bis[4-(carbazol-9-yl)phenyl]fluorene;
1,3-bis(carbazol-9-yl)benzene (mCP); and
2,2-bis(4-carbazol-9-ylphenyl)adamantane (Ad-Cz).

Aside from the above carbazole derivatives, compounds having a triphenylsilyl group and having a triarylamine skeleton in the molecule, typified by 9-[4-(carbazol-9-yl)phenyl]-9-[4-(triphenylsilyl)phenyl]-9H-fluorene, are also usable as materials for the formation of the electron blocking layer.

Hole Blocking Layer:

The hole blocking layer is to be provided, as appropriate, between the electron transport layer and the luminous layer, although not shown in FIG. 1, and is formed to block the transmission of holes from the luminous layer, thereby increasing the luminous efficiency. Compounds having hole blocking function, such as phenanthroline derivatives, e.g., bathocuproine (BCP), metal complexes of quinolinol derivatives, e.g., bis(2-methyl-8-quinolinolato) (4-phenylphenolato)aluminum(III) (BAlq), various rare earth complexes, triazole derivatives, triazine derivatives, and oxadiazole derivatives, are used as materials for the formation of the hole blocking layer.

<Hole Transport Layer of Two-Layer Structure>

The organic EL device of the present invention uses the arylamine compound represented by the general formula (1) as the hole transport layer. As stated earlier, the hole transport layer containing such an arylamine compound can be configured as a two-layer structure.

That is, as shown in FIG. 1, it is preferred that the hole transport layer is configured as a two-layer structure in which it is divided into the first hole transport layer 4 located beside the anode 2, and the second hole transport layer 5 located beside the luminous layer 6, and the arylamine represented by the general formula (1) is contained in the second hole transport layer 5. In this case, an arylamine different from that used in the second hole transport layer 5 is used in the first hole transport layer 4.

If the hole transport layer is divided into two layers, as above, the second hole transport layer 5 on the side of the luminous layer 6 shows very high electron blocking properties as well as hole transport properties. This is because the arylamine compound represented by the general formula (1) shows high electron blocking properties in addition to hole transport properties. Thus, the second hole transport layer 5 is provided adjacently to the luminous layer 6 as shown in FIG. 1, in particular, whereby the carrier balance in the luminous layer 6 can be held at a higher level. This is very advantageous in improving the properties of the organic EL device.

In such a two-layer structure, the second hole transport layer 5 is formed from the arylamine compound represented by the general formula (1). On the other hand, the first hole transport layer 4 is formed from a triarylamine derivative different from the arylamine compound used in the formation of the second hole transport layer 5, because the triarylamine derivative exhibits excellent hole transport properties.

The triarylamine derivative used to form the first hole transport layer 4 may be the arylamine compound represented by the general formula (1), if it is different from the one used for the formation of the second hole transport layer 5. Since electron blocking properties are not strictly required of the first hole transport layer 4, however, it is desirable to form the first hole transport layer 4 with the use of a publicly known triarylamine derivative which is used as a hole transport material.

Such a publicly known triarylamine derivative has a molecular structure in which two triarylamine skeletons are bound together by a single bond or a divalent hydrocarbon group, and has 2 to 6 triarylamine skeletons in the molecule.

In the present invention, the first hole transport layer 4 can be formed using a triarylamine derivative represented by the following general formula (3) or (4) from the viewpoint of excellent thin film stability, heat resistance, and ease of synthesis as well as hole transport properties. Such a triarylamine derivative can be used alone, or a mixture of two or more.

The triarylamine derivative represented by the general formula (3):

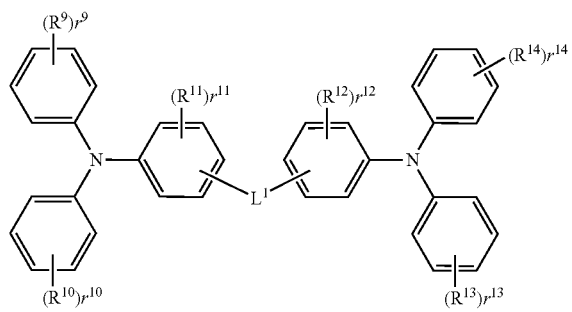

(3)

The triarylamine derivative represented by the general formula (3) has two triarylamine skeletons.

In the general formula (3), $r^9$ to $r^{14}$ are each an integer showing the number of each of the substituents $R^9$ to $R^{14}$ bound to the aromatic ring, $r^9$, $r^{10}$, $r^{13}$ and $r^{14}$ are each an integer of 0 to 5, and $r^{11}$ and $r^{12}$ are each an integer of 0 to 4.

The substituents $R^9$ to $R^{14}$ bound to the aromatic rings each represent a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, a monovalent aromatic hydrocarbon group, a monovalent aromatic heterocyclic group, or an aryloxy group.

If these substituents are each present in plural numbers on the same benzene ring, the plurality of the substituents are preferably present independently of each other. However, the plurality of the substituents may bind to each other via a single bond, a methylene group optionally having a substituent, an oxygen atom, or a sulfur atom to form a ring. For example, the plurality of substituents may be bound together to form a naphthalene ring.

Concrete examples of the alkyl group, the cycloalkyl group, the alkenyl group, the alkyloxy group, the cycloalkyloxy group, or the aryloxy group represented by the substituents $R^9$ to $R^{14}$ include the same groups as those illustrated in connection with $R^1$ to $R^7$ in the general formula (2a). Examples of the monovalent aromatic hydrocarbon group or the monovalent aromatic heterocyclic group include the same groups as those illustrated in connection with $Ar^1$ to $Ar^4$ of the general formula (1).

The substituents $R^9$ to $R^{14}$, like the groups $R^1$ to $R^7$ or the groups $Ar^1$ to $Ar^4$, may further have substituents. Such substituents are preferably present independently of each other, but may bind to each other via a single bond, a methylene group optionally having a substituent, an oxygen atom, or a sulfur atom to form a ring.

In the general formula (3), $L^1$ is a bridge group connecting the two arylamine skeletons, and represents a single bond, or a divalent group represented by the following structural formula (B), (C), (D), (E), (F) or (G):

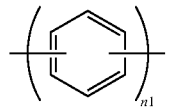

(B)

where n1 denotes an integer of 1 to 4.

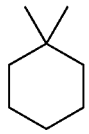

(C)

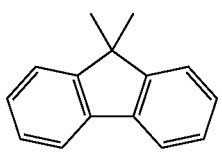

(D)

—CH$_2$—  (E)

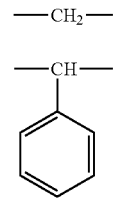

(F)

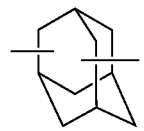

(G)

Concrete examples of the triarylamine derivative represented by the general formula (3) include the compounds (3-1) to (3-41) having the structural formulas shown in FIGS. 92 to 99.

The triarylamine derivative represented by the formula (4):

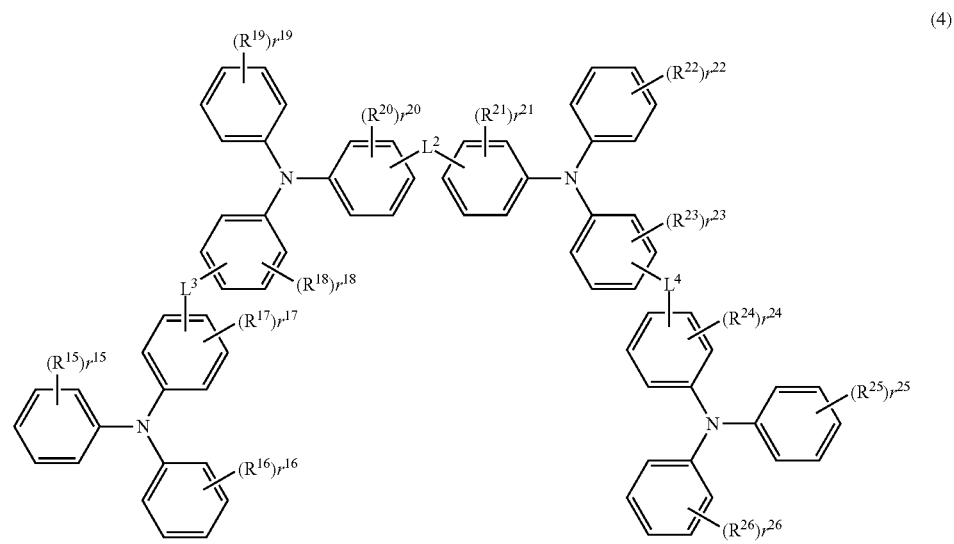

(4)

The triarylamine derivative represented by the general formula (4) has four triarylamine skeletons.

In the general formula (4), $r^{15}$ to $r^{26}$ are each an integer showing the number of each of the substituents $R^{15}$ to $R^{26}$ bound to the aromatic rings, $r^{15}$, $r^{16}$, $r^{19}$, $r^{22}$, $r^{25}$ and $r^{26}$ are each an integer of 0 to 5, and $r^{17}$, $r^{18}$, $r^{20}$, $r^{21}$, $r^{23}$ and $r^{24}$ are each an integer of 0 to 4.

The substituents $R^{15}$ to $R^{26}$ bound to the aromatic rings each represent a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, a monovalent aromatic hydrocarbon group, a monovalent aromatic heterocyclic group, or an aryloxy group.

If these substituents are each present in plural numbers on the same benzene ring, the plurality of substituents are preferably present independently of each other. However, the plurality of substituents may bind to each other via a single bond, a methylene group optionally having a substituent, an oxygen atom, or a sulfur atom to form a ring. For example, the plurality of substituents may be bound together to form a naphthalene ring.

Concrete examples of the alkyl group, the cycloalkyl group, the alkenyl group, the alkyloxy group, the cycloalkyloxy group, or the aryloxy group represented by the substituents $R^{15}$ to $R^{26}$ include the same groups as those illustrated in connection with $R^1$ to $R^7$ in the general formula (2a). Examples of the monovalent aromatic hydrocarbon group or the monovalent aromatic heterocyclic group include the same groups as those illustrated in connection with $Ar^1$ to $Ar^4$ of the general formula (1).

The substituents $R^{15}$ to $R^{26}$, like the groups $R^1$ to $R^7$ or the groups $Ar^1$ to $Ar^4$, may further have substituents. Such substituents are preferably present independently of each other, but may bind to each other via a single bond, a methylene group optionally having a substituent, an oxygen atom, or a sulfur atom to form a ring.

In the general formula (4), $L^2$ to $L^4$ are each a bridge group connecting the two arylamine skeletons, and each represent a single bond, a divalent group represented by the following structural formula (B'), or the same group as the divalent group represented by (C), (D), (E), (F) or (G) in the general formula (3).

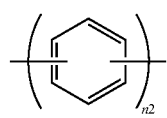
(B')

where n2 denotes an integer of 1 to 3.

Concrete examples of the triarylamine derivative represented by the general formula (4) include the compounds (4-1) to (4-17) having the structural formulas shown in FIGS. 100 to 103.

In the present invention, the various triarylamine derivatives illustrated above can be synthesized by methods publicly known per se (see, for example, JP-A-7-126615, JP-A-08-048656, and JP-A-2005-108804).

The total thickness (t1+t2), the sum of the thickness t1 of the first hole transport layer 4 formed using the above triarylamine derivative and the thickness t2 of the second hole transport layer 5 formed using the arylamine compound of the general formula (1), is preferably in the range of 20 to 300 nm, further in the range of 50 to 200 nm, particularly in the range of 50 to 150 nm.

With the organic EL device of the present invention having the aforementioned structure, the materials for an organic EL device, which are excellent in hole and electron injection/transport performances, thin film stability, and durability, are combined in consideration of the carrier balance. Compared with conventional organic EL devices, therefore, the organic EL device of the invention is improved in the efficiency of transport of holes from the hole transport layer to the luminous layer, and is also improved in the efficiency of transport of electrons from the electron transport layer to the luminous layer. In case the hole transport layer is configured as the first hole transport layer-second hole transport layer two-layered structure, moreover, the carrier balance is further improved, a further increase in the luminous efficiency and a further decrease in the driving voltage are obtained, and the durability of the organic EL device is further enhanced.

According to the present invention, as described above, an organic EL device with high efficiency, low driving voltage, and long service life can be achieved.

EXAMPLES

The present invention will now be described by the following Experimental Examples.

Example 1

Synthesis of N,N-bis(biphenyl-4-yl)-N-(6-phenylbiphenyl-3-yl)amine (compound 1-1)

(First Step)

| | |
|---|---|
| A nitrogen-purged reaction vessel was charged with N,N-bis(biphenyl-4-yl)amine | 40.5 g, |
| 3-bromobiphenyl | 28.0 g, |
| t-butoxysodium | 13.7 g, and |
| toluene | 400 mL. |

With the mixture being ultrasonically irradiated for 30 minutes, a nitrogen gas was passed therethrough.
Then,

| | |
|---|---|
| palladium acetate | 0.54 g, and |
| a 50% (w/v) toluene solution of t-butylphosphine | 1.46 g | were added. The mixture was heated, and stirred for 4 hours at 95° C.

After insolubles were removed by filtration, the filtrate was heated, and subjected to adsorption purification using silica gel at 100° C., followed by hot filtration. The filtrate was cooled to room temperature with stirring, and precipitated solids were collected by filtration to obtain
N,N-bis(biphenyl-4-yl)-N-(biphenyl-3-yl)amine as greenish white solids 50.2 g (yield 88%).

(Second Step)

| | |
|---|---|
| A nitrogen-purged reaction vessel was charged with triarylamine obtained above | 50.0 g, and |
| dimethylformamide | 500 mL, | and the mixture was cooled in an ice bath.

Then,

| | |
|---|---|
| N-bromosuccinimide | 22.1 g | was slowly added, followed by stirring the mixture for 4 hours. Then, methanol was added, and a precipitated crude product was collected by filtration.

Then, reflux washing using ethyl acetate was performed to obtain

N,N-bis(biphenyl-4-yl)-N-(6-bromobiphenyl-3-yl)amine as a pink powder 40.2 g (yield 69%).

(Third Step)

| | |
|---|---|
| Then, a nitrogen-purged reaction vessel was charged with N,N-bis(biphenyl-4-yl)-N-(6-bromobiphenyl-3-yl)amine obtained above | 11.8 g, |
| toluene | 94 mL, |
| phenylboronic acid an aqueous solution of 5.9 g potassium carbonate dissolved in 36 ml. water. | 2.7 g, and |

With the mixture being ultrasonically irradiated for 30 minutes, a nitrogen gas was passed therethrough.

Then,

| | |
|---|---|
| tetrakis(triphenylphosphine)palladium | 0.74 g | was added. The mixture was heated, and stirred for 18 hours at 72° C. The mixture was cooled to room temperature, and an organic layer was collected by liquid separation. The collected matter was washed with water, successively washed with a saturated saline solution, then dried by using anhydrous magnesium sulfate, and concentrated to obtain a crude product.

Subsequent purification using column chromatography gave

N,N-bis(biphenyl-4-yl)-N-(6-phenylbiphenyl-3-yl)amine as a white powder 8.4 g (yield 72%).

The resulting amine compound is the compound (1-1) represented by the following formula:

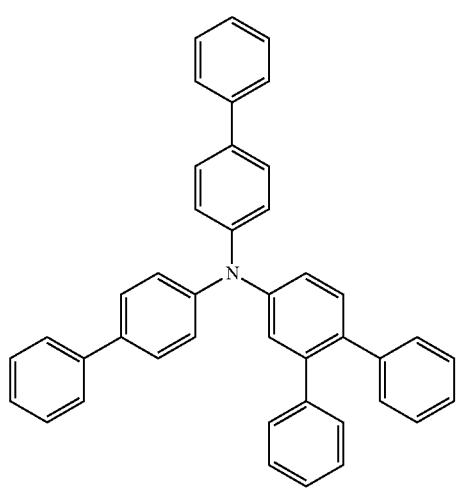

(1-1)

pm-substituted benzene ring: 1

Figure 2:
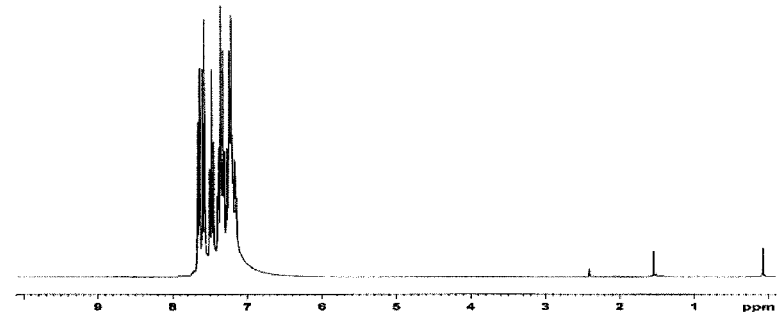
FIG. 2 is a $^1$H-NMR chart diagram of the compound (1-1) of Example 1.

In connection with the white powder obtained above, its structure was identified using NMR. Its NMR chart is shown in FIG. 2.

In $^1$H-NMR (CDCl$_3$), the following signals of 31 hydrogens were detected:

δ (ppm) = 7.56-7.68 (7H)

7.45-7.52 (4H)

7.14-7.41 (20H)

Example 2

Synthesis of N,N-bis(biphenyl-4-yl)-N-{6-(naphthyl-1-yl)biphenyl-3-yl}amine (compound 1-2)

Reactions were performed under the same conditions as in Example 1, except that phenylboronic acid used in the third step of Example 1 was replaced by 1-naphthylboronic acid. As a result, the following product was obtained:

N,N-bis(biphenyl-4-yl)-N-{6-(naphthyl-1-yl)biphenyl-3-yl}amine as a white powder 9.2 g (yield 61%).

The resulting amine compound is the compound (1-2) represented by the following formula:

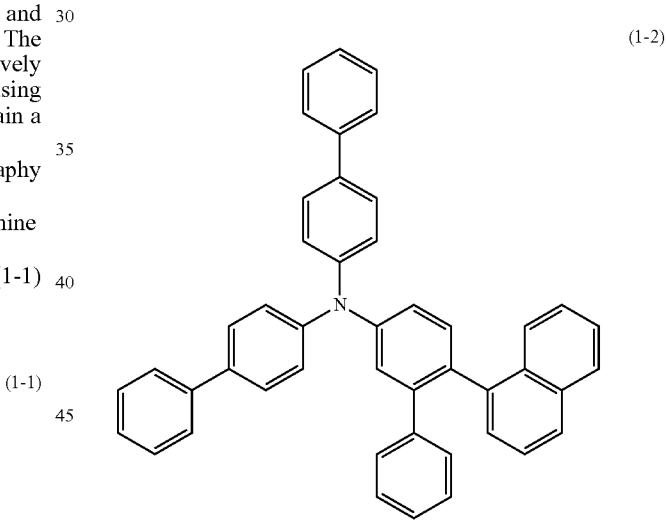

(1-2)

pm-substituted benzene ring: 1

Figure 3:
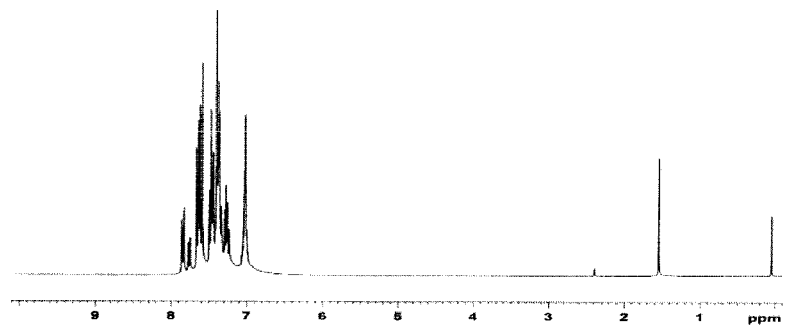
FIG. 3 is a $^1$H-NMR chart diagram of the compound (1-2) of Example 2.

In connection with the white powder obtained above, its structure was identified using NMR. Its NMR chart is shown in FIG. 3.

In $^1$H-NMR (CDCl$_3$), the following signals of 33 hydrogens were detected:

δ (ppm) = 7.84-7.87 (3H)

7.67-7.83 (6H)

7.26-7.64 (18H)

7.02-7.04 (6H)

Example 3

Synthesis of N,N-bis(biphenyl-4-yl)-N-{6-(9,9-dimethylfluoren-2-yl)biphenyl-3-yl}amine (compound 1-3)

Reactions were performed under the same conditions as in Example 1, except that phenylboronic acid used in the third step of Example 1 was replaced by (9,9-dimethylfluoren-2-yl)boronic acid. As a result, the following product was obtained:
N,N-bis(biphenyl-4-yl)-N-{6-(9,9-dimethylfluoren-2-yl)biphenyl-3-yl}amine as a white powder 9.0 g (yield 57%).

The resulting amine compound is the compound (1-3) represented by the following formula:

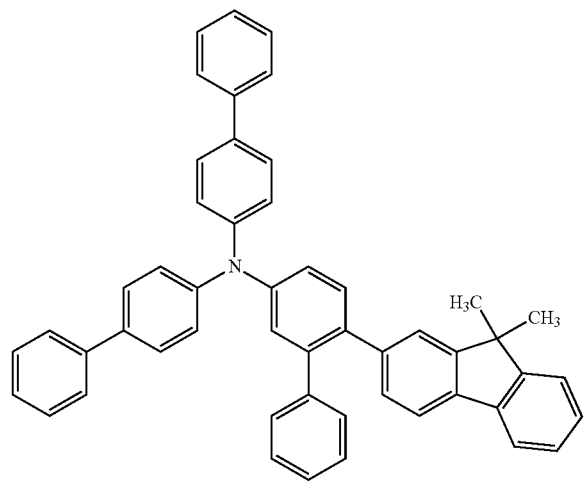

(1-3)

pm-substituted benzene ring: 1

Figure 4:
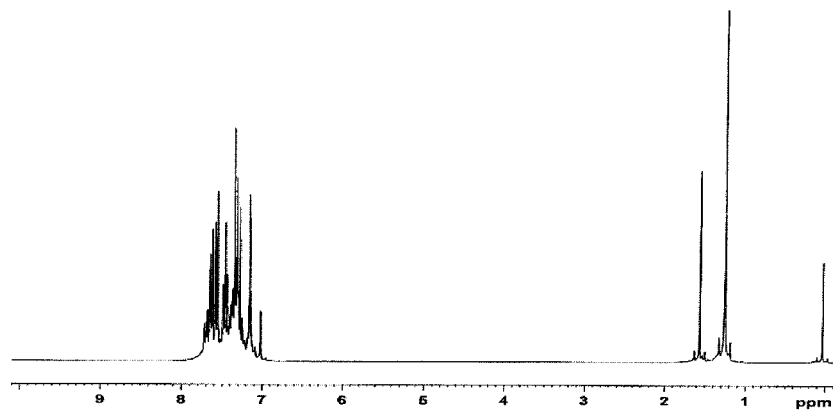
FIG. 4 is a $^1$H-NMR chart diagram of the compound (1-3) of Example 3.

In connection with the white powder obtained above, its structure was identified using NMR. Its NMR chart is shown in FIG. 4.

In $^1$H-NMR (CDCl$_3$), the following signals of 39 hydrogens were detected:

$\delta$ (ppm) = 7.56-7.64 (10H)

7.26-7.50 (18H)

7.02-7.16 (5H)

1.26 (6H)

Example 4

Synthesis of N,N-bis(6-phenylbiphenyl-3-yl)-N-(biphenyl-4-yl)amine (compound 1-94)

(First Step)

| | |
|---|---|
| A nitrogen-purged reaction vessel was charged with benzamide | 13.0 g, |
| 3-bromobiphenyl | 52.5 g, |
| potassium carbonate | 44.5 g, |
| sodium hydrogen sulfite | 3.4 g, |
| phenanthroline monohydrate | 2.2 g, |
| copper powder | 0.68 g, |
| dodecylbenzene | 13 mL, and |
| toluene | 30 mL. |

The mixture was heated with stirring, and refluxed for 19 hours, with toluene being removed. The system was cooled, and toluene was added, whereafter insolubles were removed by filtration. Washing with water and washing with a saturated saline solution were sequentially performed. Then, the residue was dried by using anhydrous magnesium sulfate, and concentrated to obtain a crude product.

Then, the crude product was purified using column chromatography to obtain
N,N-bis(biphenyl-3-yl)benzamide as a yellow viscous substance 41.7 g (yield 91%).

(Second Step)

| | |
|---|---|
| A reaction vessel was charged with N,N-bis(biphenyl-3-yl)benzamide obtained above | 41.7 g, |
| isoamyl alcohol | 36 mL, |
| water | 12 mL, and |
| potassium hydroxide | 7.6 g. |

The mixture was heated with stirring, and refluxed for 48 hours. The mixture was cooled to room temperature and, after water and toluene were added, an organic layer was collected by liquid separation. The collected matter was washed with water, successively washed with a saturated saline solution, then dried by using anhydrous magnesium sulfate, and concentrated to obtain a crude product.

Subsequently, the crude product was purified using column chromatography to obtain
N,N-bis(biphenyl-3-yl)amine as a brown viscous substance 25.3 g (yield 80%).

(Third Step)

| | |
|---|---|
| A nitrogen-purged reaction vessel was charged with N,N-bis(biphenyl-3-yl)amine obtained above | 25.2 g, |
| toluene | 250 mL, |
| 4-bromobiphenyl | 20.5 g, and |
| t-butoxysodium | 9.0 g. |

With the mixture being ultrasonically irradiated for 30 minutes, a nitrogen gas was passed therethrough.
Then,

| | |
|---|---|
| palladium acetate | 0.35 g, and |
| a 50% (w/v) toluene solution of t-butylphosphine | 0.95 g | were added. The mixture was heated, and stirred for 14 hours at 95° C. After insolubles were removed by filtration, washing with water and washing with a saturated saline solution were sequentially performed. Then, the residue was dried by using anhydrous magnesium sulfate, and concentrated to obtain a crude product.

Subsequently, purification using column chromatography was performed to obtain
N,N-bis(biphenyl-3-yl)-N-(biphenyl-4-yl)amine as a yellowish white powder 31.6 g (yield 85%).

(Fourth Step)

| | |
|---|---|
| A nitrogen-purged reaction vessel was charged with N,N-bis(biphenyl-3-yl)-N-(biphenyl-4-yl)amine obtained above | 31.5 g, and |
| dimethylformamide | 320 mL, | and the mixture was cooled in an ice bath.
Then,

| | |
|---|---|
| N-bromosuccinimide | 26.0 g | was slowly added, and the mixture was stirred for 5 hours. Water was added, and a crude product precipitated was collected by filtration. The precipitate was washed with methanol, and purified using column chromatography to purify
N,N-bis(6-bromobiphenyl-3-yl)-N-(biphenyl-4-yl)amine as a white powder 36.9 g (yield 88%).
(Fifth Step)
Reactions were performed in the same manner as in the third step of Example 1, except that bis(biphenyl-4-yl)-(6-bromobiphenyl-3-yl)amine used in the third step of Example 1 was replaced by N,N-bis(6-bromobiphenyl-3-yl)-N-(biphenyl-4-yl)amine obtained above. As a result, the following product was obtained:
N,N-bis(6-phenylbiphenyl-3-yl)-N-(biphenyl-4-yl)amine as a white powder 10.2 g (yield 73%).
The resulting amine compound is the compound (1-94) represented by the following formula:

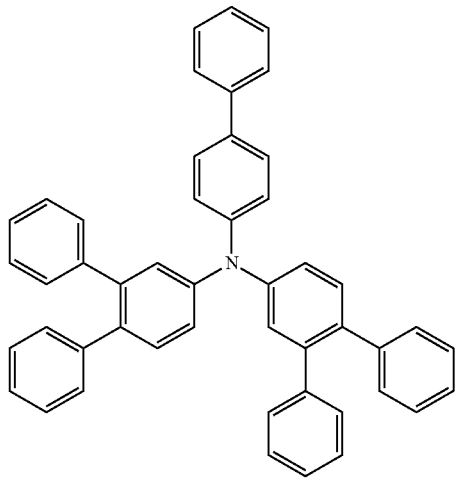

Figure 5:
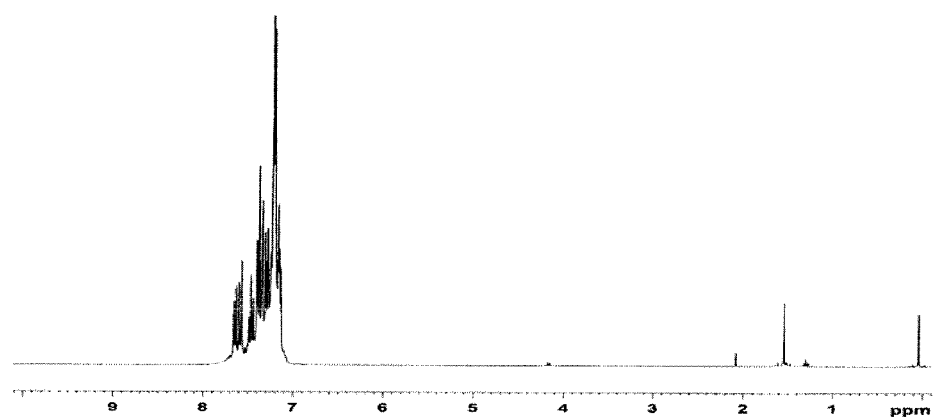
FIG. 5 is a $^1$H-NMR chart diagram of the compound (1-94) of Example 4.

(1-94)

pm-substituted benzene rings: 2
In connection with the white powder obtained above, its structure was identified using NMR. Its NMR chart is shown in FIG. 5.
In $^1$H-NMR (CDCl$_3$), the following signals of 35 hydrogens were detected:

$\delta$ (ppm) = 7.57-7.66 (4H)

7.10-7.49 (31H)

Example 5

Synthesis of tris(6-phenylbiphenyl-3-yl)amine (compound 1-129)

(First Step)

| | |
|---|---|
| A nitrogen-purged reaction vessel was charged with | 10.4 g, |
| 3-aminobiphenyl | |
| toluene | 250 mL, |
| 3-bromobiphenyl | 30.0 g, and |
| t-butoxysodium | 13.1 g. |

With the mixture being ultrasonically irradiated for 30 minutes, a nitrogen gas was passed therethrough.
Then,

| | |
|---|---|
| tris(dibenzylideneacetone)palladium | 2.25 g, and |
| a 50% (w/v) toluene solution of t-butylphosphine | 1.50 g | were added. The mixture was heated, and stirred for 3 hours at 95° C. After insolubles were removed by filtration, washing with water and washing with a saturated saline solution were sequentially performed. Then, the collected matter was dried by using anhydrous magnesium sulfate, and concentrated to obtain a crude product.
Further, the crude product was purified using column chromatography to obtain
tris(biphenyl-3-yl)amine as a white powder 24.6 g (yield 85%).
(Second Step)

| | |
|---|---|
| A nitrogen-purged reaction vessel was charged with tris(biphenyl-3-yl)amine obtained above | 24.5 g, and |
| dimethylformamide | 245 mL, | and the mixture was cooled in an ice bath.
Then,

| | |
|---|---|
| N-bromosuccinimide | 30.4 g | was slowly added, followed by stirring the mixture for 7 hours. Toluene was added, and washing with water and washing with a saturated saline solution were sequentially performed. Then, the residue was dried over anhydrous magnesium sulfate, and concentrated to obtain a crude product.
The crude product was purified using column chromatography to obtain
tris(6-bromobiphenyl-3-yl)amine as a white powder 33.6 g (yield 92%).

(Third Step)

Reactions were performed in the same manner as in the third step of Example 1, except that bis(biphenyl-4-yl)-(6-bromobiphenyl-3-yl)amine used in the third step of Example 1 was replaced by tris(6-bromobiphenyl-3-yl)amine obtained above. As a result, the following product was obtained:

tris(6-phenylbiphenyl-3-yl)amine as a white powder 11.1 g (yield 75%).

The resulting amine compound is the compound (1-129) represented by the following formula:

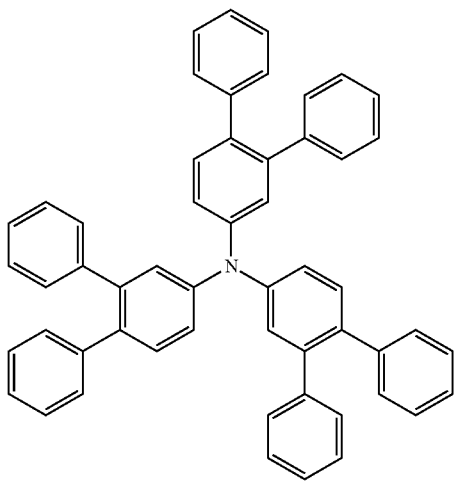

(1-129)

pm-substituted benzene rings: 3

Figure 6:
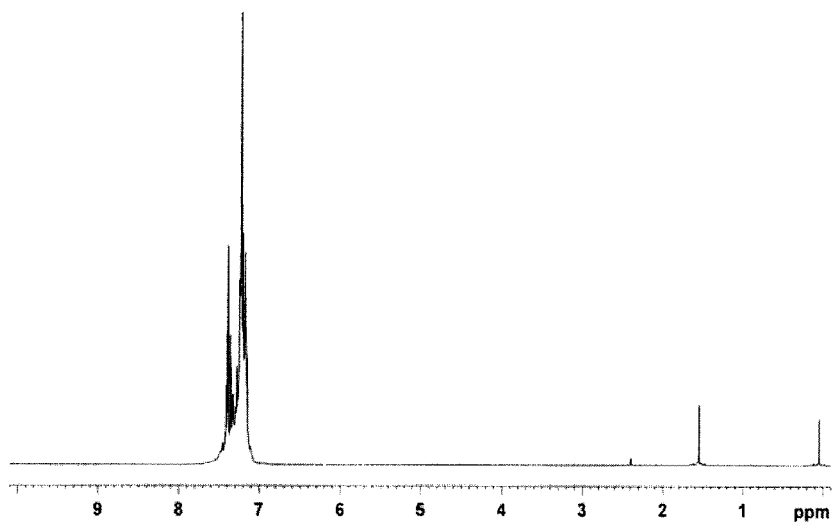
FIG. 6 is a $^1$H-NMR chart diagram of the compound (1-129) of Example 5.

In connection with the white powder obtained above, its structure was identified using NMR. Its NMR chart is shown in FIG. 6.

In $^1$H-NMR (CDCl$_3$), the following signals of 39 hydrogens were detected:

$\delta$ (ppm) = 7.35-7.42 (6H)

7.15-7.35 (33H)

Example 6

Synthesis of N,N-bis(biphenyl-4-yl)-N-(6-phenyl-1,1':4',1''-terphenyl-4-yl)amine (compound 1-4)

Reactions were performed under the same conditions as in Example 1, except that phenylboronic acid used in the third step of Example 1 was replaced by 4-biphenylboronic acid. As a result, the following product was obtained:

N,N-bis(biphenyl-4-yl)-N-(6-phenyl-1,1':4',1''-terphenyl-4-yl)amine as a white powder 8.4 g (yield 76%).

The resulting amine compound is the compound (1-4) represented by the following formula:

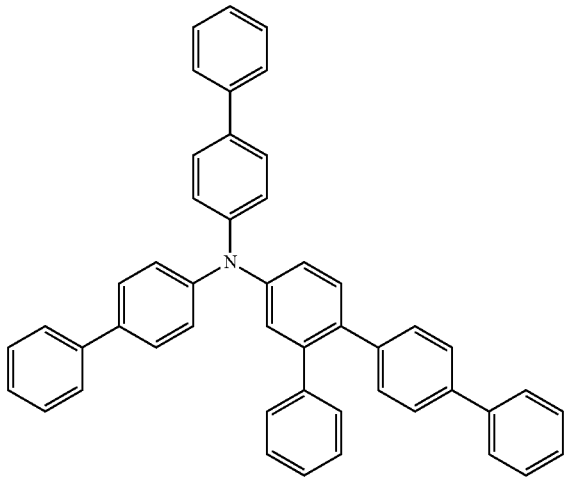

(1-4)

pm-substituted benzene ring: 1

Figure 7:
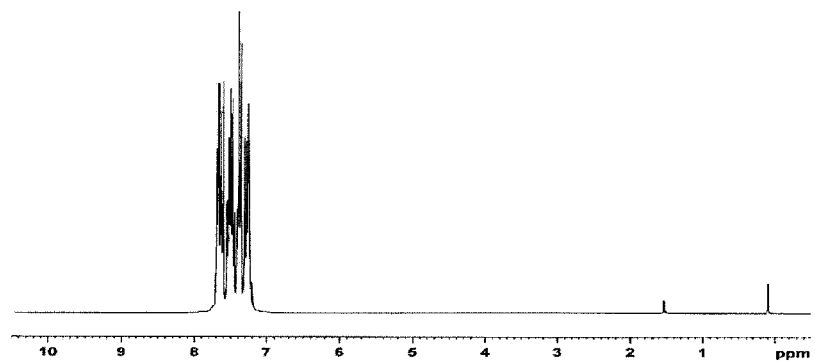
FIG. 7 is a $^1$H-NMR chart diagram of the compound (1-4) of Example 6.

In connection with the white powder obtained above, its structure was identified using NMR. Its NMR chart is shown in FIG. 7.

In $^1$H-NMR (CDCl$_3$), the following signals of 35 hydrogens were detected:

$\delta$ (ppm) = 7.60-7.68 (10H)

7.45-7.50 (9H)

7.30-7.39 (8H)

7.22-7.28 (8H)

Example 7

Synthesis of N,N-bis(biphenyl-4-yl)-N-(6-phenyl-1,1':4',1'':4'',1'''-quaterphenyl-4-yl)amine (compound 1-9)

Reactions were performed under the same conditions as in Example 1, except that phenylboronic acid used in the third step of Example 1 was replaced by p-terphenylboronic acid pinacol ester. As a result, the following product was obtained:

N,N-bis(biphenyl-4-yl)-N-(6-phenyl-1,1':4',1'':4'',1'''-quaterphenyl-4-yl)amine as a white powder 7.6 g (yield 75%).

The resulting amine compound is the compound (1-9) represented by the following formula:

The resulting amine compound is the compound (1-56) represented by the following formula:

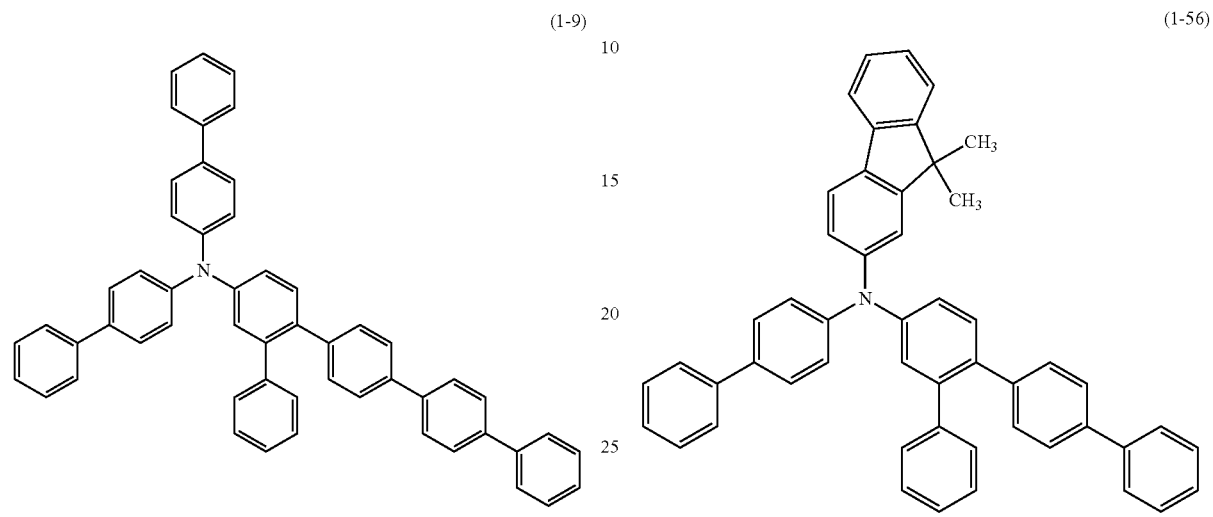

(1-9)

(1-56)

pm-substituted benzene ring: 1

Figure 8:
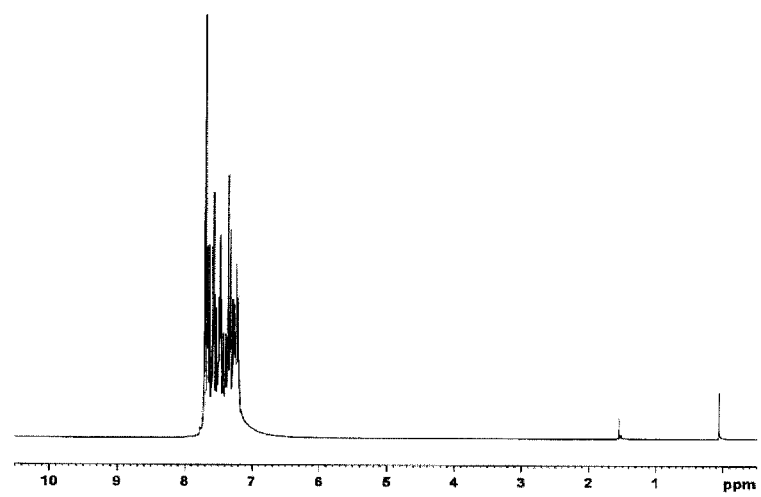
FIG. 8 is a $^1$H-NMR chart diagram of the compound (1-9) of Example 7.

In connection with the white powder obtained above, its structure was identified using NMR. Its NMR chart is shown in FIG. 8.

In $^1$H-NMR (CDCl$_3$), the following signals of 39 hydrogens were detected:

$\delta$ (ppm) = 7.40-7.55 (20H)

7.30-7.39 (7H)

7.19-7.29 (12H)

pm-substituted benzene ring: 1

Figure 9:
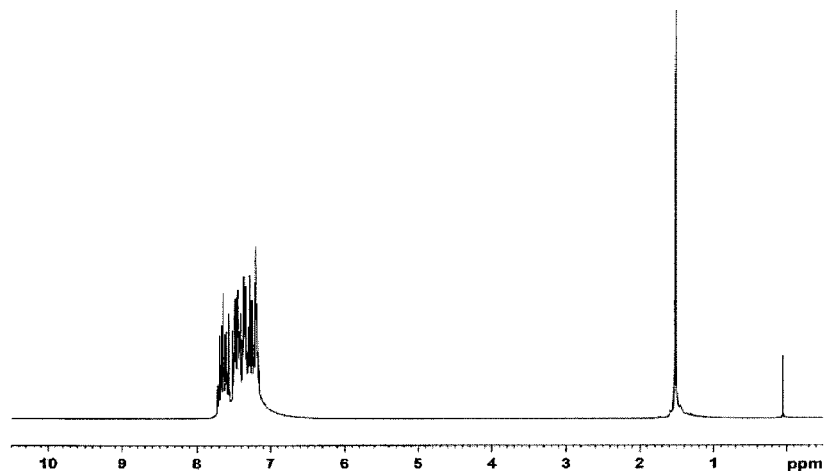
FIG. 9 is a $^1$H-NMR chart diagram of the compound (1-56) of Example 8.

In connection with the white powder obtained above, its structure was identified using NMR. Its NMR chart is shown in FIG. 9.

In $^1$H-NMR (CDCl$_3$), the following signals of 39 hydrogens were detected:

$\delta$ (ppm) = 7.57-7.70 (7H)

7.18-7.52 (26H)

1.52 (6H)

Example 8

Synthesis of N-4-biphenyl-N-(9,9-dimethylfluoren-2-yl)-N-(6-phenyl-1,1':4',1''-terphenyl-4-yl)amine (compound 1-56)

Reactions were performed under the same conditions as in the third step of Example 1, except that N-4-biphenyl-N-(6-bromobiphenyl-3-yl)-N-(9,9-dimethylfluoren-2-yl)amine, and 4-biphenyboronic acid were used instead of N,N-bis(biphenyl-4-yl)-N-(6-bromobiphenyl-3-yl)amine and phenylboronic acid in the third step of Example 1. As a result, the following product was obtained:

N-4-biphenyl-N-(9,9-dimethylfluoren-2-yl)-N-(6-phenyl-1,1':4',1''-terphenyl-4-yl)amine as a white powder 17.8 g (yield 89%).

Example 9

Synthesis of N-4-biphenyl-N-(1,1':4',1''-terphenyl-4-yl)-N-(6-phenyl-1,1':4',1''-terphenyl-4-yl)amine (compound 1-68)

Reactions were performed under the same conditions as in the third step of Example 1, except that N-4-biphenyl-N-(6-bromobiphenyl-3-yl)-N-(4-bromophenyl)amine, and 4-biphenyboronic acid were used instead of N,N-bis(biphenyl-4-yl)-N-(6-bromobiphenyl-3-yl)amine and phenylboronic acid in the third step of Example 1. As a result, the following product was obtained:

N-4-biphenyl-N-(1,1':4',1''-terphenyl-4-yl)-N-(6-phenyl-1,1':4',1''-terphenyl-4-yl)amine as a white powder 6.4 g (yield 55%).

The resulting amine compound is the compound (1-68) represented by the following formula:

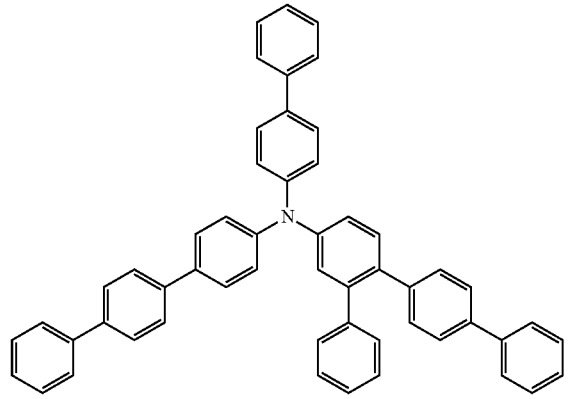

(1-68)

pm-substituted benzene ring: 1

Figure 10:
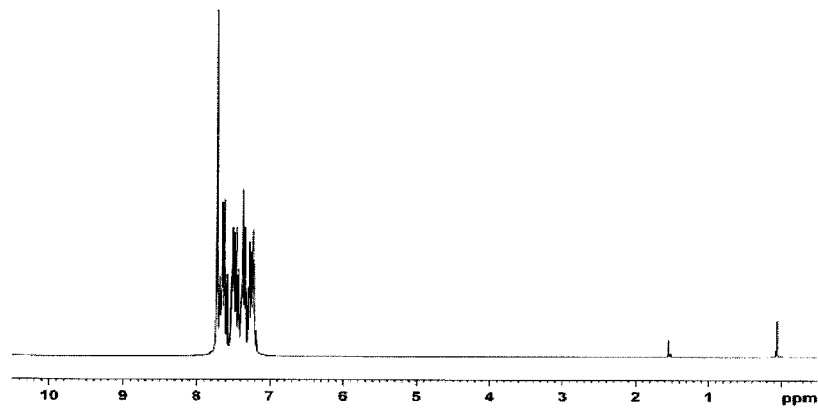
FIG. 10 is a $^1$H-NMR chart diagram of the compound (1-68) of Example 9.

In connection with the white powder obtained above, its structure was identified using NMR. Its NMR chart is shown in FIG. 10.

In $^1$H-NMR (CDCl$_3$), the following signals of 39 hydrogens were detected:

$\delta$ (ppm) = 7.58-7.79 (15H)

7.42-7.53 (9H)

7.20-7.40 (15H)

Example 10

Synthesis of N,N-bis(biphenyl-4-yl)-N-(6-phenyl-1,1':4',1''-terphenyl-3-yl)amine (compound 1-90)

Reactions were performed under the same conditions as in the third step of Example 1, except that N,N-bis(biphenyl-4-yl)-N-(6-bromo-1,1':4',1''-terphenyl-3-yl)amine was used instead of N,N-bis(biphenyl-4-yl)-N-(6-bromobiphenyl-3-yl)amine in the third step of Example 1. As a result, the following product was obtained:

N,N-bis(biphenyl-4-yl)-N-(6-phenyl-1,1':4',1''-terphenyl-3-yl)amine as a white powder 6.8 g (yield 84%).

The resulting amine compound is the compound (1-90) represented by the following formula:

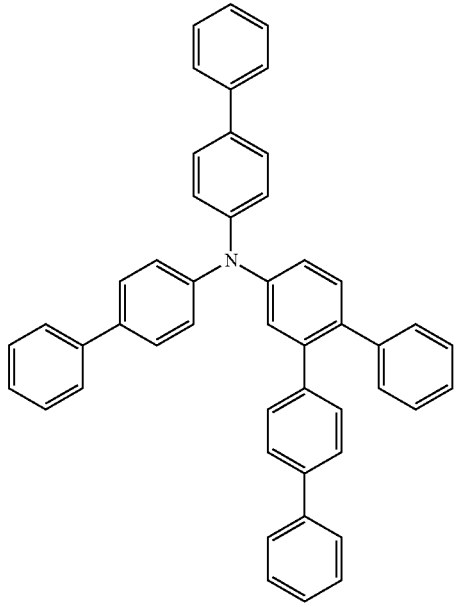

(1-90)

pm-substituted benzene ring: 1

Figure 11:
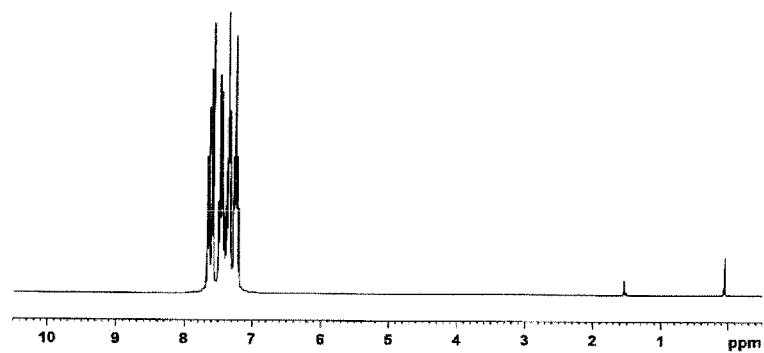
FIG. 11 is a $^1$H-NMR chart diagram of the compound (1-90) of Example 10.

In connection with the white powder obtained above, its structure was identified using NMR. Its NMR chart is shown in FIG. 11.

In $^1$H-NMR (CDCl$_3$), the following signals of 35 hydrogens were detected:

$\delta$ (ppm) = 7.58-7.66 (10H)

7.34-7.48 (17H)

7.20-7.28 (8H)

Example 11

Synthesis of N,N-bis(biphenyl-4-yl)-N-(6-phenyl-1,1':2',1''-terphenyl-3-yl)amine (compound 1-92)

Reactions were performed under the same conditions as in the third step of Example 1, except that N,N-bis(biphenyl-4-yl)-N-(6-bromo-1,1':2',1''-terphenyl-3-yl)amine was used instead of N,N-bis(biphenyl-4-yl)-N-(6-bromobiphenyl-3-yl)amine in the third step of Example 1. As a result, the following product was obtained:

N,N-bis(biphenyl-4-yl)-N-(6-phenyl-1,1':2',1''-terphenyl-3-yl)amine as a white powder 4.8 g (yield 40%).

The resulting amine compound is the compound (1-92) represented by the following formula:

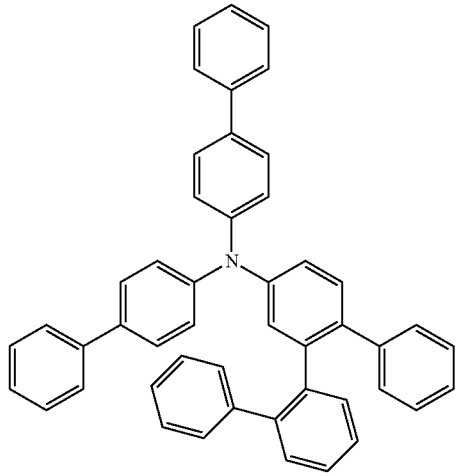

(1-92)

pm-substituted benzene ring: 1

Figure 12:
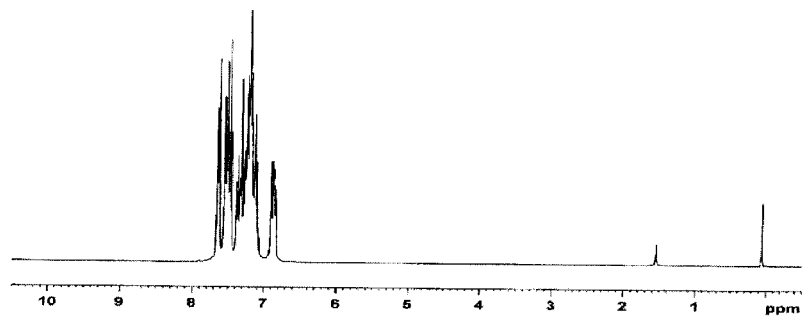
FIG. 12 is a $^1$H-NMR chart diagram of the compound (1-92) of Example 11.

In connection with the white powder obtained above, its structure was identified using NMR. Its NMR chart is shown in FIG. 12.

In $^1$H-NMR (CDCl$_3$), the following signals of 35 hydrogens were detected:

$\delta$ (ppm) = 7.62-7.68 (4H)
7.46-7.58 (8H)
7.09-7.39 (19H)
6.84-6.91 (4H)

Example 12

Synthesis of N-4-biphenyl-N-{4-(naphthalen-1-yl)phenyl}-N-(6-phenyl-1,1':4',1''-terphenyl-4-yl)amine (compound 1-134)

Reactions were performed under the same conditions as in the third step of Example 1, except that N-4-biphenyl-N-(6-bromobiphenyl-3-yl)-N-{4-(naphthalen-1-yl)phenyl}amine, and 4-biphenyboronic acid were used instead of N,N-bis(biphenyl-4-yl)-N-(6-bromobiphenyl-3-yl)amine and phenylboronic acid in the third step of Example 1. As a result, the following product was obtained:

N-4-biphenyl-N-{4-(naphthalen-1-yl)phenyl}-N-(6-phenyl-1,1':4',1''-terphenyl-4-yl)amine as a white powder 7.5 g (yield 60%).

The resulting amine compound is the compound (1-134) represented by the following formula:

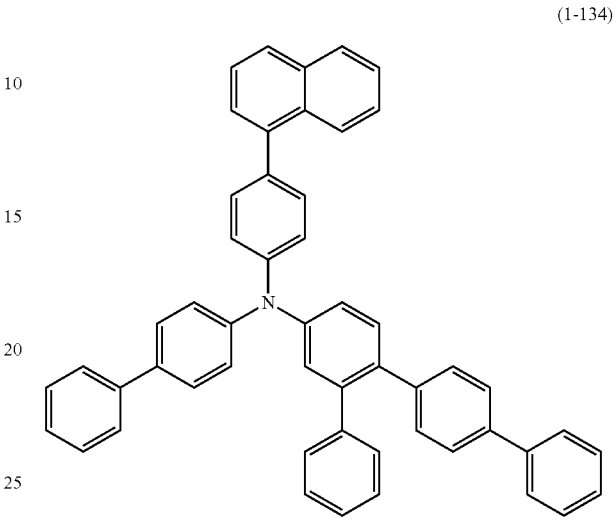

(1-134)

pm-substituted benzene ring: 1

Figure 13:
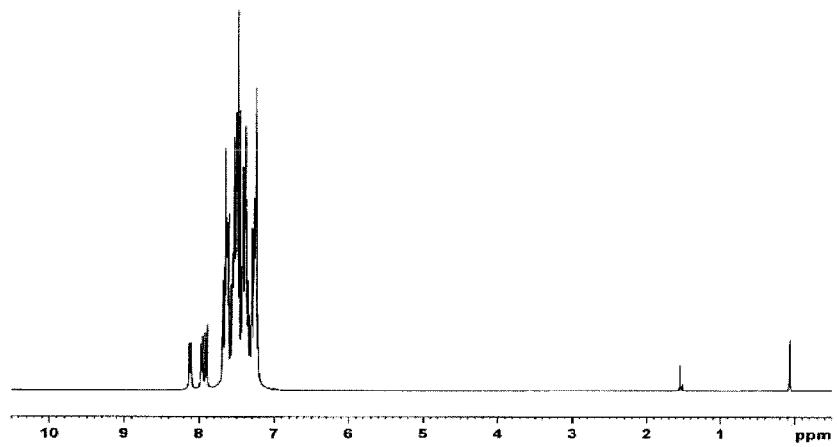
FIG. 13 is a $^1$H-NMR chart diagram of the compound (1-134) of Example 12.

In connection with the white powder obtained above, its structure was identified using NMR. Its NMR chart is shown in FIG. 13.

In $^1$H-NMR (CDCl$_3$), the following signals of 37 hydrogens were detected:

$\delta$ (ppm) = 8.08-8.12 (1H)
7.86-7.98 (2H)
7.21-7.64 (34H)

Example 13

Synthesis of N-4-biphenyl-N-{4-(naphthalen-1-yl)phenyl}-N-(6-phenyl-1,1':4',1'':4'',1'''-quaterphenyl-4-yl)amine (compound 1-135)

Reactions were performed under the same conditions as in the third step of Example 1, except that N-4-biphenyl-N-(6-bromobiphenyl-3-yl)-N-{4-(naphthalen-1-yl)phenyl}amine, and p-terphenylboronic acid pinacol ester were used instead of N,N-bis(biphenyl-4-yl)-N-(6-bromobiphenyl-3-yl)amine and phenylboronic acid in the third step of Example 1. As a result, the following product was obtained:

N-4-biphenyl-N-{4-(naphthalen-1-yl)phenyl}-N-(6-phenyl-1,1':4',1'':4'',1'''-quaterphenyl-4-yl)amine as a white powder 9.0 g (yield 56%).

The resulting amine compound is the compound (1-135) represented by the following formula:

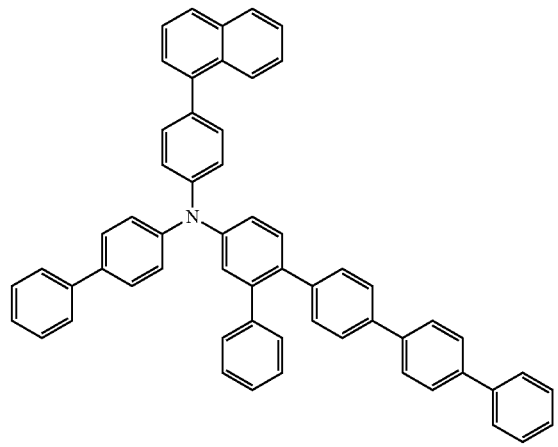

(1-135)

pm-substituted benzene ring: 1

Figure 14:
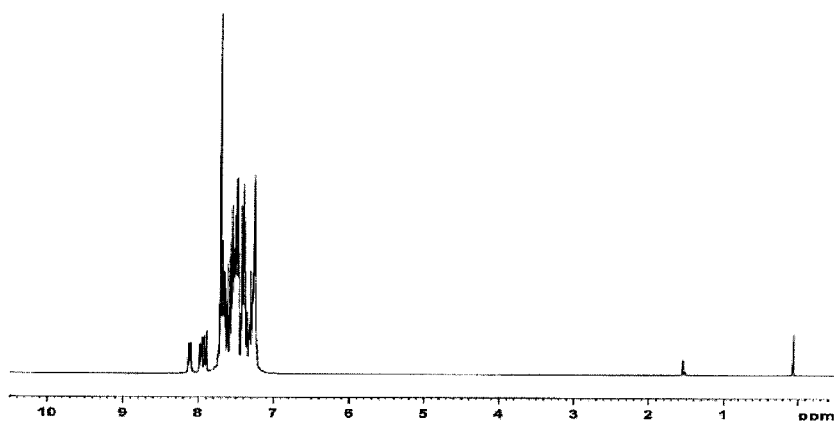
FIG. 14 is a $^1$H-NMR chart diagram of the compound (1-135) of Example 13.

In connection with the white powder obtained above, its structure was identified using NMR. Its NMR chart is shown in FIG. 14.

In $^1$H-NMR (CDCl$_3$), the following signals of 41 hydrogens were detected:

$\delta$ (ppm) = 8.08-8.12 (1H)
7.86-7.98 (2H)
7.22-7.71 (38H)

Example 14

Synthesis of N,N-bis{4-(naphthalen-1-yl)phenyl}-N-(6-phenyl-1,1':4',1''-terphenyl-4-yl)amine (compound 1-136)

Reactions were performed under the same conditions as in the third step of Example 1, except that N,N-bis{4-(naphthalen-1-yl)phenyl}-N-(6-bromobiphenyl-3-yl)amine, and 4-biphenylboronic acid were used instead of N,N-bis(biphenyl-4-yl)-N-(6-bromobiphenyl-3-yl)amine and phenylboronic acid in the third step of Example 1. As a result, the following product was obtained:

N,N-bis{4-(naphthalen-1-yl)phenyl}-N-(6-phenyl-1,1':4',1''-terphenyl-4-yl)amine as a white powder 10.6 g (yield 79%).

The resulting amine compound is the compound (1-136) represented by the following formula:

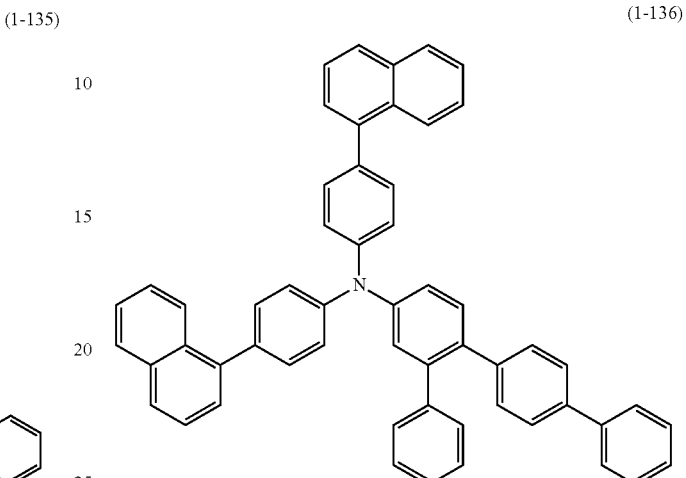

(1-136)

pm-substituted benzene ring: 1

Figure 15:
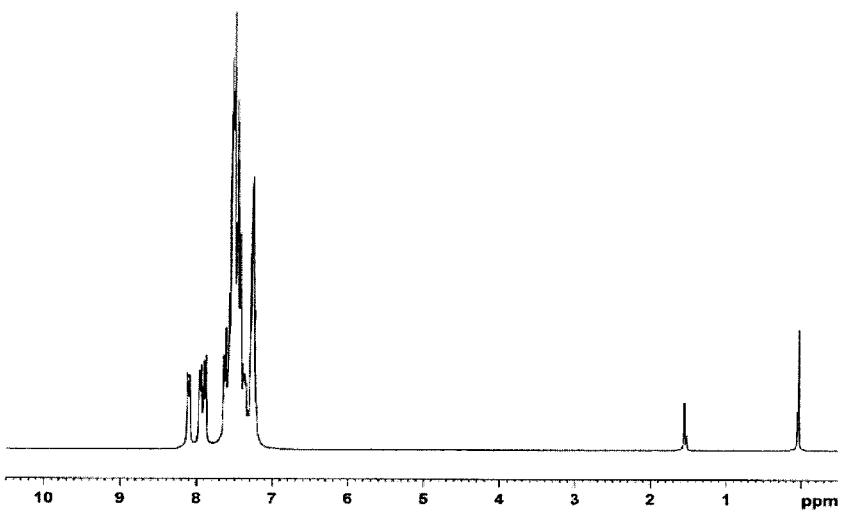
FIG. 15 is a $^1$H-NMR chart diagram of the compound (1-136) of Example 14.

In connection with the white powder obtained above, its structure was identified using NMR. Its NMR chart is shown in FIG. 15.

In $^1$H-NMR (CDCl$_3$), the following signals of 39 hydrogens were detected:

$\delta$ (ppm) = 8.08-8.14 (2H)
7.88-7.96 (4H)
7.24-7.64 (33H)

Example 15

Synthesis of N,N-bis{4-(naphthalen-1-yl)phenyl}-N-{6-phenyl-4''-(naphthalen-1-yl)biphenyl-4-yl}amine (compound 1-137)

Reactions were performed under the same conditions as in the third step of Example 1, except that N,N-bis{4-(naphthalen-1-yl)phenyl}-N-(6-bromobiphenyl-3-yl)amine, and 4-(naphthalen-2-yl)phenylboronic acid were used instead of N,N-bis(biphenyl-4-yl)-N-(6-bromobiphenyl-3-yl)amine and phenylboronic acid in the third step of Example 1. As a result, the following product was obtained:

N,N-bis{4-(naphthalen-1-yl)phenyl}-N-{6-phenyl-4''-(naphthalen-1-yl)biphenyl-4-yl}amine as a white powder 9.7 g (yield 74%).

The resulting amine compound is the compound (1-137) represented by the following formula:

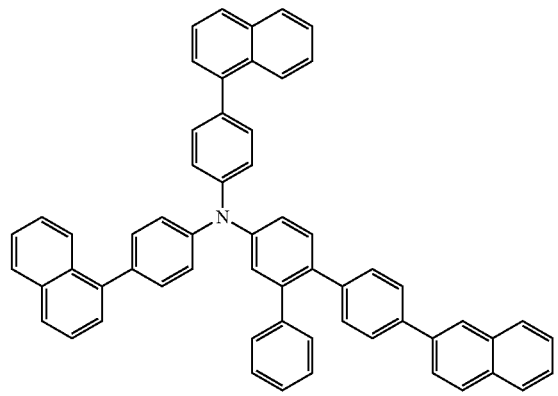

(1-137)

pm-substituted benzene ring: 1

Figure 16:
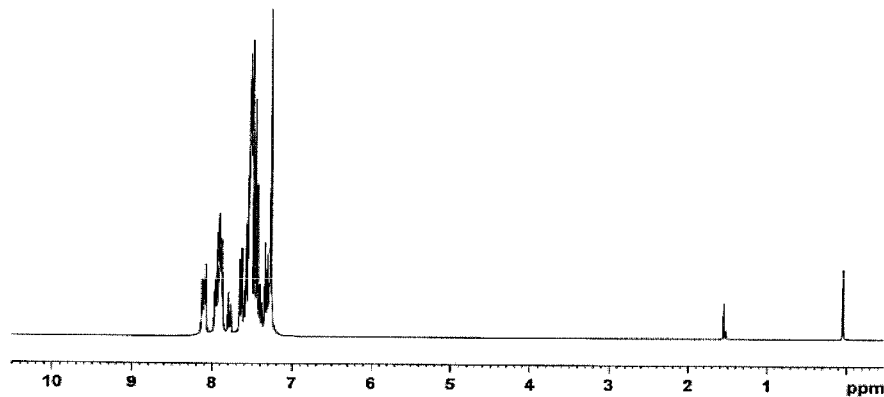
FIG. 16 is a $^1$H-NMR chart diagram of the compound (1-137) of Example 15.

In connection with the white powder obtained above, its structure was identified using NMR. Its NMR chart is shown in FIG. 16.

In $^1$H-NMR (CDCl$_3$), the following signals of 41 hydrogens were detected:

$\delta$ (ppm) = 8.08-8.14 (3H)

7.66-7.97 (8H)

7.28-7.66 (30H)

Example 16

Synthesis of N,N-bis{4-(naphthalen-1-yl)phenyl}-N-(6-phenyl-1,1':4',1":4",1'''-quaterphenyl-4-yl)amine (compound 1-138)

Reactions were performed under the same conditions as in the third step of Example 1, except that N,N-bis{4-(naphthalen-1-yl)phenyl}-N-(6-bromobiphenyl-3-yl)amine, and p-terphenylboronic acid pinacol ester were used instead of N,N-bis(biphenyl-4-yl)-N-(6-bromobiphenyl-3-yl)amine and phenylboronic acid in the third step of Example 1. As a result, the following product was obtained:

N,N-bis{4-(naphthalen-1-yl)phenyl}-N-(6-phenyl-1,1':4',1":4",1'''-quaterphenyl-4-yl)amine as a white powder 6.2 g (yield 63%).

The resulting amine compound is the compound (1-138) represented by the following formula:

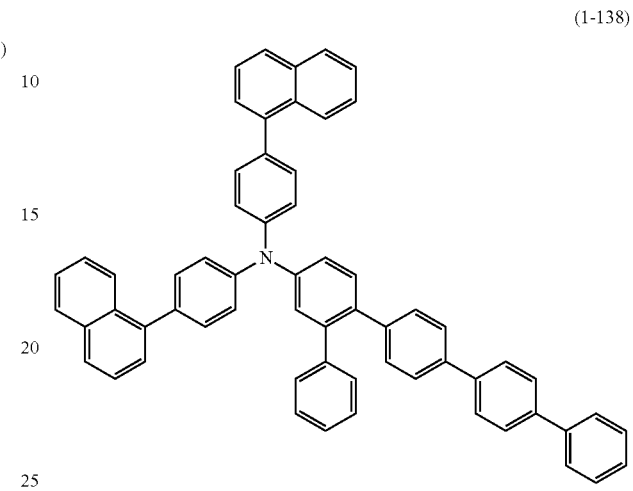

(1-138)

pm-substituted benzene ring: 1

Figure 17:
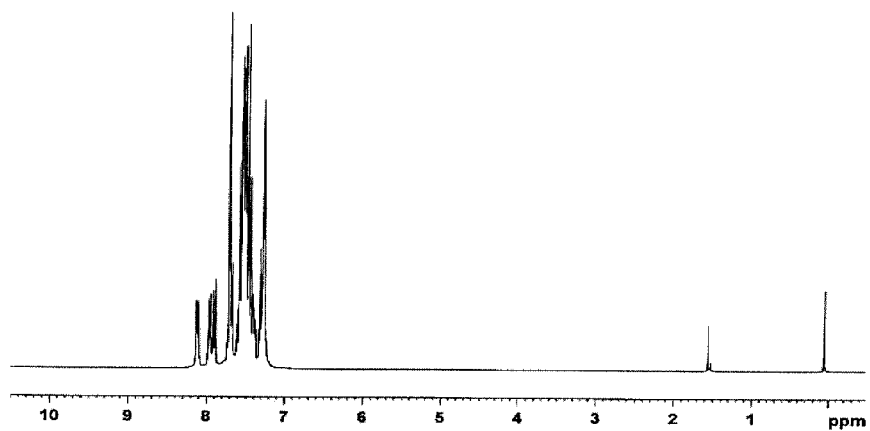
FIG. 17 is a $^1$H-NMR chart diagram of the compound (1-138) of Example 16.

In connection with the white powder obtained above, its structure was identified using NMR. Its NMR chart is shown in FIG. 17.

In $^1$H-NMR (CDCl$_3$), the following signals of 43 hydrogens were detected:

$\delta$ (ppm) = 8.08-8.14 (3H)

7.89-7.95 (4H)

7.25-7.71 (36H)

Example 17

Synthesis of N,N-bis{4-(naphthalen-1-yl)phenyl}-N-(6-phenyl-1,1':3',1"-terphenyl-4-yl)amine (compound 1-139)

Reactions were performed under the same conditions as in the third step of Example 1, except that N,N-bis{4-(naphthalen-1-yl)phenyl}-N-(6-bromobiphenyl-3-yl)amine, and 3-biphenylboronic acid were used instead of N,N-bis(biphenyl-4-yl)-N-(6-bromobiphenyl-3-yl)amine and phenylboronic acid in the third step of Example 1. As a result, the following product was obtained:

N,N-bis{4-(naphthalen-1-yl)phenyl}-N-(6-phenyl-1,1':3',1"-terphenyl-4-yl)amine as a white powder 4.9 g (yield 48%).

The resulting amine compound is the compound (1-139) represented by the following formula:

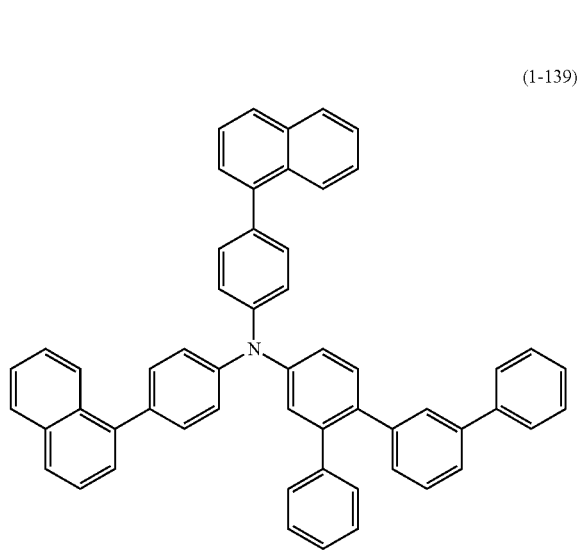 [SMILES: c1ccc(-c2cccc(-c3ccc(N(c4ccc(-c5cccc6ccccc56)cc4)c4ccc(-c5cccc6ccccc56)cc4)cc3-c3ccccc3)c2)cc1]

(1-139)

pm-substituted benzene ring: 1

Figure 18:
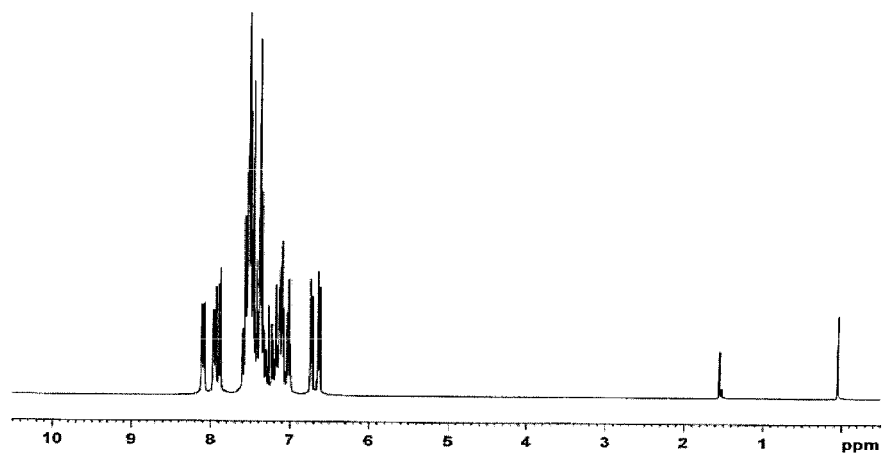
FIG. 18 is a $^1$H-NMR chart diagram of the compound (1-139) of Example 17.

In connection with the white powder obtained above, its structure was identified using NMR. Its NMR chart is shown in FIG. 18.

In $^1$H-NMR (CDCl$_3$), the following signals of 39 hydrogens were detected:

$\delta$ (ppm) = 8.08-8.12 (2H)
7.86-7.94 (4H)
7.00-7.57 (29H)
6.63-6.75 (4H)

Example 18

Synthesis of N-4-biphenyl-N-{4-(naphthalen-2-yl)phenyl}-N-(6-phenyl-1,1':4',1''-terphenyl-4-yl)amine (compound 1-140)

Reactions were performed under the same conditions as in the third step of Example 1, except that N-4-biphenyl-N-(6-bromobiphenyl-3-yl)-N-{4-(naphthalen-2-yl)phenyl}amine, and 4-biphenylboronic acid were used instead of N,N-bis(biphenyl-4-yl)-N-(6-bromobiphenyl-3-yl)amine and phenylboronic acid in the third step of Example 1. As a result, the following product was obtained:

N-4-biphenyl-N-{4-(naphthalen-2-yl)phenyl}-N-(6-phenyl-1,1':4',1''-terphenyl-4-yl)amine as a white powder 4.9 g (yield 44%).

The resulting amine compound is the compound (1-140) represented by the following formula:

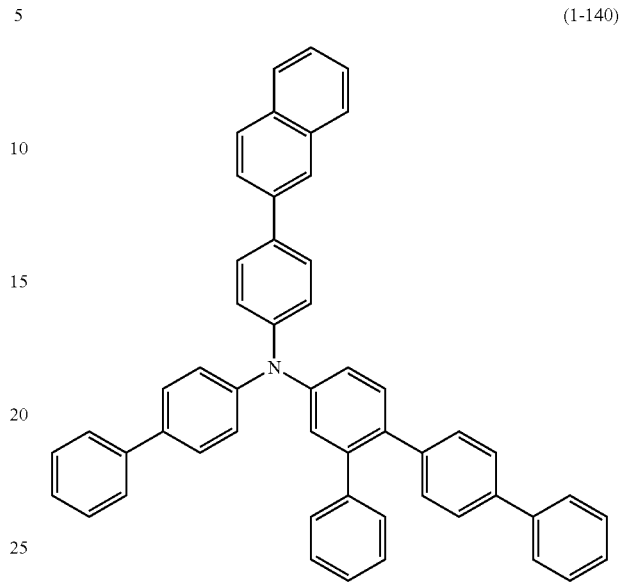

(1-140)

pm-substituted benzene ring: 1

Figure 19:
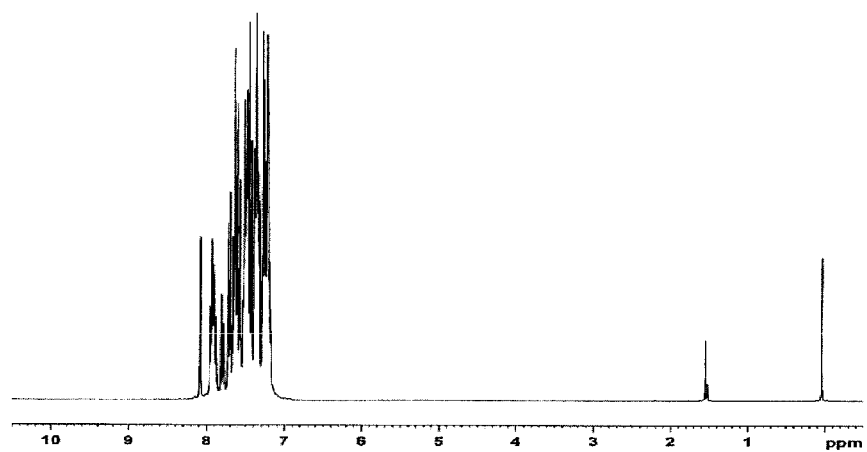
FIG. 19 is a $^1$H-NMR chart diagram of the compound (1-140) of Example 18.

In connection with the white powder obtained above, its structure was identified using NMR. Its NMR chart is shown in FIG. 19.

In $^1$H-NMR (CDCl$_3$), the following signals of 37 hydrogens were detected:

$\delta$ (ppm) = 7.73 (1H)
7.61-7.70 (3H)
7.54-7.58 (1H)
7.19-7.52 (32H)

Example 19

Synthesis of N-4-biphenyl-N-{4-(naphthalen-2-yl)phenyl}-N-(6-phenyl-1,1':4',1''-terphenyl-3-yl)amine (compound 1-141)

Reactions were performed under the same conditions as in the third step of Example 1, except that N-4-biphenyl-N-{4-(naphthalen-2-yl)phenyl}-N-(6-bromo-1,1':4',1''-terphenyl-3-yl)amine was used instead of N,N-bis(biphenyl-4-yl)-N-(6-bromobiphenyl-3-yl)amine in the third step of Example 1. As a result, the following product was obtained:

N-4-biphenyl-N-{4-(naphthalen-2-yl)phenyl}-N-(6-phenyl-1,1':4',1''-terphenyl-3-yl)amine as a white powder 5.8 g (yield 56%).

The resulting amine compound is the compound (1-141) represented by the following formula:

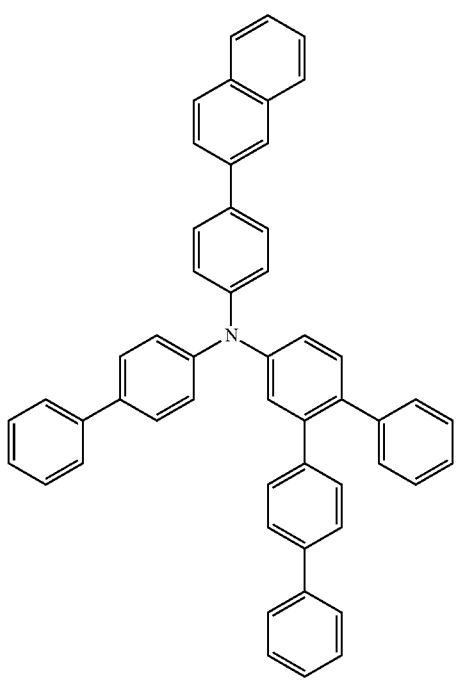

(1-141)

pm-substituted benzene ring: 1

Figure 20:
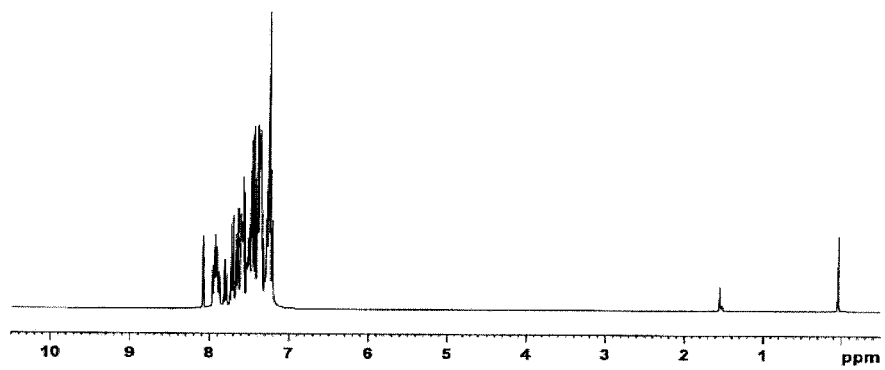
FIG. 20 is a $^1$H-NMR chart diagram of the compound (1-141) of Example 19.

In connection with the white powder obtained above, its structure was identified using NMR. Its NMR chart is shown in FIG. 20.

In $^1$H-NMR (CDCl$_3$), the following signals of 37 hydrogens were detected:

$\delta$ (ppm) = 8.08 (1H)
7.81-7.96 (3H)
7.79-7.81 (1H)
7.21-7.73 (32H)

Example 20

Synthesis of N-4-biphenyl-N-{4-(naphthalen-2-yl)phenyl}-N-{6-phenyl-4'-(naphthalen-2-yl)biphenyl-3-yl)amine (compound 1-142)

Reactions were performed under the same conditions as in the third step of Example 1, except that N-4-biphenyl-N-{4-(naphthalen-2-yl)phenyl}-N-{6-bromo-4'-(naphthalen-2-yl)biphenyl-3-yl}amine was used instead of N,N-bis(biphenyl-4-yl)-N-(6-bromobiphenyl-3-yl)amine in the third step of Example 1. As a result, the following product was obtained:

N-4-biphenyl-N-{4-(naphthalen-2-yl)phenyl}-N-{6-phenyl-4'-(naphthalen-2-yl)biphenyl-3-yl)amine as a white powder 10.0 g (yield 81%).

The resulting amine compound is the compound (1-142) represented by the following formula:

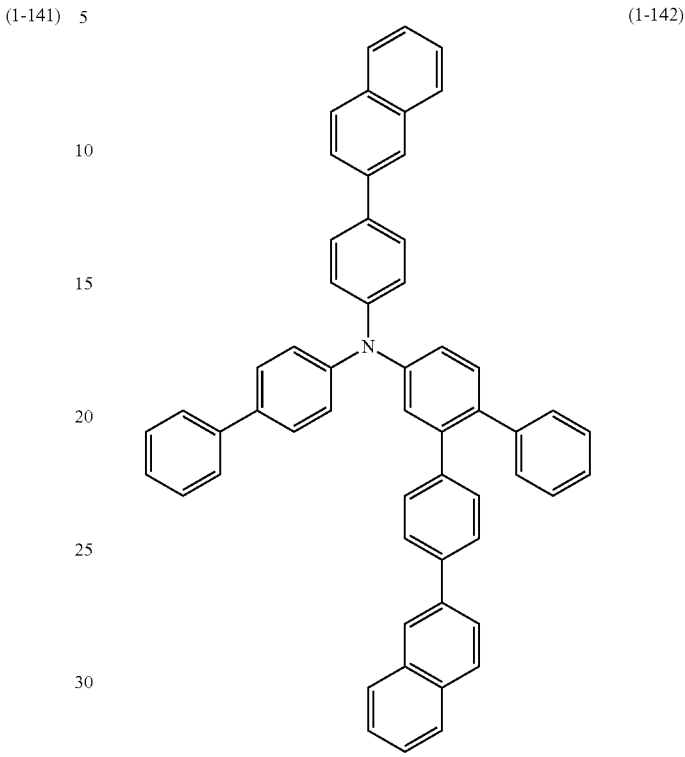

(1-142)

pm-substituted benzene ring: 1

Figure 21:
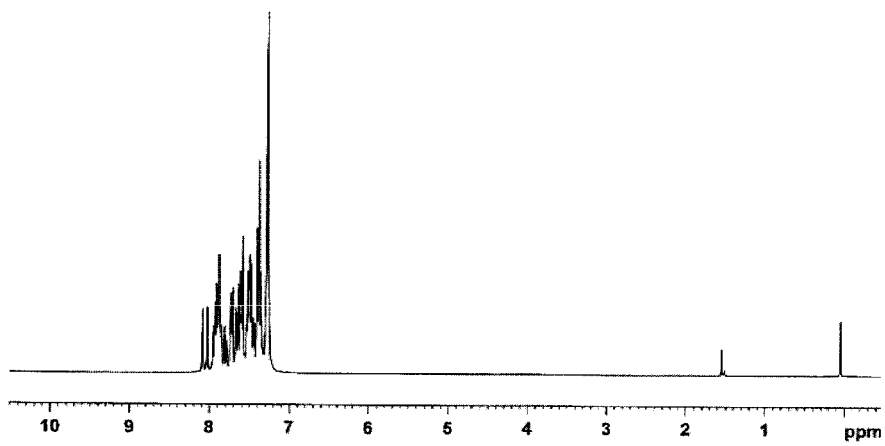
FIG. 21 is a $^1$H-NMR chart diagram of the compound (1-142) of Example 20.

In connection with the white powder obtained above, its structure was identified using NMR. Its NMR chart is shown in FIG. 21.

In $^1$H-NMR (CDCl$_3$), the following signals of 39 hydrogens were detected:

$\delta$ (ppm) = 8.04-8.10 (2H)
7.78-7.96 (8H)
7.24-7.65 (29H)

Example 21

Synthesis of N-4-biphenyl-N-(9,9-diphenylfluoren-2-yl)-N-(6-phenylbiphenyl-3-yl)amine (compound 1-143)

Reactions were performed under the same conditions as in the third step of Example 1, except that N-4-biphenyl-N-(6-bromobiphenyl-3-yl)-N-(9,9-diphenylfluoren-2-yl)amine was used instead of N,N-bis(biphenyl-4-yl)-N-(6-bromobiphenyl-3-yl)amine in the third step of Example 1. As a result, the following product was obtained:

N-4-biphenyl-N-(9,9-diphenylfluoren-2-yl)-N-(6-phenylbiphenyl-3-yl)amine as a white powder 11.0 g (yield 61%).

The resulting amine compound is the compound (1-143) represented by the following formula:

(1-143)

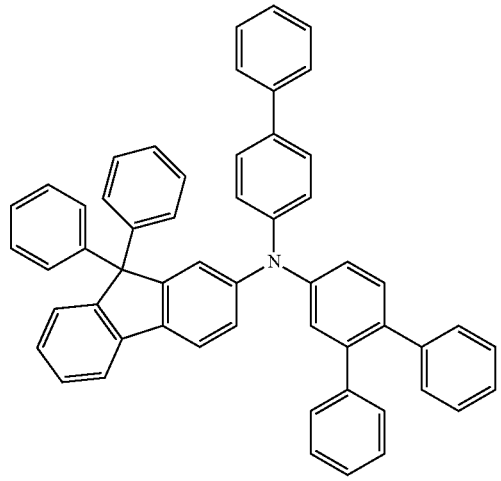

pm-substituted benzene ring: 1

Figure 22:
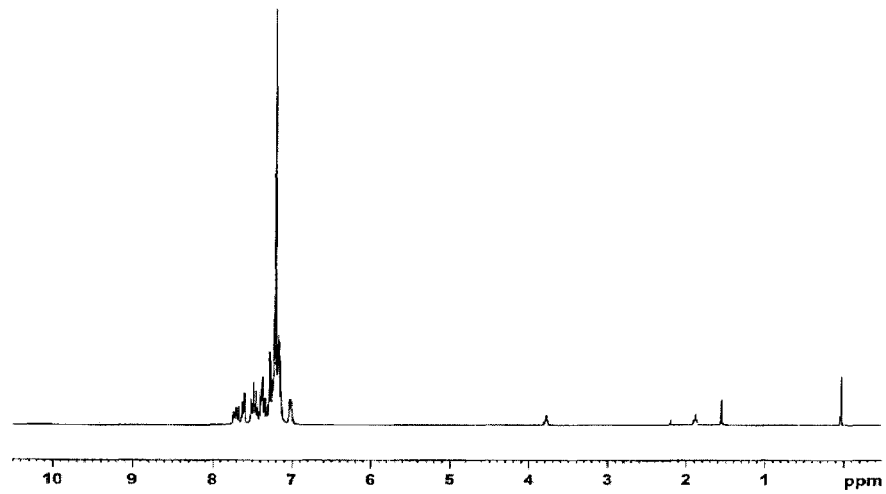
FIG. 22 is a 1H-NMR chart diagram of the compound (1-143) of Example 21.

In connection with the white powder obtained above, its structure was identified using NMR. Its NMR chart is shown in FIG. 22.

In $^1$H-NMR (CDCl$_3$), the following signals of 39 hydrogens were detected:

$\delta$ (ppm) = 7.60-7.74 (4H)
7.14-7.52 (33H)
7.00-7.03 (2H)

Example 22

Synthesis of N-4-biphenyl-N-(9,9-diphenylfluoren-2-yl)-N-(6-phenyl-1,1':4',1''-terphenyl-4-yl)amine (compound 1-144)

Reactions were performed under the same conditions as in the third step of Example 1, except that N-4-biphenyl-N-(6-bromobiphenyl-3-yl)-N-(9,9-diphenylfluoren-2-yl)amine, and 4-biphenylboronic acid were used instead of N,N-bis(biphenyl-4-yl)-N-(6-bromobiphenyl-3-yl)amine and phenylboronic acid in the third step of Example 1. As a result, the following product was obtained:

N-4-biphenyl-N-(9,9-diphenylfluoren-2-yl)-N-(6-phenyl-1,1':4',1''-terphenyl-4-yl)amine as a white powder 6.5 g (yield 71%).

The resulting amine compound is the compound (1-144) represented by the following formula:

(1-144)

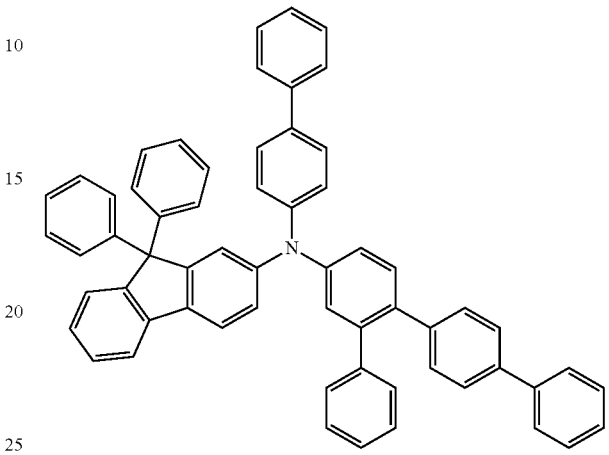

pm-substituted benzene ring: 1

Figure 23:
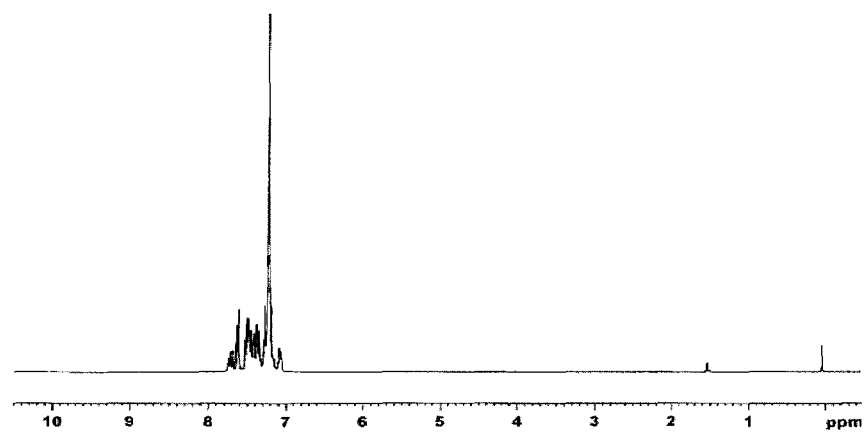
FIG. 23 is a $^1$H-NMR chart diagram of the compound (1-144) of Example 22.

In connection with the white powder obtained above, its structure was identified using NMR. Its NMR chart is shown in FIG. 23.

In $^1$H-NMR (CDCl$_3$), the following signals of 43 hydrogens were detected:

$\delta$ (ppm) = 7.61-7.77 (6H)
7.20-7.51 (34H)
7.06-7.11 (3H)

Example 23

Synthesis of N-4-biphenyl-N-(9,9-diphenylfluoren-2-yl)-N-(6-phenyl-1,1':3',1''-terphenyl-4-yl)amine (compound 1-145)

Reactions were performed under the same conditions as in the third step of Example 1, except that N-4-biphenyl-N-(6-bromobiphenyl-3-yl)-N-(9,9-diphenylfluoren-2-yl)amine, and 3-biphenylboronic acid were used instead of N,N-bis(biphenyl-4-yl)-N-(6-bromobiphenyl-3-yl)amine and phenylboronic acid in the third step of Example 1. As a result, the following product was obtained:

N-4-biphenyl-N-(9,9-diphenylfluoren-2-yl)-N-(6-phenyl-1,1':3',1''-terphenyl-4-yl)amine as a white powder 8.0 g (yield 87%).

The resulting amine compound is the compound (1-145) represented by the following formula:

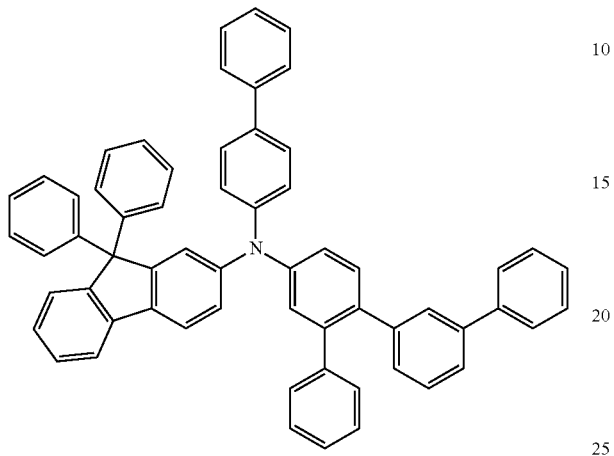

(1-145)

pm-substituted benzene ring: 1

Figure 24:
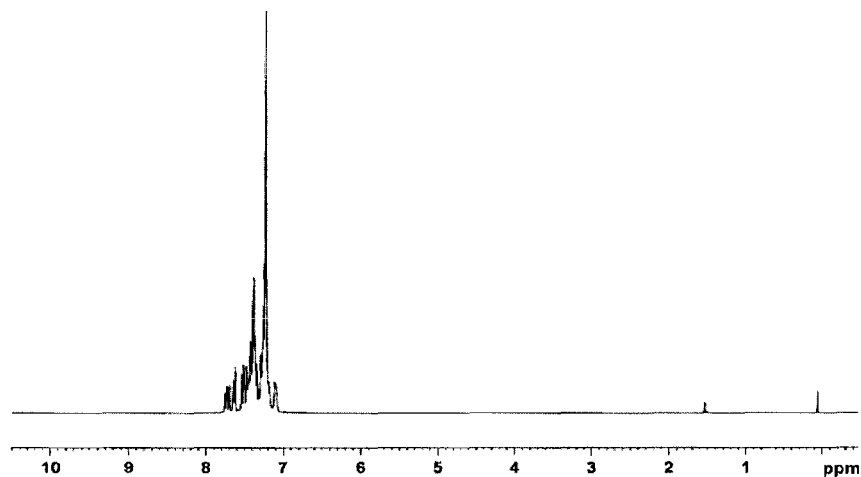
FIG. 24 is a $^1$H-NMR chart diagram of the compound (1-145) of Example 23.

In connection with the white powder obtained above, its structure was identified using NMR. Its NMR chart is shown in FIG. 24.

In $^1$H-NMR (CDCl$_3$), the following signals of 43 hydrogens were detected:

$\delta$ (ppm) = 7.70-7.76 (2H)
7.63-7.65 (2H)
7.18-7.54 (36H)
7.08-7.12 (3H)

Example 24

Synthesis of N-4-biphenyl-N-(9,9-diphenylfluoren-2-yl)-N-(6-phenyl-1,1':2',1"-terphenyl-4-yl)amine (compound 1-146)

Reactions were performed under the same conditions as in the third step of Example 1, except that N-4-biphenyl-N-(6-bromobiphenyl-3-yl)-N-(9,9-diphenylfluoren-2-yl)amine, and 2-biphenylboronic acid were used instead of N,N-bis(biphenyl-4-yl)-N-(6-bromobiphenyl-3-yl)amine and phenylboronic acid in the third step of Example 1. As a result, the following product was obtained:

N-4-biphenyl-N-(9,9-diphenylfluoren-2-yl)-N-(6-phenyl-1,1':2',1"-terphenyl-4-yl)amine as a white powder 5.2 g (yield 57%).

The resulting amine compound is the compound (1-146) represented by the following formula:

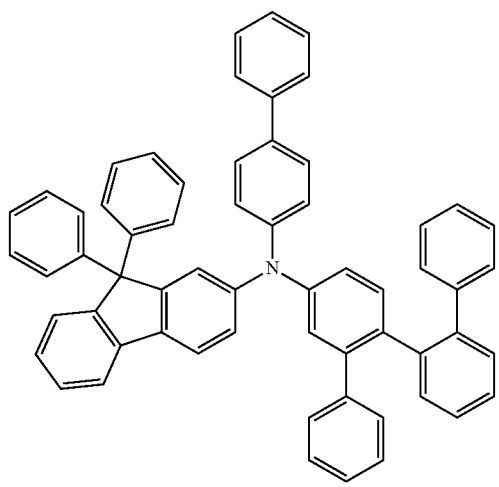

(1-146)

pm-substituted benzene ring: 1

Figure 25:
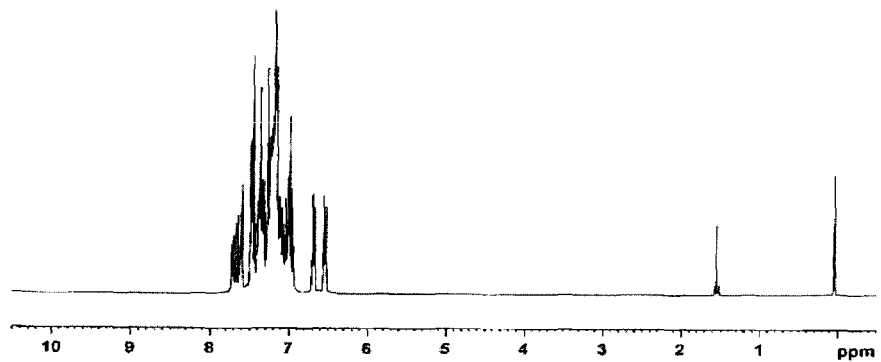
FIG. 25 is a $^1$H-NMR chart diagram of the compound (1-146) of Example 24.

In connection with the white powder obtained above, its structure was identified using NMR. Its NMR chart is shown in FIG. 25.

In $^1$H-NMR (CDCl$_3$), the following signals of 43 hydrogens were detected:

$\delta$ (ppm) = 7.60-7.74 (4H)
6.95-7.49 (35H)
6.68-6.71 (2H)
6.54-6.57 (2H)

Example 25

Synthesis of N,N-bis(biphenyl-4-yl)-N-{6-phenyl-4'-(naphthalen-1-yl)biphenyl-3-yl}amine (compound 1-147)

Reactions were performed under the same conditions as in the third step of Example 1, except that N,N-bis(biphenyl-4-yl)-N-{6-bromo-4'-(naphthalen-1-yl)biphenyl-3-yl}amine was used instead of N,N-bis(biphenyl-4-yl)-N-(6-bromobiphenyl-3-yl)amine in the third step of Example 1. As a result, the following product was obtained:

N,N-bis(biphenyl-4-yl)-N-{6-phenyl-4'-(naphthalen-1-yl)biphenyl-3-yl}amine as a white powder 5.4 g (yield 33%).

The resulting amine compound is the compound (1-147) represented by the following formula:

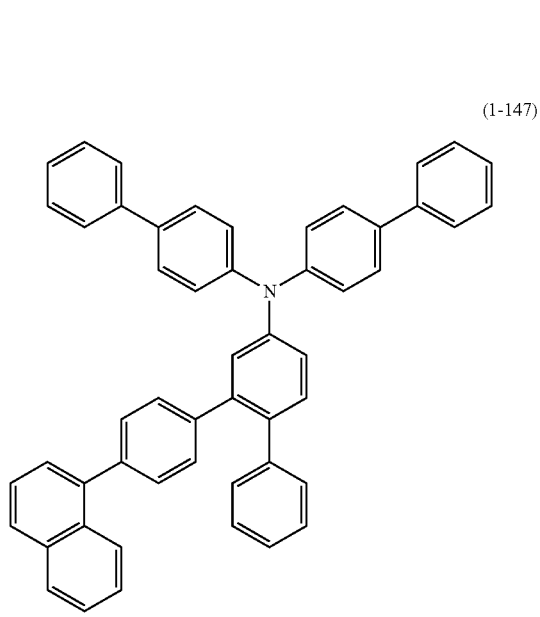 [SMILES: c1ccc(-c2ccc(N(c3ccc(-c4ccccc4)cc3)c3ccc(-c4ccccc4)c(-c4ccc(-c5cccc6ccccc56)cc4)c3)cc2)cc1]
(1-147)

pm-substituted benzene ring: 1

Figure 26:
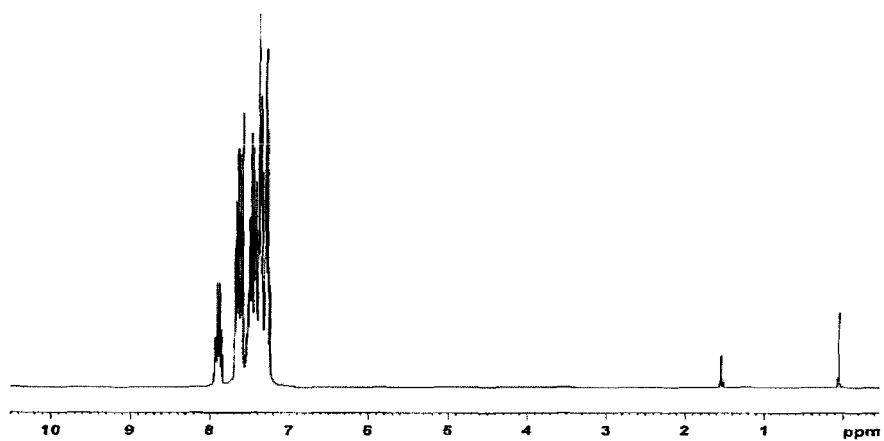
FIG. 26 is a 1H-NMR chart diagram of the compound (1-147) of Example 25.

In connection with the white powder obtained above, its structure was identified using NMR. Its NMR chart is shown in FIG. 26.

In $^1$H-NMR (CDC$_3$), the following signals of 37 hydrogens were detected:

δ (ppm) = 7.84-7.95 (3H)
7.24-7.67 (34H)

Example 26

Synthesis of N,N-bis(biphenyl-4-yl)-N-{6-(biphenyl-4-yl)-1,1':4',1"-terphenyl-3-yl}amine (compound 1-148)

Reactions were performed under the same conditions as in the third step of Example 1, except that N,N-bis(biphenyl-4-yl)-N-(6-bromo-1,1':4',1"-terphenyl-3-yl)amine, and 4-biphenylboronic acid were used instead of N,N-bis(biphenyl-4-yl)-N-(6-bromobiphenyl-3-yl)amine and phenylboronic acid in the third step of Example 1. As a result, the following product was obtained:

N,N-bis(biphenyl-4-yl)-N-{6-(biphenyl-4-yl)-1,1':4',1"-terphenyl-3-yl}amine as a white powder 9.4 g (yield 84%).

The resulting amine compound is the compound (1-148) represented by the following formula:

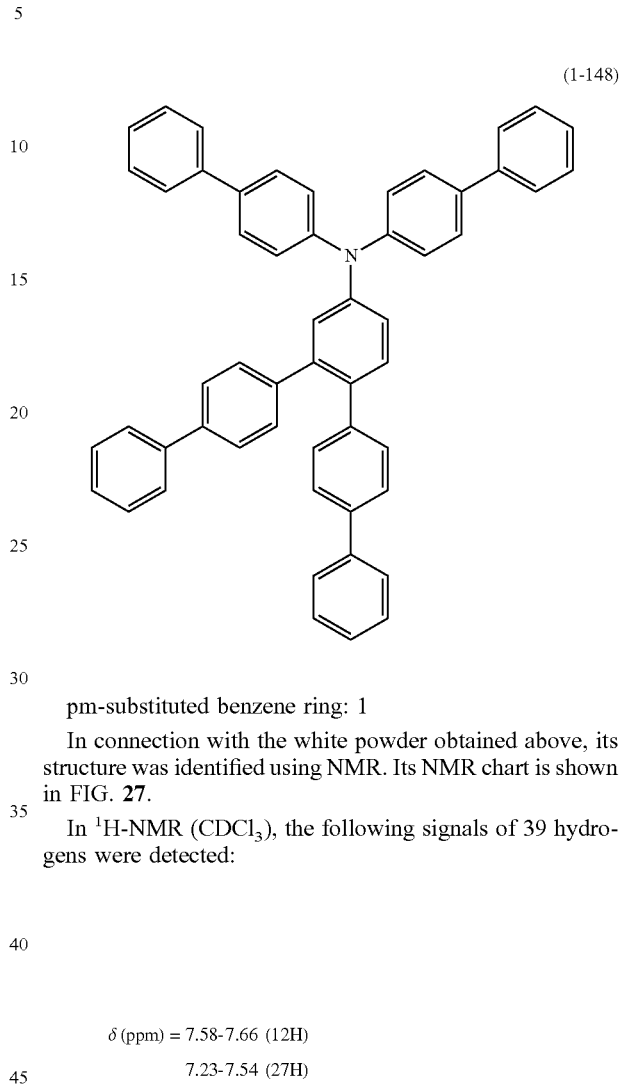
(1-148)

pm-substituted benzene ring: 1

Figure 27:
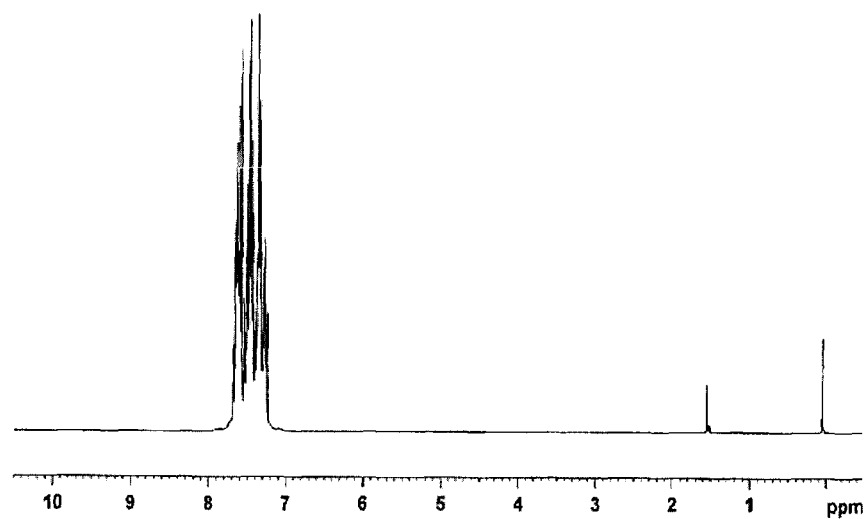
FIG. 27 is a $^1$H-NMR chart diagram of the compound (1-148) of Example 26.

In connection with the white powder obtained above, its structure was identified using NMR. Its NMR chart is shown in FIG. 27.

In $^1$H-NMR (CDCl$_3$), the following signals of 39 hydrogens were detected:

δ (ppm) = 7.58-7.66 (12H)
7.23-7.54 (27H)

Example 27

Synthesis of N,N-bis(biphenyl-4-yl)-N-{6-(biphenyl-3-yl)-1,1':4',1"-terphenyl-3-yl}amine (compound 1-149)

Reactions were performed under the same conditions as in the third step of Example 1, except that N,N-bis(biphenyl-4-yl)-N-(6-bromo-1,1':4',1"-terphenyl-3-yl)amine, and 3-biphenylboronic acid were used instead of N,N-bis(biphenyl-4-yl)-N-(6-bromobiphenyl-3-yl)amine and phenylboronic acid in the third step of Example 1. As a result, the following product was obtained:

N,N-bis(biphenyl-4-yl)-N-{6-(biphenyl-3-yl)-1,1':4',1"-terphenyl-3-yl}amine as a white powder 9.6 g (yield 86%).

The resulting amine compound is the compound (1-149) represented by the following formula:

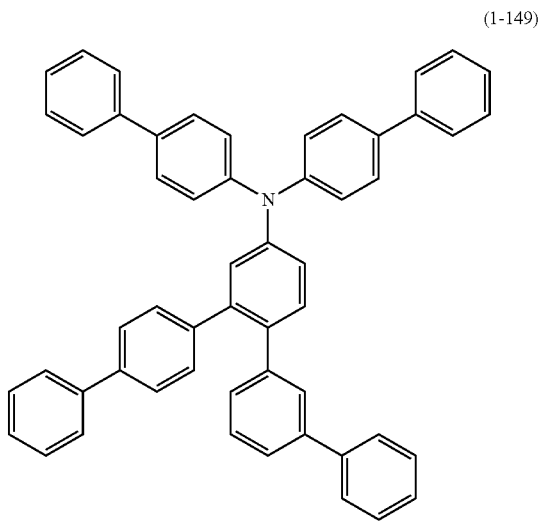 [SMILES: c1ccc(-c2ccc(-c3cc(N(c4ccc(-c5ccccc5)cc4)c4ccc(-c5ccccc5)cc4)ccc3-c3cccc(-c4ccccc4)c3)cc2)cc1]

(1-149)

pm-substituted benzene ring: 1

Figure 28:
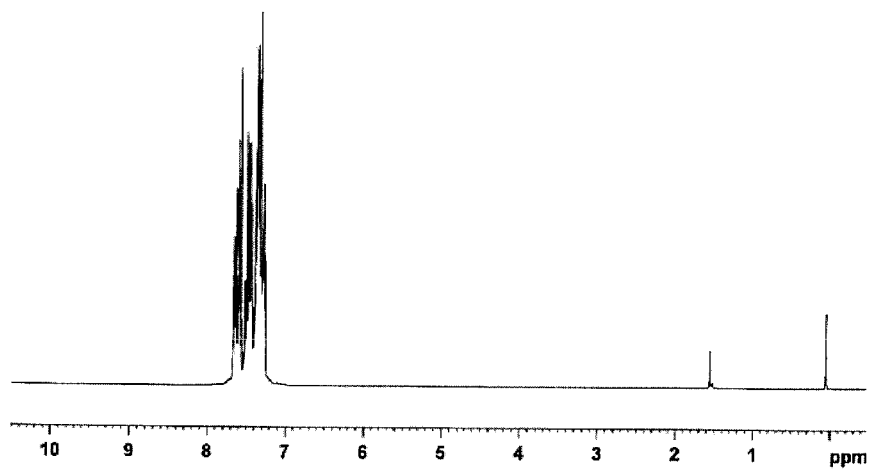
FIG. 28 is a 1H-NMR chart diagram of the compound (1-149) of Example 27.

In connection with the white powder obtained above, its structure was identified using NMR. Its NMR chart is shown in FIG. 28.

In $^1$H-NMR (CDCl$_3$), the following signals of 39 hydrogens were detected:

$\delta$ (ppm) = 7.58-7.66 (10H)
7.26-7.52 (29H)

Example 28

Synthesis of N,N-bis(biphenyl-4-yl)-N-{6-(biphenyl-2-yl)-1,1':4',1''-terphenyl-3-yl}amine (compound 1-150)

Reactions were performed under the same conditions as in the third step of Example 1, except that N,N-bis(biphenyl-4-yl)-N-(6-bromo-1,1':4',1''-terphenyl-3-yl)amine, and 2-biphenylboronic acid were used instead of N,N-bis(biphenyl-4-yl)-N-(6-bromobiphenyl-3-yl)amine and phenylboronic acid in the third step of Example 1. As a result, the following product was obtained:

N,N-bis(biphenyl-4-yl)-N-{6-(biphenyl-2-yl)-1,1':4',1''-terphenyl-3-yl}amine as a white powder 9.6 g (yield 86%).

The resulting amine compound is the compound (1-150) represented by the following formula:

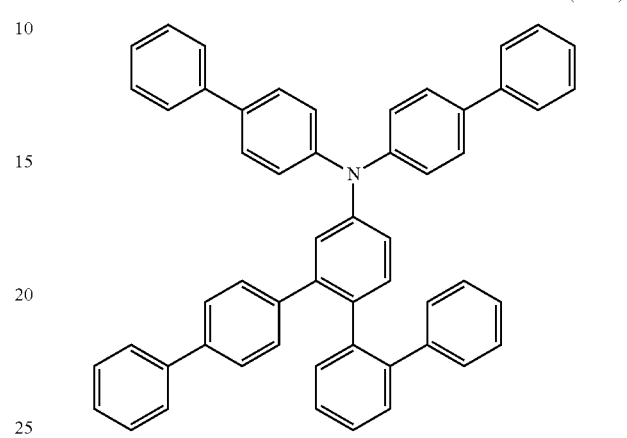

(1-150)

pm-substituted benzene ring: 1

Figure 29:
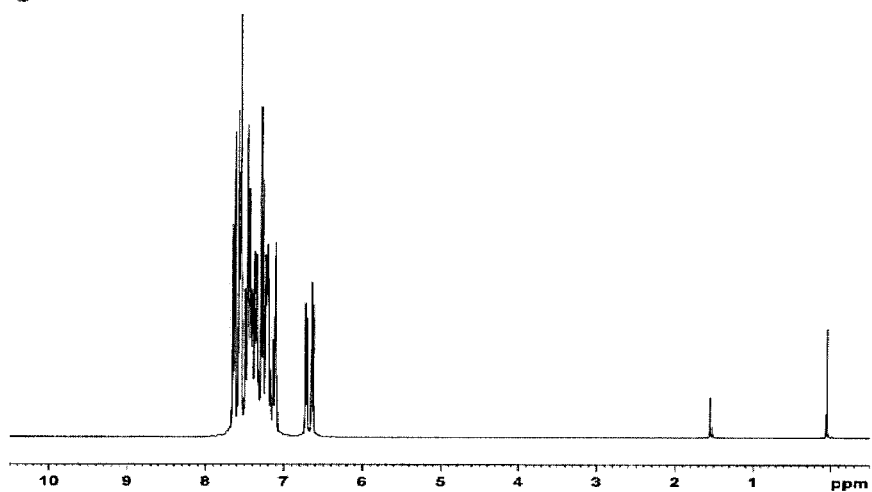
FIG. 29 is a ¹H-NMR chart diagram of the compound (1-150) of Example 28.

In connection with the white powder obtained above, its structure was identified using NMR. Its NMR chart is shown in FIG. 29.

In $^1$H-NMR (CDCl$_3$), the following signals of 39 hydrogens were detected:

$\delta$ (ppm) = 7.54-7.66 (10H)
7.08-7.49 (25H)
6.63-6.74 (4H)

Example 29

Synthesis of N,N-bis(9,9-dimethylfluoren-2-yl)-N-(6-phenyl-1,1':4',1''-terphenyl-4-yl)amine (compound 1-151)

Reactions were performed under the same conditions as in the third step of Example 1, except that N,N-bis(9,9-dimethylfluoren-2-yl)-N-(6-bromobiphenyl-3-yl)amine, and 4-biphenylboronic acid were used instead of N,N-bis(biphenyl-4-yl)-N-(6-bromobiphenyl-3-yl)amine and phenylboronic acid in the third step of Example 1. As a result, the following product was obtained:

N,N-bis(9,9-dimethylfluoren-2-yl)-N-(6-phenyl-1,1':4',1''-terphenyl-4-yl)amine as a white powder 16.7 g (yield 92%).

The resulting amine compound is the compound (1-151) represented by the following formula:

The resulting amine compound is the compound (1-152) represented by the following formula:

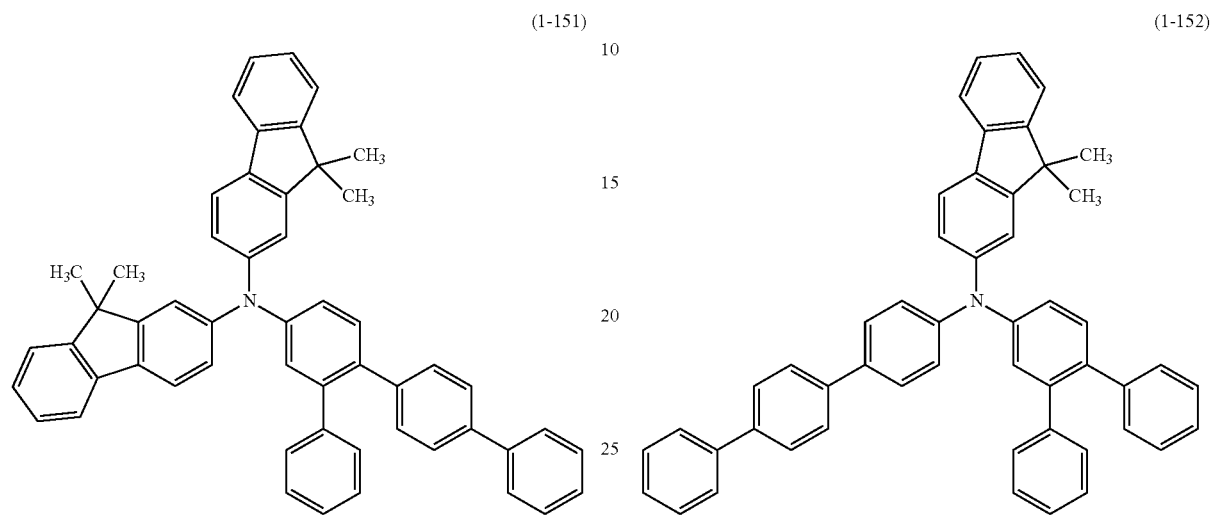

(1-151)

(1-152)

pm-substituted benzene ring: 1

Figure 30:
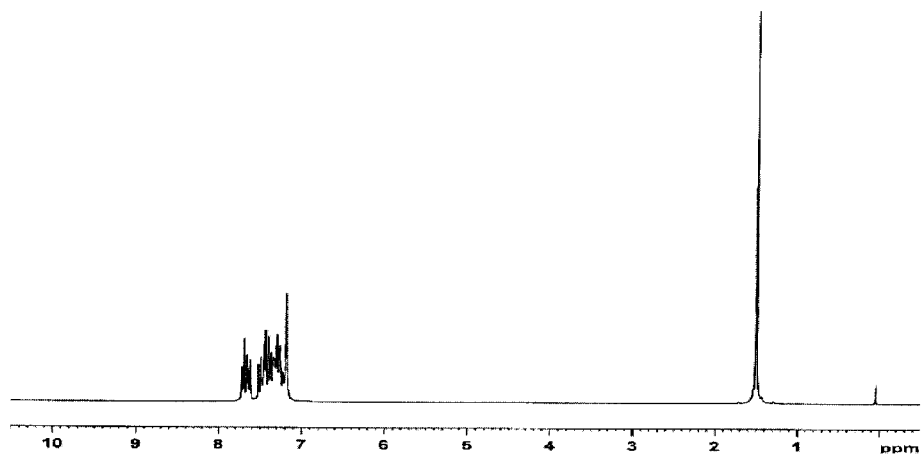
FIG. 30 is a ¹H-NMR chart diagram of the compound (1-151) of Example 29.

In connection with the white powder obtained above, its structure was identified using NMR. Its NMR chart is shown in FIG. 30.

In $^1$H-NMR (CDCl$_3$), the following signals of 43 hydrogens were detected:

$\delta$ (ppm) = 7.62-7.70 (6H)
7.19-7.52 (25H)
1.50 (12H)

pm-substituted benzene ring: 1

Figure 31:
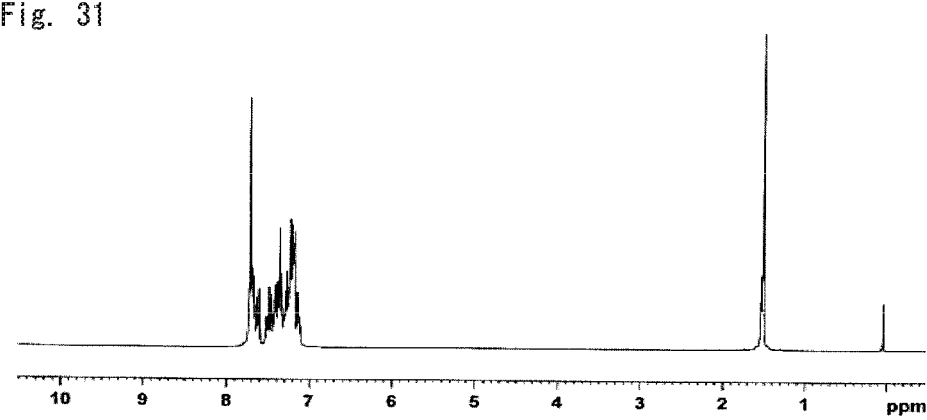
FIG. 31 is a ¹H-NMR chart diagram of the compound (1-152) of Example 30.

In connection with the white powder obtained above, its structure was identified using NMR. Its NMR chart is shown in FIG. 31.

In $^1$H-NMR (CDCl$_3$), the following signals of 39 hydrogens were detected:

$\delta$ (ppm) = 7.61-7.69 (10H)
7.12-7.52 (23H)
1.51 (6H)

Example 30

Synthesis of N-(9,9-dimethylfluoren-2-yl)-N-(6-phenylbiphenyl-3-yl)-N-(1,1':4',1''-terphenyl-4-yl)amine (compound 1-152)

Reactions were performed under the same conditions as in the third step of Example 1, except that N-(6-bromobiphenyl-3-yl)-N-(9,9-dimethylfluoren-2-yl)-N-(1,1':4',1''-terphenyl-4-yl)amine was used instead of N,N-bis(biphenyl-4-yl)-N-(6-bromobiphenyl-3-yl)amine in the third step of Example 1. As a result, the following product was obtained:

N-(9,9-dimethylfluoren-2-yl)-N-(6-phenylbiphenyl-3-yl)-N-(1,1':4',1''-terphenyl-4-yl)amine as a white powder 18.3 g (yield 74%).

Example 31

Synthesis of N-(9,9-dimethylfluoren-2-yl)-N-{4-(naphthalen-2-yl)phenyl}-N-(6-phenylbiphenyl-3-yl)amine (compound 1-153)

Reactions were performed under the same conditions as in the third step of Example 1, except that N-(6-bromobiphenyl-3-yl)-N-(9,9-dimethylfluoren-2-yl)-N-{4-(naphthalen-2-yl)phenyl}amine was used instead of N,N-bis(biphenyl-4-yl)-N-(6-bromobiphenyl-3-yl)amine in the third step of Example 1. As a result, the following product was obtained:

N-(9,9-dimethylfluoren-2-yl)-N-{4-(naphthalen-2-yl)phenyl}-N-(6-phenylbiphenyl-3-yl)amine as a white powder 8.8 g (yield 63%).

The resulting amine compound is the compound (1-153) represented by the following formula:

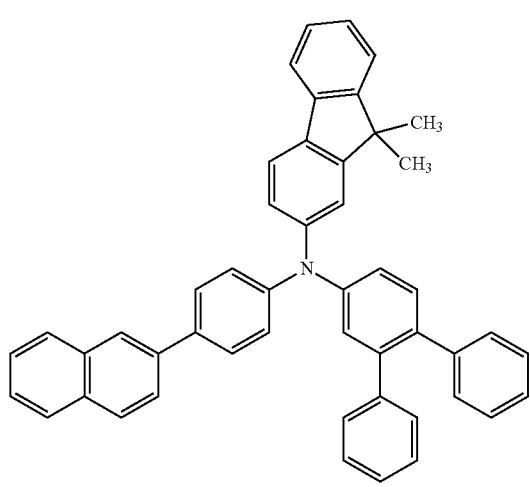

(1-153)

pm-substituted benzene ring: 1

Figure 32:
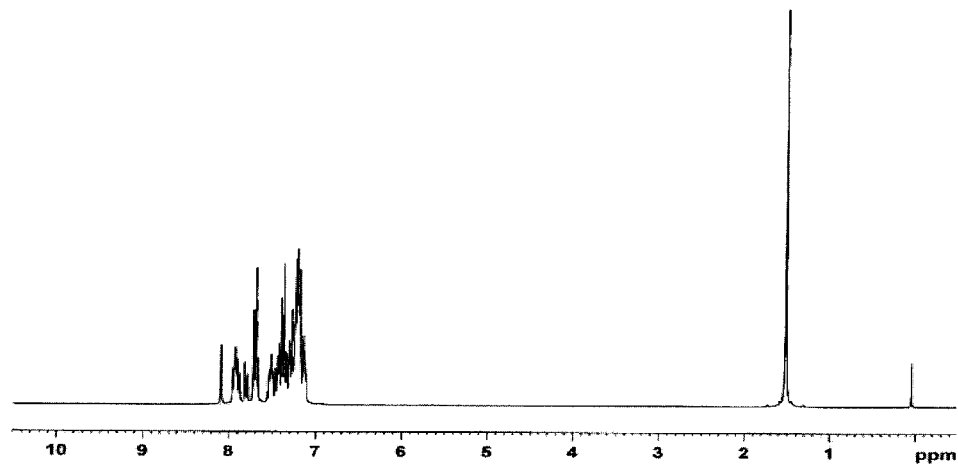
FIG. 32 is a ¹H-NMR chart diagram of the compound (1-153) of Example 31.

In connection with the white powder obtained above, its structure was identified using NMR. Its NMR chart is shown in FIG. 32.

In $^1$H-NMR (CDCl$_3$), the following signals of 37 hydrogens were detected:

$\delta$ (ppm) = 8.08 (1H)
7.76-7.94 (4H)
7.60-7.71 (4H)
7.13-7.54 (22H)
1.52 (6H)

Example 32

Synthesis of N-(9,9-dimethylfluoren-2-yl)-N-{4-(naphthalen-2-yl)phenyl}-N-(6-phenyl-1,1':4',1''-terphenyl-4-yl)amine (compound 1-154)

Reactions were performed under the same conditions as in the third step of Example 1, except that N-(6-bromobiphenyl-3-yl)-N-(9,9-dimethylfluoren-2-yl)-N-{4-(naphthalen-2-yl)phenyl}amine, and 4-biphenylboronic acid were used instead of N,N-bis(biphenyl-4-yl)-N-(6-bromobiphenyl-3-yl)amine and phenylboronic acid in the third step of Example 1. As a result, the following product was obtained:

N-(9,9-dimethylfluoren-2-yl)-N-{4-(naphthalen-2-yl)phenyl}-N-(6-phenyl-1,1':4',1''-terphenyl-4-yl)amine as a white powder 10.4 g (yield 67%).

The resulting amine compound is the compound (1-154) represented by the following formula:

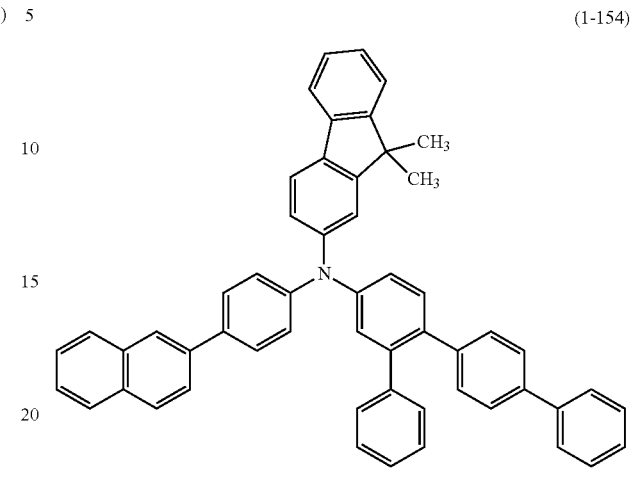

(1-154)

pm-substituted benzene ring: 1

Figure 33:
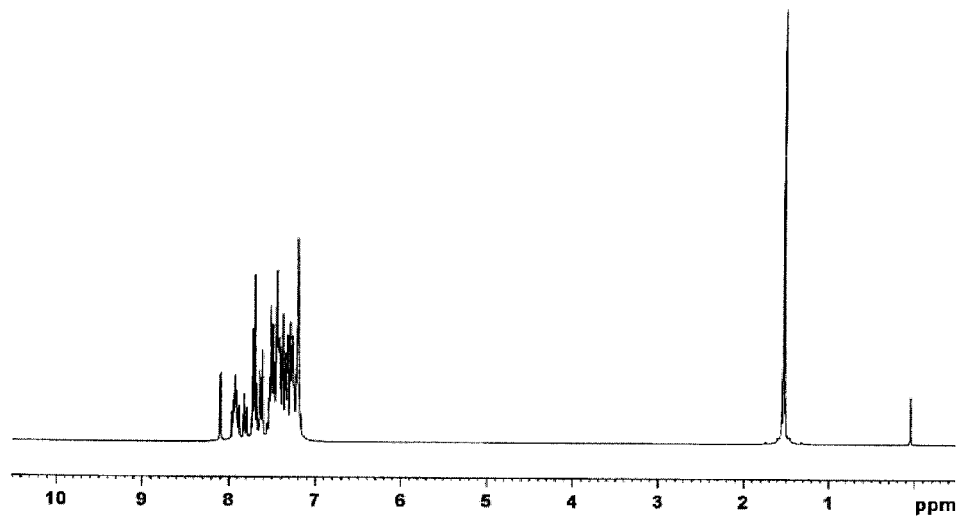
FIG. 33 is a ¹H-NMR chart diagram of the compound (1-154) of Example 32.

In connection with the white powder obtained above, its structure was identified using NMR. Its NMR chart is shown in FIG. 33.

In $^1$H-NMR (CDCl$_3$), the following signals of 41 hydrogens were detected:

$\delta$ (ppm) = 8.12 (1H)
7.78-7.92 (4H)
7.60-7.71 (6H)
7.21-7.54 (24H)
1.53 (6H)

Example 33

Synthesis of N-4-biphenyl-N-(9,9-dimethylfluoren-2-yl)-N-(6-phenyl-4'-(naphthalen-1-yl)biphenyl-4-yl)amine (compound 1-155)

Reactions were performed under the same conditions as in the third step of Example 1, except that N-4-biphenyl-N-(6-bromobiphenyl-3-yl)-N-(9,9-dimethylfluoren-2-yl)amine, and 4-(naphthalen-1-yl)phenylboronic acid were used instead of N,N-bis(biphenyl-4-yl)-N-(6-bromobiphenyl-3-yl)amine and phenylboronic acid in the third step of Example 1. As a result, the following product was obtained:

N-4-biphenyl-N-(9,9-dimethylfluoren-2-yl)-N-(6-phenyl-4'-(naphthalen-1-yl)biphenyl-4-yl)amine as a white powder 17.8 g (yield 89%).

The resulting amine compound is the compound (1-155) represented by the following formula:

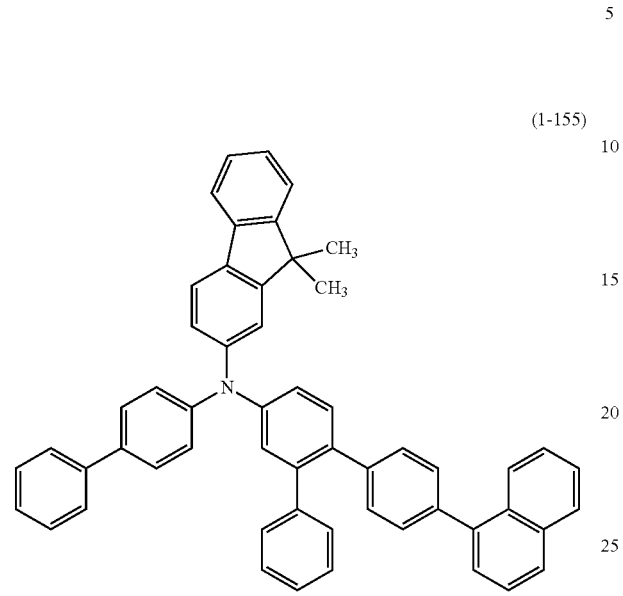

(1-155)

pm-substituted benzene ring: 1

Figure 34:
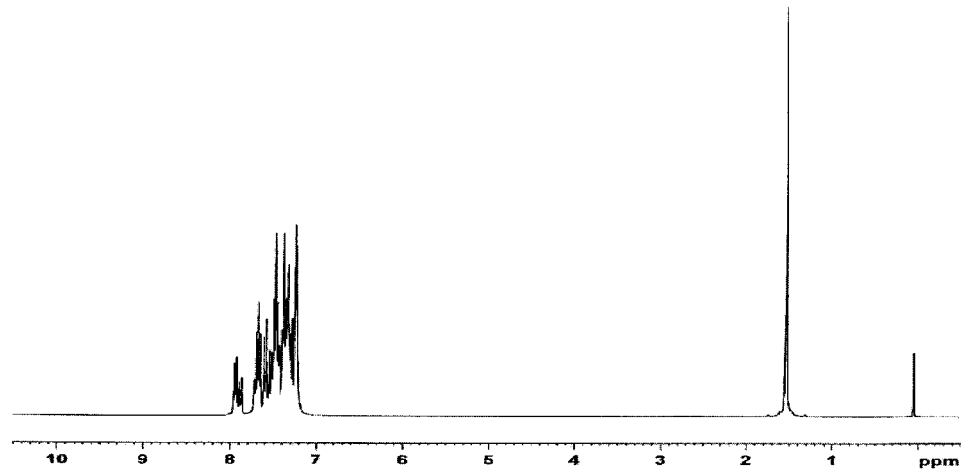
FIG. 34 is a ¹H-NMR chart diagram of the compound (1-155) of Example 33.

In connection with the white powder obtained above, its structure was identified using NMR. Its NMR chart is shown in FIG. 34.

In $^1$H-NMR (CDCl$_3$), the following signals of 41 hydrogens were detected:

$\delta$ (ppm) = 7.85-7.96 (3H)
7.18-7.74 (32H)
1.53 (6H)

Example 34

Synthesis of N-(9,9-dimethylfluoren-2-yl)-N-{4-(naphthalen-1-yl)phenyl}-N-(6-phenylbiphenyl-3-yl)amine (compound 1-156)

Reactions were performed under the same conditions as in the third step of Example 1, except that N-(6-bromobiphenyl-3-yl)-N-(9,9-dimethylfluoren-2-yl)-N-{4-(naphthalen-1-yl)phenyl}amine was used instead of N,N-bis(biphenyl-4-yl)-N-(6-bromobiphenyl-3-yl)amine in the third step of Example 1. As a result, the following product was obtained:

N-(9,9-dimethylfluoren-2-yl)-N-{4-(naphthalen-1-yl)phenyl}-N-(6-phenylbiphenyl-3-yl)amine as a white powder 17.8 g (yield 89%).

The resulting amine compound is the compound (1-156) represented by the following formula:

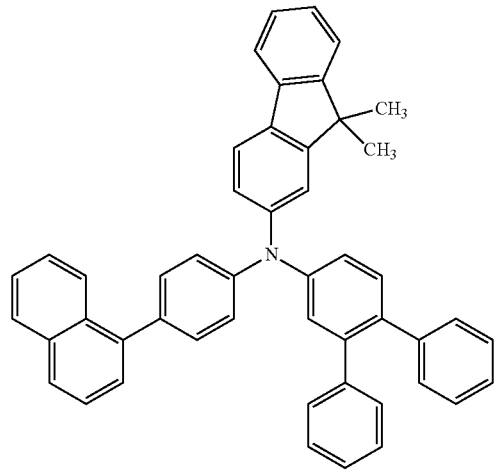

(1-156)

pm-substituted benzene ring: 1

Figure 35:
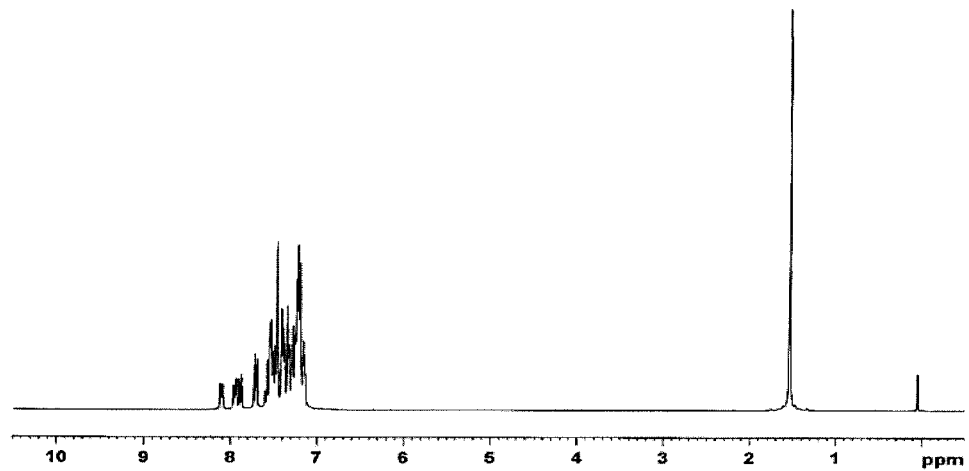
FIG. 35 is a ¹H-NMR chart diagram of the compound (1-156) of Example 34.

In connection with the white powder obtained above, its structure was identified using NMR. Its NMR chart is shown in FIG. 35.

In $^1$H-NMR (CDCl$_3$), the following signals of 37 hydrogens were detected:

$\delta$ (ppm) = 8.10-8.13 (1H)
7.86-7.94 (2H)
7.72-7.75 (2H)
7.14-7.58 (26H)

Example 35

Synthesis of N-(9,9-dimethylfluoren-2-yl)-N-{4-(naphthalen-1-yl)phenyl}-N-(6-phenyl-1,1':4',1''-terphenyl-4-yl)amine (compound 1-157)

Reactions were performed under the same conditions as in the third step of Example 1, except that N-(6-bromobiphenyl-3-yl)-N-(9,9-dimethylfluoren-2-yl)-N-{4-(naphthalen-1-yl)phenyl}amine, and 4-biphenylboronic acid were used instead of N,N-bis(biphenyl-4-yl)-N-(6-bromobiphenyl-3-yl)amine and phenylboronic acid in the third step of Example 1. As a result, the following product was obtained:

N-(9,9-dimethylfluoren-2-yl)-N-{4-(naphthalen-1-yl)phenyl}-N-(6-phenyl-1,1':4',1''-terphenyl-4-yl)amine as a white powder 19.9 g (yield 89%).

The resulting amine compound is the compound (1-157) represented by the following formula:

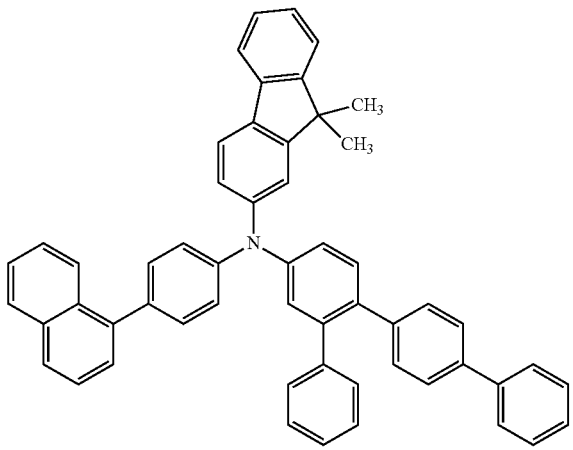

(1-157)

pm-substituted benzene ring: 1

Figure 36:
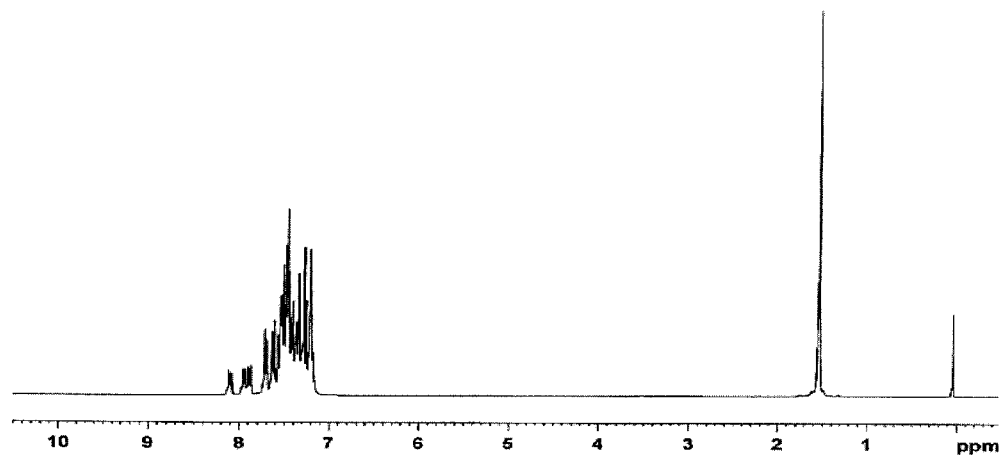
FIG. 36 is a ¹H-NMR chart diagram of the compound (1-157) of Example 35.

In connection with the white powder obtained above, its structure was identified using NMR. Its NMR chart is shown in FIG. 36.

In $^1$H-NMR (CDCl$_3$), the following signals of 41 hydrogens were detected:

$\delta$ (ppm) = 8.07-8.13 (1H)
7.88-7.96 (2H)
7.16-7.72 (32H)
1.54 (6H)

Example 36

Synthesis of N-4-biphenyl-N-{4-(9,9-dimethylfluoren-2-yl)phenyl}-N-{6-phenyl-1,1':3',1''-terphenyl-4-yl)amine (compound 1-158)

Reactions were performed under the same conditions as in the third step of Example 1, except that N-4-biphenyl-N-(6-bromobiphenyl-3-yl)-N-{4-(9,9-dimethylfluoren-2-yl)phenyl}amine, and 3-biphenylboronic acid were used instead of N,N-bis(biphenyl-4-yl)-N-(6-bromobiphenyl-3-yl)amine and phenylboronic acid in the third step of Example 1. As a result, the following product was obtained:

N-4-biphenyl-N-{4-(9,9-dimethylfluoren-2-yl)phenyl}-N-{6-phenyl-1,1':3',1''-terphenyl-4-yl}amine as a white powder 8.7 g (yield 49%).

The resulting amine compound is the compound (1-158) represented by the following formula:

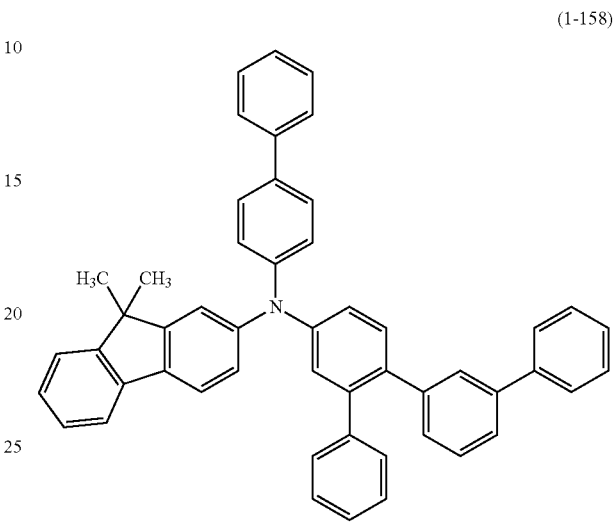

(1-158)

pm-substituted benzene ring: 1

Figure 37:
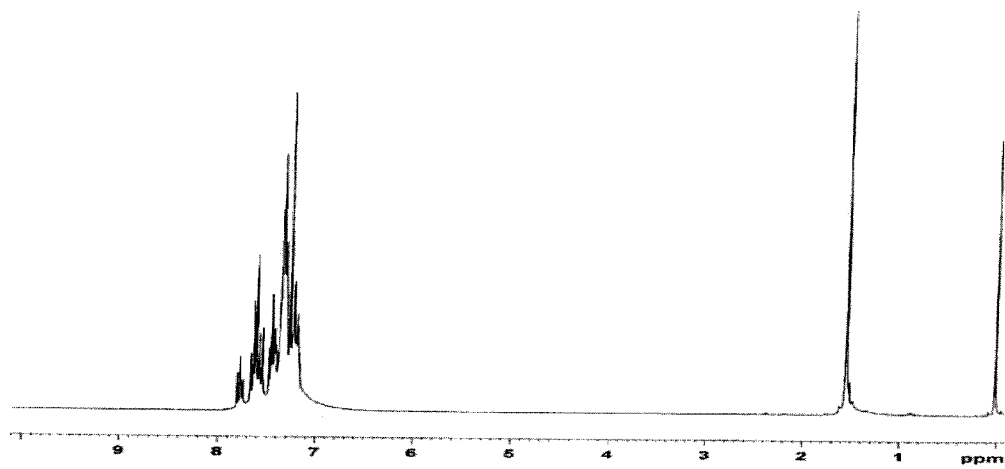
FIG. 37 is a ¹H-NMR chart diagram of the compound (1-158) of Example 36.

In connection with the white powder obtained above, its structure was identified using NMR. Its NMR chart is shown in FIG. 37.

In $^1$H-NMR (CDCl$_3$), the following signals of 43 hydrogens were detected:

$\delta$ (ppm) = 7.74-7.82 (2H)
7.58-7.76 (6H)
7.16-7.48 (29H)
1.57 (6H)

Example 37

Synthesis of N,N-bis{4-(naphthalen-2-yl)phenyl}-N-(6-phenyl-1,1':4',1''-terphenyl-3-yl)amine (compound 1-159)

Reactions were performed under the same conditions as in the third step of Example 1, except that N,N-bis{4-(naphthalen-2-yl)phenyl}-N-(6-bromo-1,1':4',1''-terphenyl-3-yl)amine was used instead of N,N-bis(biphenyl-4-yl)-N-(6-bromobiphenyl-3-yl)amine in the third step of Example 1. As a result, the following product was obtained:

N,N-bis{4-(naphthalen-2-yl)phenyl}-N-(6-phenyl-1,1':4',1''-terphenyl-3-yl)amine as a white powder 5.1 g (yield 65%).

The resulting amine compound is the compound (1-159) represented by the following formula:

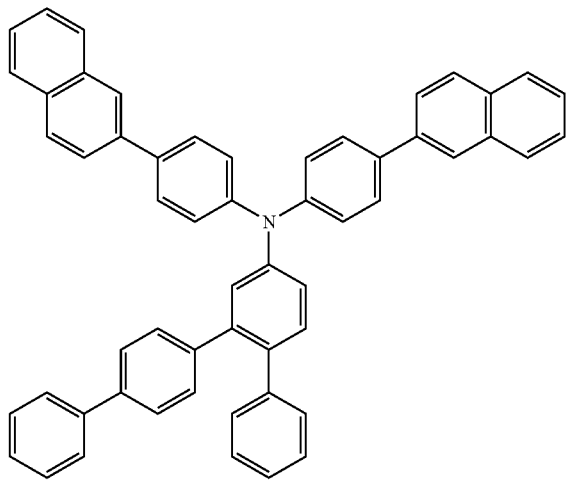

(1-159)

pm-substituted benzene ring: 1

Figure 38:
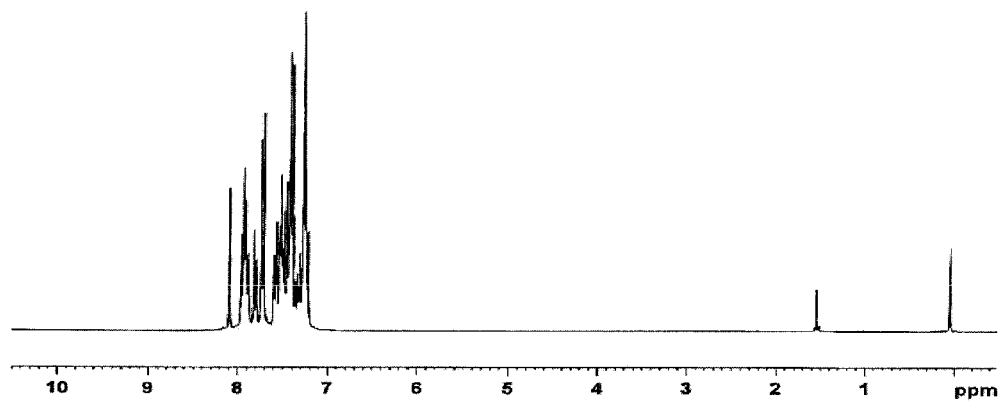
FIG. 38 is a ¹H-NMR chart diagram of the compound (1-159) of Example 37.
Figure 39:
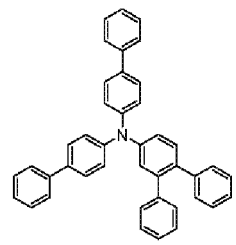
FIG. 39 is a drawing showing the structural formulas of Compound Nos. (1-1) to (1-5) among the arylamine compounds of the general formula (1).
Figure 39:
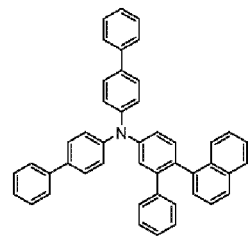
Figure 39:
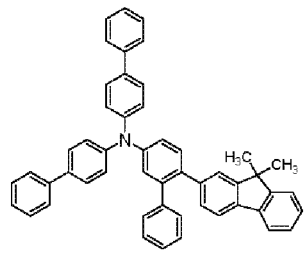
Figure 39:
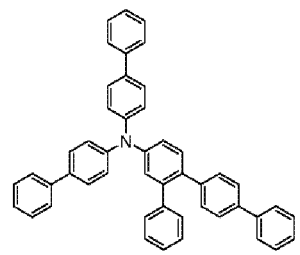
Figure 39:
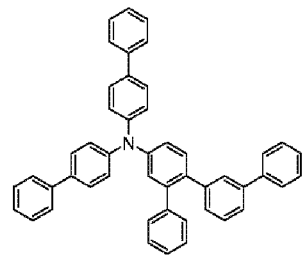
Figure 40:
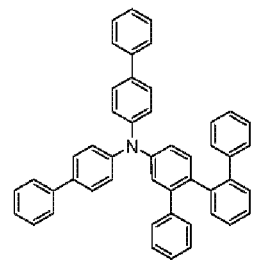
FIG. 40 is a drawing showing the structural formulas of Compound Nos. (1-6) to (1-9) among the arylamine compounds of the general formula (1).
Figure 40:
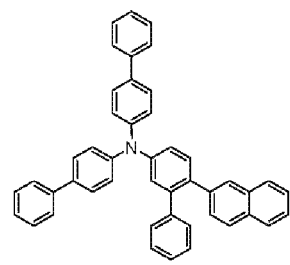
Figure 40:
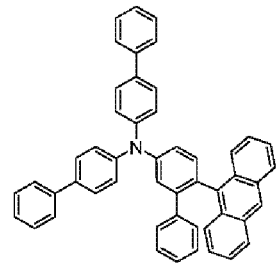
Figure 40:
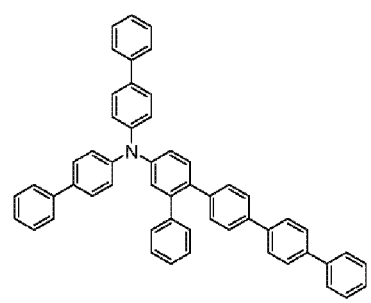
Figure 41:
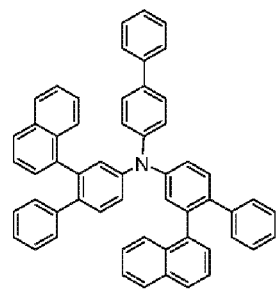
FIG. 41 is a drawing showing the structural formulas of Compound Nos. (1-10) to (1-13) among the arylamine compounds of the general formula (1).
Figure 41:
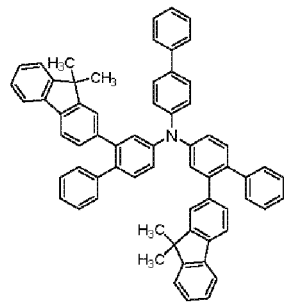
Figure 41:
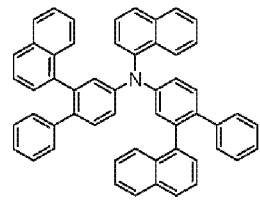
Figure 41:
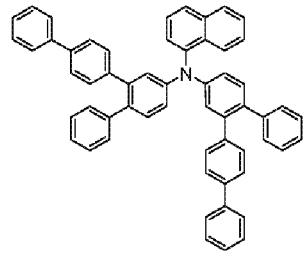
Figure 42:
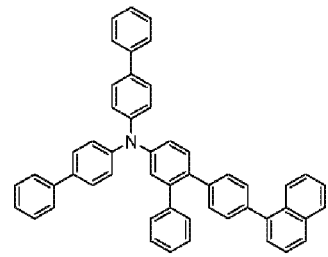
FIG. 42 is a drawing showing the structural formulas of Compound Nos. (1-14) to (1-17) among the arylamine compounds of the general formula (1).
Figure 42:
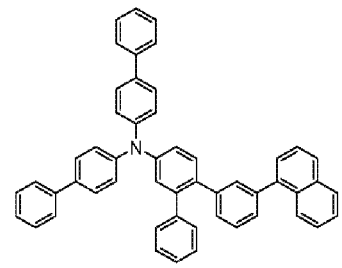
Figure 42:
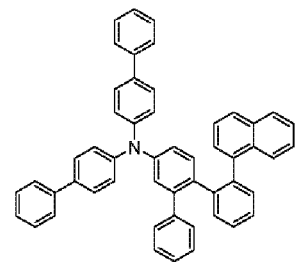
Figure 42:
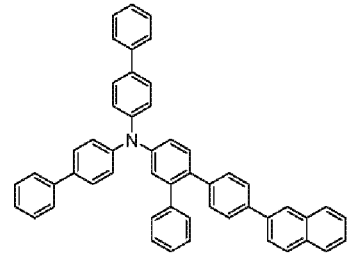
Figure 43:
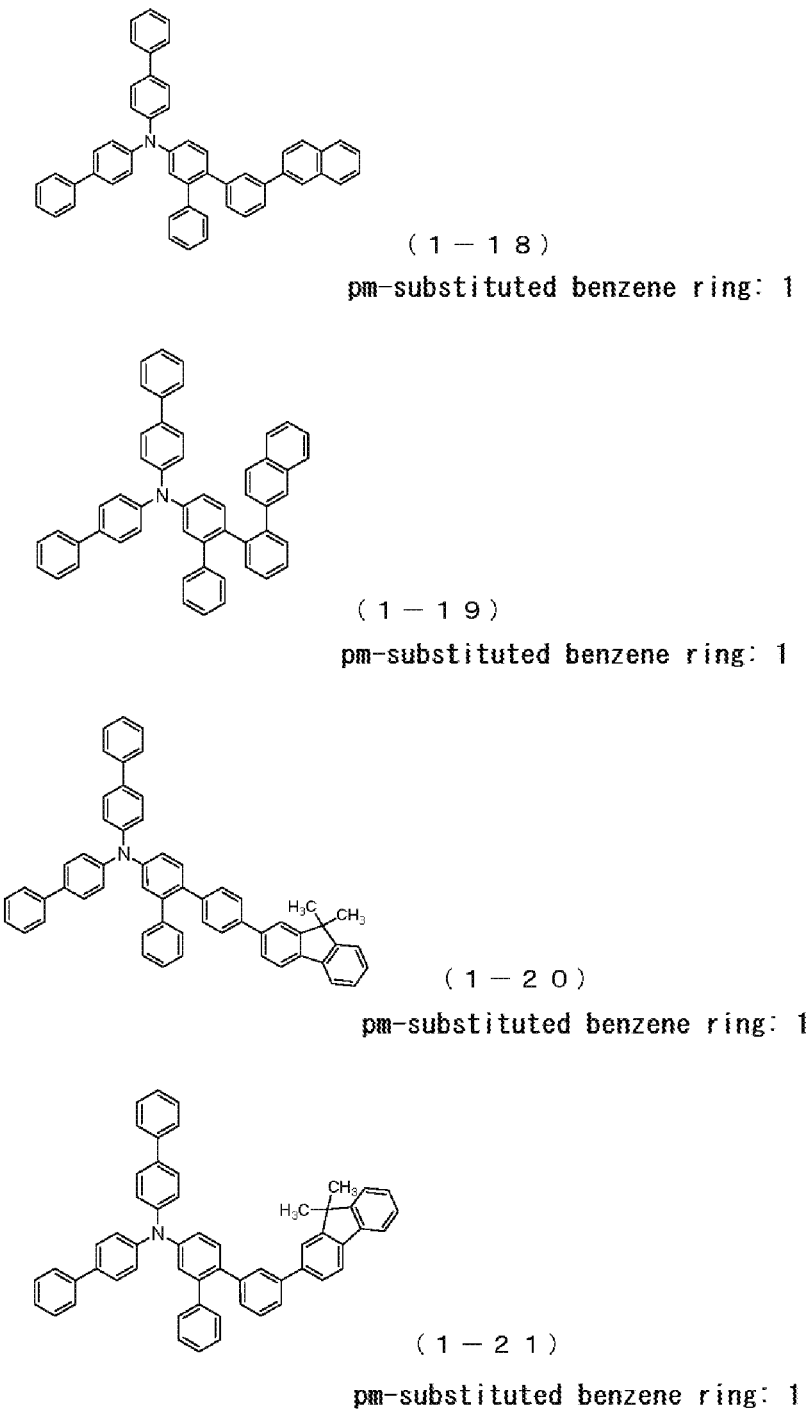
FIG. 43 is a drawing showing the structural formulas of Compound Nos. (1-18) to (1-21) among the arylamine compounds of the general formula (1).
Figure 44:
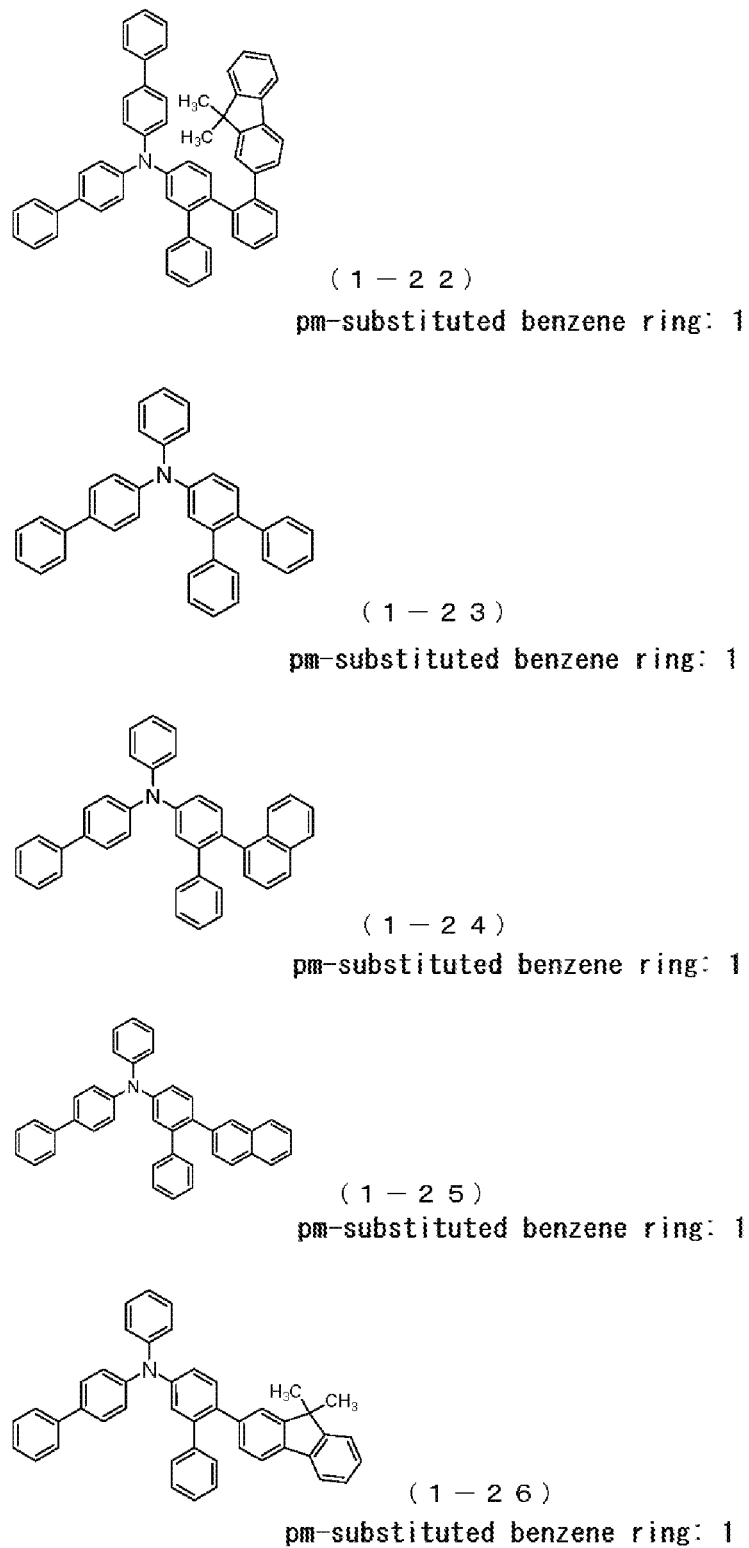
FIG. 44 is a drawing showing the structural formulas of Compound Nos. (1-22) to (1-26) among the arylamine compounds of the general formula (1).
Figure 45:
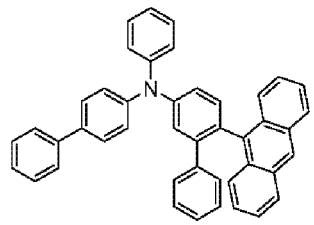
FIG. 45 is a drawing showing the structural formulas of Compound Nos. (1-27) to (1-31) among the arylamine compounds of the general formula (1).
Figure 45:
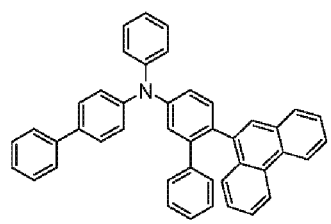
Figure 45:
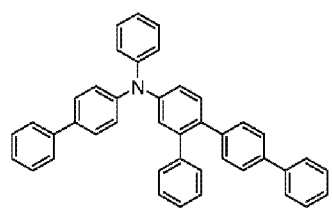
Figure 45:
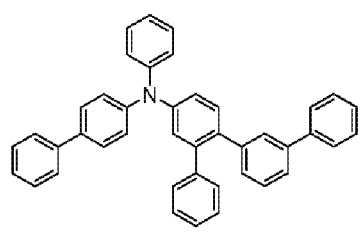
Figure 45:
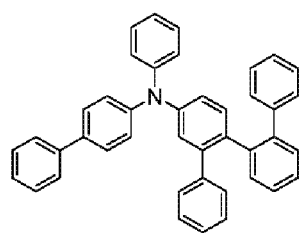
Figure 46:
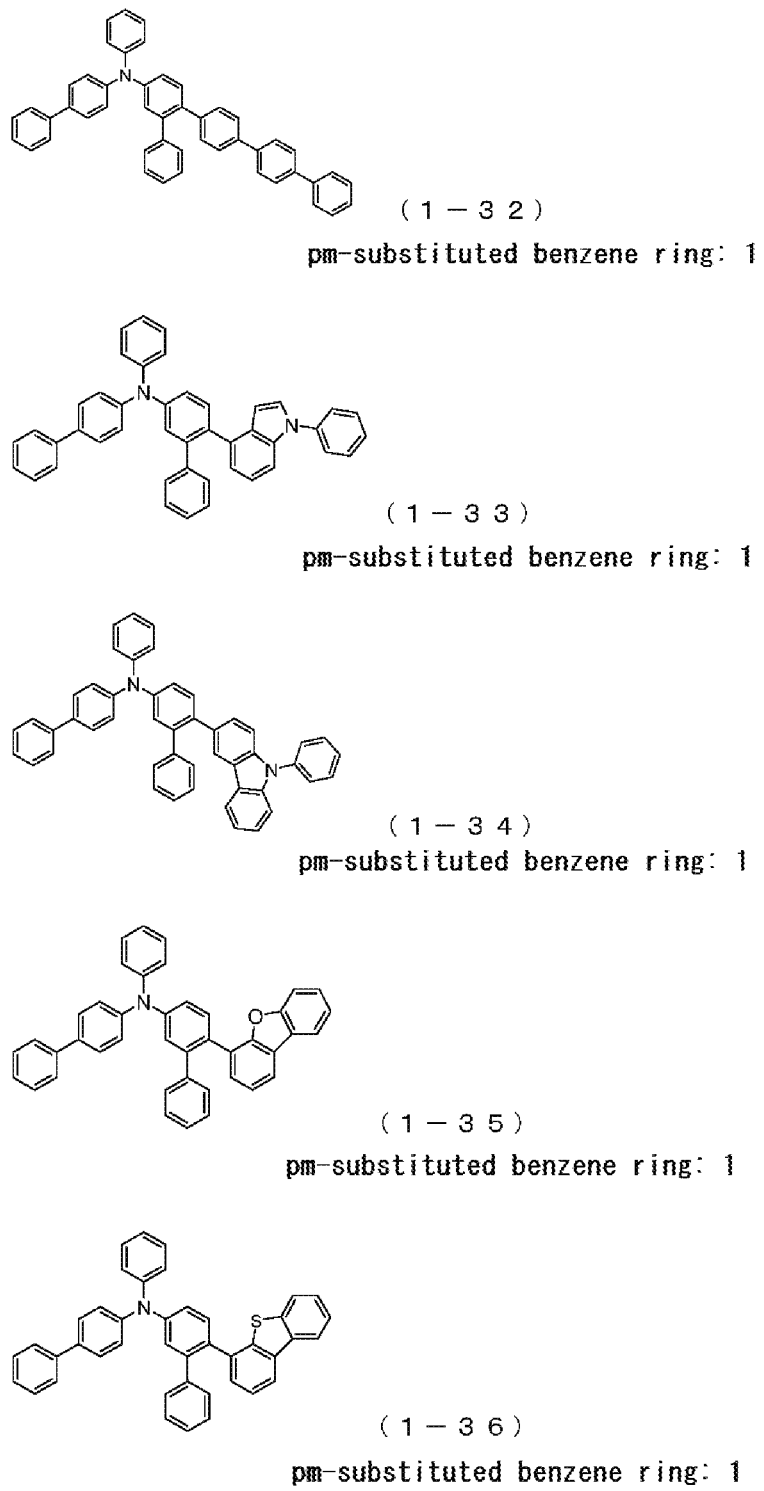
FIG. 46 is a drawing showing the structural formulas of Compound Nos. (1-32) to (1-36) among the arylamine compounds of the general formula (1).
Figure 47:
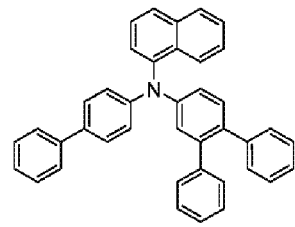
FIG. 47 is a drawing showing the structural formulas of Compound Nos. (1-37) to (1-41) among the arylamine compounds of the general formula (1).
Figure 47:
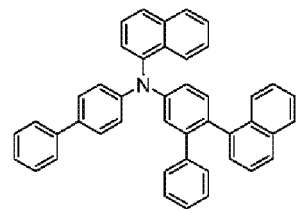
Figure 47:
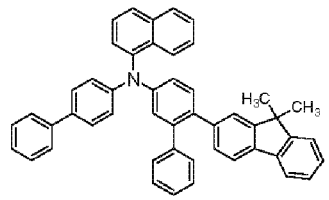
Figure 47:
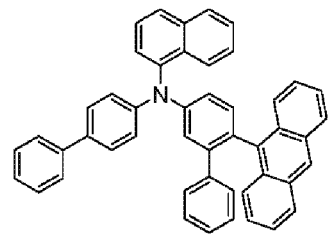
Figure 47:
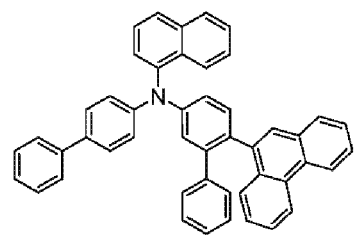
Figure 48:
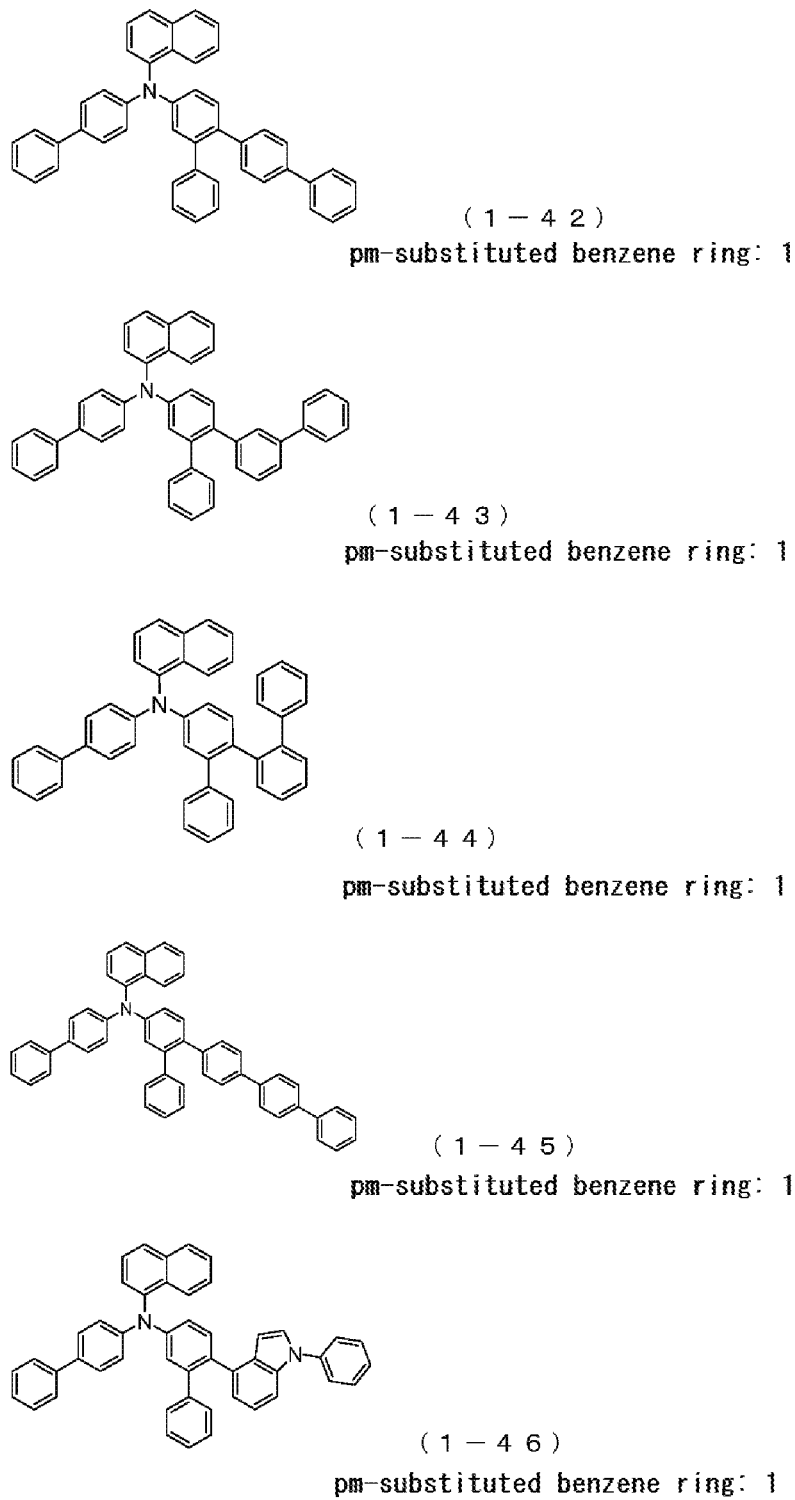
FIG. 48 is a drawing showing the structural formulas of Compound Nos. (1-42) to (1-46) among the arylamine compounds of the general formula (1).
Figure 49:
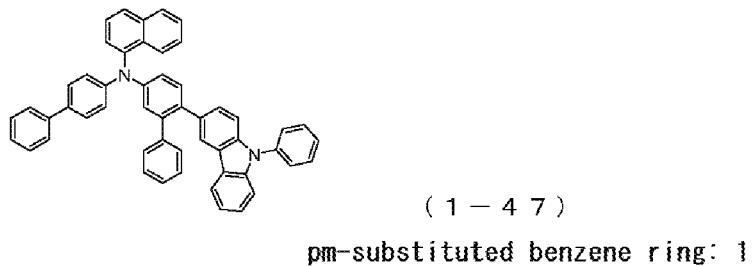
FIG. 49 is a drawing showing the structural formulas of Compound Nos. (1-47) to (1-51) among the arylamine compounds of the general formula (1).
Figure 49:
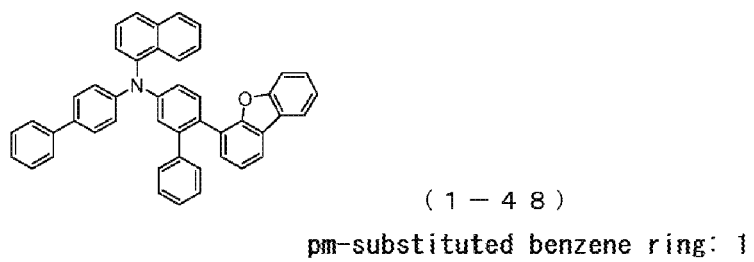
Figure 49:
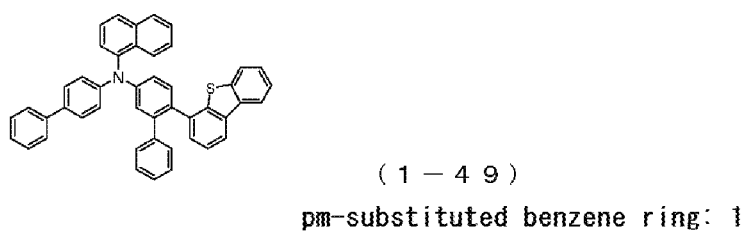
Figure 49:
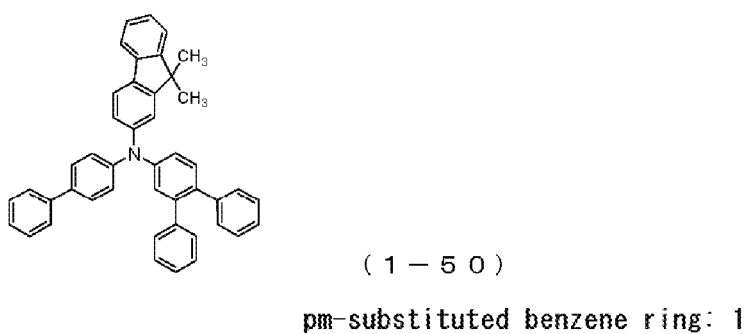
Figure 49:
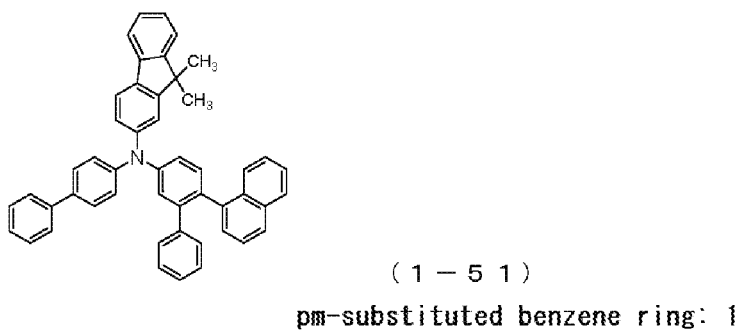
Figure 50:
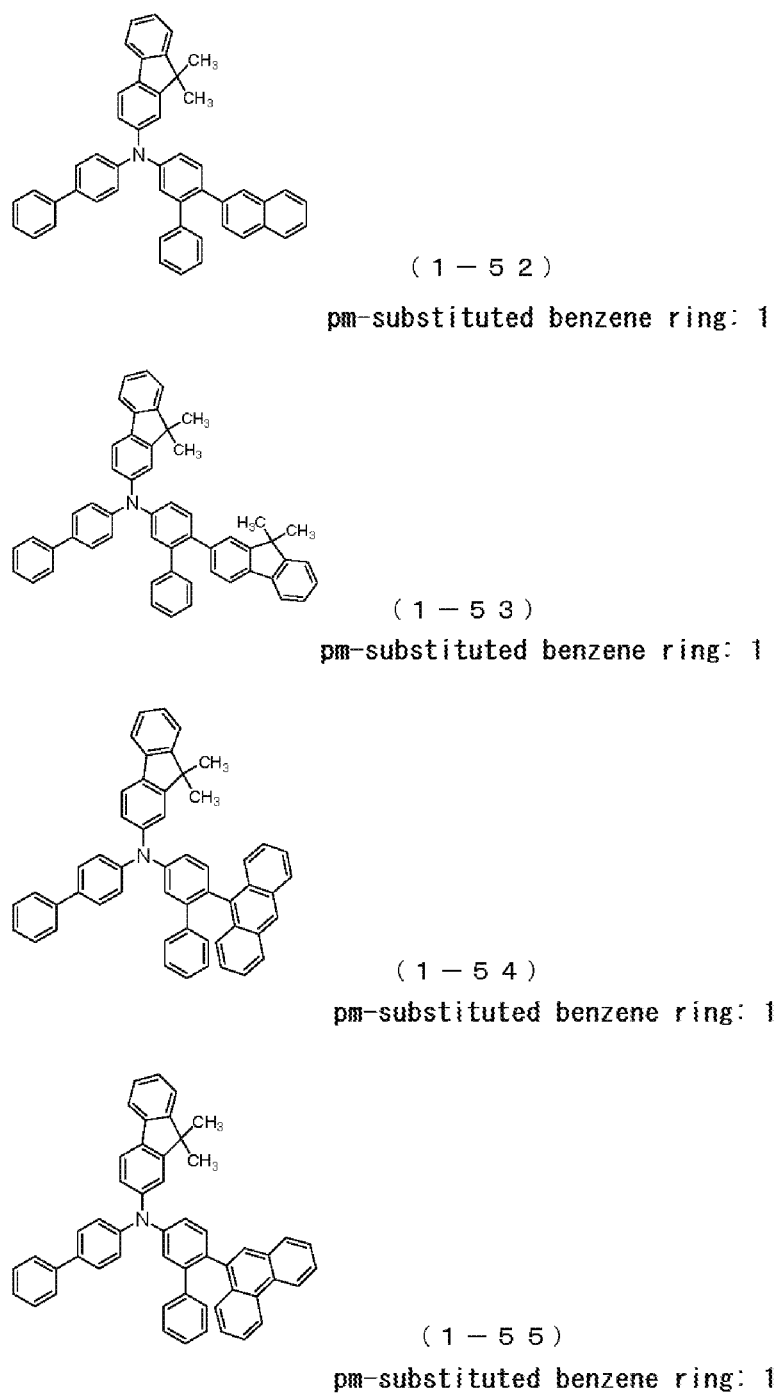
FIG. 50 is a drawing showing the structural formulas of Compound Nos. (1-52) to (1-55) among the arylamine compounds of the general formula (1).
Figure 51:
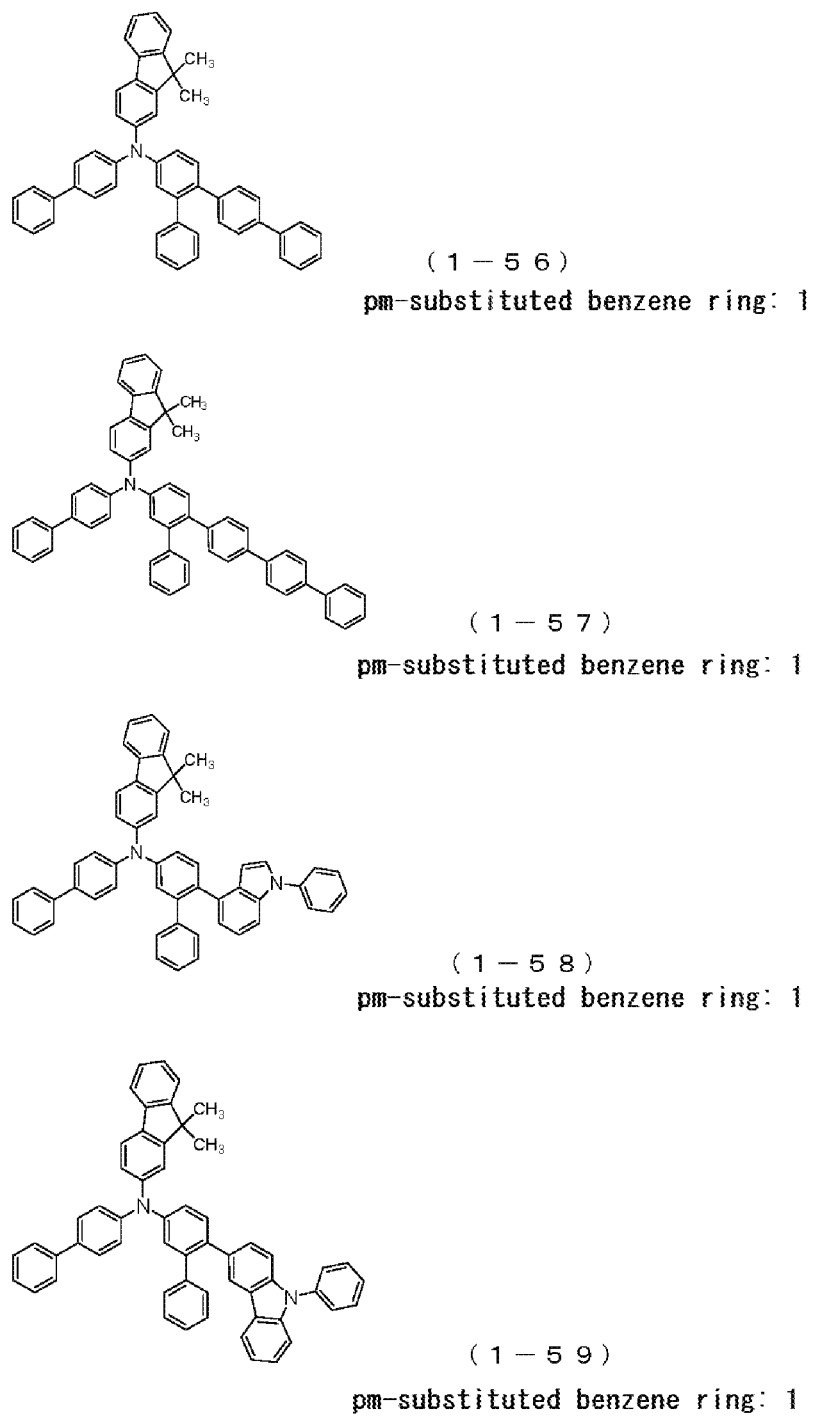
FIG. 51 is a drawing showing the structural formulas of Compound Nos. (1-56) to (1-59) among the arylamine compounds of the general formula (1).
Figure 52:
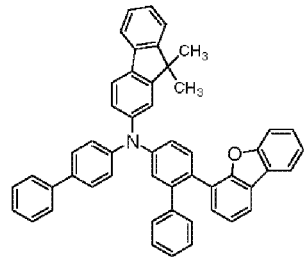
FIG. 52 is a drawing showing the structural formulas of Compound Nos. (1-60) to (1-64) among the arylamine compounds of the general formula (1).
Figure 52:
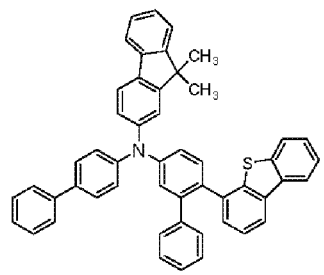
Figure 52:
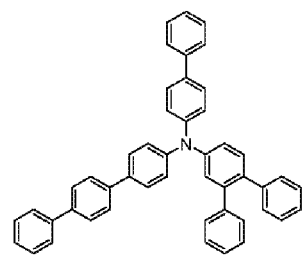
Figure 52:
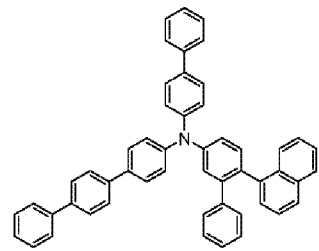
Figure 52:
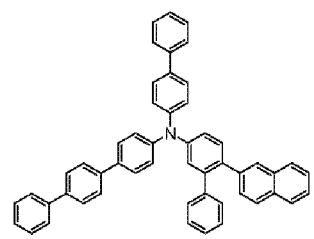
Figure 53:
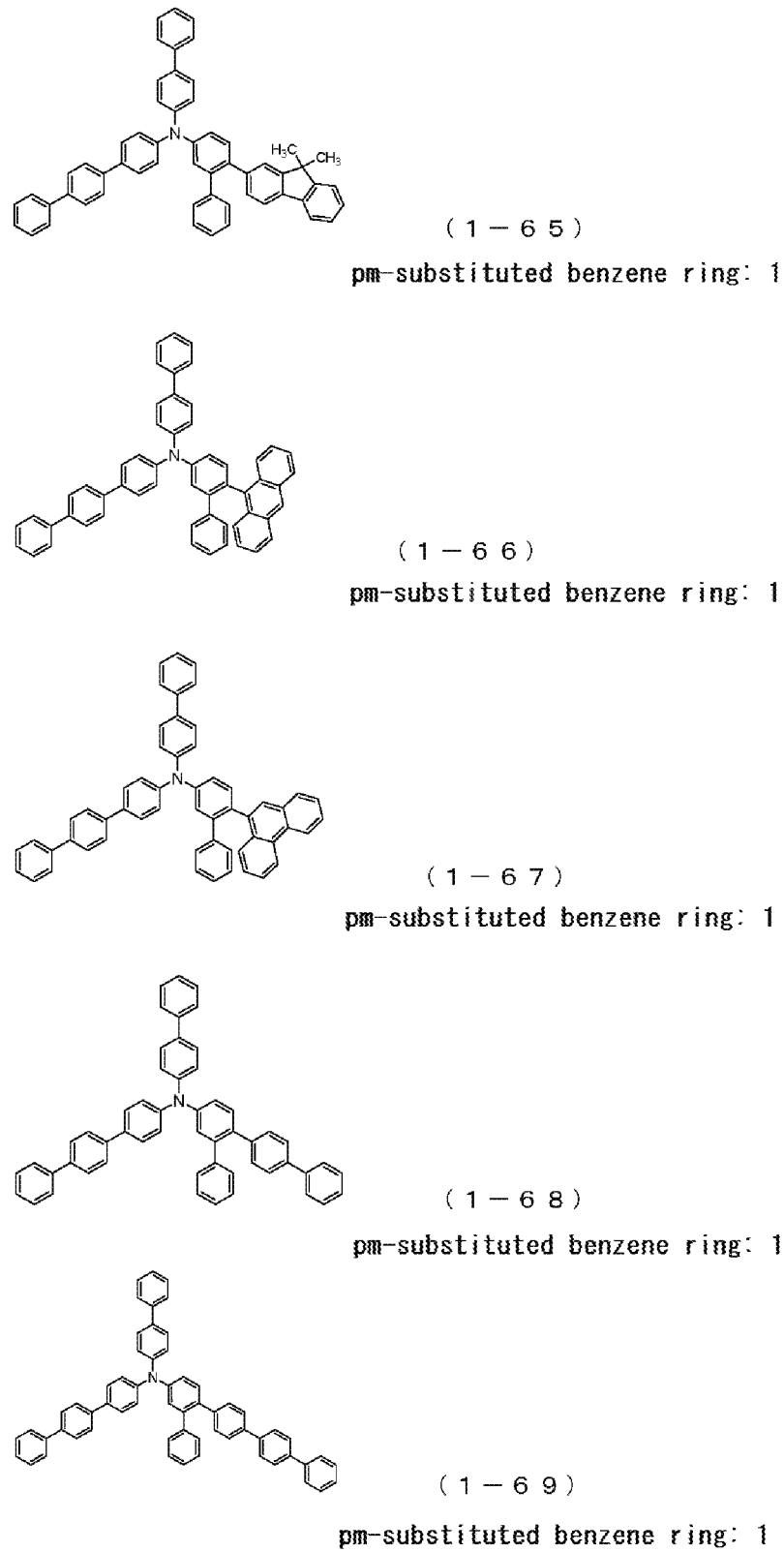
FIG. 53 is a drawing showing the structural formulas of Compound Nos. (1-65) to (1-69) among the arylamine compounds of the general formula (1).
Figure 54:
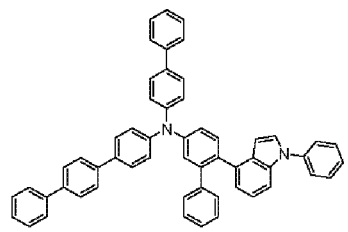
FIG. 54 is a drawing showing the structural formulas of Compound Nos. (1-70) to (1-74) among the arylamine compounds of the general formula (1).
Figure 54:
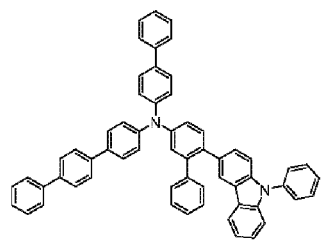
Figure 54:
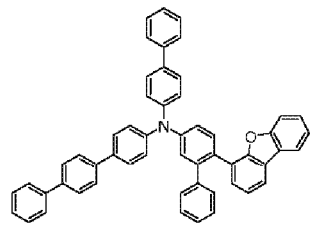
Figure 54:
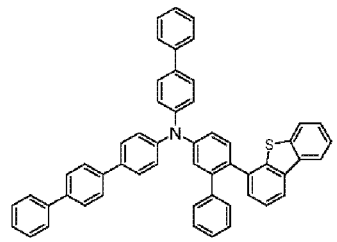
Figure 54:
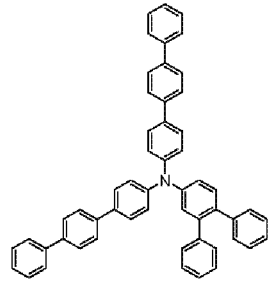
Figure 55:
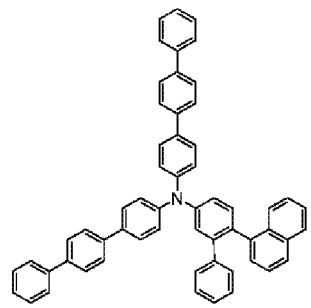
FIG. 55 is a drawing showing the structural formulas of Compound Nos. (1-75) to (1-78) among the arylamine compounds of the general formula (1).
Figure 55:
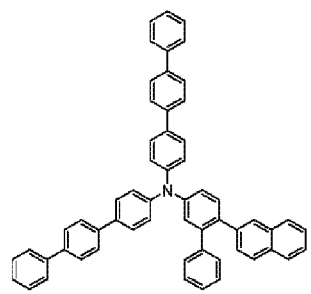
Figure 55:
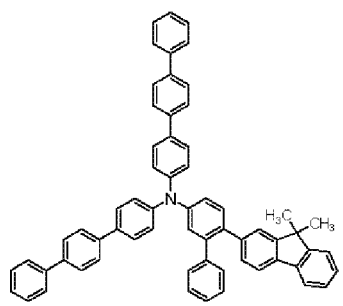
Figure 55:
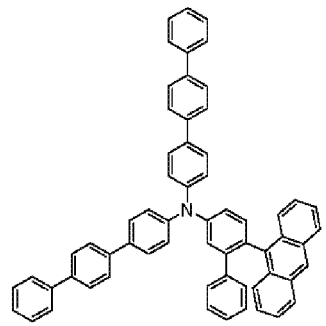
Figure 56:
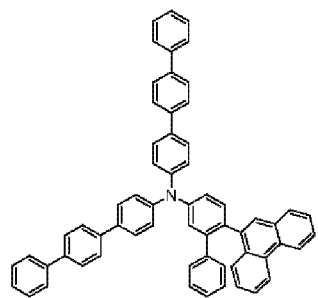
FIG. 56 is a drawing showing the structural formulas of Compound Nos. (1-79) to (1-82) among the arylamine compounds of the general formula (1).
Figure 56:
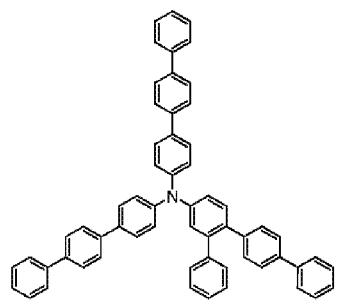
Figure 56:
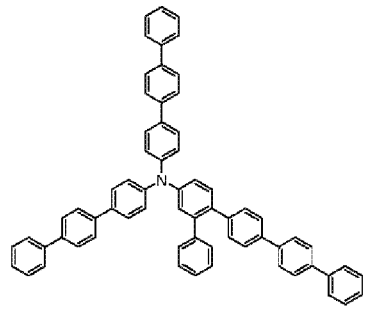
Figure 56:
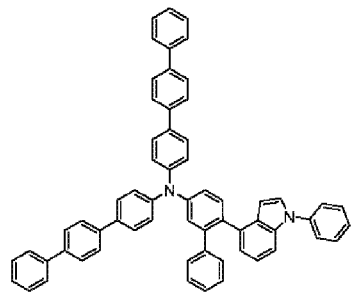
Figure 57:
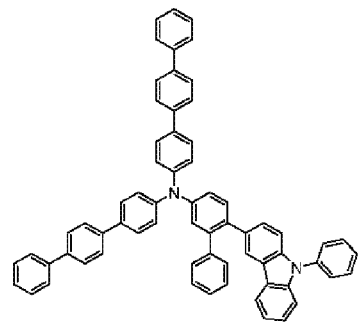
FIG. 57 is a drawing showing the structural formulas of Compound Nos. (1-83) to (1-86) among the arylamine compounds of the general formula (1).
Figure 57:
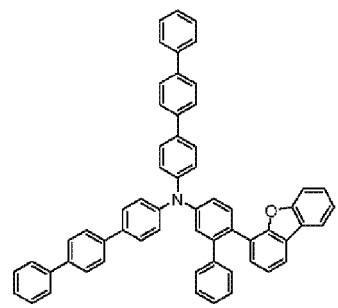
Figure 57:
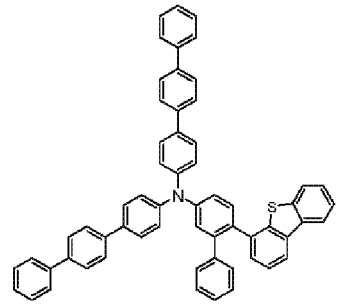
Figure 57:
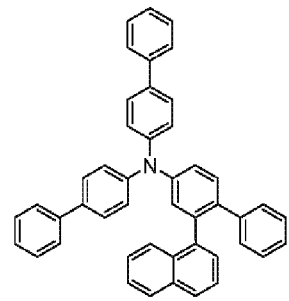
Figure 58:
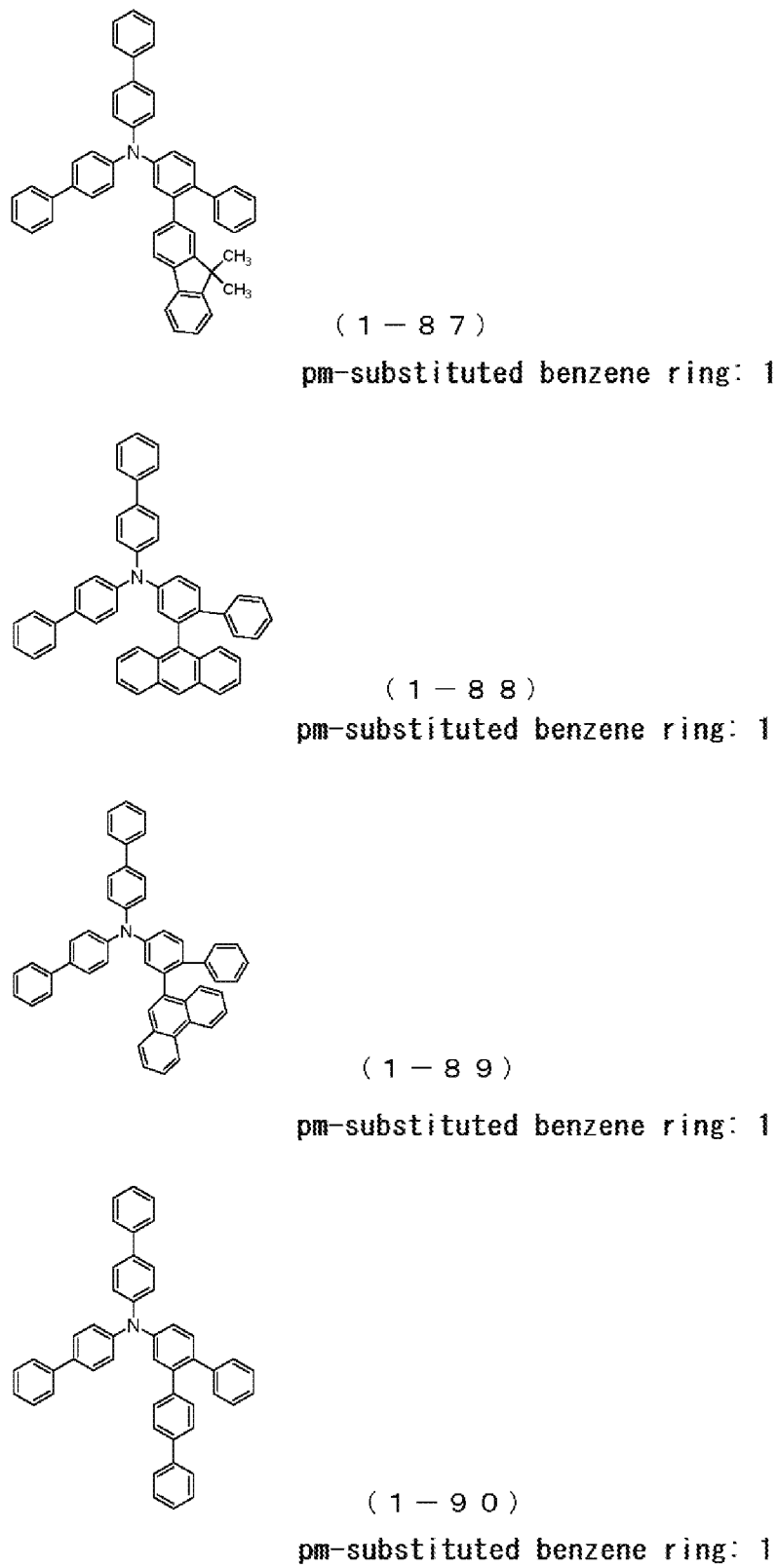
FIG. 58 is a drawing showing the structural formulas of Compound Nos. (1-87) to (1-90) among the arylamine compounds of the general formula (1).
Figure 59:
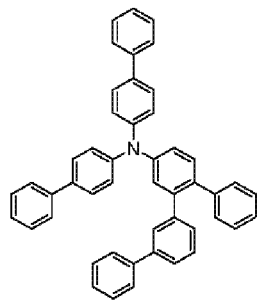
FIG. 59 is a drawing showing the structural formulas of Compound Nos. (1-91) to (1-94) among the arylamine compounds of the general formula (1).
Figure 59:
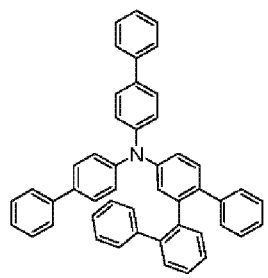
Figure 59:
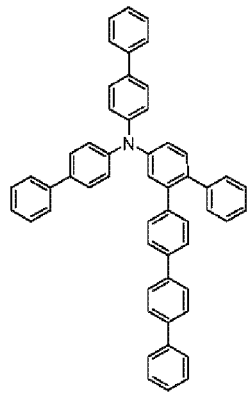
Figure 59:
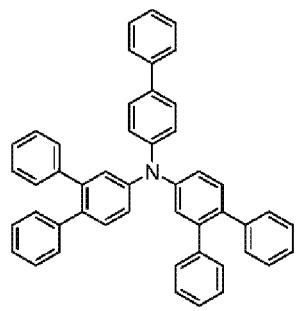
Figure 60:
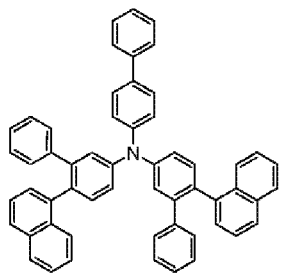
FIG. 60 is a drawing showing the structural formulas of Compound Nos. (1-95) to (1-98) among the arylamine compounds of the general formula (1).
Figure 60:
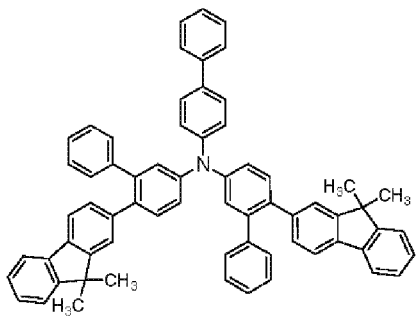
Figure 60:
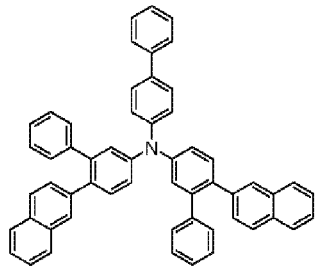
Figure 60:
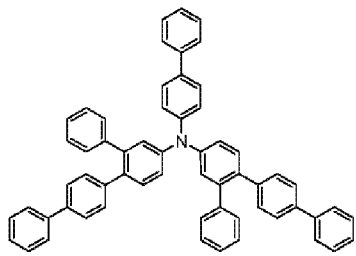
Figure 61:
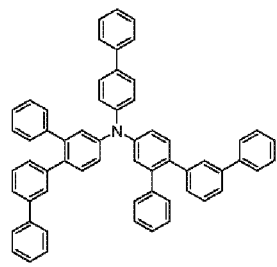
FIG. 61 is a drawing showing the structural formulas of Compound Nos. (1-99) to (1-103) among the arylamine compounds of the general formula (1).
Figure 61:
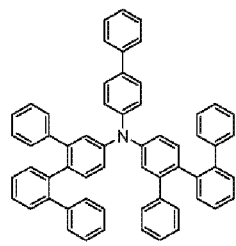
Figure 61:
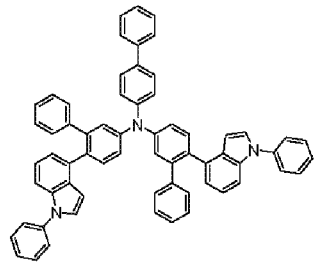
Figure 61:
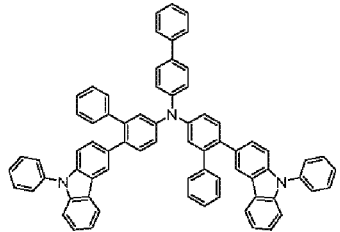
Figure 61:
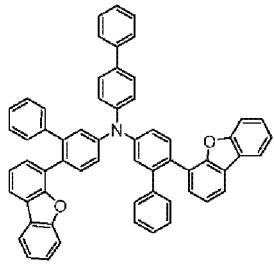
Figure 62:
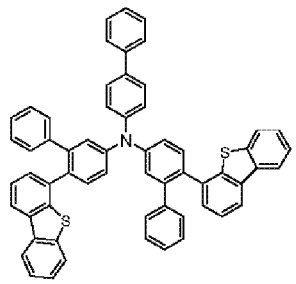
FIG. 62 is a drawing showing the structural formulas of Compound Nos. (1-104) to (1-108) among the arylamine compounds of the general formula (1).
Figure 62:
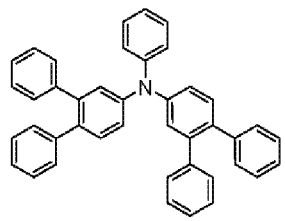
Figure 62:
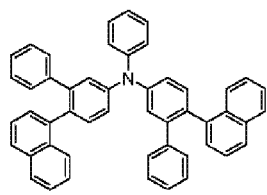
Figure 62:
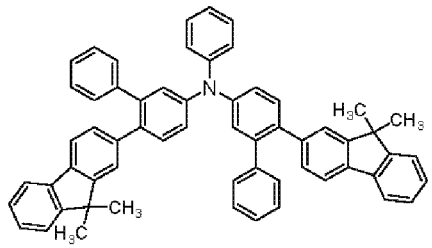
Figure 62:
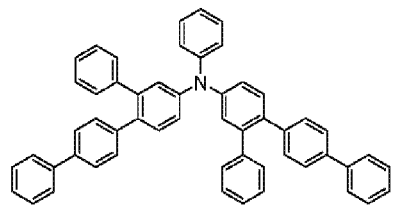
Figure 63:
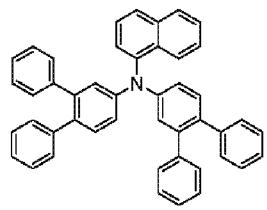
FIG. 63 is a drawing showing the structural formulas of Compound Nos. (1-109) to (1-112) among the arylamine compounds of the general formula (1).
Figure 63:
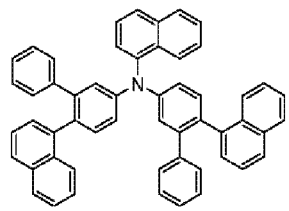
Figure 63:
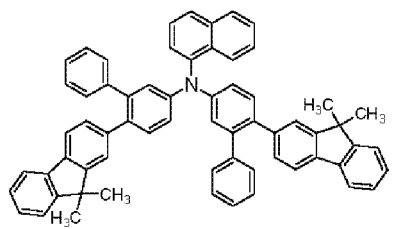
Figure 63:
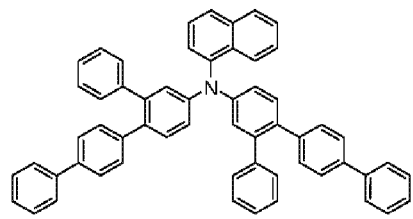
Figure 64:
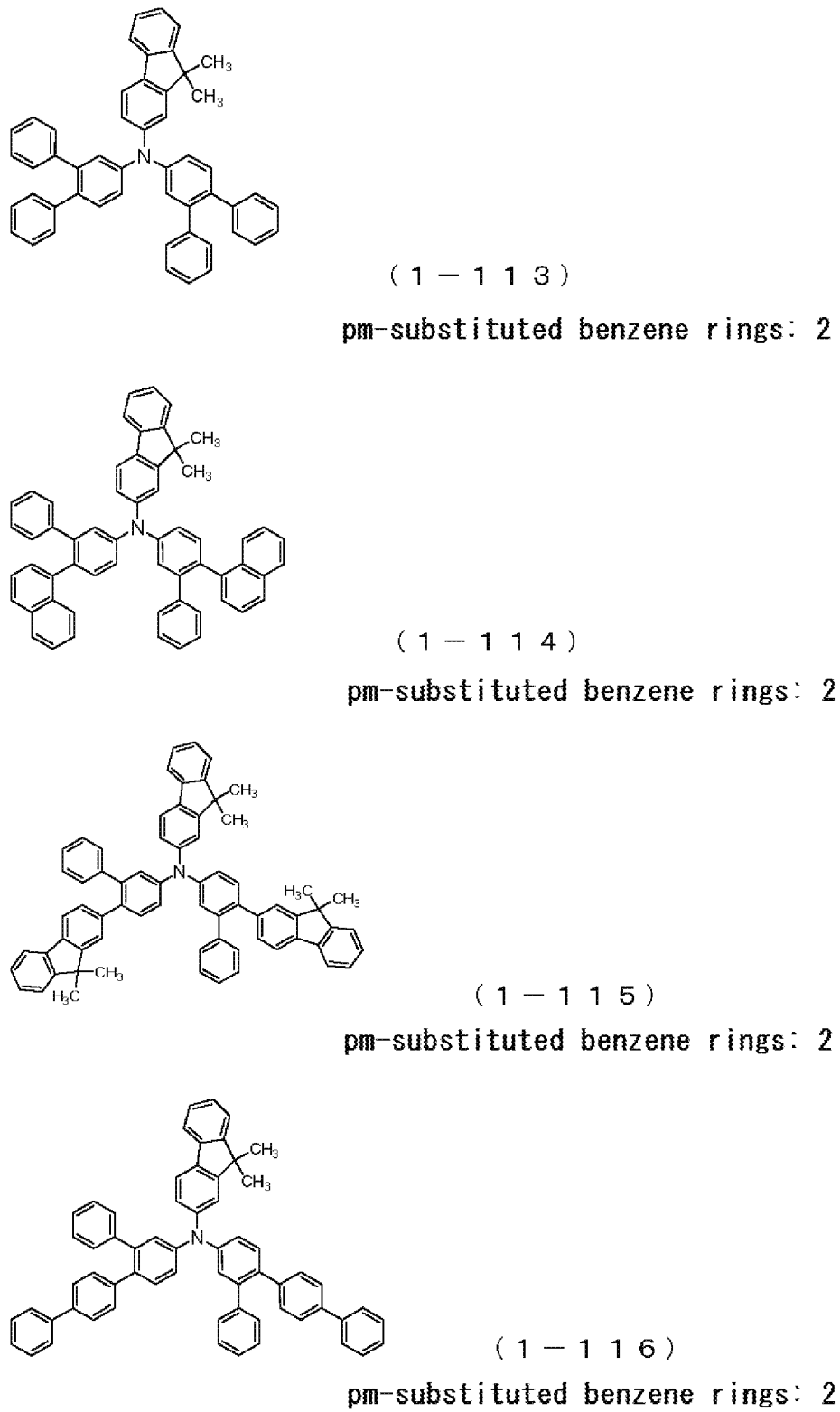
FIG. 64 is a drawing showing the structural formulas of Compound Nos. (1-113) to (1-116) among the arylamine compounds of the general formula (1).
Figure 65:
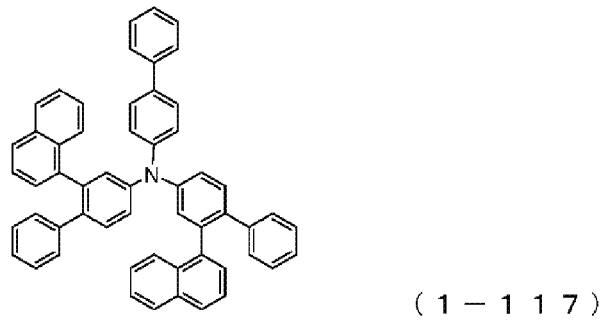
FIG. 65 is a drawing showing the structural formulas of Compound Nos. (1-117) to (1-120) among the arylamine compounds of the general formula (1).
Figure 65:
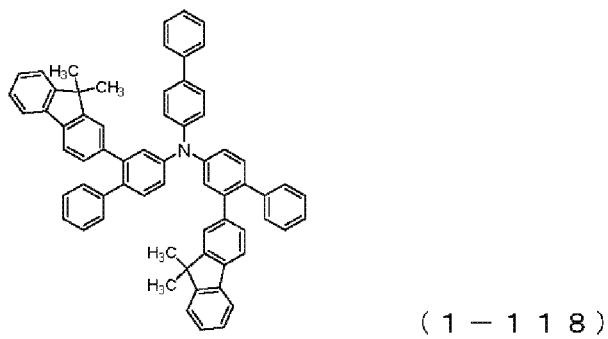
Figure 65:
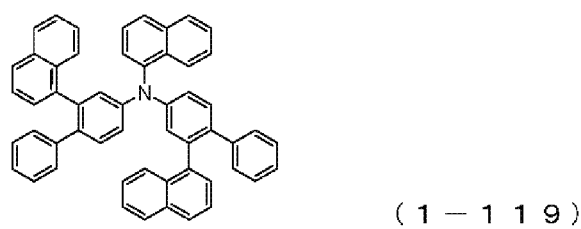
Figure 65:
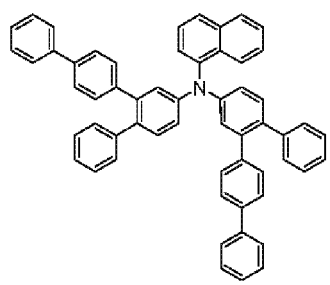
Figure 66:
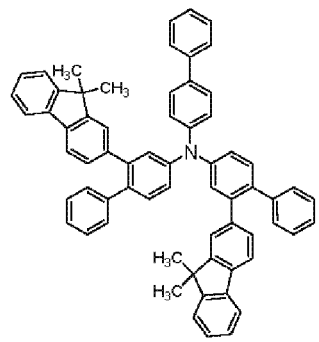
FIG. 66 is a drawing showing the structural formulas of Compound Nos. (1-121) to (1-124) among the arylamine compounds of the general formula (1).
Figure 66:
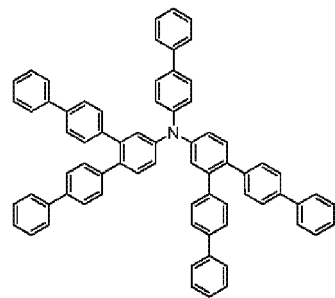
Figure 66:
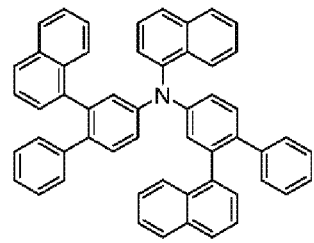
Figure 66:
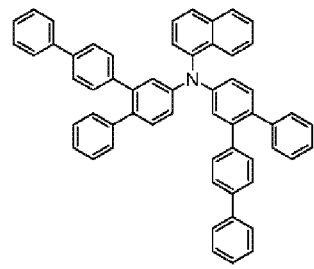
Figure 67:
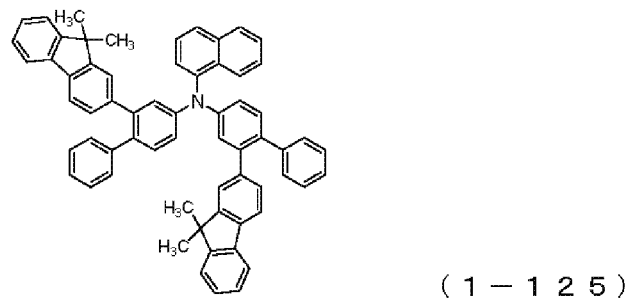
FIG. 67 is a drawing showing the structural formulas of Compound Nos. (1-125) to (1-126) among the arylamine compounds of the general formula (1).
Figure 67:
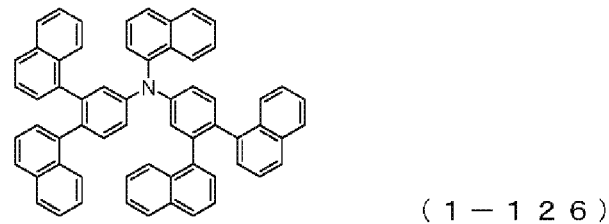
Figure 68:
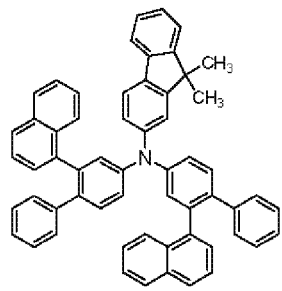
FIG. 68 is a drawing showing the structural formulas of Compound Nos. (1-127) to (1-130) among the arylamine compounds of the general formula (1).
Figure 68:
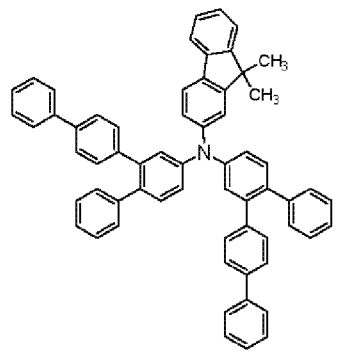
Figure 68:
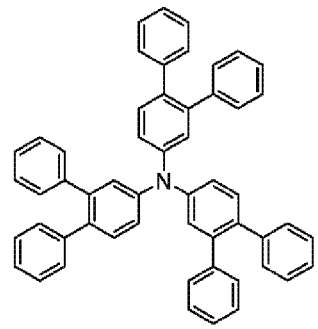
Figure 68:
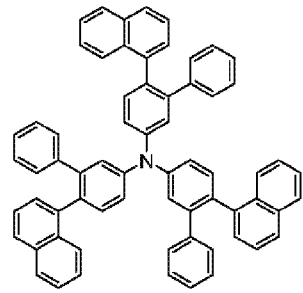
Figure 69:
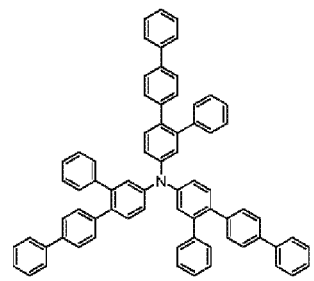
FIG. 69 is a drawing showing the structural formulas of Compound Nos. (1-131) to (1-133) among the arylamine compounds of the general formula (1).
Figure 69:
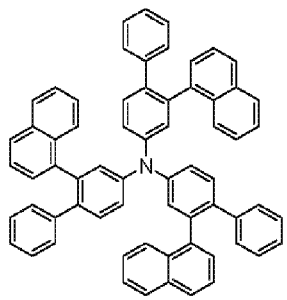
Figure 69:
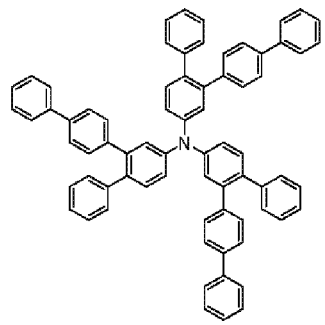
Figure 70:
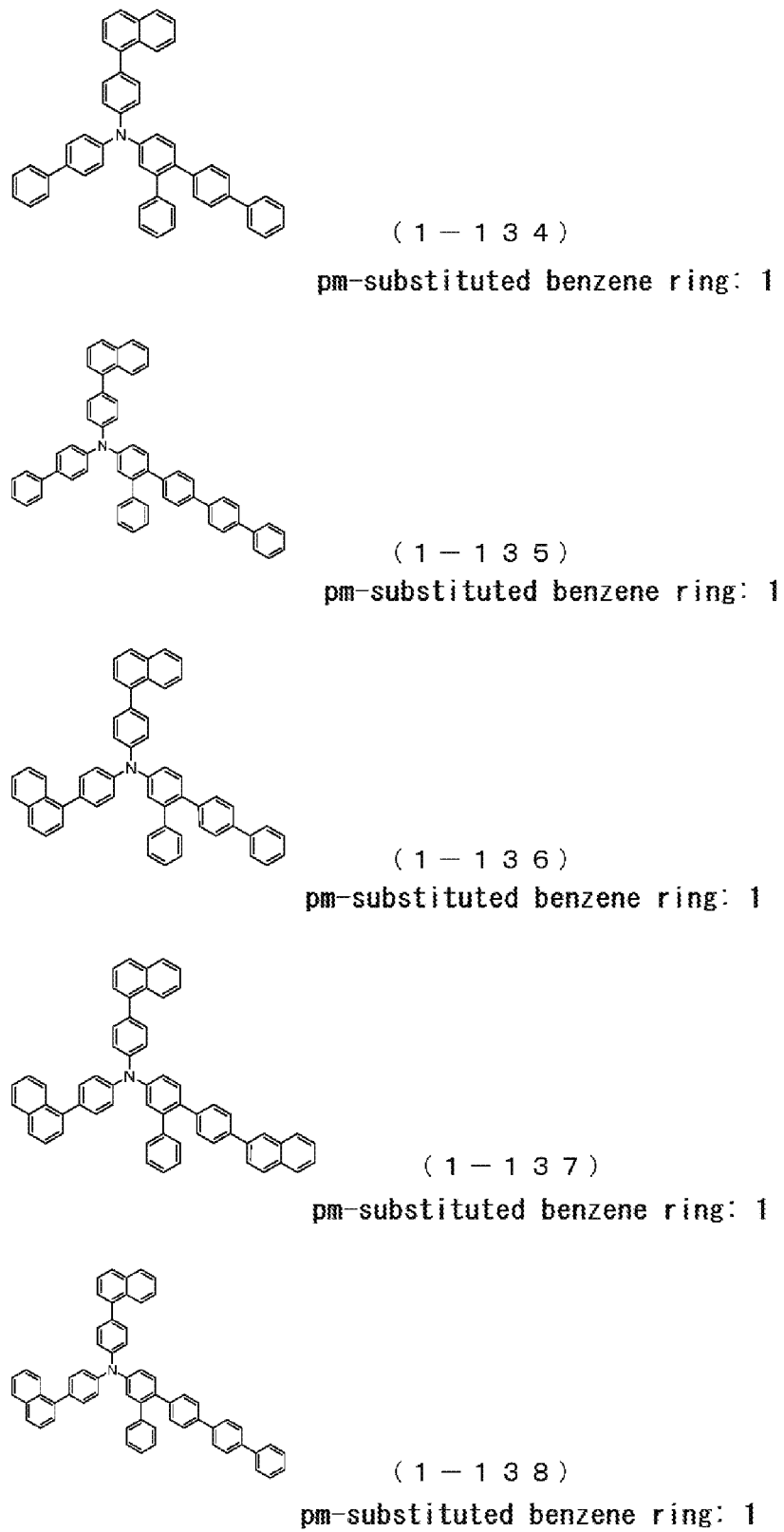
FIG. 70 is a drawing showing the structural formulas of Compound Nos. (1-134) to (1-138) among the arylamine compounds of the general formula (1).
Figure 71:
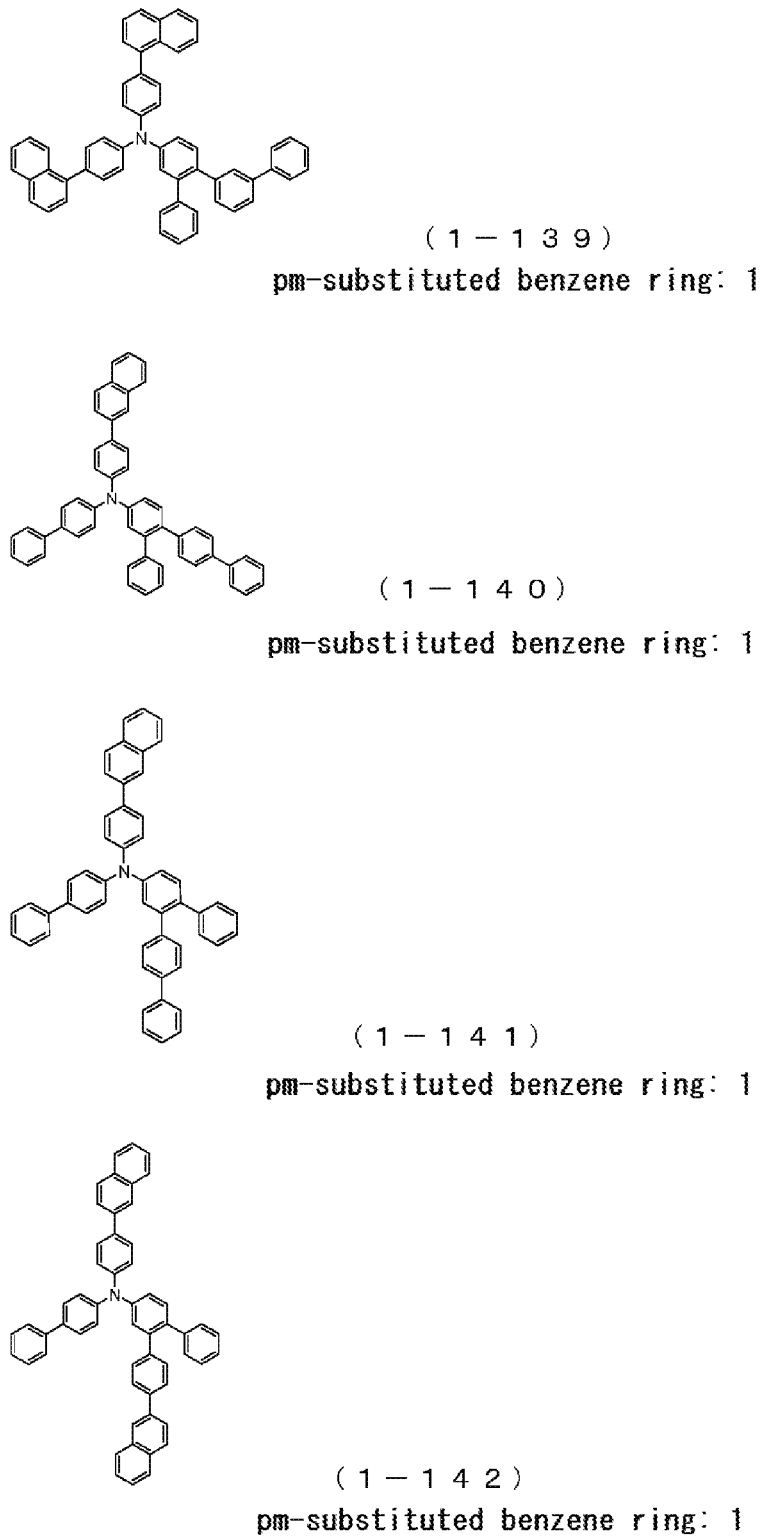
FIG. 71 is a drawing showing the structural formulas of Compound Nos. (1-139) to (1-142) among the arylamine compounds of the general formula (1).
Figure 72:
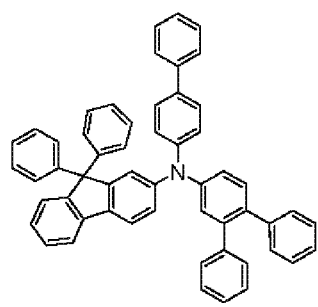
FIG. 72 is a drawing showing the structural formulas of Compound Nos. (1-143) to (1-146) among the arylamine compounds of the general formula (1).
Figure 72:
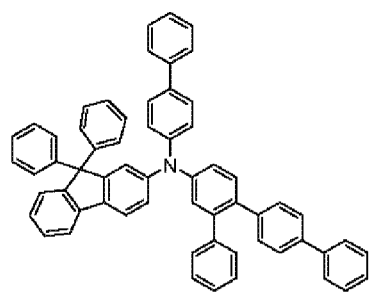
Figure 72:
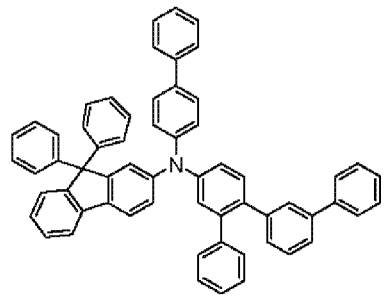
Figure 72:
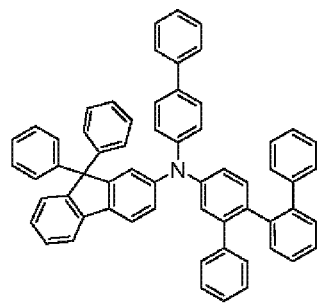
Figure 73:
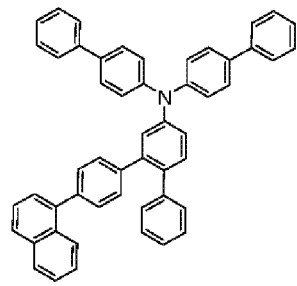
FIG. 73 is a drawing showing the structural formulas of Compound Nos. (1-147) to (1-150) among the arylamine compounds of the general formula (1).
Figure 73:
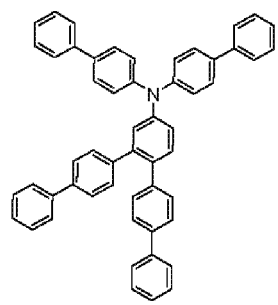
Figure 73:
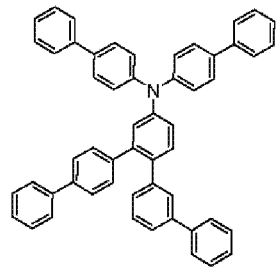
Figure 73:
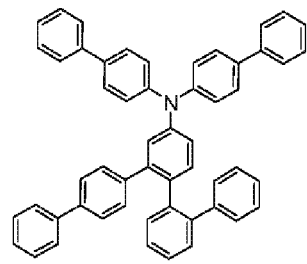
Figure 74:
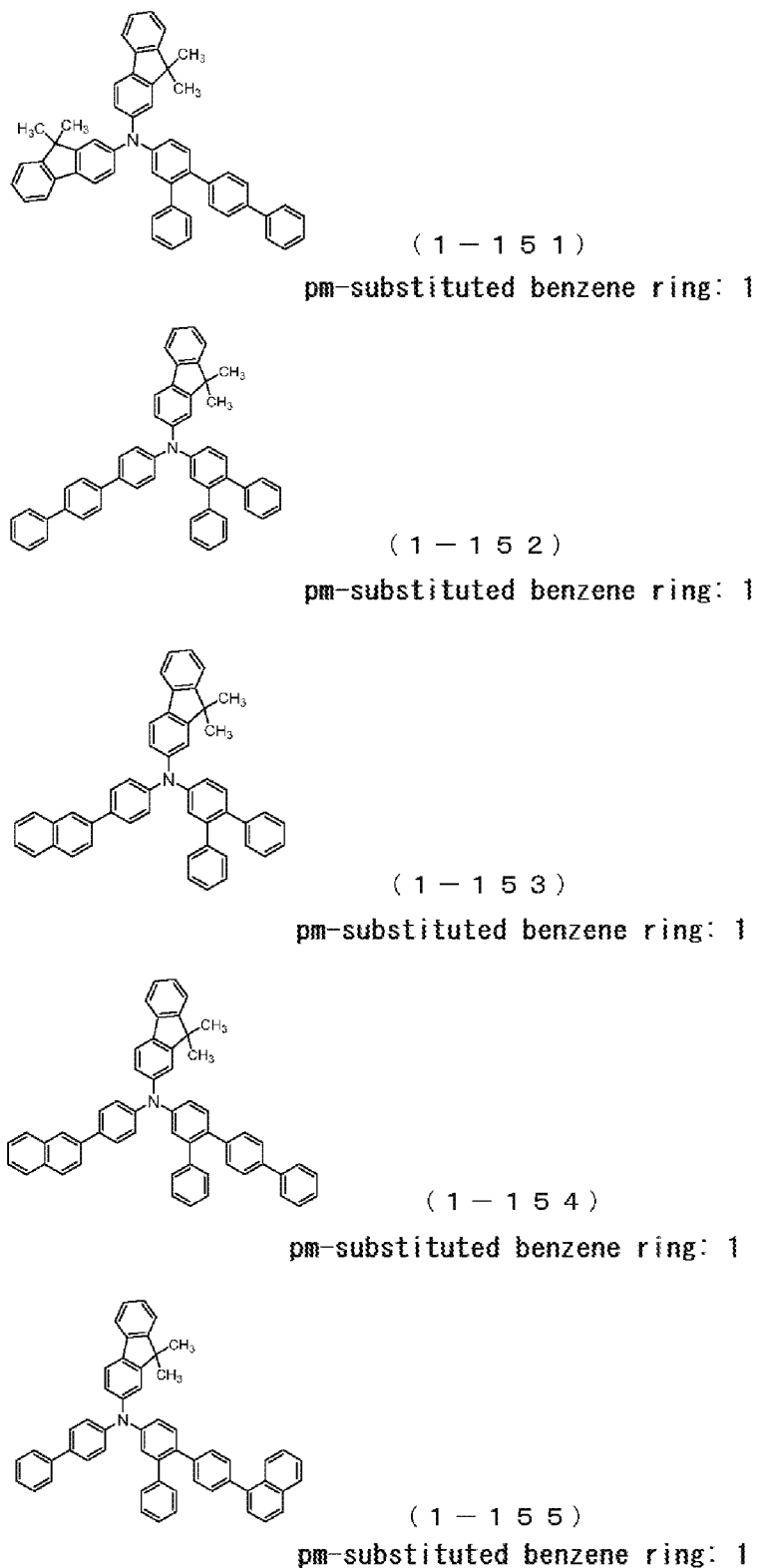
FIG. 74 is a drawing showing the structural formulas of Compound Nos. (1-151) to (1-155) among the arylamine compounds of the general formula (1).
Figure 75:
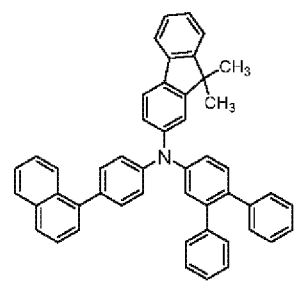
FIG. 75 is a drawing showing the structural formulas of Compound Nos. (1-156) to (1-159) among the arylamine compounds of the general formula (1).
Figure 75:
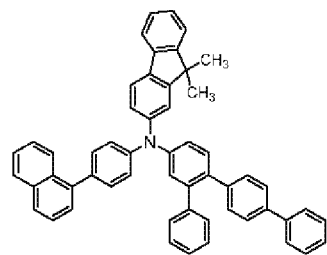
Figure 75:
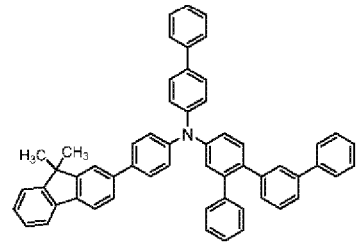
Figure 75:
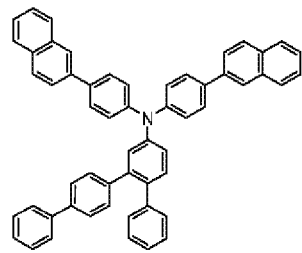
Figure 76:
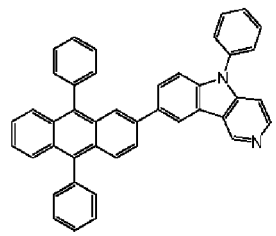
FIG. 76 is a drawing showing the structural formulas of Compound Nos. (2a-1) to (2a-5) among the anthracene derivatives of the general formula (2a).
Figure 76:
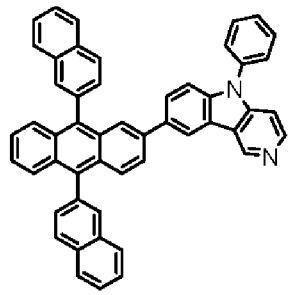
Figure 76:
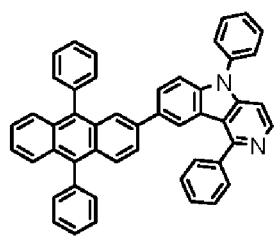
Figure 76:
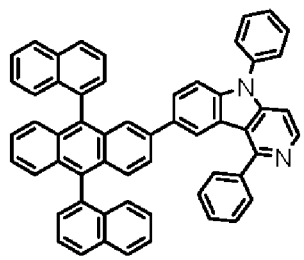
Figure 76:
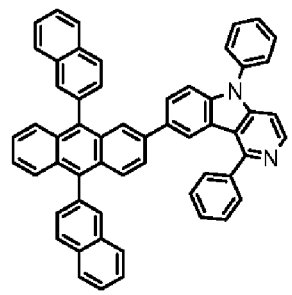
Figure 77:
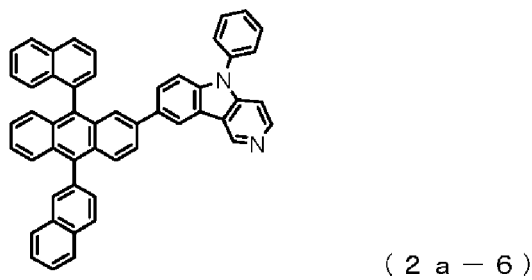
FIG. 77 is a drawing showing the structural formulas of Compound Nos. (2a-6) to (2a-10) among the anthracene derivatives of the general formula (2a).
Figure 77:
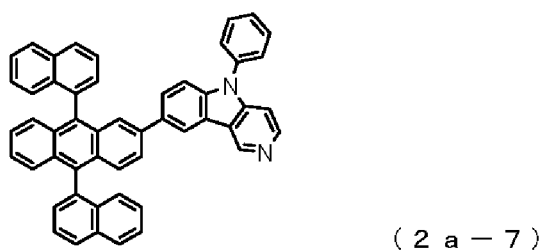
Figure 77:
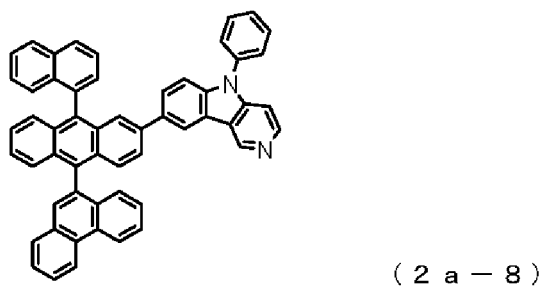
Figure 77:
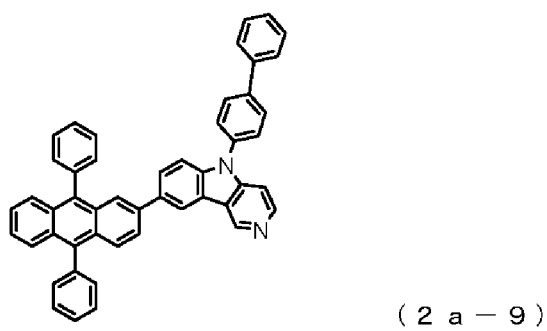
Figure 77:
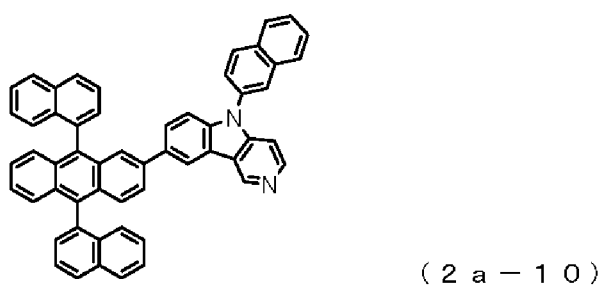
Figure 78:
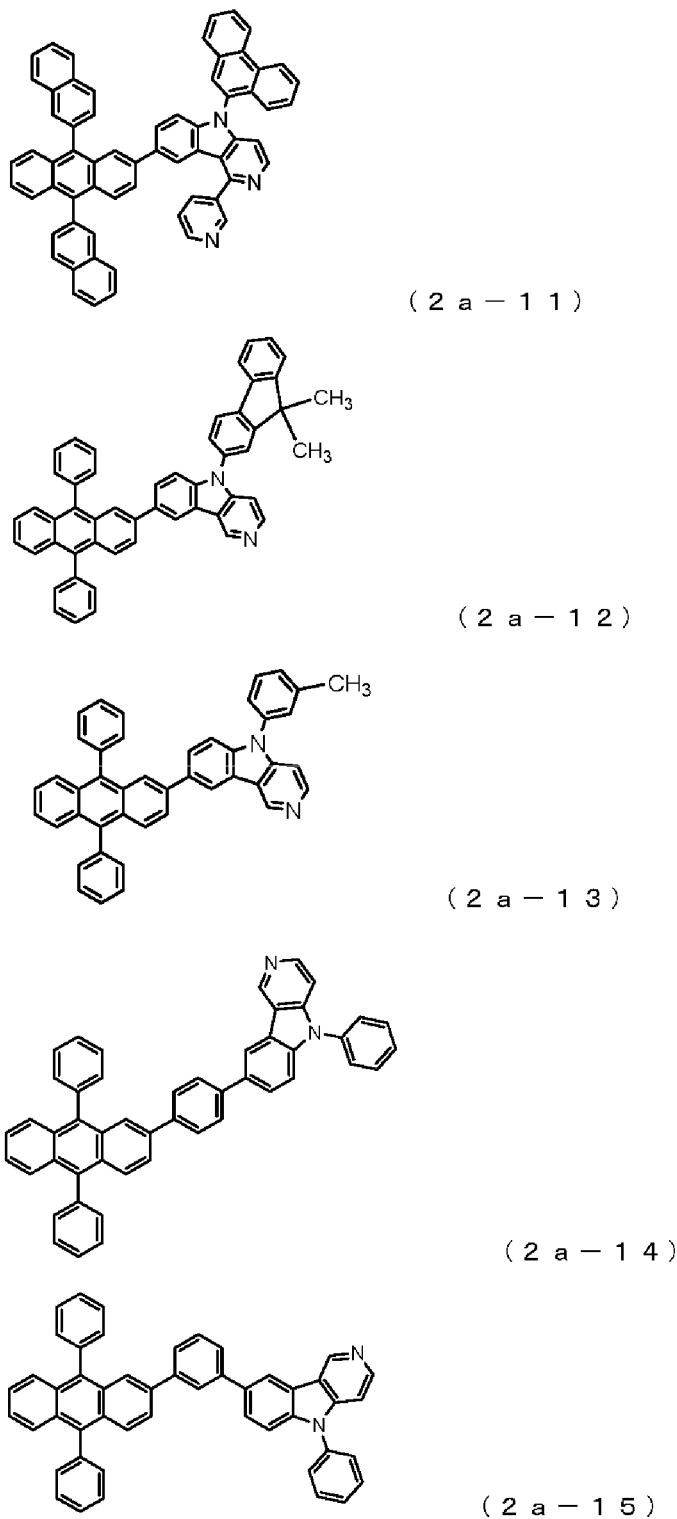
FIG. 78 is a drawing showing the structural formulas of Compound Nos. (2a-11) to (2a-15) among the anthracene derivatives of the general formula (2a).
Figure 79:
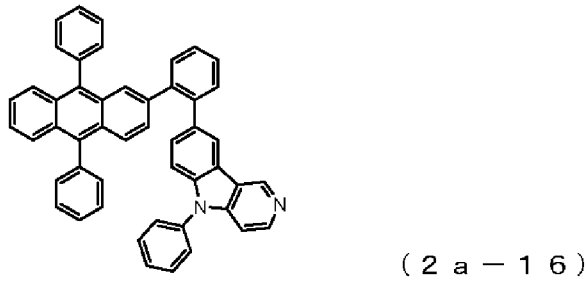
FIG. 79 is a drawing showing the structural formulas of Compound Nos. (2a-16) to (2a-20) among the anthracene derivatives of the general formula (2a).
Figure 79:
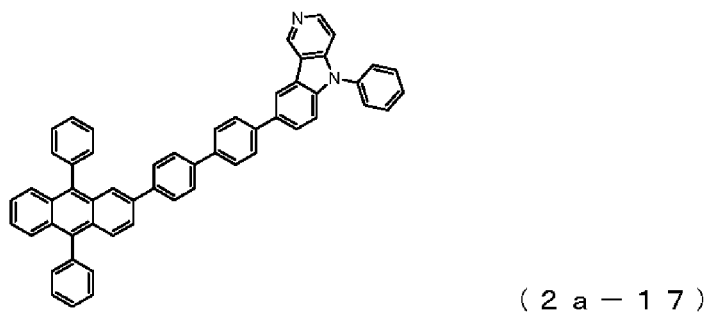
Figure 79:
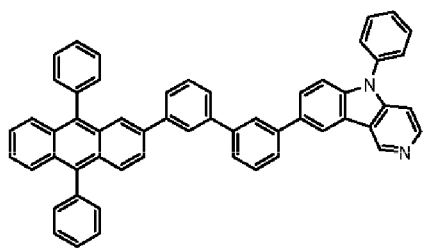
Figure 79:
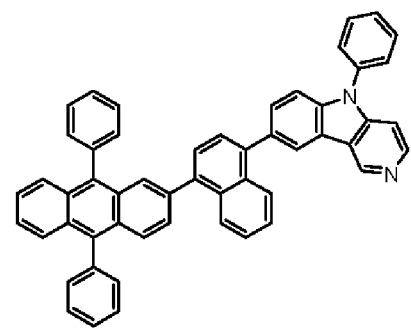
Figure 79:
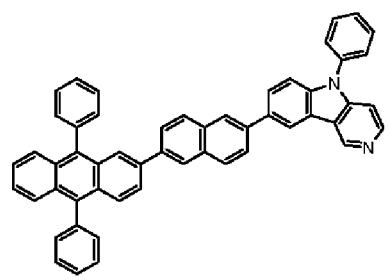
Figure 80:
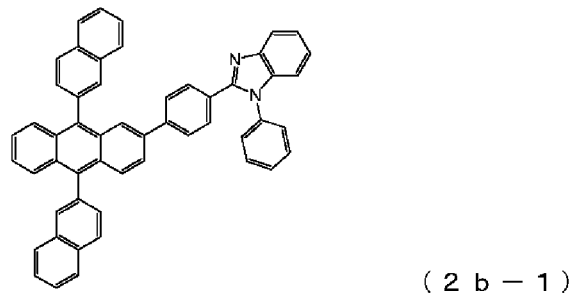
FIG. 80 is a drawing showing the structural formulas of Compound Nos. (2b-1) to (2b-5) among the anthracene derivatives of the general formula (2b).
Figure 80:
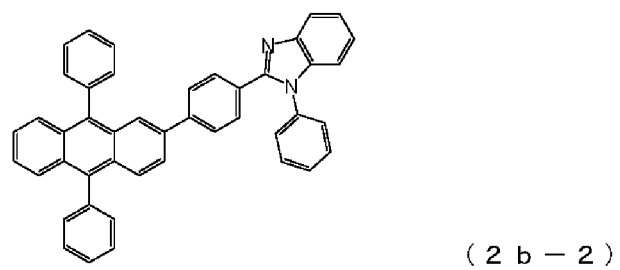
Figure 80:
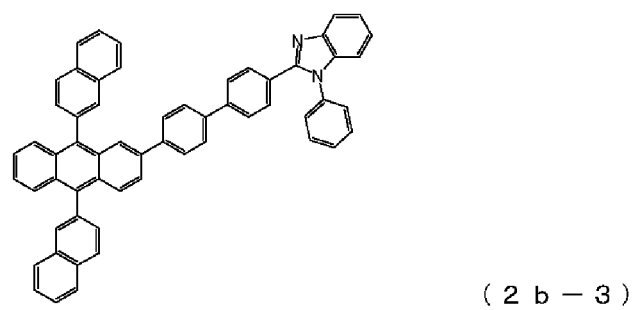
Figure 80:
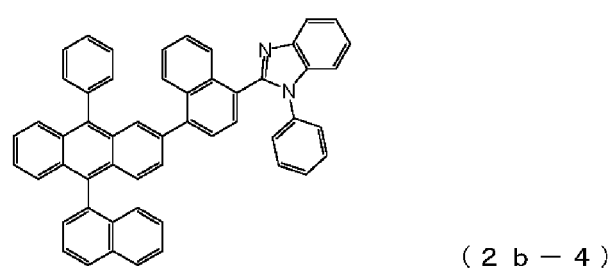
Figure 80:
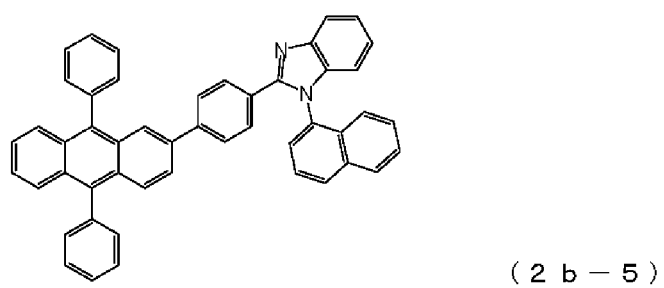
Figure 81:
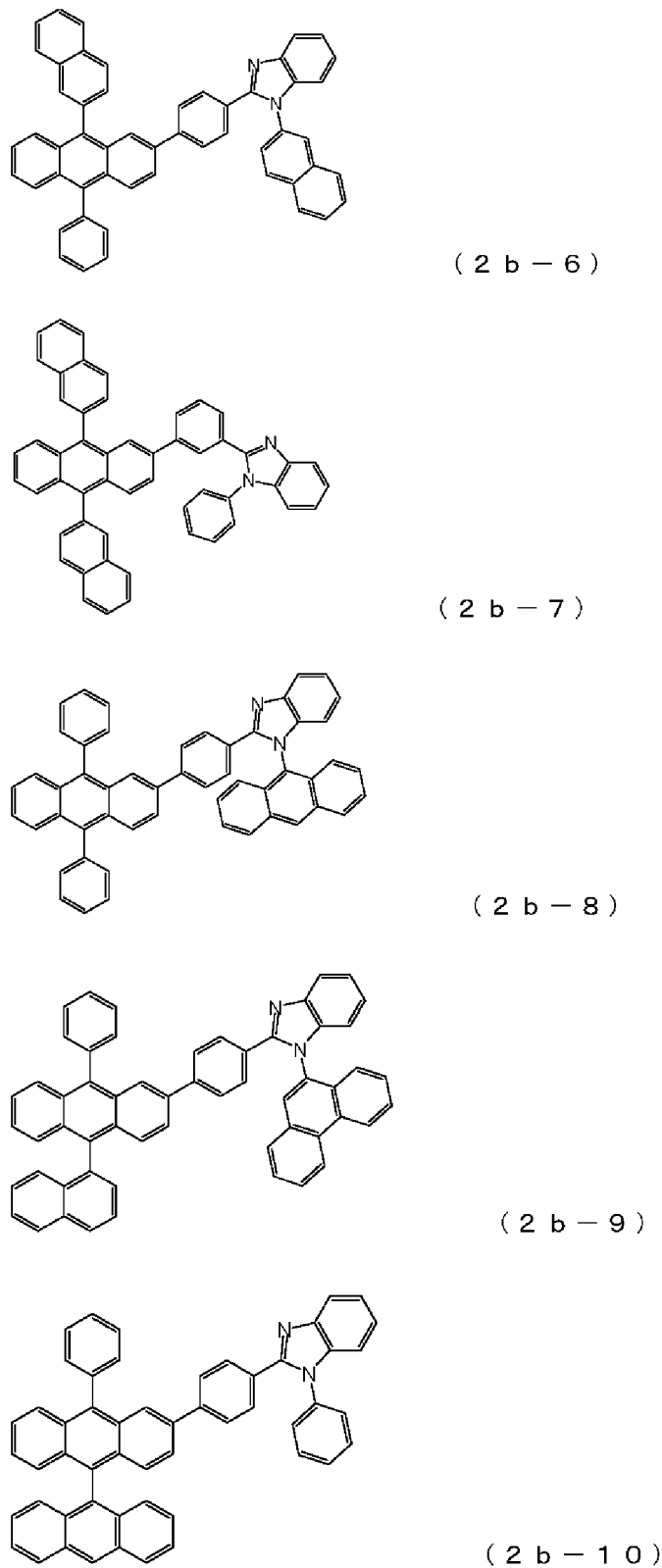
FIG. 81 is a drawing showing the structural formulas of Compound Nos. (2b-6) to (2b-10) among the anthracene derivatives of the general formula (2b).
Figure 82:
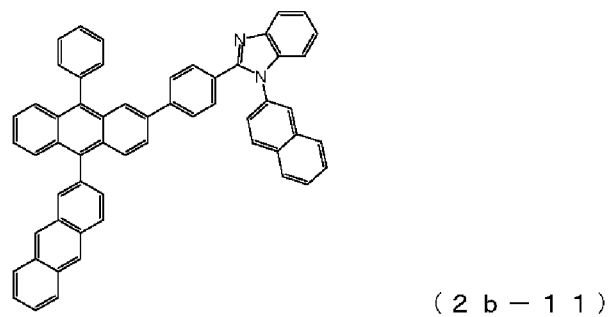
FIG. 82 is a drawing showing the structural formulas of Compound Nos. (2b-11) to (2b-15) among the anthracene derivatives of the general formula (2b).
Figure 82:
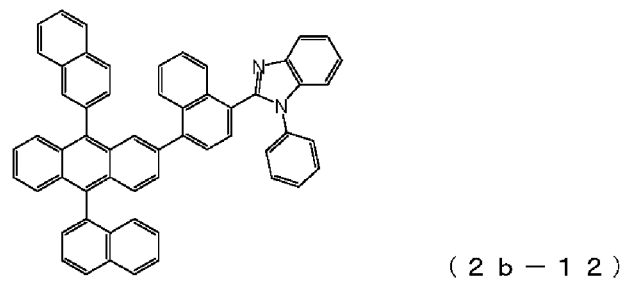
Figure 82:
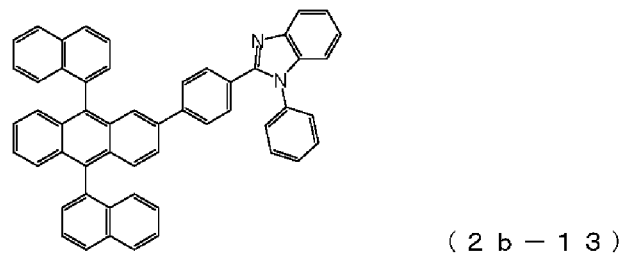
Figure 82:
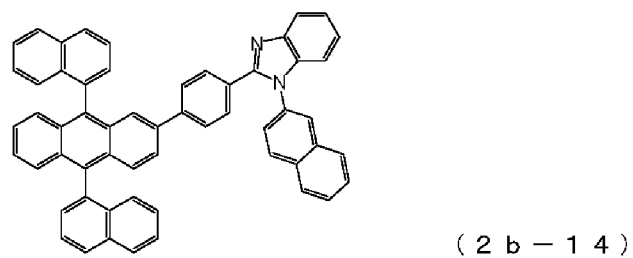
Figure 82:
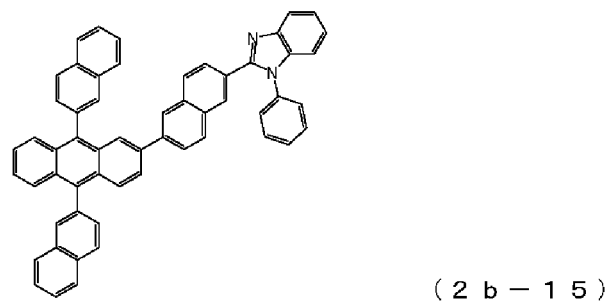
Figure 83:
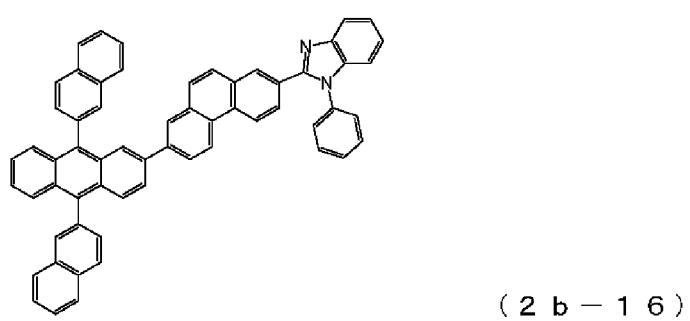
FIG. 83 is a drawing showing the structural formula of Compound No. (2b-16) among the anthracene derivatives of the general formula (2b).
Figure 84:
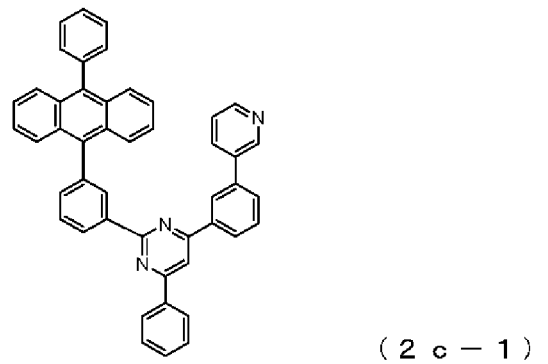
FIG. 84 is a drawing showing the structural formulas of Compound Nos. (2c-1) to (2c-4) among the anthracene derivatives of the general formula (2c).
Figure 84:
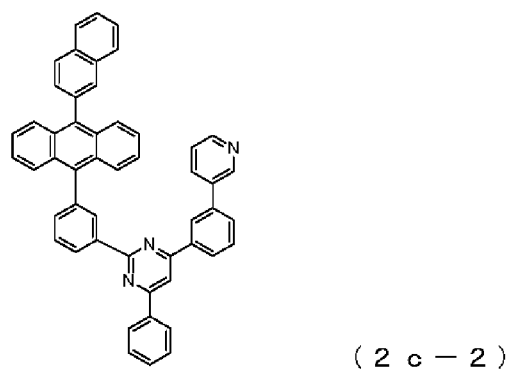
Figure 84:
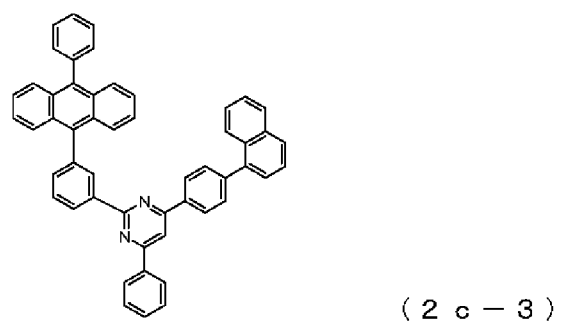
Figure 84:
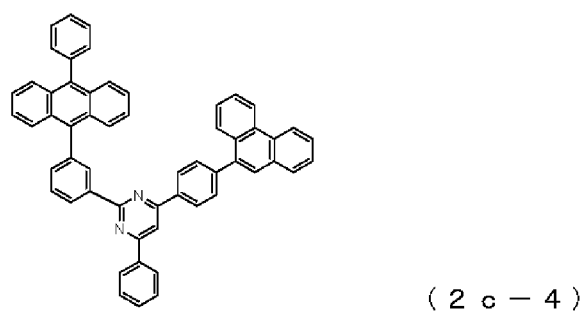
Figure 85:
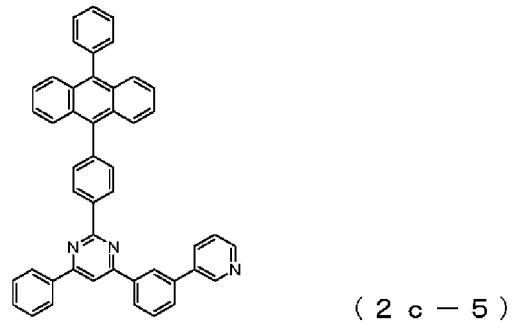
FIG. 85 is a drawing showing the structural formulas of Compound Nos. (2c-5) to (2c-8) among the anthracene derivatives of the general formula (2c).
Figure 85:
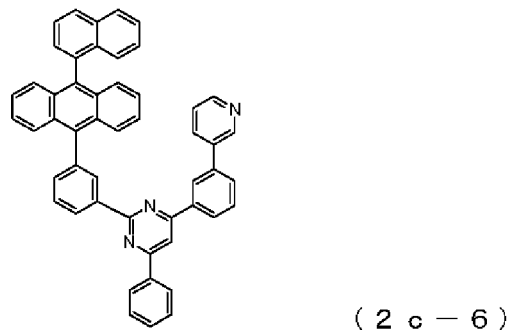
Figure 85:
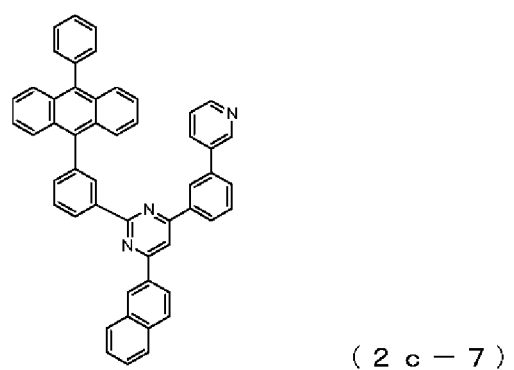
Figure 85:
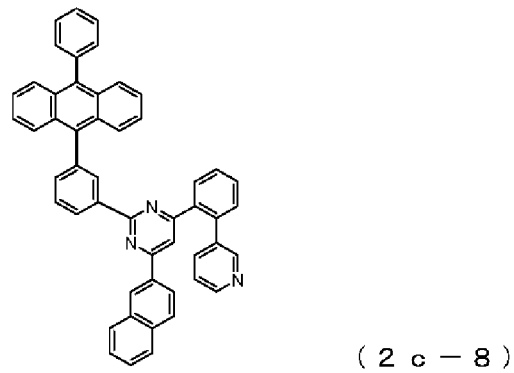
Figure 86:
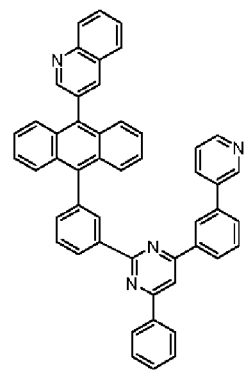
FIG. 86 is a drawing showing the structural formulas of Compound Nos. (2c-9) to (2c-12) among the anthracene derivatives of the general formula (2c).
Figure 86:
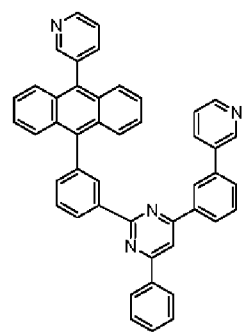
Figure 86:
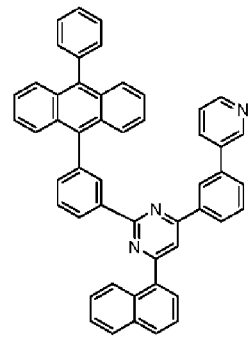
Figure 86:
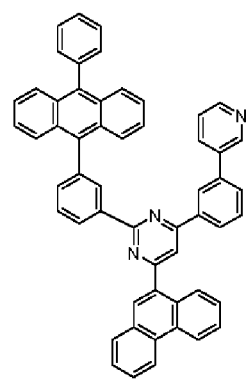
Figure 87:
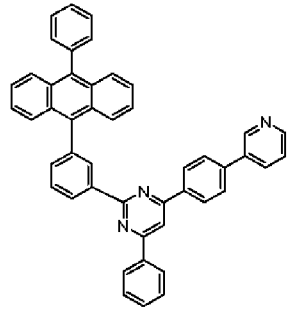
FIG. 87 is a drawing showing the structural formulas of Compound Nos. (2c-13) to (2c-16) among the anthracene derivatives of the general formula (2c).
Figure 87:
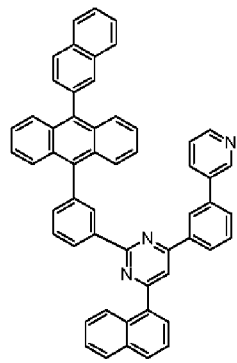
Figure 87:
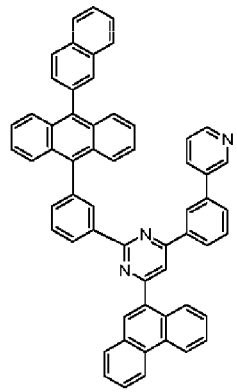
Figure 87:
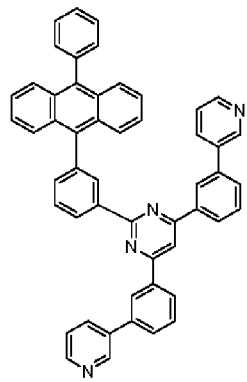
Figure 88:
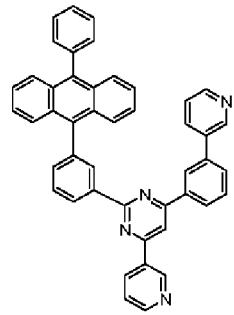
FIG. 88 is a drawing showing the structural formulas of Compound Nos. (2c-17) to (2c-20) among the anthracene derivatives of the general formula (2c).
Figure 88:
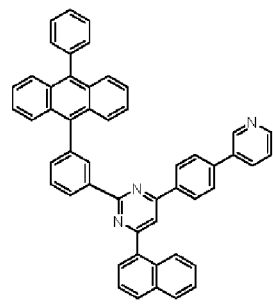
Figure 88:
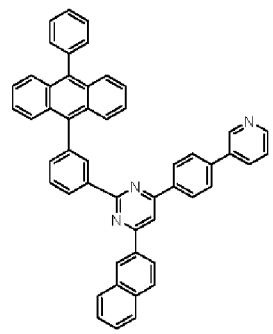
Figure 88:
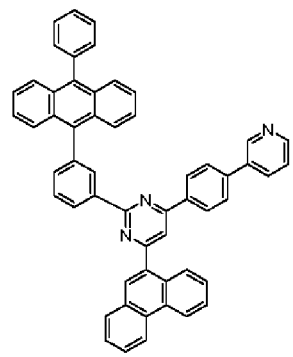
Figure 89:
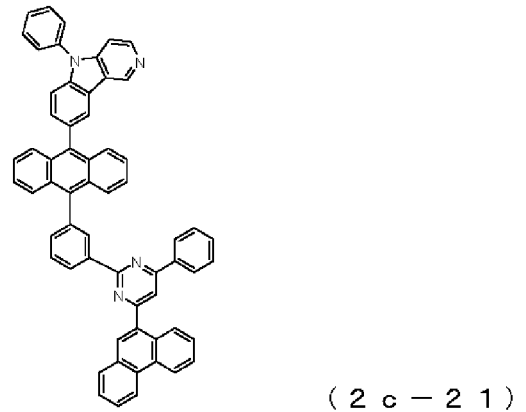
FIG. 89 is a drawing showing the structural formulas of Compound Nos. (2c-21) to (2c-24) among the anthracene derivatives of the general formula (2c).
Figure 89:
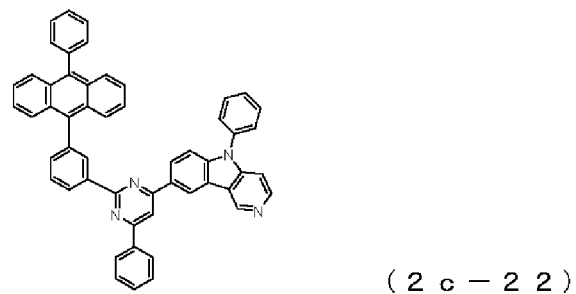
Figure 89:
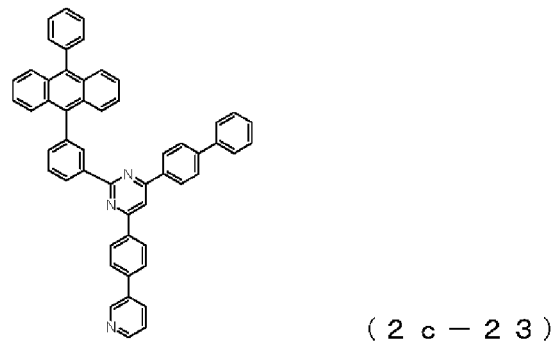
Figure 89:
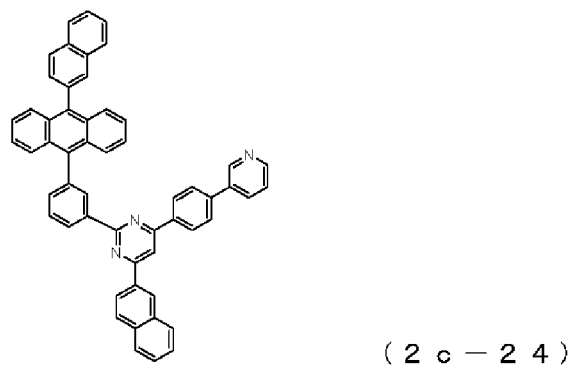
Figure 90:
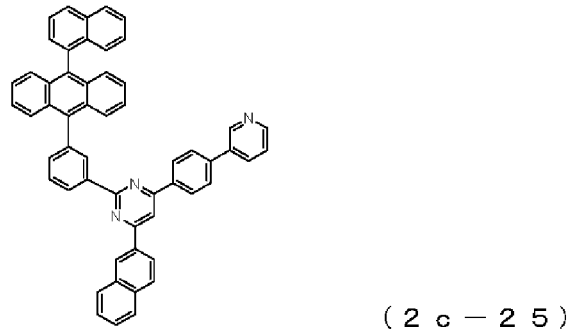
FIG. 90 is a drawing showing the structural formulas of Compound Nos. (2c-25) to (2c-28) among the anthracene derivatives of the general formula (2c).
Figure 90:
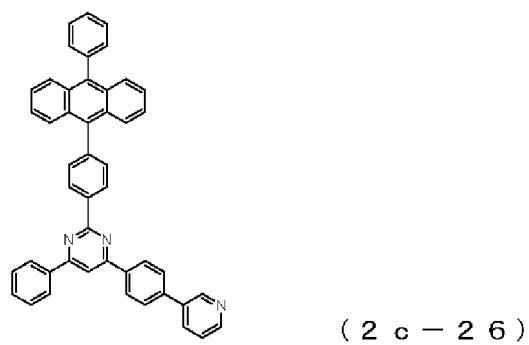
Figure 90:
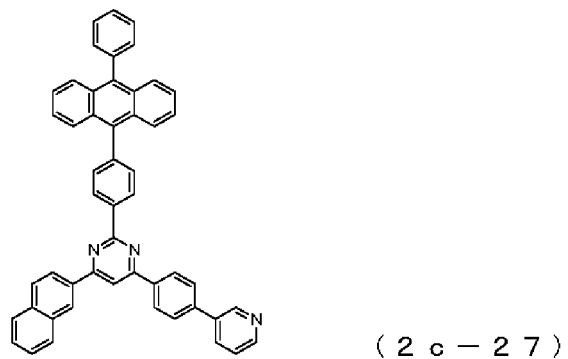
Figure 90:
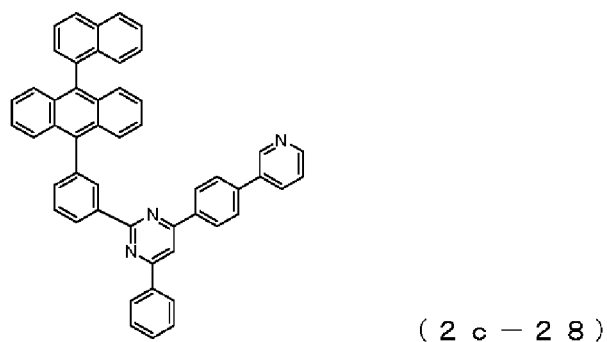
Figure 91:
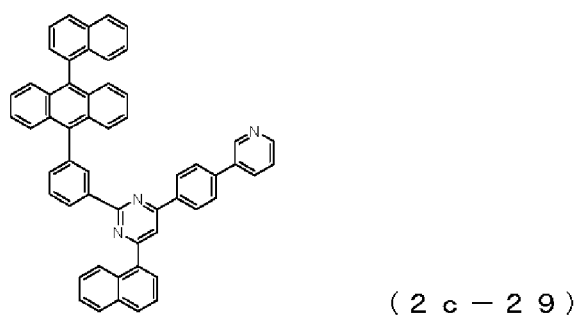
FIG. 91 is a drawing showing the structural formulas of Compound Nos. (2c-29) to (2c-30) among the anthracene derivatives of the general formula (2c).
Figure 91:
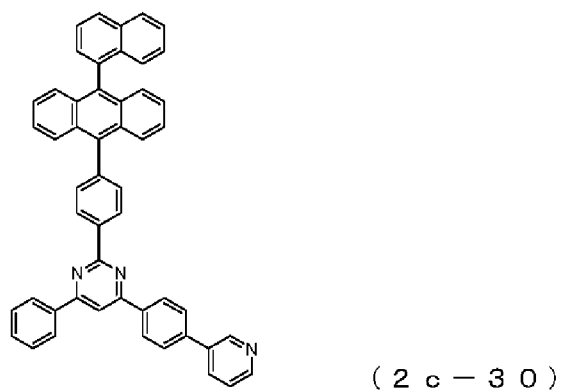
Figure 92:
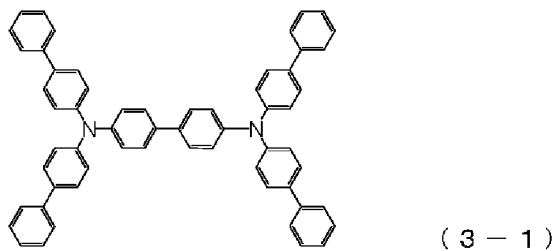
FIG. 92 is a drawing showing the structural formulas of Compound Nos. (3-1) to (3-5) among the triarylamine derivatives of the general formula (3).
Figure 92:
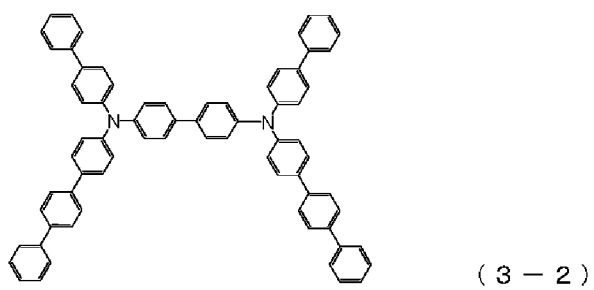
Figure 92:
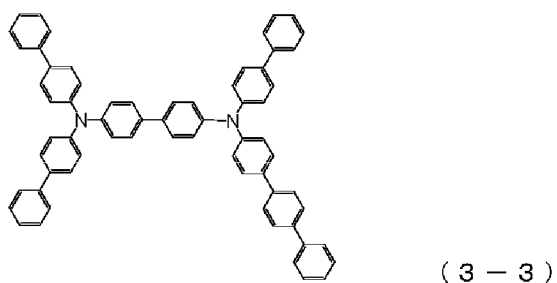
Figure 92:
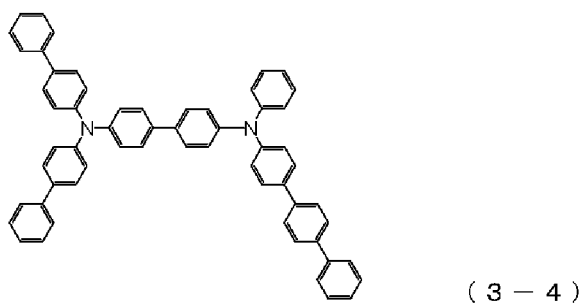
Figure 92:
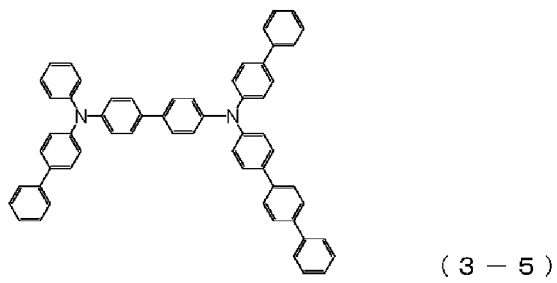
Figure 93:
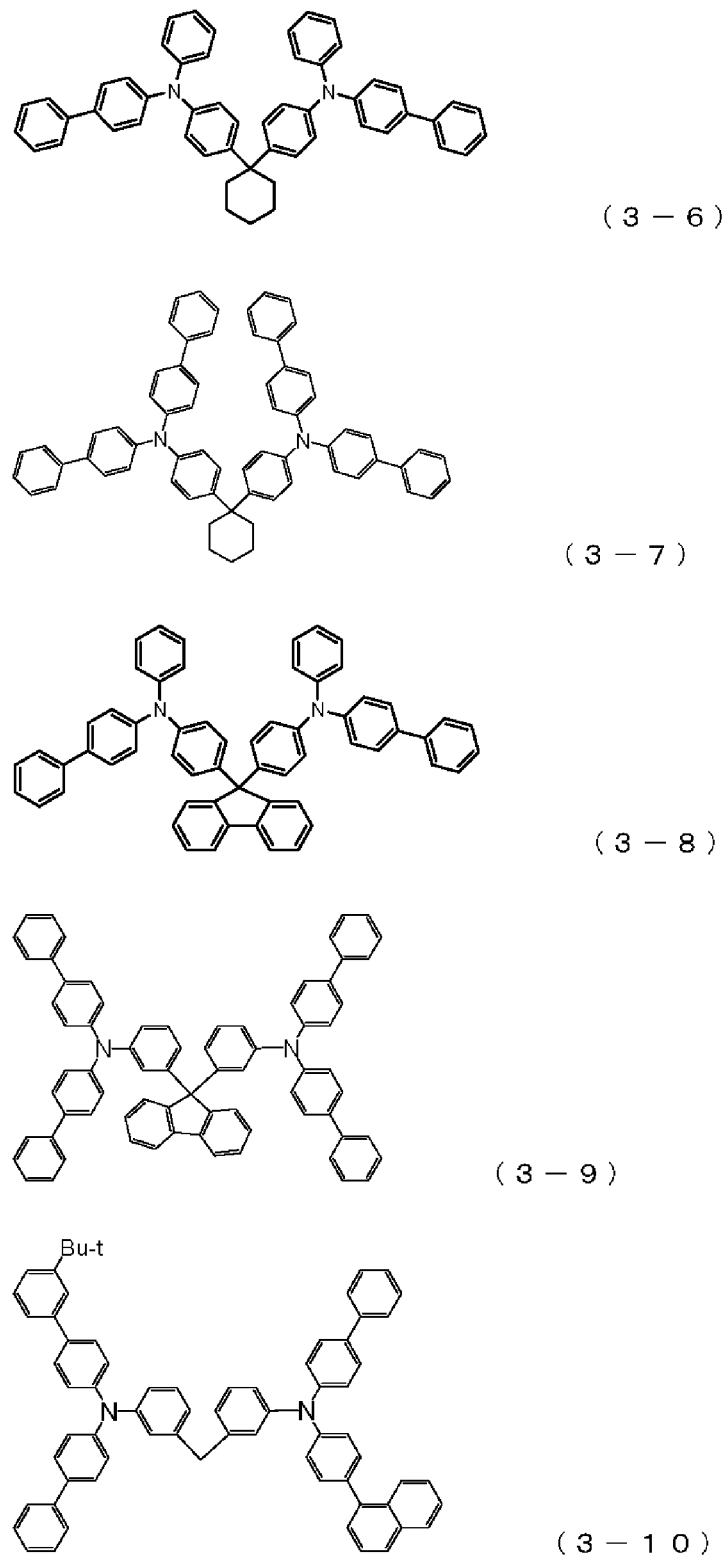
FIG. 93 is a drawing showing the structural formulas of Compound Nos. (3-6) to (3-10) among the triarylamine derivatives of the general formula (3).
Figure 94:
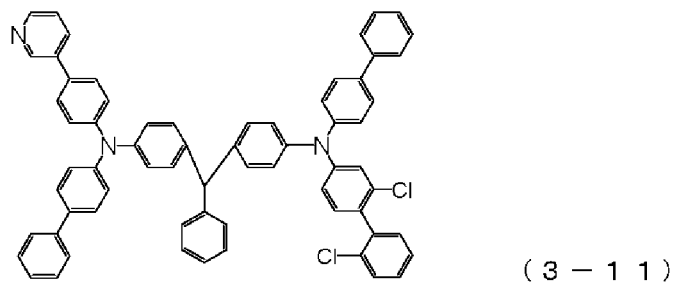
FIG. 94 is a drawing showing the structural formulas of Compound Nos. (3-11) to (3-15) among the triarylamine derivatives of the general formula (3).
Figure 94:
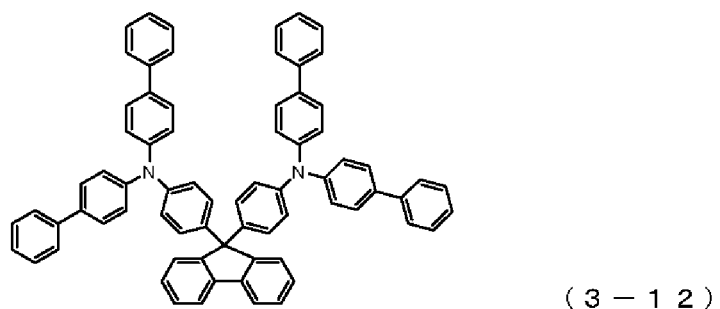
Figure 94:
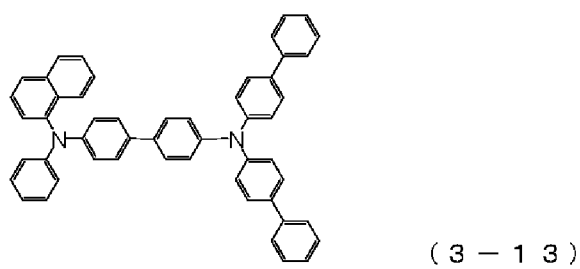
Figure 94:
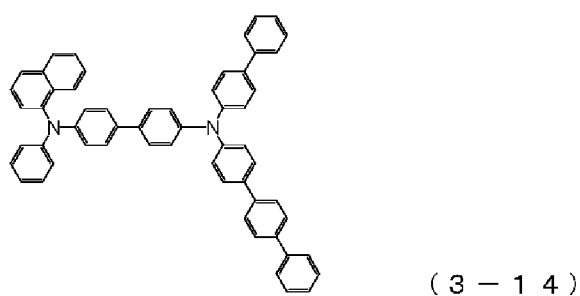
Figure 94:
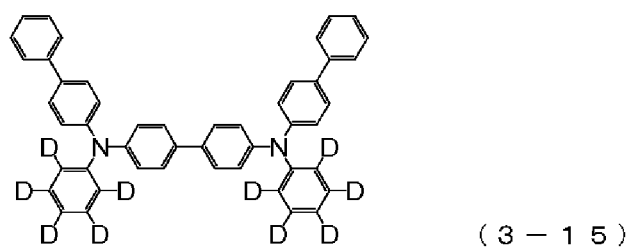
Figure 95:
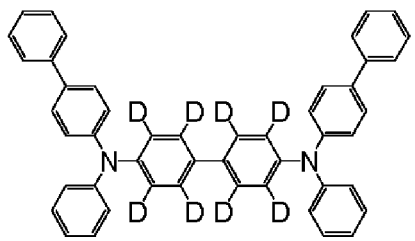
FIG. 95 is a drawing showing the structural formulas of Compound Nos. (3-16) to (3-20) among the triarylamine derivatives of the general formula (3).
Figure 95:
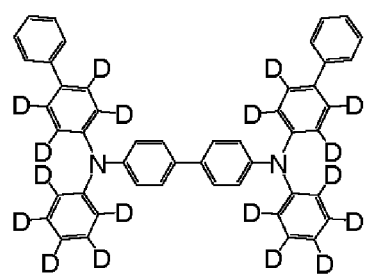
Figure 95:
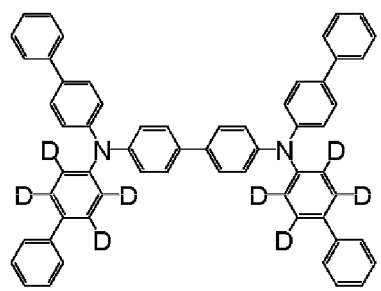
Figure 95:
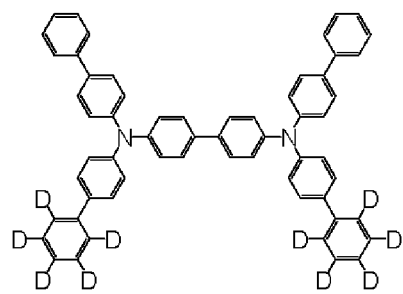
Figure 95:
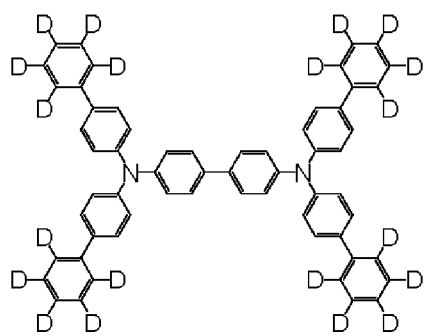
Figure 96:
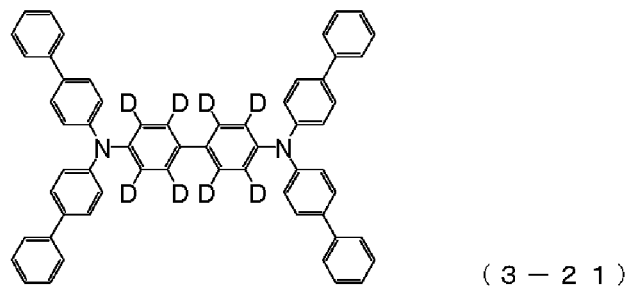
FIG. 96 is a drawing showing the structural formulas of Compound Nos. (3-21) to (3-25) among the triarylamine derivatives of the general formula (3).
Figure 96:
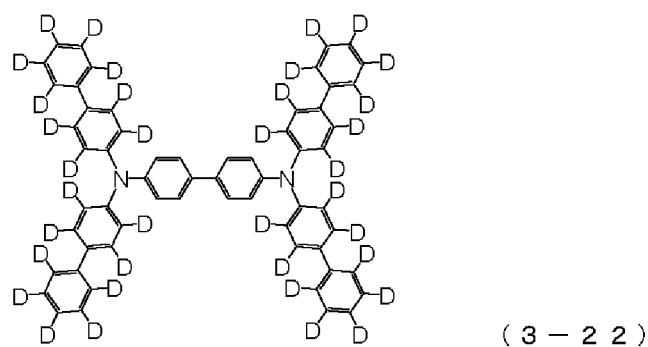
Figure 96:
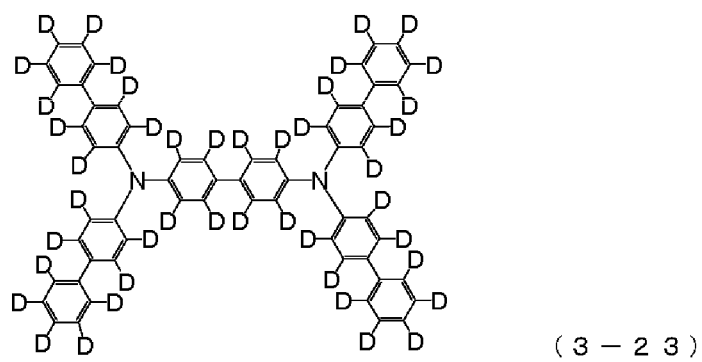
Figure 96:
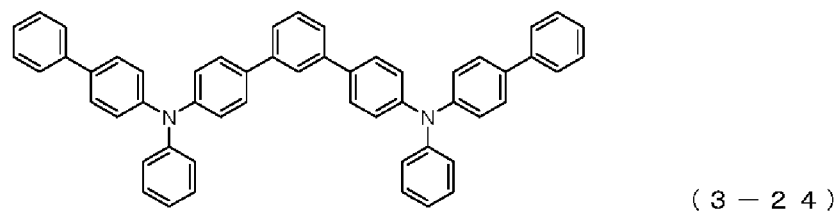
Figure 96:
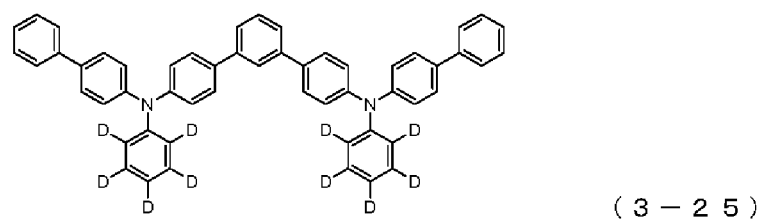
Figure 97:
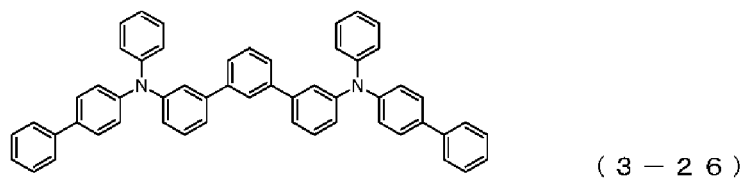
FIG. 97 is a drawing showing the structural formulas of Compound Nos. (3-26) to (3-31) among the triarylamine derivatives of the general formula (3).
Figure 97:
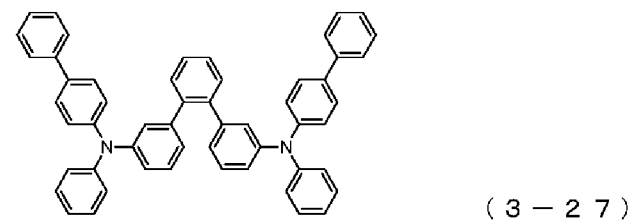
Figure 97:
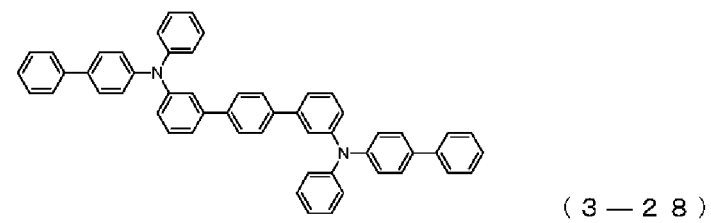
Figure 97:
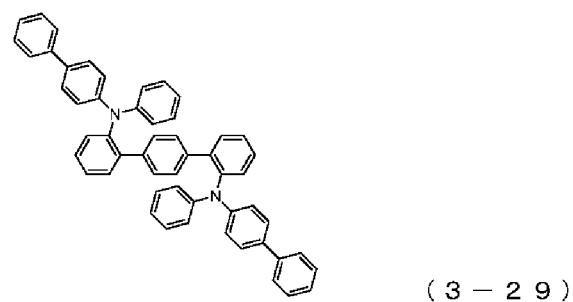
Figure 97:
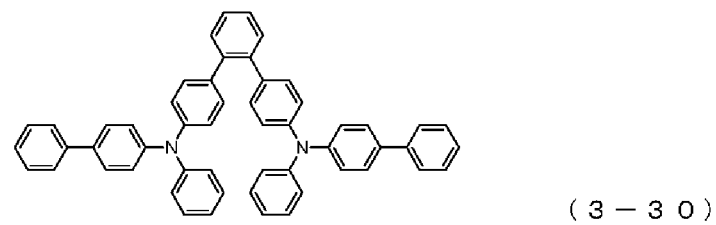
Figure 97:
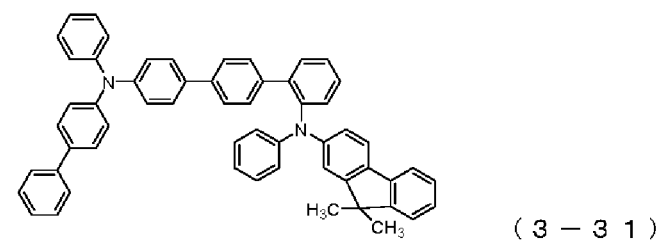
Figure 98:
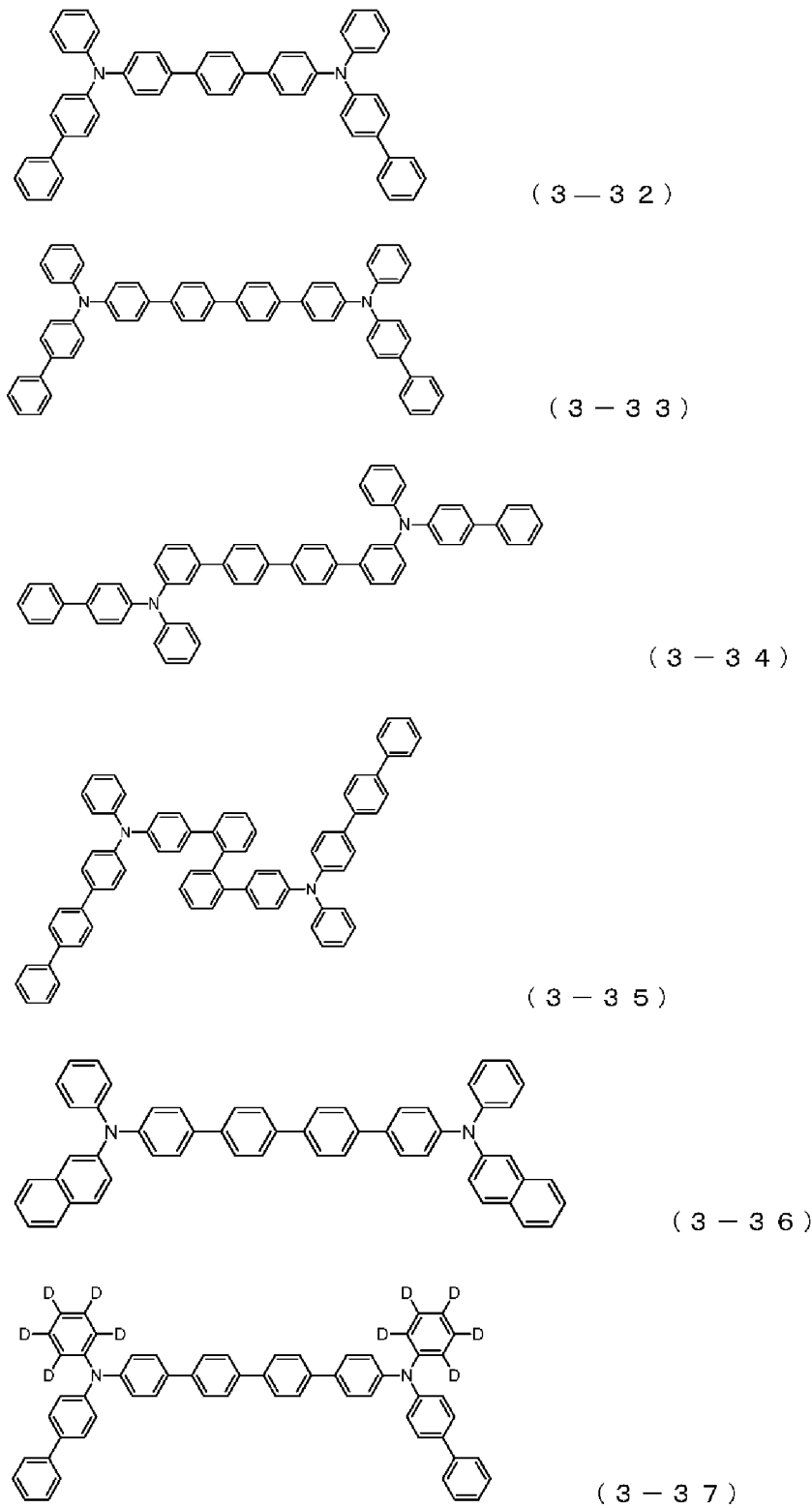
FIG. 98 is a drawing showing the structural formulas of Compound Nos. (3-32) to (3-37) among the triarylamine derivatives of the general formula (3).
Figure 99:
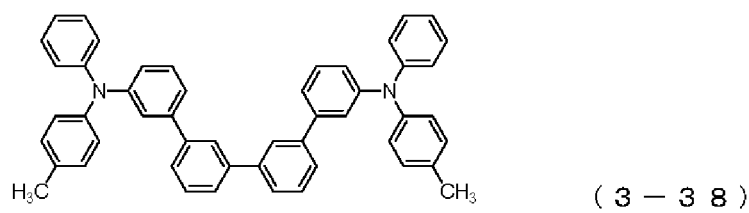
FIG. 99 is a drawing showing the structural formulas of Compound Nos. (3-38) to (3-41) among the triarylamine derivatives of the general formula (3).
Figure 99:
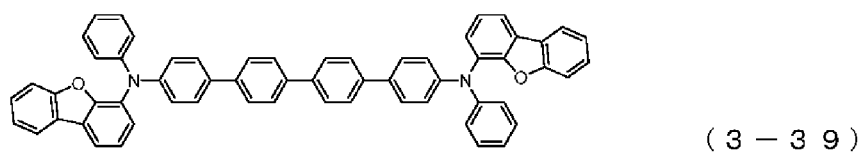
Figure 99:
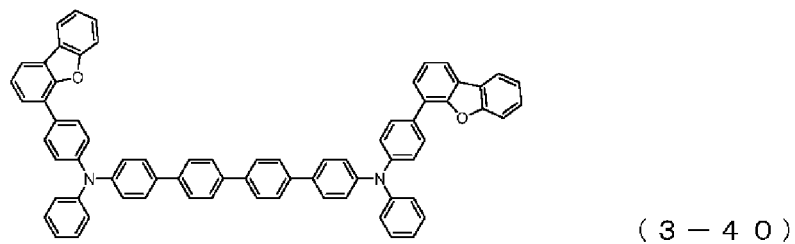
Figure 99:
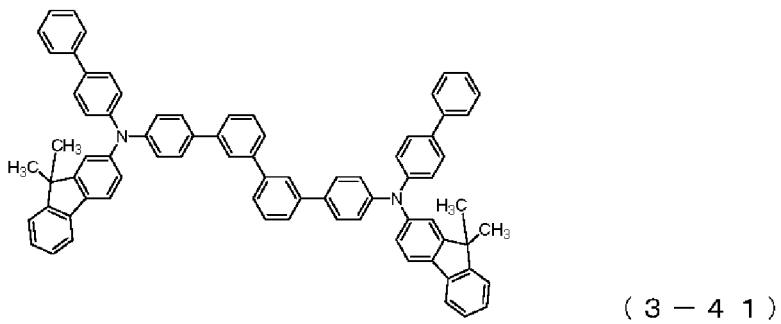
Figure 100:
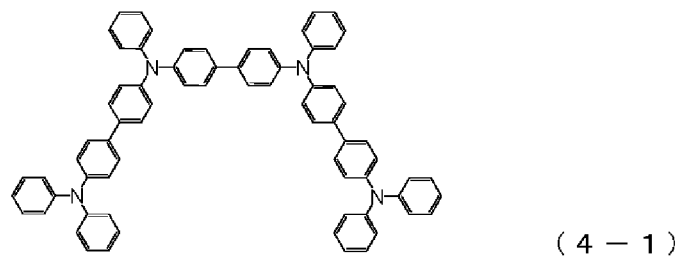
FIG. 100 is a drawing showing the structural formulas of Compound Nos. (4-1) to (4-5) among the triarylamine derivatives of the general formula (4).
Figure 100:
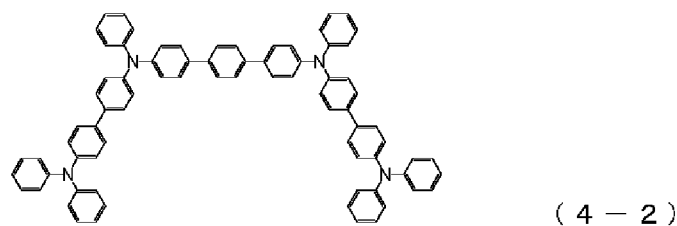
Figure 100:
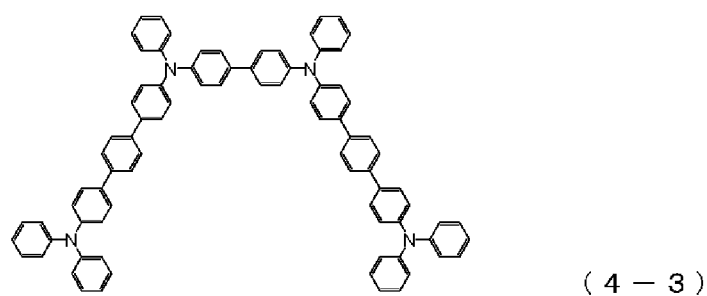
Figure 100:
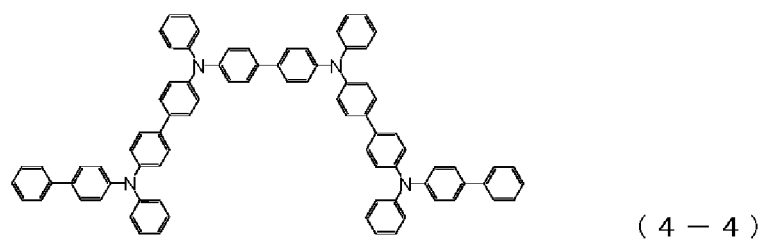
Figure 100:
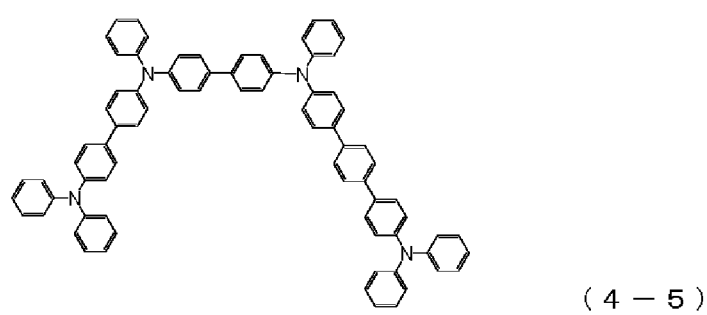
Figure 101:
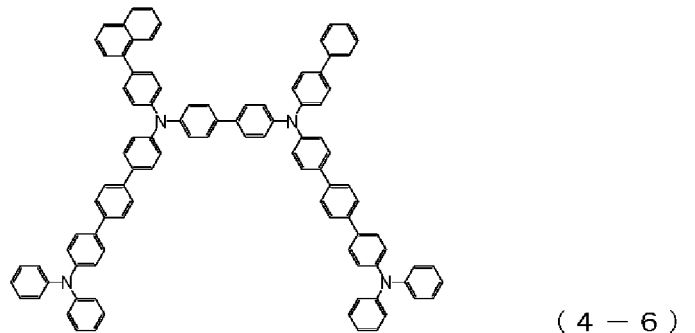
FIG. 101 is a drawing showing the structural formulas of Compound Nos. (4-6) to (4-10) among the triarylamine derivatives of the general formula (4).
Figure 101:
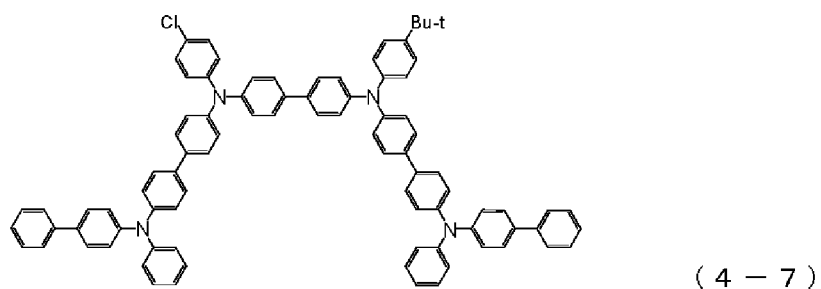
Figure 101:
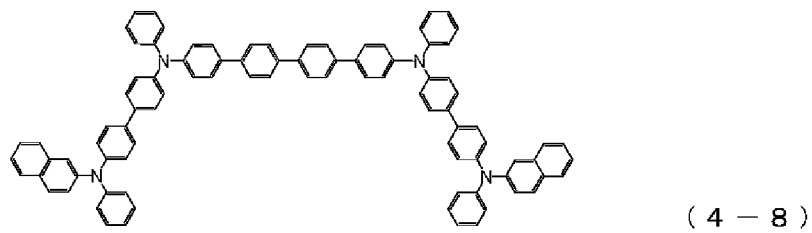
Figure 101:
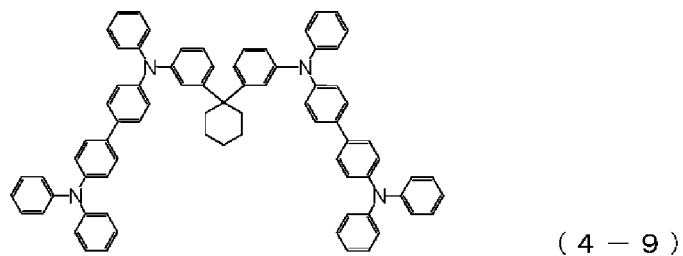
Figure 101:
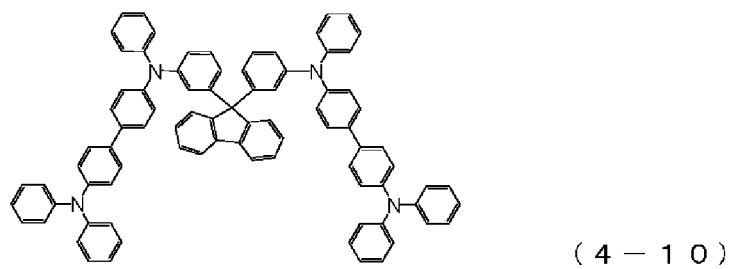
Figure 102:
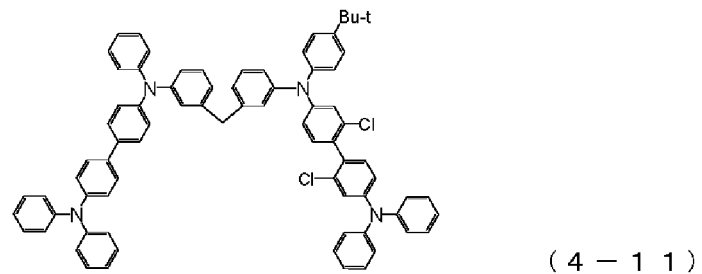
FIG. 102 is a drawing showing the structural formulas of Compound Nos. (4-11) to (4-15) among the triarylamine derivatives of the general formula (4).
Figure 102:
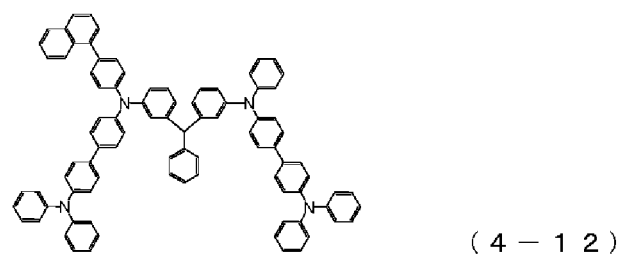
Figure 102:
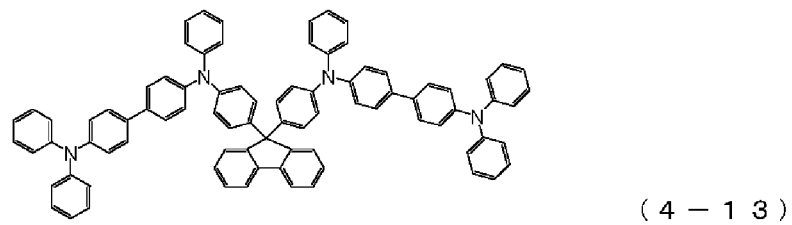
Figure 102:
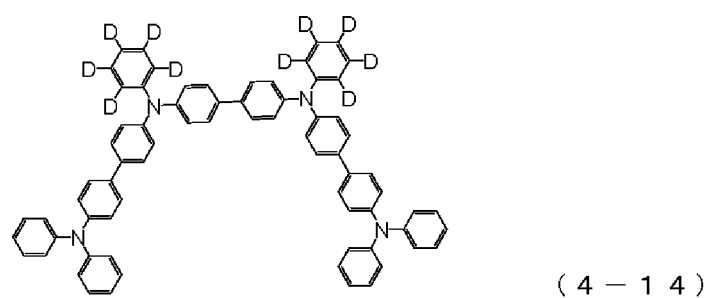
Figure 102:
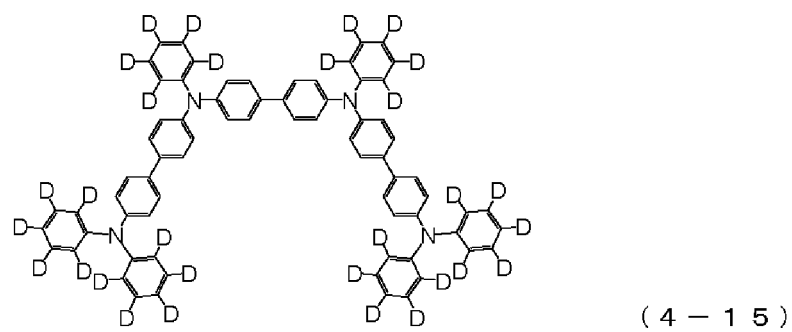
Figure 103:
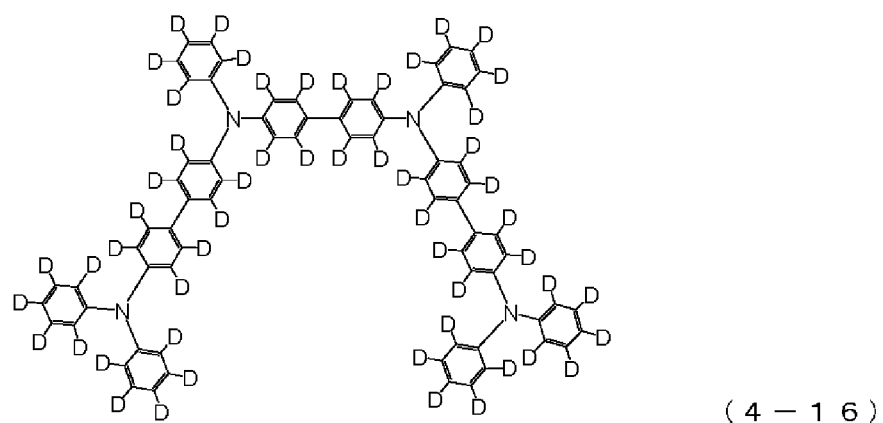
FIG. 103 is a drawing showing the structural formulas of Compound Nos. (4-16) to (4-17) among the triarylamine derivatives of the general formula (4).
Figure 103:
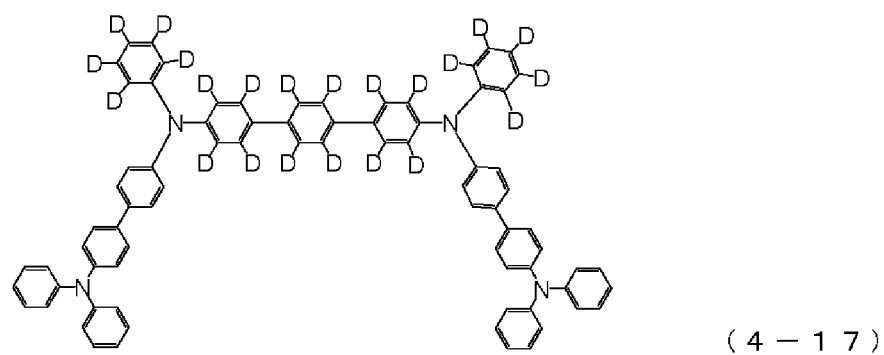

In connection with the white powder obtained above, its structure was identified using NMR. Its NMR chart is shown in FIG. 38.

In $^1$H-NMR (CDCl$_3$), the following signals of 39 hydrogens were detected:

$\delta$ (ppm) = 8.10 (1H)
7.87-7.96 (4H)
7.71-7.84 (6H)
7.22-7.60 (26H)

Example 38

The various arylamine compounds represented by the general formula (1), which were synthesized in the Examples, were measured for the glass transition point by a high sensitivity differential scanning calorimeter (DSC3100S, produced by Bruker AXS K.K.). The results are shown below.

The glass transition point is a parameter serving as an index to stability in a thin film state and heat resistance.

|  | Glass transition point |
|---|---|
| Compound (1-2): Example 2 | 103° C. |
| Compound (1-3): Example 3 | 115° C. |
| Compound (1-94): Example 4 | 101° C. |
| Compound (1-129): Example 5 | 112° C. |
| Compound (1-4): Example 6 | 104° C. |
| Compound (1-9): Example 7 | 117° C. |
| Compound (1-56): Example 8 | 116° C. |
| Compound (1-68): Example 9 | 116° C. |
| Compound (1-90): Example 10 | 106° C. |
| Compound (1-134): Example 12 | 109° C. |
| Compound (1-135): Example 13 | 121° C. |
| Compound (1-136): Example 14 | 117° C. |
| Compound (1-137): Example 15 | 120° C. |
| Compound (1-138): Example 16 | 125° C. |
| Compound (1-139): Example 17 | 107° C. |
| Compound (1-140): Example 18 | 110° C. |
| Compound (1-141): Example 19 | 112° C. |
| Compound (1-142): Example 20 | 119° C. |
| Compound (1-147): Example 25 | 111° C. |
| Compound (1-148): Example 26 | 119° C. |
| Compound (1-149): Example 27 | 107° C. |
| Compound (1-150): Example 28 | 110° C. |
| Compound (1-151): Example 29 | 114° C. |
| Compound (1-153): Example 31 | 108° C. |
| Compound (1-154): Example 32 | 122° C. |
| Compound (1-155): Example 33 | 119° C. |
| Compound (1-156): Example 34 | 109° C. |
| Compound (1-157): Example 35 | 122° C. |
| Compound (1-158): Example 36 | 112° C. |
| Compound (1-159): Example 37 | 116° C. |

The above results show that the arylamine compounds represented by the general formula (1) have a glass transition point of 100° C. or higher, demonstrating that they are stable in a thin film state.

Example 39

In connection with each of the various arylamine compounds represented by the general formula (1), which were synthesized in the Examples, a vapor deposited film with a film thickness of 100 nm was prepared on an ITO substrate, and its work function was measured using an ionization potential measuring device (PYS-202, produced by Sumitomo Heavy Industries, Ltd.). The results are shown below.

The work function is a parameter serving as an index to hole transport properties.

|  | Work function |
|---|---|
| Compound (1-1): Example 1 | 5.68 eV |
| Compound (1-2): Example 2 | 5.72 eV |
| Compound (1-3): Example 3 | 5.66 eV |
| Compound (1-94): Example 4 | 5.72 eV |
| Compound (1-129): Example 5 | 5.75 eV |
| Compound (1-4): Example 6 | 5.67 eV |
| Compound (1-9): Example 7 | 5.70 eV |
| Compound (1-56): Example 8 | 5.62 eV |
| Compound (1-68): Example 9 | 5.66 eV |
| Compound (1-90): Example 10 | 5.71 eV |
| Compound (1-92): Example 11 | 5.70 eV |
| Compound (1-134): Example 12 | 5.71 eV |
| Compound (1-135): Example 13 | 5.71 eV |
| Compound (1-136): Example 14 | 5.72 eV |
| Compound (1-137): Example 15 | 5.72 eV |
| Compound (1-138): Example 16 | 5.73 eV |
| Compound (1-139): Example 17 | 5.73 eV |
| Compound (1-140): Example 18 | 5.69 eV |
| Compound (1-141): Example 19 | 5.70 eV |
| Compound (1-142): Example 20 | 5.71 eV |
| Compound (1-143): Example 21 | 5.66 eV |
| Compound (1-144): Example 22 | 5.67 eV |
| Compound (1-145): Example 23 | 5.68 eV |
| Compound (1-146): Example 24 | 5.67 eV |
| Compound (1-147): Example 25 | 5.72 eV |
| Compound (1-148): Example 26 | 5.70 eV |
| Compound (1-149): Example 27 | 5.71 eV |
| Compound (1-150): Example 28 | 5.72 eV |
| Compound (1-151): Example 29 | 5.55 eV |
| Compound (1-152): Example 30 | 5.61 eV |
| Compound (1-153): Example 31 | 5.62 eV |
| Compound (1-154): Example 32 | 5.62 eV |
| Compound (1-155): Example 33 | 5.63 eV |
| Compound (1-156): Example 34 | 5.62 eV |
| Compound (1-157): Example 35 | 5.63 eV |

-continued

|  | Work function |
|---|---|
| Compound (1-158): Example 36 | 5.64 eV |
| Compound (1-159): Example 37 | 5.69 eV |

The above results demonstrate that the arylamine compounds represented by the general formula (1) show a suitable energy level as compared with a work function of 5.4 eV which an ordinary hole transport material such as NPD or TPD has. Thus, these compounds are found to have satisfactory hole transport capability.

Example 40

An organic EL device of the structure shown in FIG. 1, namely, an organic EL device having a transparent anode (ITO electrode) 2, a hole injection layer 3, a first hole transport layer 4, a second hole transport layer 5, a luminous layer 6, an electron transport layer 7, an electron injection layer 8, and a cathode (aluminum electrode) 9 formed on a transparent substrate (glass substrate) 1, was prepared by vapor deposition in accordance with the procedure described below.

First of all, an ITO-equipped glass substrate comprising an ITO electrode (transparent anode 2) with a film thickness of 150 nm formed on a glass substrate (transparent substrate 1) was provided.

This glass substrate 1 was ultrasonically cleaned for 20 minutes in isopropyl alcohol, and then dried for 10 minutes on a hot plate heated to 200° C. Then, the glass substrate with ITO was subjected to UV/ozone treatment for 15 minutes. Then, the ITO-equipped glass substrate was mounted within a vacuum deposition machine, and the pressure was reduced to 0.001 Pa or lower.

Then, a film of a compound (HIM-1) represented by the following structural formula, was formed in a film thickness of 5 nm as the hole injection layer 3 so as to cover the transparent anode 2.

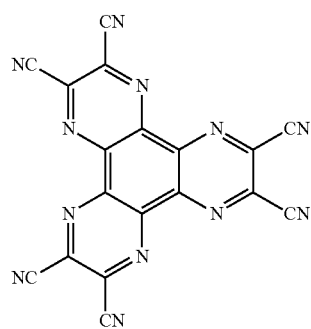
(HIM-1)

On the hole injection layer 3, the arylamine compound (3-1) having two triarylamine skeletons in the molecule of the following structural formula was formed in a film thickness of 60 nm as the first hole transport layer 4.

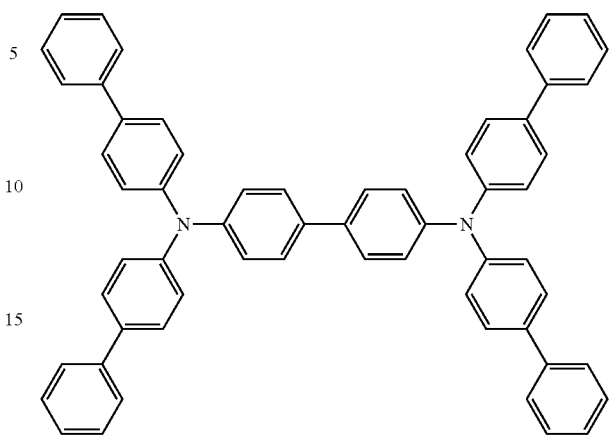
(3-1)

On the so formed first hole transport layer 4, the arylamine compound (1-1) synthesized in Example 1 was formed in a film thickness of 5 nm as the second hole transport layer 5.

On the second hole transport layer 5, a pyrene derivative (EMD-1) of the following structural formula and an anthracene derivative (EMH-1) of the following structural formula were binary vapor deposited at such vapor deposition rates that the vapor deposition rate ratio was EMD-1:EMH-1=5:95, whereby the luminous layer 6 was formed in a film thickness of 20 nm.

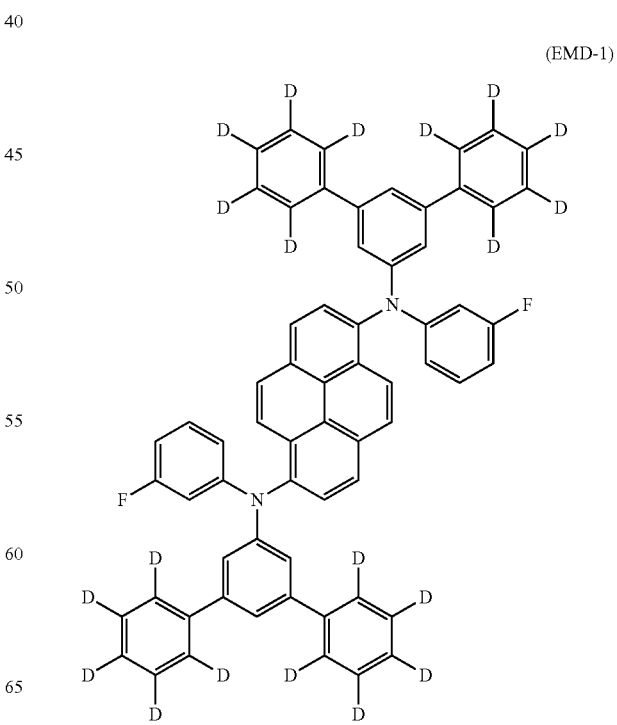
(EMD-1)

-continued

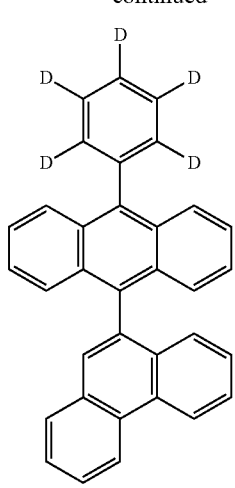

(EMH-1)

On this luminous layer 6, an anthracene derivative (2a-1) of the following structural formula and a compound (ETM-1) of the following structural formula were binary vapor deposited at such vapor deposition rates that the vapor deposition rate ratio was the 2a-1:ETM-1=50:50, whereby the electron transport layer 7 was formed in a film thickness of 30 nm.

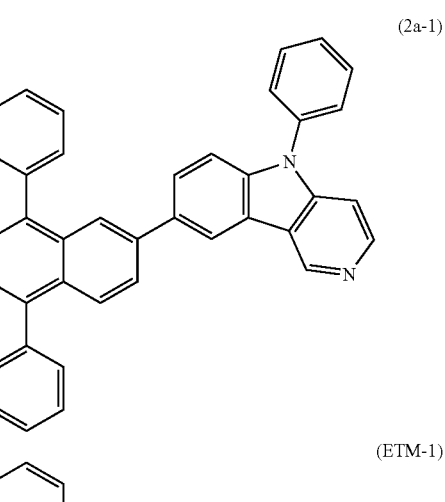

(2a-1)

(ETM-1)

On the electron transport layer 7, a film of lithium fluoride was formed in a film thickness of 1 nm as the electron injection layer 8.

Finally, aluminum was vapor deposited to a film thickness of 100 nm to form the cathode 9.

The so prepared organic EL device was measured for the properties at normal temperature in the atmosphere. The layer configuration of the resulting organic EL device is shown in Table 1, and the results of the measurements of the light emission characteristics when a direct current voltage was applied are summarized in Table 4.

Among the properties measured, the device service life was measured as the period of time until the emission luminance attenuated to 1900 cd/m$^2$ (corresponding to 95%, with the initial luminance taken as 100%: 95% attenuation) when constant current driving was performed, with the emission luminance at the start of light emission (initial luminance) being set at 2000 cd/m$^2$.

Example 41

An organic EL device was prepared in the same manner as in Example 40, except that the compound (1-4) synthesized in Example 6 was used instead of the compound (1-1) to form the second hole transport layer 5 with a film thickness of 5 nm. The so prepared organic EL device was measured for the properties at normal temperature in the atmosphere. The layer configuration of the resulting organic EL device is shown in Table 1, and the results of the measurement of the light emission characteristics when a direct current voltage was applied are summarized in Table 4.

Example 42

An organic EL device was prepared in the same manner as in Example 40, except that the compound (1-9) synthesized in Example 7 was used instead of the compound (1-1) to form the second hole transport layer 5 with a film thickness of 5 nm.

The so prepared organic EL device was measured for the properties at normal temperature in the atmosphere. The layer configuration of the resulting organic EL device is shown in Table 1, and the results of the measurement of the light emission characteristics when a direct current voltage was applied are summarized in Table 4.

Example 43

An organic EL device was prepared in the same manner as in Example 40, except that the compound (1-56) synthesized in Example 8 was used instead of the compound (1-1) to form the second hole transport layer 5 with a film thickness of 5 nm.

The so prepared organic EL device was measured for the properties at normal temperature in the atmosphere. The layer configuration of the resulting organic EL device is shown in Table 1, and the results of the measurement of the light emission characteristics when a direct current voltage was applied are summarized in Table 4.

Example 44

An organic EL device was prepared in the same manner as in Example 40, except that the compound (1-68) synthesized in Example 9 was used instead of the compound (1-1) to form the second hole transport layer 5 with a film thickness of 5 nm.

The so prepared organic EL device was measured for the properties at normal temperature in the atmosphere. The layer configuration of the resulting organic EL device is shown in Table 1, and the results of the measurement of the light emission characteristics when a direct current voltage was applied are summarized in Table 4.

Example 45

An organic EL device was prepared in the same manner as in Example 40, except that the compound (1-90) synthesized in Example 10 was used instead of the compound (1-1) to form the second hole transport layer 5 with a film thickness of 5 nm.

The so prepared organic EL device was measured for the properties at normal temperature in the atmosphere. The layer configuration of the resulting organic EL device is shown in Table 1, and the results of the measurement of the light emission characteristics when a direct current voltage was applied are summarized in Table 4.

Example 46

An organic EL device was prepared in the same manner as in Example 40, except that the compound (1-92) synthesized in Example 11 was used instead of the compound (1-1) to form the second hole transport layer 5 with a film thickness of 5 nm.

The so prepared organic EL device was measured for the properties at normal temperature in the atmosphere. The layer configuration of the resulting organic EL device is shown in Table 1, and the results of the measurement of the light emission characteristics when a direct current voltage was applied are summarized in Table 4.

Example 47

An organic EL device was prepared in the same manner as in Example 40, except that the compound (1-134) synthesized in Example 12 was used instead of the compound (1-1) to form the second hole transport layer 5 with a film thickness of 5 nm.

The so prepared organic EL device was measured for the properties at normal temperature in the atmosphere. The layer configuration of the resulting organic EL device is shown in Table 1, and the results of the measurement of the light emission characteristics when a direct current voltage was applied are summarized in Table 4.

Example 48

An organic EL device was prepared in the same manner as in Example 40, except that the compound (1-135) synthesized in Example 13 was used instead of the compound (1-1) to form the second hole transport layer 5 with a film thickness of 5 nm.

The so prepared organic EL device was measured for the properties at normal temperature in the atmosphere. The layer configuration of the resulting organic EL device is shown in Table 1, and the results of the measurement of the light emission characteristics when a direct current voltage was applied are summarized in Table 4.

Example 49

An organic EL device was prepared in the same manner as in Example 40, except that the compound (1-136) synthesized in Example 14 was used instead of the compound (1-1) to form the second hole transport layer 5 with a film thickness of 5 nm.

The so prepared organic EL device was measured for the properties at normal temperature in the atmosphere. The layer configuration of the resulting organic EL device is shown in Table 1, and the results of the measurement of the light emission characteristics when a direct current voltage was applied are summarized in Table 4.

Example 50

An organic EL device was prepared in the same manner as in Example 40, except that the compound (1-137) synthesized in Example 15 was used instead of the compound (1-1) to form the second hole transport layer 5 with a film thickness of 5 nm.

The so prepared organic EL device was measured for the properties at normal temperature in the atmosphere. The layer configuration of the resulting organic EL device is shown in Table 1, and the results of the measurement of the light emission characteristics when a direct current voltage was applied are summarized in Table 4.

Example 51

An organic EL device was prepared in the same manner as in Example 40, except that the compound (1-138) synthesized in Example 16 was used instead of the compound (1-1) to form the second hole transport layer 5 with a film thickness of 5 nm.

The so prepared organic EL device was measured for the properties at normal temperature in the atmosphere. The layer configuration of the resulting organic EL device is shown in Table 1, and the results of the measurement of the light emission characteristics when a direct current voltage was applied are summarized in Table 4.

Example 52

An organic EL device was prepared in the same manner as in Example 40, except that the compound (1-139) synthesized in Example 17 was used instead of the compound (1-1) to form the second hole transport layer 5 with a film thickness of 5 nm.

The so prepared organic EL device was measured for the properties at normal temperature in the atmosphere. The layer configuration of the resulting organic EL device is shown in Table 1, and the results of the measurement of the light emission characteristics when a direct current voltage was applied are summarized in Table 4.

Example 53

An organic EL device was prepared in the same manner as in Example 40, except that the compound (1-140) synthesized in Example 18 was used instead of the compound (1-1) to form the second hole transport layer 5 with a film thickness of 5 nm.

The so prepared organic EL device was measured for the properties at normal temperature in the atmosphere. The layer configuration of the resulting organic EL device is shown in Table 1, and the results of the measurement of the light emission characteristics when a direct current voltage was applied are summarized in Table 4.

Example 54

An organic EL device was prepared in the same manner as in Example 40, except that the compound (1-141) synthesized in Example 19 was used instead of the compound (1-1) to form the second hole transport layer 5 with a film thickness of 5 nm.

The so prepared organic EL device was measured for the properties at normal temperature in the atmosphere. The layer configuration of the resulting organic EL device is shown in Table 1, and the results of the measurement of the light emission characteristics when a direct current voltage was applied are summarized in Table 4.

Example 55

An organic EL device was prepared in the same manner as in Example 40, except that the compound (1-142) syn-

Example 56

An organic EL device was prepared in the same manner as in Example 40, except that the compound (1-143) synthesized in Example 21 was used instead of the compound (1-1) to form the second hole transport layer 5 with a film thickness of 5 nm.

The so prepared organic EL device was measured for the properties at normal temperature in the atmosphere. The layer configuration of the resulting organic EL device is shown in Table 1, and the results of the measurement of the light emission characteristics when a direct current voltage was applied are summarized in Table 4.

Example 57

An organic EL device was prepared in the same manner as in Example 40, except that the compound (1-144) synthesized in Example 22 was used instead of the compound (1-1) to form the second hole transport layer 5 with a film thickness of 5 nm.

The so prepared organic EL device was measured for the properties at normal temperature in the atmosphere. The layer configuration of the resulting organic EL device is shown in Table 1, and the results of the measurement of the light emission characteristics when a direct current voltage was applied are summarized in Table 4.

Example 58

An organic EL device was prepared in the same manner as in Example 40, except that the compound (1-145) synthesized in Example 23 was used instead of the compound (1-1) to form the second hole transport layer 5 with a film thickness of 5 nm.

The so prepared organic EL device was measured for the properties at normal temperature in the atmosphere. The layer configuration of the resulting organic EL device is shown in Table 2, and the results of the measurement of the light emission characteristics when a direct current voltage was applied are summarized in Table 5.

Example 59

An organic EL device was prepared in the same manner as in Example 40, except that the compound (1-146) synthesized in Example 24 was used instead of the compound (1-1) to form the second hole transport layer 5 with a film thickness of 5 nm.

The so prepared organic EL device was measured for the properties at normal temperature in the atmosphere. The layer configuration of the resulting organic EL device is shown in Table 2, and the results of the measurement of the light emission characteristics when a direct current voltage was applied are summarized in Table 5.

Example 60

An organic EL device was prepared in the same manner as in Example 40, except that the compound (1-147) synthesized in Example 25 was used instead of the compound (1-1) to form the second hole transport layer 5 with a film thickness of 5 nm.

The so prepared organic EL device was measured for the properties at normal temperature in the atmosphere. The layer configuration of the resulting organic EL device is shown in Table 2, and the results of the measurement of the light emission characteristics when a direct current voltage was applied are summarized in Table 5.

Example 61

An organic EL device was prepared in the same manner as in Example 40, except that the compound (1-148) synthesized in Example 26 was used instead of the compound (1-1) to form the second hole transport layer 5 with a film thickness of 5 nm.

The so prepared organic EL device was measured for the properties at normal temperature in the atmosphere. The layer configuration of the resulting organic EL device is shown in Table 2, and the results of the measurement of the light emission characteristics when a direct current voltage was applied are summarized in Table 5.

Example 62

An organic EL device was prepared in the same manner as in Example 40, except that the compound (1-149) synthesized in Example 27 was used instead of the compound (1-1) to form the second hole transport layer 5 with a film thickness of 5 nm.

The so prepared organic EL device was measured for the properties at normal temperature in the atmosphere. The layer configuration of the resulting organic EL device is shown in Table 2, and the results of the measurement of the light emission characteristics when a direct current voltage was applied are summarized in Table 5.

Example 63

An organic EL device was prepared in the same manner as in Example 40, except that the compound (1-150) synthesized in Example 28 was used instead of the compound (1-1) to form the second hole transport layer 5 with a film thickness of 5 nm.

The so prepared organic EL device was measured for the properties at normal temperature in the atmosphere. The layer configuration of the resulting organic EL device is shown in Table 2, and the results of the measurement of the light emission characteristics when a direct current voltage was applied are summarized in Table 5.

Example 64

An organic EL device was prepared in the same manner as in Example 40, except that the compound (1-151) synthesized in Example 29 was used instead of the compound (1-1) to form the second hole transport layer 5 with a film thickness of 5 nm.

The so prepared organic EL device was measured for the properties at normal temperature in the atmosphere. The layer configuration of the resulting organic EL device is shown in Table 2, and the results of the measurement of the light emission characteristics when a direct current voltage was applied are summarized in Table 5.

Example 65

An organic EL device was prepared in the same manner as in Example 40, except that the compound (1-152) syn-

Example 66

An organic EL device was prepared in the same manner as in Example 40, except that the compound (1-153) synthesized in Example 31 was used instead of the compound (1-1) to form the second hole transport layer 5 with a film thickness of 5 nm.

The so prepared organic EL device was measured for the properties at normal temperature in the atmosphere. The layer configuration of the resulting organic EL device is shown in Table 2, and the results of the measurement of the light emission characteristics when a direct current voltage was applied are summarized in Table 5.

Example 67

An organic EL device was prepared in the same manner as in Example 40, except that the compound (1-154) synthesized in Example 32 was used instead of the compound (1-1) to form the second hole transport layer 5 with a film thickness of 5 nm.

The so prepared organic EL device was measured for the properties at normal temperature in the atmosphere. The layer configuration of the resulting organic EL device is shown in Table 2, and the results of the measurement of the light emission characteristics when a direct current voltage was applied are summarized in Table 5.

Example 68

An organic EL device was prepared in the same manner as in Example 40, except that the compound (1-155) synthesized in Example 33 was used instead of the compound (1-1) to form the second hole transport layer 5 with a film thickness of 5 nm.

The so prepared organic EL device was measured for the properties at normal temperature in the atmosphere. The layer configuration of the resulting organic EL device is shown in Table 2, and the results of the measurement of the light emission characteristics when a direct current voltage was applied are summarized in Table 5.

Example 69

An organic EL device was prepared in the same manner as in Example 40, except that the compound (1-156) synthesized in Example 34 was used instead of the compound (1-1) to form the second hole transport layer 5 with a film thickness of 5 nm.

The so prepared organic EL device was measured for the properties at normal temperature in the atmosphere. The layer configuration of the resulting organic EL device is shown in Table 2, and the results of the measurement of the light emission characteristics when a direct current voltage was applied are summarized in Table 5.

Example 70

An organic EL device was prepared in the same manner as in Example 40, except that the compound (1-157) synthesized in Example 35 was used instead of the compound (1-1) to form the second hole transport layer 5 with a film thickness of 5 nm.

The so prepared organic EL device was measured for the properties at normal temperature in the atmosphere. The layer configuration of the resulting organic EL device is shown in Table 2, and the results of the measurement of the light emission characteristics when a direct current voltage was applied are summarized in Table 5.

Example 71

An organic EL device was prepared in the same manner as in Example 40, except that the compound (1-158) synthesized in Example 36 was used instead of the compound (1-1) to form the second hole transport layer 5 with a film thickness of 5 nm. The so prepared organic EL device was measured for the properties at normal temperature in the atmosphere. The layer configuration of the resulting organic EL device is shown in Table 2, and the results of the measurement of the light emission characteristics when a direct current voltage was applied are summarized in Table 5.

Example 72

An organic EL device was prepared in the same manner as in Example 40, except that the compound (1-159) synthesized in Example 37 was used instead of the compound (1-1) to form the second hole transport layer 5 with a film thickness of 5 nm.

The so prepared organic EL device was measured for the properties at normal temperature in the atmosphere. The layer configuration of the resulting organic EL device is shown in Table 2, and the results of the measurement of the light emission characteristics when a direct current voltage was applied are summarized in Table 5.

Example 73

An organic EL device was prepared in the same manner as in Example 40, except that an anthracene derivative (2c-23) of the following structural formula was used instead of the anthracene derivative (2a-1), and this anthracene derivative (2c-23) and the compound (ETM-1) were binary vapor deposited at such vapor deposition rates that the vapor deposition rate ratio was (2c-23):(ETM-1)=50:50, whereby the electron transport layer 7 with a film thickness of 30 nm was formed.

(2c-23)

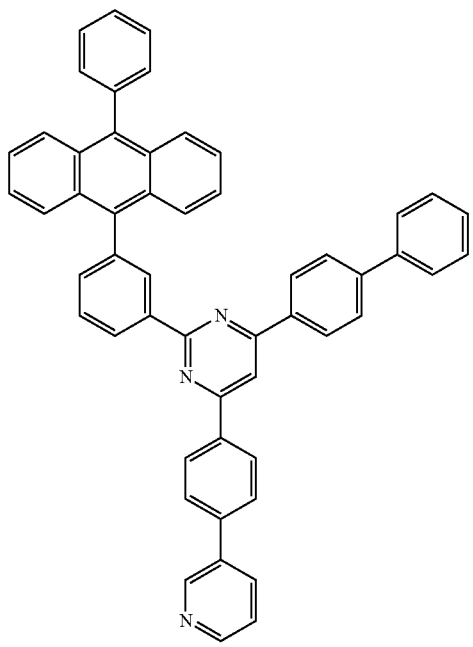

The so prepared organic EL device was measured for the properties at normal temperature in the atmosphere. The layer configuration of the resulting organic EL device is shown in Table 2, and the results of the measurement of the light emission characteristics when a direct current voltage was applied are summarized in Table 5.

Example 74

An organic EL device was prepared in the same manner as in Example 73, except that the compound (1-4) synthesized in Example 6 was used instead of the compound (1-1) to form the second hole transport layer 5 with a film thickness of 5 nm.

The so prepared organic EL device was measured for the properties at normal temperature in the atmosphere. The layer configuration of the resulting organic EL device is shown in Table 2, and the results of the measurement of the light emission characteristics when a direct current voltage was applied are summarized in Table 5.

Example 75

An organic EL device was prepared in the same manner as in Example 73, except that the compound (1-9) synthesized in Example 7 was used instead of the compound (1-1) to form the second hole transport layer 5 with a film thickness of 5 nm.

The so prepared organic EL device was measured for the properties at normal temperature in the atmosphere. The layer configuration of the resulting organic EL device is shown in Table 2, and the results of the measurement of the light emission characteristics when a direct current voltage was applied are summarized in Table 5.

Comparative Example 1

An organic EL device was prepared in the same manner as in Example 40, except that the arylamine compound (3-1) having two triphenylamine structures in the molecule was used instead of the compound (1-1) to form the second hole transport layer 5 with a film thickness of 5 nm.

In this case, the first hole transport layer 4 and the second hole transport layer 5 function as an integral hole transport layer (thickness 65 nm).

The so prepared organic EL device was measured for the properties at normal temperature in the atmosphere. The layer configuration of the resulting organic EL device is shown in Table 3, and the results of the measurement of the light emission characteristics when a direct current voltage was applied are summarized in Table 6.

Comparative Example 2

An organic EL device was prepared in the same manner as in Example 40, except that the compound (HTM-1) of the following structural formula was used instead of the compound (1-1) to form the second hole transport layer 5 with a film thickness of 5 nm.

(HTM-1)

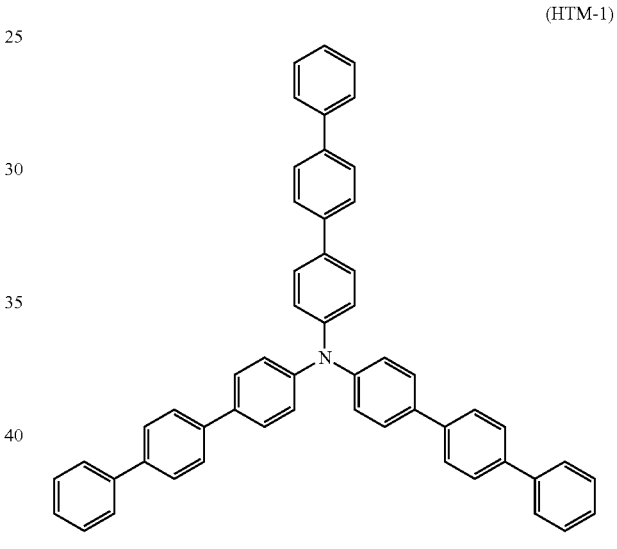

The so prepared organic EL device was measured for the properties at normal temperature in the atmosphere. The layer configuration of the resulting organic EL device is shown in Table 3, and the results of the measurement of the light emission characteristics when a direct current voltage was applied are summarized in Table 6.

Comparative Example 3

An organic EL device was prepared in the same manner as in Example 40, except that an arylamine compound (HTM-2) of the following structural formula was used instead of the above arylamine compound (3-1) to form the first hole transport layer 4 with a film thickness of 60 nm, and the above arylamine compound (HTM-2) was used instead of the compound (1-1) to form the second hole transport layer 5 with a film thickness of 5 nm.

In this case, the first hole transport layer 4 and the second hole transport layer 5 function as an integral hole transport layer (thickness 65 nm).

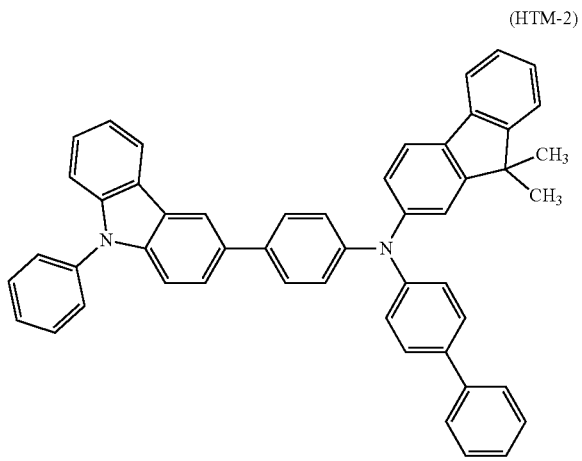 [SMILES: CC1(C)c2ccccc2-c2ccc(N(c3ccc(-c4ccccc4)cc3)c3ccc(-c4ccc5c(c4)c4ccccc4n5-c4ccccc4)cc3)cc21]
(HTM-2)

The so prepared organic EL device was measured for the properties at normal temperature in the atmosphere. The layer configuration of the resulting organic EL device is shown in Table 3, and the results of the measurement of the light emission characteristics when a direct current voltage was applied are summarized in Table 6.

Comparative Example 4

An organic EL device was prepared in the same manner as in Example 73, except that the above arylamine compound (HTM-2) was used instead of the compound (1-1) to form the second hole transport layer 4 with a film thickness of 5 nm.

In this case, the first hole transport layer 4 and the second hole transport layer 5 function as an integral hole transport layer (thickness 65 nm).

The so prepared organic EL device was measured for the properties at normal temperature in the atmosphere. The layer configuration of the resulting organic EL device is shown in Table 3, and the results of the measurement of the light emission characteristics when a direct current voltage was applied are summarized in Table 6.

TABLE 1

|        | First hole transport layer | Second hole transport layer | Luminous layer | Electron transport layer |
|--------|----------------------------|------------------------------|----------------|---------------------------|
| Ex. 40 | Compound 3-1 | Compound 1-1   | EMD-1/EMH-1 | Compound 2a-1/ETM-1 |
| Ex. 41 | Compound 3-1 | Compound 1-4   | EMD-1/EMH-1 | Compound 2a-1/ETM-1 |
| Ex. 42 | Compound 3-1 | Compound 1-9   | EMD-1/EMH-1 | Compound 2a-1/ETM-1 |
| Ex. 43 | Compound 3-1 | Compound 1-56  | EMD-1/EMH-1 | Compound 2a-1/ETM-1 |
| Ex. 44 | Compound 3-1 | Compound 1-68  | EMD-1/EMH-1 | Compound 2a-1/ETM-1 |
| Ex. 45 | Compound 3-1 | Compound 1-90  | EMD-1/EMH-1 | Compound 2a-1/ETM-1 |
| Ex. 46 | Compound 3-1 | Compound 1-92  | EMD-1/EMH-1 | Compound 2a-1/ETM-1 |
| Ex. 47 | Compound 3-1 | Compound 1-134 | EMD-1/EMH-1 | Compound 2a-1/ETM-1 |
| Ex. 48 | Compound 3-1 | Compound 1-135 | EMD-1/EMH-1 | Compound 2a-1/ETM-1 |
| Ex. 49 | Compound 3-1 | Compound 1-136 | EMD-1/EMH-1 | Compound 2a-1/ETM-1 |
| Ex. 50 | Compound 3-1 | Compound 1-137 | EMD-1/EMH-1 | Compound 2a-1/ETM-1 |
| Ex. 51 | Compound 3-1 | Compound 1-138 | EMD-1/EMH-1 | Compound 2a-1/ETM-1 |
| Ex. 52 | Compound 3-1 | Compound 1-139 | EMD-1/EMH-1 | Compound 2a-1/ETM-1 |
| Ex. 53 | Compound 3-1 | Compound 1-140 | EMD-1/EMH-1 | Compound 2a-1/ETM-1 |
| Ex. 54 | Compound 3-1 | Compound 1-141 | EMD-1/EMH-1 | Compound 2a-1/ETM-1 |
| Ex. 55 | Compound 3-1 | Compound 1-142 | EMD-1/EMH-1 | Compound 2a-1/ETM-1 |
| Ex. 56 | Compound 3-1 | Compound 1-143 | EMD-1/EMH-1 | Compound 2a-1/ETM-1 |
| Ex. 57 | Compound 3-1 | Compound 1-144 | EMD-1/EMH-1 | Compound 2a-1/ETM-1 |

TABLE 2

|        | First hole transport layer | Second hole transport layer | Luminous layer | Electron transport layer |
|--------|----------------------------|------------------------------|----------------|---------------------------|
| Ex. 58 | Compound 3-1 | Compound 1-145 | EMD-1/EMH-1 | Compound 2a-1/ETM-1 |
| Ex. 59 | Compound 3-1 | Compound 1-146 | EMD-1/EMH-1 | Compound 2a-1/ETM-1 |
| Ex. 60 | Compound 3-1 | Compound 1-147 | EMD-1/EMH-1 | Compound 2a-1/ETM-1 |
| Ex. 61 | Compound 3-1 | Compound 1-148 | EMD-1/EMH-1 | Compound 2a-1/ETM-1 |
| Ex. 62 | Compound 3-1 | Compound 1-149 | EMD-1/EMH-1 | Compound 2a-1/ETM-1 |
| Ex. 63 | Compound 3-1 | Compound 1-150 | EMD-1/EMH-1 | Compound 2a-1/ETM-1 |
| Ex. 64 | Compound 3-1 | Compound 1-151 | EMD-1/EMH-1 | Compound 2a-1/ETM-1 |
| Ex. 65 | Compound 3-1 | Compound 1-152 | EMD-1/EMH-1 | Compound 2a-1/ETM-1 |
| Ex. 66 | Compound 3-1 | Compound 1-153 | EMD-1/EMH-1 | Compound 2a-1/ETM-1 |
| Ex. 67 | Compound 3-1 | Compound 1-154 | EMD-1/EMH-1 | Compound 2a-1/ETM-1 |
| Ex. 68 | Compound 3-1 | Compound 1-155 | EMD-1/EMH-1 | Compound 2a-1/ETM-1 |
| Ex. 69 | Compound 3-1 | Compound 1-156 | EMD-1/EMH-1 | Compound 2a-1/ETM-1 |
| Ex. 70 | Compound 3-1 | Compound 1-157 | EMD-1/EMH-1 | Compound 2a-1/ETM-1 |
| Ex. 71 | Compound 3-1 | Compound 1-158 | EMD-1/EMH-1 | Compound 2a-1/ETM-1 |
| Ex. 72 | Compound 3-1 | Compound 1-159 | EMD-1/EMH-1 | Compound 2a-1/ETM-1 |
| Ex. 73 | Compound 3-1 | Compound 1-1   | EMD-1/EMH-1 | Compound 2c-23/ETM-1 |
| Ex. 74 | Compound 3-1 | Compound 1-4   | EMD-1/EMH-1 | Compound 2c-23/ETM-1 |
| Ex. 75 | Compound 3-1 | Compound 1-9   | EMD-1/EMH-1 | Compound 2c-23/ETM-1 |

TABLE 3

|  | First hole transport layer | Second hole transport layer | Luminous layer | Electron transport layer |
|---|---|---|---|---|
| Comp. Ex. 1 | Compound 3-1 | Compound 3-1 | EMD-1/EMH-1 | Compound 2a-1/ETM-1 |
| Comp. Ex. 2 | Compound 3-1 | HTM-1 | EMD-1/EMH-1 | Compound 2a-1/ETM-1 |
| Comp. Ex. 3 | HTM-2 | HTM-2 | EMD-1/EMH-1 | Compound 2a-1/ETM-1 |
| Comp. Ex. 4 | Compound 3-1 | Compound 3-1 | EMD-1/EMH-1 | Compound 2c-23/ETM-1 |

TABLE 4

|  | *1 | *2 | *3 | *4 | *5 |
|---|---|---|---|---|---|
| Ex. 40 | 3.90 | 748 | 7.47 | 6.01 | 162 |
| Ex. 41 | 3.93 | 794 | 7.93 | 6.34 | 205 |
| Ex. 42 | 4.01 | 801 | 8.01 | 6.28 | 184 |
| Ex. 43 | 3.90 | 800 | 8.00 | 6.45 | 125 |
| Ex. 44 | 3.99 | 826 | 8.26 | 6.50 | 134 |
| Ex. 45 | 3.92 | 822 | 8.21 | 6.59 | 133 |
| Ex. 46 | 3.93 | 801 | 8.00 | 6.40 | 178 |
| Ex. 47 | 3.96 | 861 | 8.61 | 6.83 | 158 |
| Ex. 48 | 3.99 | 840 | 8.41 | 6.63 | 162 |
| Ex. 49 | 3.96 | 865 | 8.66 | 6.87 | 150 |
| Ex. 50 | 3.98 | 871 | 8.71 | 6.87 | 135 |
| Ex. 51 | 3.97 | 838 | 8.40 | 6.64 | 135 |
| Ex. 52 | 4.00 | 834 | 8.33 | 6.54 | 130 |
| Ex. 53 | 3.96 | 817 | 8.18 | 6.48 | 229 |
| Ex. 54 | 3.93 | 831 | 8.30 | 6.64 | 216 |
| Ex. 55 | 3.92 | 841 | 8.41 | 6.75 | 173 |
| Ex. 56 | 3.99 | 813 | 8.13 | 6.40 | 174 |
| Ex. 57 | 3.94 | 819 | 8.18 | 6.53 | 222 |

*1: Voltage [V] (@10 mA/cm$^2$)
*2: Luminance [cd/m$^2$] (@10 mA/cm$^2$)
*3: Luminous efficiency [cd/A] (@10 mA/cm$^2$)
*4: Power efficiency [lm/W] (@10 mA/cm$^2$)
*5: Device lifetime 95% attenuation (hrs)

TABLE 5

|  | *1 | *2 | *3 | *4 | *5 |
|---|---|---|---|---|---|
| Ex. 58 | 3.93 | 830 | 8.29 | 6.64 | 205 |
| Ex. 59 | 3.93 | 844 | 8.43 | 6.75 | 153 |
| Ex. 60 | 3.92 | 833 | 8.33 | 6.68 | 145 |
| Ex. 61 | 3.92 | 855 | 8.55 | 6.86 | 115 |
| Ex. 62 | 3.98 | 883 | 8.83 | 6.97 | 116 |
| Ex. 63 | 3.94 | 880 | 8.82 | 7.04 | 142 |
| Ex. 64 | 3.90 | 820 | 8.21 | 6.65 | 123 |
| Ex. 65 | 3.98 | 826 | 8.26 | 6.52 | 136 |
| Ex. 66 | 3.97 | 834 | 8.34 | 6.60 | 153 |
| Ex. 67 | 3.95 | 841 | 8.41 | 6.70 | 154 |
| Ex. 68 | 3.93 | 866 | 8.66 | 6.93 | 153 |
| Ex. 69 | 3.91 | 848 | 8.48 | 6.81 | 130 |
| Ex. 70 | 3.92 | 865 | 8.64 | 6.92 | 124 |
| Ex. 71 | 3.96 | 861 | 8.61 | 6.83 | 125 |
| Ex. 72 | 3.92 | 850 | 8.50 | 6.82 | 158 |
| Ex. 73 | 3.91 | 822 | 8.22 | 6.61 | 196 |
| Ex. 74 | 3.92 | 865 | 8.64 | 6.91 | 227 |
| Ex. 75 | 3.99 | 857 | 8.57 | 6.72 | 214 |

*1: Voltage [V] (@10 mA/cm$^2$)
*2: Luminance [cd/m$^2$] (@10 mA/cm$^2$)
*3: Luminous efficiency [cd/A] (@10 mA/cm$^2$)
*4: Power efficiency [lm/W] (@10 mA/cm$^2$)
*5: Device lifetime 95% attenuation (hrs)

TABLE 6

|  | *1 | *2 | *3 | *4 | *5 |
|---|---|---|---|---|---|
| Comp. Ex. 1 | 3.88 | 688 | 6.89 | 5.60 | 59 |
| Comp. Ex. 2 | 3.92 | 722 | 7.21 | 5.79 | 54 |
| Comp. Ex. 3 | 3.97 | 654 | 6.51 | 5.37 | 67 |
| Comp. Ex. 4 | 3.85 | 695 | 6.96 | 5.68 | 78 |

*1: Voltage [V] (@10 mA/cm$^2$)
*2: Luminance [cd/m$^2$] (@10 mA/cm$^2$)
*3: Luminous efficiency [cd/A] (@10 mA/cm$^2$)
*4: Power efficiency [lm/W] (@10 mA/cm$^2$)
*5: Device lifetime 95% attenuation (hrs)

As will be understood from the above experimental results, shown in Tables 1 to 6, the luminous efficiency when an electric current was flowed at a current density of 10 mA/cm$^2$ showed values of 6.51 to 7.21 cd/A in the organic EL devices of Comparative Examples 1 to 4, but showed high values of 7.47 to 8.83 cd/A in all of the organic EL devices of Examples 40 to 75.

The power efficiency was 5.37 to 5.79 lm/W in Comparative Examples 1 to 4, while this parameter was as high as 6.01 to 7.04 lm/W in all of Examples 40 to 75.

Service life of the device (95% attenuation) was 54 to 78 hours in Comparative Examples 1 to 4, but was 115 to 229 hours in Examples 40 to 75, showing much longer service life.

INDUSTRIAL APPLICABILITY

The organic EL devices of the present invention using the arylamine compound having the specific structure represented by the general formula (1) is increased in luminous efficiency, can improve durability, and can be put to uses such as domestic electrical appliances and illumination.

EXPLANATIONS OF LETTERS OR NUMERALS

1: Transparent substrate
2: Transparent electrode (anode)
3: Hole injection layer
4: First hole transport layer
5: Second hole transport layer
6: Luminous layer
7: Electron Transport layer
8: Electron injection layer
9: Cathode

The invention claimed is:

1. An organic electroluminescent device having an anode, a hole transport layer, a luminous layer, an electron transport layer, and a cathode in this order, wherein the hole transport layer contains an arylamine compound represented by the following formula (1):

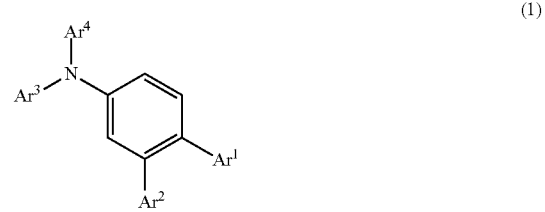

(1)

where

Ar¹ represents an unsubstituted phenyl group, an unsubstituted biphenylyl group, an unsubstituted terphenylyl group, or a phenyl group having a naphthyl group as a substituent;

Ar² represents an unsubstituted phenyl group an unsubstituted biphenylyl group; and Ar³ and Ar⁴ each represents an unsubstituted biphenylyl group, an unsubstituted terphenylyl group, a phenyl group having a naphthyl group or a fluorenyl group as a substituent, or a fluorenyl group having a methyl group or a phenyl group as a substituent.

2. The organic electroluminescent device according to claim 1, wherein the electron transport layer contains an anthracene derivative represented by the following formula (2):

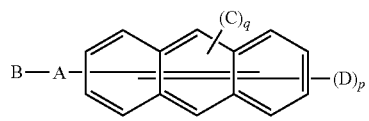

(2)

where

A represents a divalent aromatic hydrocarbon group, a divalent aromatic heterocyclic group, or a single bond, B represents a monovalent aromatic heterocyclic group, C represents a monovalent aromatic hydrocarbon group or a monovalent aromatic heterocyclic group, D represents a hydrogen atom, a deuterium atom, a fluorine atom, a chlorine atom, a cyano group, or an alkyl group having 1 to 6 carbon atoms, and p and q are such that p denotes an integer of 7 or 8, and q denotes an integer of 1 or 2, provided that p and q total 9.

3. The organic electroluminescent device according to claim 2, wherein the anthracene derivative is represented by the following formula (2a):

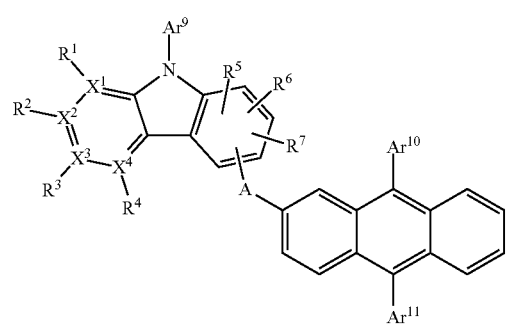

(2a)

where

A is as defined in the formula (2),

Ar⁹, Ar¹⁰, and Ar¹¹ each represents a monovalent aromatic hydrocarbon group or a monovalent aromatic heterocyclic group, $R^1$ to $R^7$ each represents a hydrogen atom, a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, a monovalent aromatic hydrocarbon group, a monovalent aromatic heterocyclic group, or an aryloxy group, and these groups may bind to each other via a single bond, a methylene group optionally having a substituent, an oxygen atom, or a sulfur atom to form a ring, and $X^1$, $X^2$, $X^3$, and $X^4$ each represents a carbon atom or a nitrogen atom, provided that only one of $X^1$, $X^2$, $X^3$, and $X^4$ represents a nitrogen atom, and any of $R^1$ to $R^4$, including a hydrogen atom, does not bind to the nitrogen atom.

4. The organic electroluminescent device according to claim 2, wherein the anthracene derivative is represented by the following formula (2b):

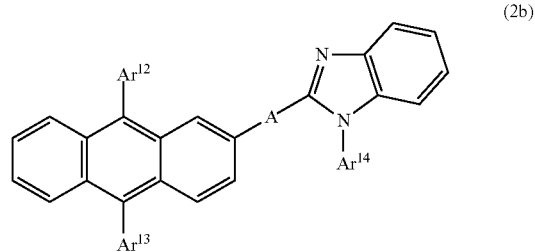

(2b)

where

A is as defined in the formula (2), and

Ar¹², Ar¹³, and Ar¹⁴ each represents a monovalent aromatic hydrocarbon group or a monovalent aromatic heterocyclic group.

5. The organic electroluminescent device according to claim 2, wherein the anthracene derivative is represented by the following formula (2c):

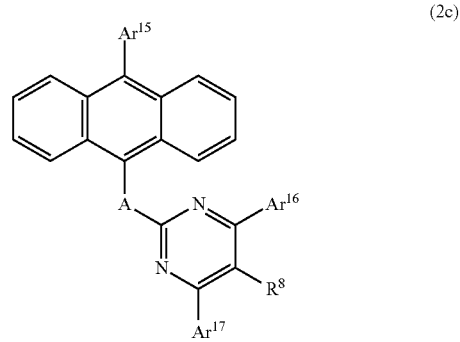

(2c)

where

A is as defined in the formula (2), $Ar^{15}$, $Ar^{16}$, and $Ar^{17}$ each represents a monovalent aromatic hydrocarbon group or a monovalent aromatic heterocyclic group, and $R^8$ represents a hydrogen atom, a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, a monovalent aromatic hydrocarbon group, a monovalent aromatic heterocyclic group, or an aryloxy group.

6. The organic electroluminescent device according to claim 1, wherein the hole transport layer has a two-layer structure having a first hole transport layer and a second hole transport layer, and the second hole transport layer is located beside the luminous layer, and contains the arylamine compound.

7. The organic electroluminescent device according to claim 6, wherein the first hole transport layer contains a triarylamine derivative different from the arylamine compound contained in the second hole transport layer, and the triarylamine derivative has a molecular structure comprising two triarylamine skeletons coupled together by a single bond or a divalent hydrocarbon group, and has 2 to 6 triarylamine skeletons in the entire molecule.

8. The organic electroluminescent device according to claim 7, wherein the triarylamine derivative contained in the first hole transport layer is represented by the following formula (3):

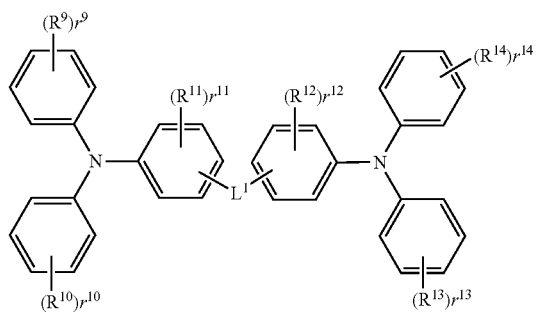
(3)

where $r^9$, $r^{10}$, $r^{13}$, and $r^{14}$ each denotes an integer of 0 to 5, $r^{11}$ and $r^{12}$ each denotes an integer of 0 to 4, $R^9$ to $R^{14}$ each represents a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, a monovalent aromatic hydrocarbon group, a monovalent aromatic heterocyclic group, or an aryloxy group and, if a plurality of these groups are present on an identical benzene ring, these groups may bind to each other via a single bond, a methylene group optionally having a substituent, an oxygen atom, or a sulfur atom to form a ring, and $L^1$ represents a single bond, or a divalent group represented by the following structural formula (B), (C), (D), (E), (F), or (G):

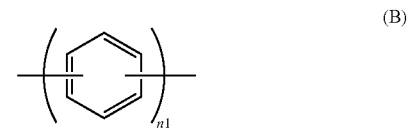
(B)

where n1 denotes an integer of 1 to 4,

(C)

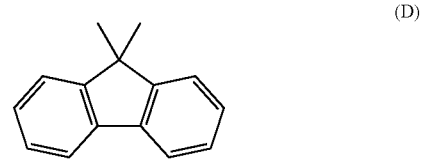
(D)

—CH$_2$— (E)

(F)

(G)

9. The organic electroluminescent device according to claim 7, wherein the triarylamine derivative contained in the first hole transport layer is represented by the following formula (4):

(4)

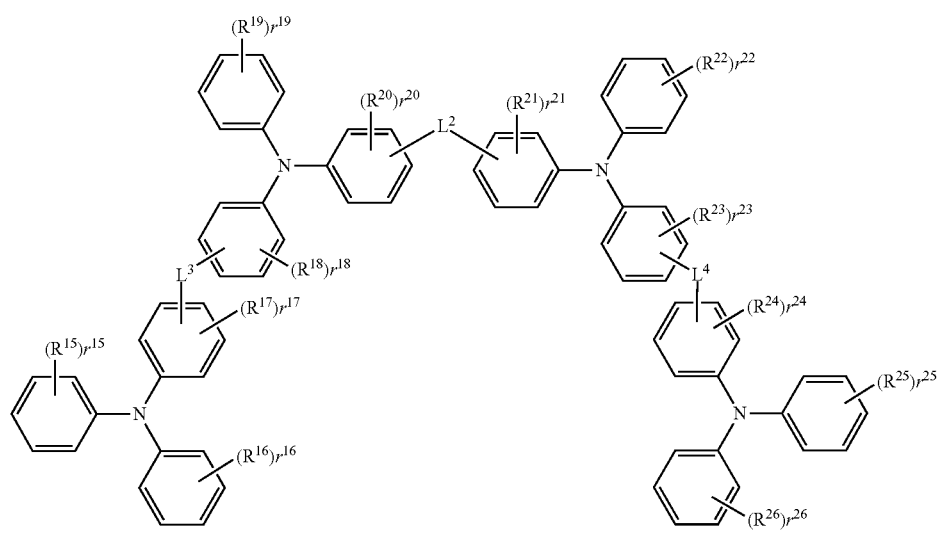

where
$r^{15}$, $r^{16}$, $r^{19}$, $r^{22}$, and $r^{26}$ each denotes an integer of 0 to 5, $r^{17}$, $r^{18}$, $r^{20}$, $r^{21}$, $r^{23}$, and $r^{24}$ each denotes an integer of 0 to 4, $R^{15}$ to $R^{26}$ each represents a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, a monovalent aromatic hydrocarbon group, a monovalent aromatic heterocyclic group, or an aryloxy group and, if a plurality of these groups are present on an identical benzene ring, these groups may bind to each other via a single bond, a methylene group optionally having a substituent, an oxygen atom, or a sulfur atom to form a ring, and $L^2$, $L^3$ and $L^4$ each represent a single bond, or a divalent group represented by the following structural formula (B'), (C), (D), (E), (F) or (G):

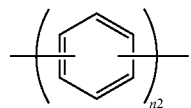 (B')

where n2 denotes an integer of 1 to 3, (C)

(D)

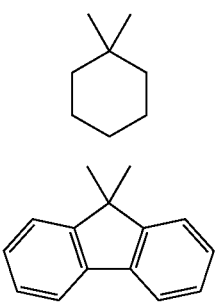

-continued

—CH$_2$— (E)

—CH— (F)

(G)

10. An arylamine compound represented by the following formula (1):

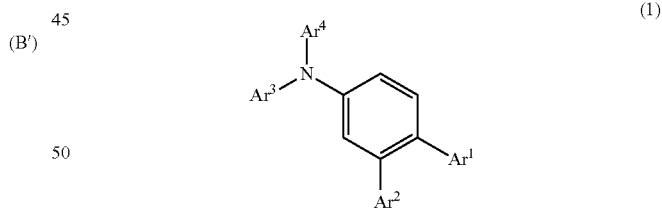 (1)

where
Ar$^1$ represents an unsubstituted phenyl group, an unsubstituted biphenylyl group, an unsubstituted terphenylyl group, or a phenyl group having a naphthyl group as a substituent;
Ar$^2$ represents an unsubstituted phenyl group an unsubstituted biphenylyl group; and
Ar$^3$ and Ar$^4$ each represents an unsubstituted biphenylyl group, an unsubstituted terphenylyl group, a phenyl group having a naphthyl group or a fluorenyl group as a substituent, or a fluorenyl group having a methyl group or a phenyl group as a substituent.

11. An organic electroluminescent device having an anode, a hole transport layer, a luminous layer, an electron transport layer, and a cathode in this order, wherein the hole transport layer contains an arylamine compound represented by the following formula (1):

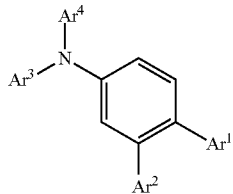
(1)

where

Ar¹ represents a phenyl group, a biphenylyl group, a terphenylyl group, a naphthyl group, a phenanthrenyl group, or a fluorenyl group;

Ar² represents an unsubstituted phenyl group an unsubstituted biphenylyl group; and Ar³ and Ar⁴ each represents an unsubstituted biphenylyl group, an unsubstituted terphenylyl group, a phenyl group having a naphthyl group or a fluorenyl group as a substituent, or a fluorenyl group having a methyl group or a phenyl group as a substituent, wherein the hole transport layer has a two-layer structure having a first hole transport layer and a second hole transport layer, and the second hole transport layer is located beside the luminous layer, and contains the arylamine compound, wherein the first hole transport layer contains a triarylamine derivative different from the arylamine compound contained in the second hole transport layer, and the triarylamine derivative has a molecular structure comprising two triarylamine skeletons coupled together by a single bond or a divalent hydrocarbon group, and has 2 to 6 triarylamine skeletons in the entire molecule.

12. The organic electroluminescent device according to claim 11, wherein the triarylamine derivative contained in the first hole transport layer is represented by the following formula (3):

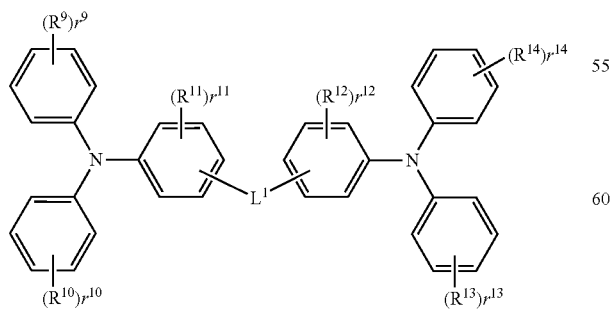
(3)

where $r^9$, $r^{10}$, $r^{13}$, and $r^{14}$ each denotes an integer of 0 to 5, $r^{11}$ and $r^{12}$, each denotes an integer of 0 to 4, $R^9$ to $R^{14}$ each represents a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, a monovalent aromatic hydrocarbon group, a monovalent aromatic heterocyclic group, or an aryloxy group and, if a plurality of these groups are present on an identical benzene ring, these groups may bind to each other via a single bond, a methylene group optionally having a substituent, an oxygen atom, or a sulfur atom to form a ring, and L¹ represents a single bond, or a divalent group represented by the following structural formula (B), (C), (D), (E), (F), or (G):

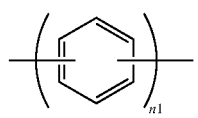
(B)

where n1 denotes an integer of 1 to 4,

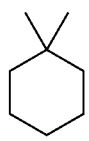
(C)

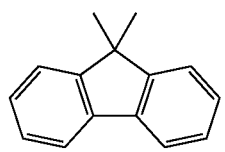
(D)

—CH₂— (E)

—CH— (F)

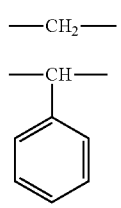

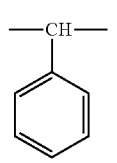
(G)

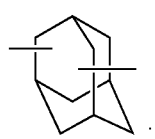

13. The organic electroluminescent device according to claim 11, wherein the triarylamine derivative contained in the first hole transport layer is represented by the following formula (4):

(4)

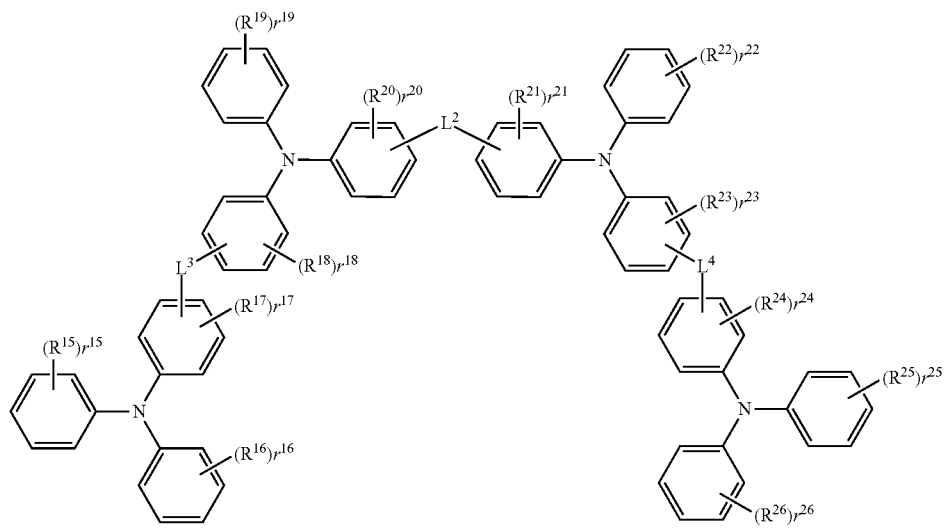

where
$r^{15}$, $r^{16}$, $r^{19}$, $r^{22}$, $r^{25}$, and $r^{26}$ each denotes an integer of 0 to 5, $r^{17}$, $r^{18}$, $r^{20}$, $r^{21}$, $r^{23}$, and $r^{24}$ each denote an integer of 0 to 4, $R^{15}$ to $R^{26}$ each represents a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, a monovalent aromatic hydrocarbon group, a monovalent aromatic heterocyclic group, or an aryloxy group and, if a plurality of these groups are present on an identical benzene ring, these groups may bind to each other via a single bond, a methylene group optionally having a substituent, an oxygen atom, or a sulfur atom to form a ring, and $L^2$, $L^3$, and $L^4$ each represents a single bond, or a divalent group represented by the following structural formula (B'), (C), (D), (E), (F), or (G):

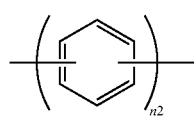 (B')

where n2 denotes an integer of 1 to 3,

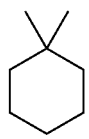 (C)

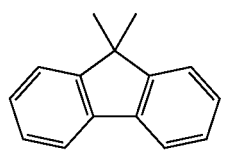 (D)

—CH$_2$— (E)

—CH— (F)
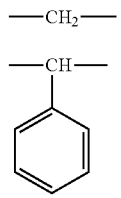

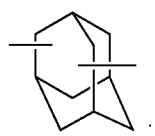 (G)

\* \* \* \* \*

UNITED STATES PATENT AND TRADEMARK OFFICE
CERTIFICATE OF CORRECTION

PATENT NO. : 10,818,844 B2
APPLICATION NO. : 15/324133
DATED : October 27, 2020
INVENTOR(S) : N. Yokoyama et al.

Page 1 of 1

It is certified that error appears in the above-identified patent and that said Letters Patent is hereby corrected as shown below:

On the Title Page
Abstract, Line 5, please change "each represent" to -- each represents --

In the Claims
Column 94, Line 59 (Claim 10, Line 8) please change "phenyl group an" to -- phenyl group or an --
Column 95, Line 24 (Claim 11, Line 12) please change "$Ar^1$" to -- $Ar^4$ --

Signed and Sealed this
Sixth Day of April, 2021

Drew Hirshfeld
*Performing the Functions and Duties of the*
*Under Secretary of Commerce for Intellectual Property and*
*Director of the United States Patent and Trademark Office*